United States Patent
Dong et al.

(10) Patent No.: US 12,122,832 B2
(45) Date of Patent: Oct. 22, 2024

(54) TIM-3-TARGETING ANTIBODIES AND USES THEREOF

(71) Applicant: Suzhou Neologics Bioscience Co., Ltd., Suzhou (CN)

(72) Inventors: Xin Dong, SuZhou (CN); Jinyu Dong, SuZhou (CN); Binbin Wang, SuZhou (CN); Dong Wang, SuZhou (CN); Yu Zhang, Hefei (CN); Liegang Shao, SuZhou (CN); Qian Gao, SuZhou (CN); Haojie Wang, SuZhou (CN); Jun Ma, NanJing (CN); Baiyang Wang, Princeton, NJ (US)

(73) Assignee: SUZHOU NEOLOGICS BIOSCIENCE CO., LTD., Suzhou (CN)

( * ) Notice: Subject to any disclaimer, the term of this patent is extended or adjusted under 35 U.S.C. 154(b) by 0 days.

(21) Appl. No.: 18/330,367

(22) Filed: Jun. 7, 2023

(65) Prior Publication Data
US 2023/0365685 A1     Nov. 16, 2023

Related U.S. Application Data

(63) Continuation of application No. PCT/CN2022/088770, filed on Apr. 24, 2022.

(30) Foreign Application Priority Data

Apr. 23, 2021  (WO) ................ PCT/CN2021/089261
Sep. 24, 2021  (WO) ................ PCT/CN2021/120140

(51) Int. Cl.
| | | |
|---|---|---|
| C07K 16/00 | (2006.01) | |
| A61P 35/00 | (2006.01) | |
| C07K 16/28 | (2006.01) | |
| A61K 39/00 | (2006.01) | |

(52) U.S. Cl.
CPC .......... *C07K 16/2803* (2013.01); *A61P 35/00* (2018.01); *A61K 2039/505* (2013.01); *C07K 2317/24* (2013.01); *C07K 2317/33* (2013.01); *C07K 2317/34* (2013.01); *C07K 2317/622* (2013.01); *C07K 2317/73* (2013.01); *C07K 2317/76* (2013.01); *C07K 2317/77* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 7,470,428 B2 | 12/2008 | Kuchroo et al. | |
| 8,101,176 B2 | 1/2012 | Kuchroo et al. | |
| 8,361,736 B2 | 1/2013 | Majeti et al. | |
| 8,552,156 B2 | 10/2013 | Takayanagi et al. | |
| 8,647,623 B2 | 2/2014 | Takayanagi et al. | |
| 8,697,069 B2 | 4/2014 | Kuchroo et al. | |
| 8,709,412 B2 | 4/2014 | Jones et al. | |
| 8,709,429 B2 | 4/2014 | Majeti et al. | |
| 9,103,832 B2 | 8/2015 | Takayanagi et al. | |
| 9,333,256 B2 | 5/2016 | Kuchroo et al. | |
| 9,487,591 B2 | 11/2016 | Takayanagi et al. | |
| 9,556,270 B2 | 1/2017 | Takayanagi et al. | |
| 9,958,446 B2 | 5/2018 | Takayanagi et al. | |
| 10,550,181 B2 | 2/2020 | Takayanagi et al. | |
| 2016/0311890 A1 | 10/2016 | Jones et al. | |
| 2019/0077869 A1 | 3/2019 | Fiedler et al. | |
| 2019/0225701 A1 | 7/2019 | Kuchroo et al. | |
| 2019/0248893 A1 | 8/2019 | Schebye et al. | |
| 2019/0276531 A1 | 9/2019 | Lindsted et al. | |
| 2019/0292259 A1 | 9/2019 | Damotte et al. | |
| 2019/0322746 A1 | 10/2019 | Bobilev et al. | |
| 2019/0375839 A1 | 12/2019 | Cao et al. | |
| 2019/0382480 A1 | 12/2019 | Lifke et al. | |
| 2020/0190186 A1 | 6/2020 | Schebye et al. | |
| 2020/0223921 A1 | 7/2020 | Sun et al. | |
| 2020/0297841 A1 | 9/2020 | Dijk et al. | |
| 2021/0040207 A1 | 2/2021 | Majeti et al. | |

FOREIGN PATENT DOCUMENTS

| | | |
|---|---|---|
| CN | 106132991 A | 11/2016 |
| CN | 103079644 B | 2/2017 |
| CN | 108430509 A | 8/2018 |
| CN | 108473572 A | 8/2018 |
| CN | 109266731 A | 1/2019 |
| CN | 109451741 A | 3/2019 |
| CN | 109476751 A | 3/2019 |
| CN | 109757103 A | 5/2019 |
| CN | 109790218 A | 5/2019 |
| CN | 109983032 A | 7/2019 |
| CN | 110214027 A | 9/2019 |

(Continued)

OTHER PUBLICATIONS

Almagro & Fransson, Frontiers in Bioscience 2008 (Year: 2008).*
De Genst et al., Dev Comp Immunol 2006; 30:187-98 (Year: 2006).*
Yoshinaga et al., J. Biochem 2008 (Year: 2008).*
Friedlaender A, Addeo A, Banna G. "New emerging targets in cancer immunotherapy: the role of TIM3." ESMO Open 2019;4:e000497. doi:10.1136/esmoopen-2019-000497.

(Continued)

*Primary Examiner* — Meera Natarajan
(74) *Attorney, Agent, or Firm* — Juniv LLP

(57) ABSTRACT

Disclosed herein are anti-TIM-3 antibodies and antigen-binding fragments, polynucleotides encoding the antibodies and antigen-binding fragments, and pharmaceutical compositions comprising the antibodies and antigen-binding fragments. Uses of the anti-TIM-3 antibodies and antigen-binding fragments described herein in cancer treatment are also disclosed.

Figure 1A:
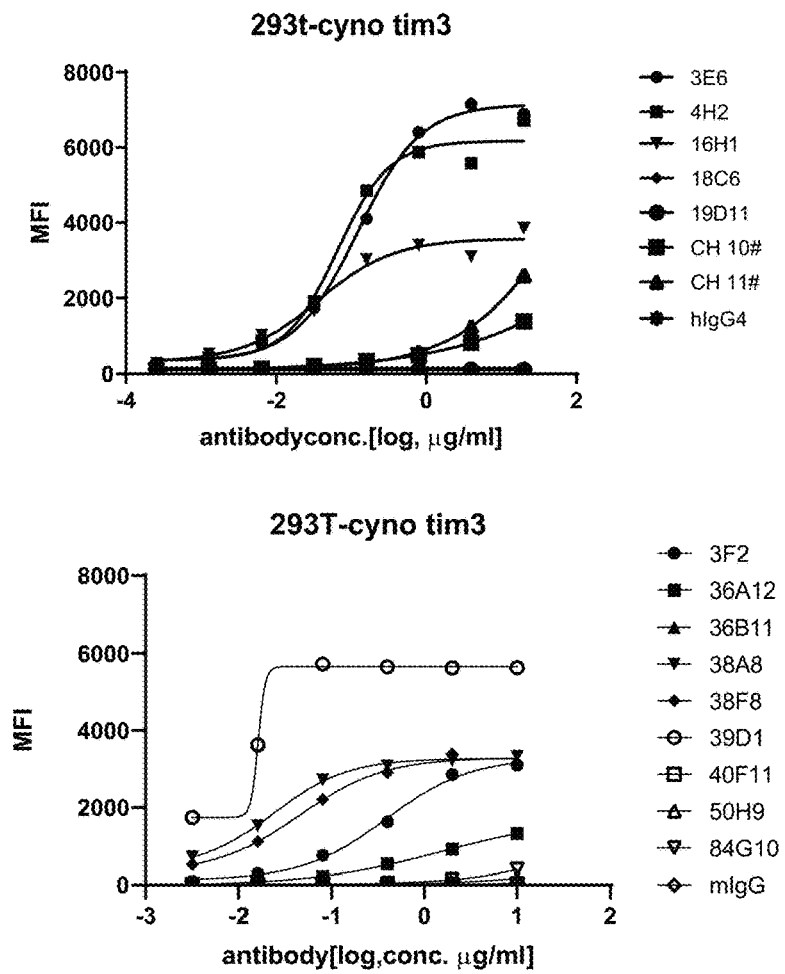

16 Claims, 10 Drawing Sheets
Specification includes a Sequence Listing.

(56) References Cited

FOREIGN PATENT DOCUMENTS

| | | |
|---|---|---|
| CN | 110305216 A | 10/2019 |
| CN | 110382000 A | 10/2019 |
| CN | 110407938 A | 11/2019 |
| CN | 110938146 A | 3/2020 |
| CN | 111050797 A | 4/2020 |
| CN | 111094982 A | 5/2020 |
| CN | 111201030 A | 5/2020 |
| CN | 111868091 A | 10/2020 |
| CN | 111886255 A | 11/2020 |
| CN | 112094348 A | 12/2020 |
| CN | 112512582 A | 3/2021 |
| CN | 112543647 A | 3/2021 |
| CN | 112566936 A | 3/2021 |
| WO | 2017193032 A9 | 2/2018 |
| WO | 2018153366 A1 | 8/2018 |
| WO | 2019046321 A1 | 3/2019 |
| WO | 2019143607 A1 | 7/2019 |
| WO | 2020038355 A1 | 2/2020 |
| WO | 2020043095 A1 | 3/2020 |
| WO | 2020070062 A1 | 4/2020 |
| WO | 2020093024 A2 | 5/2020 |
| WO | 2021053490 A1 | 3/2021 |
| WO | 2022221245 A1 | 10/2022 |

OTHER PUBLICATIONS

Yayi He, Jie Cao, Chao Zhao, Xuefei Li, Caicun Zhou & Fred R Hirsch (2018). "TIM-3, a promising target for cancer immunotherapy." OncoTargets and Therapy, 7005-7009, DOI:10.2147/OTT.S170385.

Zhihui Kuang, Li Li, Pan Zhang, Bingliang Chen, Min Wu, Haiqing Ni, Shuai Yi, Jia Zou and Junjian Liu. "A novel antibody targeting TIM-3 resulting in receptor internalization for cancer immunotherapy." Antibody Therapeutics, 2020, vol. 3, No. 4, 227-236. doi:10.1093/abt/tbaa022.

\* cited by examiner

TIM-3-TARGETING ANTIBODIES AND USES THEREOF

This application is a continuation of PCT Patent Application No. PCT/CN2022/088770, filed Apr. 24, 2022, which claims priority to PCT Patent Application No. PCT/CN2021/089261, filed Apr. 23, 2021, and PCT Patent Application No. PCT/CN2021/120140, filed Sep. 24, 2021, each of which is entirely incorporated herein by reference.

1. REFERENCE TO SEQUENCE LISTING SUBMITTED ELECTRONICALLY

This application incorporates by reference a Sequence Listing with this application entitled "135A002US03_ST26.XML" created on May 31, 2023 and having a size of 277,374 bytes.

2. FIELD

The present invention relates to molecular biology and immuno-oncology. Provided herein include anti-TIM-3-antibodies and uses thereof in treating tumors or cancers.

3. BACKGROUND

Immune checkpoint inhibitors have become a promising class of molecules for therapeutic development (e.g., those targeting PD-1, TIM-3, and CTLA-4). Despite the success of checkpoint inhibitors such as Yervov, Keytruda® and Opdivo® and others, only a fraction of the patients experience durable clinical responses to these therapies. Some tumor types have shown little response to anti-CTLA-4 or anti-PD-1/PD-L1 monotherapies in clinical trials. TIM-3 expression has been associated with cancer, but there has been limited success in the development of TIM-3-targeting therapeutic options. Accordingly, there is an unmet need for additional therapeutic options for cancer patients, especially for TIM-3-targeting agents. The compositions and methods provided herein meet these needs and provide other relative advantages.

4. SUMMARY

Provided herein are antibodies or antigen-binding fragments thereof that specifically bind human TIM-3, comprising: (a) a light chain variable region (VL) comprising (1) a light chain CDR1 (VL CDR1) having an amino acid sequence selected from the group consisting of SEQ ID NOs:86-93 and 129-137; (2) a light chain CDR2 (VL CDR2) having an amino acid sequence selected from the group consisting of SEQ ID NOs:94-100 and 138-144; and (3) a light chain CDR3 (VL CDR3) having an amino acid sequence selected from the group consisting of SEQ ID NOs:47-55, 145-153 and 198-206; or a variant thereof having up to about 3 amino acid substitutions, additions, and/or deletions in the VL CDRs; and/or (b) a heavy chain variable region (VH) comprising (1) a heavy chain CDR1 (VH CDR1) having an amino acid sequence selected from the group consisting of SEQ ID NOs:101-108 and 154-161; (2) a heavy chain CDR2 (VH CDR2) having an amino acid sequence selected from the group consisting of SEQ ID NOs:109-118 and 162-170; and (3) a heavy chain CDR3 (VH CDR3) having an amino acid sequence selected from the group consisting of SEQ ID NOs:119-128 and 171-179; or a variant thereof having up to about 3 amino acid substitutions, additions, and/or deletions in the VH CDRs.

In some embodiments of the anti-TIM-3 antibodies or antigen-binding fragments provided herein, (a) the VL CDR1, CDR2 and CDR3 have (1) the amino acid sequences of SEQ ID NOs:86, 94, and 47, respectively; (2) the amino acid sequences of SEQ ID NOs:87, 95, and 48, respectively; (3) the amino acid sequences of SEQ ID NOs:88, 96, and 49, respectively; (4) the amino acid sequences of SEQ ID NOs:89, 97, and 50, respectively; (5) the amino acid sequences of SEQ ID NOs:90, 94, and 51, respectively; (6) the amino acid sequences of SEQ ID NOs:91, 98, and 52, respectively; (7) the amino acid sequences of SEQ ID NOs:91, 98, and 53, respectively; (8) the amino acid sequences of SEQ ID NOs:92, 99, and 54, respectively; (9) the amino acid sequences of SEQ ID NOs:93, 100, and 55, respectively; (10) the amino acid sequences of SEQ ID NOs:129, 138, and 145, respectively; (11) the amino acid sequences of SEQ ID NOs:130, 139, and 146, respectively; (12) the amino acid sequences of SEQ ID NOs:131, 140, and 147, respectively; (13) the amino acid sequences of SEQ ID NOs:132, 141, and 148, respectively; (14) the amino acid sequences of SEQ ID NOs:133, 139, and 149, respectively; (15) the amino acid sequences of SEQ ID NOs:134, 142, and 150, respectively; (16) the amino acid sequences of SEQ ID NOs:135, 143, and 151, respectively; (17) the amino acid sequences of SEQ ID NOs:136, 144, and 152, respectively; (18) the amino acid sequences of SEQ ID NOs:137, 100, and 153, respectively; (19) the amino acid sequences of SEQ ID NOs:86, 94, and 198, respectively; (20) the amino acid sequences of SEQ ID NOs:86, 94, and 199, respectively; (21) the amino acid sequences of SEQ ID NOs:86, 94, and 200, respectively; (22) the amino acid sequences of SEQ ID NOs:86, 94, and 201, respectively; (23) the amino acid sequences of SEQ ID NOs:86, 94, and 202, respectively; (24) the amino acid sequences of SEQ ID NOs:86, 94, and 203, respectively; (25) the amino acid sequences of SEQ ID NOs:86, 94, and 204, respectively; (26) the amino acid sequences of SEQ ID NOs:86, 94, and 205, respectively; or (27) the amino acid sequences of SEQ ID NOs:86, 94, and 206, respectively; or a variant thereof having up to about 3 amino acid substitutions, additions, and/or deletions in the VL CDRs; and/or (b) the VH CDR1, CDR2 and CDR3 have (1) the amino acid sequences of SEQ ID NOs:101, 109, and 119, respectively; (2) the amino acid sequences of SEQ ID NOs:102, 110, and 120, respectively; (3) the amino acid sequences of SEQ ID NOs:103, 111, and 121, respectively; (4) the amino acid sequences of SEQ ID NOs:104, 112, and 122, respectively; (5) the amino acid sequences of SEQ ID NOs:105, 113, and 123, respectively; (6) the amino acid sequences of SEQ ID NOs:106, 114, and 124, respectively; (7) the amino acid sequences of SEQ ID NOs:106, 115, and 125, respectively; (8) the amino acid sequences of SEQ ID NOs:107, 116, and 126, respectively; (9) the amino acid sequences of SEQ ID NOs:108, 117, and 127, respectively; (10) the amino acid sequences of SEQ ID NOs:106, 118, and 128, respectively; (11) the amino acid sequences of SEQ ID NOs:106, 162, and 171, respectively; (12) the amino acid sequences of SEQ ID NOs:154, 163, and 172, respectively; (13) the amino acid sequences of SEQ ID NOs:155, 164, and 173, respectively; (14) the amino acid sequences of SEQ ID NOs:156, 165, and 174, respectively; (15) the amino acid sequences of SEQ ID NOs:157, 166, and 175, respectively; (16) the amino acid sequences of SEQ ID NOs:158, 167, and 176, respectively; (17) the amino acid sequences of SEQ ID NOs:159, 168, and 177, respectively; (18) the amino acid sequences of SEQ ID NOs:160, 169, and 178, respectively; or (19) the amino acid sequences of SEQ ID NOs:161, 170, and 179, respectively; or a variant thereof having up to about 3 amino acid substitutions, additions, and/or deletions in the VH CDRs.

In some embodiments of the anti-TIM-3 antibodies or antigen-binding fragments provided herein, (1) the VL CDR1. CDR2, and CDR3 have the amino acid sequences of SEQ ID NOs:86, 94, and 47, respectively, and/or the VH CDR1, CDR2, and CDR3 have the amino acid sequences of SEQ ID NOs:101, 109, and 119, respectively; (2) the VL CDR1, CDR2, and CDR3 have the amino acid sequences of SEQ ID NOs:87, 95, and 48, respectively; and/or the VH CDR1, CDR2, and CDR3 have the amino acid sequences of SEQ ID NOs:102, 110, and 120, respectively; (3) the VL CDR1, CDR2, and CDR3 have the amino acid sequences of SEQ ID NOs:88, 96, and 49, respectively; and/or the VH CDR1, CDR2, and CDR3 have the amino acid sequences of SEQ ID NOs:103, 111, and 121, respectively; (4) the VL CDR1, CDR2, and CDR3 have the amino acid sequences of SEQ ID NOs:89, 97, and 50, respectively; and/or the VH CDR1, CDR2, and CDR3 have the amino acid sequences of SEQ ID NOs:104, 112, and 122, respectively; (5) the VL CDR1, CDR2, and CDR3 have the amino acid sequences of SEQ ID NOs:90, 94, and 51, respectively; and/or the VH CDR1, CDR2, and CDR3 have the amino acid sequences of SEQ ID NOs:105, 113, and 123, respectively; (6) the VL CDR1, CDR2, and CDR3 have the amino acid sequences of SEQ ID NOs:91, 98, and 52, respectively; and/or the VH CDR1, CDR2, and CDR3 have the amino acid sequences of SEQ ID NOs:106, 114, and 124, respectively; (7) the VL CDR1, CDR2, and CDR3 have the amino acid sequences of SEQ ID NOs:91, 98, and 53, respectively; and/or the VH CDR1, CDR2, and CDR3 have the amino acid sequences of SEQ ID NOs:106, 115, and 125, respectively; (8) the VL CDR1, CDR2, and CDR3 have the amino acid sequences of SEQ ID NOs:92, 99, and 54, respectively; and/or the VH CDR1, CDR2, and CDR3 have the amino acid sequences of SEQ ID NOs:107, 116, and 126, respectively; (9) the VL CDR1, CDR2, and CDR3 have the amino acid sequences of SEQ ID NOs:93, 100, and 55, respectively; and/or the VH CDR1, CDR2, and CDR3 have the amino acid sequences of SEQ ID NOs:108, 117, and 127, respectively; (10) the VL CDR1, CDR2, and CDR3 have the amino acid sequences of SEQ ID NOs:91, 98, and 52, respectively; and/or the VH CDR1, CDR2, and CDR3 have the amino acid sequences of SEQ ID NOs:106, 118, and 128, respectively; (11) the VL CDR1, CDR2, and CDR3 have the amino acid sequences of SEQ ID NOs:129, 138, and 145, respectively; and/or the VH CDR1, CDR2, and CDR3 have the amino acid sequences of SEQ ID NOs:106, 162, and 171, respectively; (12) the VL CDR1, CDR2, and CDR3 have the amino acid sequences of SEQ ID NOs:130, 139, and 146, respectively; and/or the VH CDR1, CDR2, and CDR3 have the amino acid sequences of SEQ ID NOs:154, 163, and 172, respectively; (13) the VL CDR1, CDR2, and CDR3 have the amino acid sequences of SEQ ID NOs:131, 140, and 147, respectively; and/or the VH CDR1, CDR2, and CDR3 have the amino acid sequences of SEQ ID NOs:155, 164, and 173, respectively; (14) the VL CDR1, CDR2, and CDR3 have the amino acid sequences of SEQ ID NOs:132, 141, and 148, respectively; and/or the VH CDR1, CDR2, and CDR3 have the amino acid sequences of SEQ ID NOs:156, 165, and 174, respectively; (15) the VL CDR1, CDR2, and CDR3 have the amino acid sequences of SEQ ID NOs:133, 139, and 149, respectively; and/or the VH CDR1, CDR2, and CDR3 have the amino acid sequences of SEQ ID NOs:157, 166, and 175, respectively; (16) the VL CDR1, CDR2, and CDR3 have the amino acid sequences of SEQ ID NOs:134, 142, and 150, respectively; and/or the VH CDR1, CDR2, and CDR3 have the amino acid sequences of SEQ ID NOs:158, 167, and 176, respectively; (17) the VL CDR1, CDR2, and CDR3 have the amino acid sequences of SEQ ID NOs:135, 143, and 151, respectively; and/or the VH CDR1, CDR2, and CDR3 have the amino acid sequences of SEQ ID NOs:159, 168, and 177, respectively; (18) the VL CDR1, CDR2, and CDR3 have the amino acid sequences of SEQ ID NOs:136, 144, and 152, respectively; and/or the VH CDR1, CDR2, and CDR3 have the amino acid sequences of SEQ ID NOs:160, 169, and 178, respectively; (19) the VL CDR1, CDR2, and CDR3 have the amino acid sequences of SEQ ID NOs:137, 100, and 153, respectively; and/or the VH CDR1, CDR2, and CDR3 have the amino acid sequences of SEQ ID NOs:161, 170, and 179, respectively; (20) the VL CDR1. CDR2, and CDR3 have the amino acid sequences of SEQ ID NOs:86, 94, and 198, respectively; and/or the VH CDR1, CDR2, and CDR3 have the amino acid sequences of SEQ ID NOs:101, 109, and 119, respectively; (21) the VL CDR1, CDR2, and CDR3 have the amino acid sequences of SEQ ID NOs:86, 94, and 199, respectively; and/or the VH CDR1, CDR2, and CDR3 have the amino acid sequences of SEQ ID NOs:101, 109, and 119, respectively; (22) the VL CDR1, CDR2, and CDR3 have the amino acid sequences of SEQ ID NOs:86, 94, and 200, respectively; and/or the VH CDR1, CDR2, and CDR3 have the amino acid sequences of SEQ ID NOs:101, 109, and 119, respectively; (23) the VL CDR1, CDR2, and CDR3 have the amino acid sequences of SEQ ID NOs:86, 94, and 201, respectively; and/or the VH CDR1, CDR2, and CDR3 have the amino acid sequences of SEQ ID NOs:101, 109, and 119, respectively; (24) the VL CDR1, CDR2, and CDR3 have the amino acid sequences of SEQ ID NOs:86, 94, and 202, respectively; and/or the VH CDR1, CDR2, and CDR3 have the amino acid sequences of SEQ ID NOs:101, 109, and 119, respectively; (25) the VL CDR1, CDR2, and CDR3 have the amino acid sequences of SEQ ID NOs:86, 94, and 203, respectively; and/or the VH CDR1, CDR2, and CDR3 have the amino acid sequences of SEQ ID NOs:101, 109, and 119, respectively; (26) the VL CDR1, CDR2, and CDR3 have the amino acid sequences of SEQ ID NOs:86, 94, and 204, respectively; and/or the VH CDR1, CDR2, and CDR3 have the amino acid sequences of SEQ ID NOs:101, 109, and 119, respectively; (27) the VL CDR1, CDR2, and CDR3 have the amino acid sequences of SEQ ID NOs:86, 94, and 205, respectively; and/or the VH CDR1, CDR2, and CDR3 have the amino acid sequences of SEQ ID NOs:101, 109, and 119, respectively; or (28) the VL CDR1, CDR2, and CDR3 have the amino acid sequences of SEQ ID NOs:86, 94, and 206, respectively; and/or the VH CDR1, CDR2, and CDR3 have the amino acid sequences of SEQ ID NOs:101, 109, and 119, respectively.

In some embodiments, the anti-TIM-3 antibodies or antigen-binding fragments provided herein comprise a VL CDR1, a VL CDR2, a VH CDR1, a VH CDR2 and a VH CDR3 having the amino acid sequences of SEQ ID NOs:86, 94, 101, 109, and 119, respectively, and a VL CDR3 having an amino acid sequence selected from the group consisting of SEQ ID NOs:47 and 198-206; or a variant thereof having up to about 3 amino acid substitutions, additions, and/or deletions in the VL CDRs and up to about 3 amino acid substitutions, additions, and/or deletions in the VH CDRs. In some embodiments, the F residue of VH CDR1 (amino acid 3 of SEQ ID NO:101), H and S resides of VH CDR2 (amino acids 4 and 5 of SEQ ID NO:109), Y, R, S and W residues of VH CDR3 (amino acids 2, 3, 4, and 6 of SEQ ID NO:119), and S residue of VL CDR2 (amino acid 7 of SEQ ID NO:94) are not mutated. In some embodiments, the anti-TIM-3 antibodies or antigen-binding fragments provided herein comprise a VL CDR1, a VL CDR2, a VL CDR3, a VH CDR1, a VH CDR2 and a VH CDR3 having the amino acid sequences of SEQ ID NOs:86, 94, 47, 101, 109, and 119, respectively.

In some embodiments, provided herein are antibodies or antigen-binding fragments thereof that specifically binds human TIM-3, comprising: (a) a VL having at least 85%, at least 90%, at least 95%, at least 98%, or 100% sequence identity to an amino acid sequence selected from the group consisting of SEQ ID NOs:1-10 and 180-188; and/or (b) a VH having at least 85%, at least 90%, at least 95%, at least 98%, or 100% sequence identity to an amino acid sequence selected from the group consisting of SEQ ID NOs:11-20 and 189-197.

In some embodiments, the anti-TIM-3 antibodies or antigen-binding fragments provided herein comprise a VL and a VH, wherein the VL and VH each have at least 85%, at least 90%, at least 95%, at least 98%, or 100% sequence identity to the amino acid sequences of (1) SEQ ID NOs:1 and 11, respectively; (2) SEQ ID NOs:2 and 12, respectively; (3) SEQ ID NOs:3 and 13, respectively; (4) SEQ ID NOs:4 and 14, respectively; (5) SEQ ID NOs:5 and 15, respectively; (6) SEQ ID NOs:6 and 16, respectively; (7) SEQ ID NOs:7 and 17, respectively; (8) SEQ ID NOs:8 and 18, respectively; (9) SEQ ID NOs:9 and 19, respectively; (10) SEQ ID NOs:10 and 20, respectively; (11) SEQ ID NOs:180 and 189, respectively; (12) SEQ ID NOs:181 and 190, respectively; (13) SEQ ID NOs:182 and 191, respectively; (14) SEQ ID NOs:183 and 192, respectively; (15) SEQ ID NOs:184 and 193, respectively; (16) SEQ ID NOs:185 and 194, respectively; (17) SEQ ID NOs:186 and 195, respectively; (18) SEQ ID NOs:187 and 196, respectively; or (19) SEQ ID NOs:188 and 197, respectively. In some embodiments, the VL and VH each have at least 85%, at least 90%, at least 95%, at least 98%, or 100% sequence identity to the amino acid sequences of SEQ ID NOs:1 and 11, respectively.

In some embodiments, provided herein are antibodies or antigen-binding fragments thereof that specifically bind human TIM-3 comprising (a) a VL having at least 85%, at least 90%, at least 95%, at least 98%, or 100% sequence identity to SEQ ID NO:21 and 207-215; and/or (b) a VH having at least 85%, at least 90%, at least 95%, at least 98%, or 100% sequence identity to an amino acid sequence selected from the group consisting of SEQ ID NOs:22-29.

In some embodiments, provided herein are antibodies or antigen-binding fragments thereof that specifically bind human TIM-3, comprising (a) a VL comprising VL CDR1, CDR2, and CDR3 from a VL having an amino acid sequence selected from the group consisting of SEQ ID NOs:1-10 and 180-188; and/or (b) a VH comprising VH CDR1, CDR2, and CDR3 from a VH having an amino acid sequence selected from group consisting of SEQ ID NOs:11-20 and 189-197.

In some embodiments, the anti-TIM-3 antibodies or antigen-binding fragments provided herein comprise (1) a VL comprising VL CDR1, CDR2, and CDR3 from a VL having the amino acid sequence of SEQ ID NO:1, and/or a VH comprising VH CDR1, CDR2, and CDR3 from a VH having the amino acid sequence of SEQ ID NO: 1; (2) a VL comprising VL CDR1, CDR2, and CDR3 from a VL having the amino acid sequence of SEQ ID NO:2, and/or a VH comprising VH CDR1. CDR2, and CDR3 from a VH having the amino acid sequence of SEQ ID NO:12; (3) a VL comprising VL CDR1, CDR2, and CDR3 from a VL having the amino acid sequence of SEQ ID NO:3, and/or a VH comprising VH CDR1, CDR2, and CDR3 from a VH having the amino acid sequence of SEQ ID NO:13; (4) a VL comprising VL CDR1, CDR2, and CDR3 from a VL having the amino acid sequence of SEQ ID NO:4, and/or a VH comprising VH CDR1, CDR2, and CDR3 from a VH having the amino acid sequence of SEQ ID NO:14; (5) a VL comprising VL CDR1, CDR2, and CDR3 from a VL having the amino acid sequence of SEQ ID NO:5, and/or a VH comprising VH CDR1, CDR2, and CDR3 from a VH having the amino acid sequence of SEQ ID NO:15; (6) a VL comprising VL CDR1, CDR2, and CDR3 from a VL having the amino acid sequence of SEQ ID NO:6, and/or a VH comprising VH CDR1, CDR2, and CDR3 from a VH having the amino acid sequence of SEQ ID NO:16; (7) a VL comprising VL CDR1, CDR2, and CDR3 from a VL having the amino acid sequence of SEQ ID NO:7, and/or a VH comprising VH CDR1. CDR2, and CDR3 from a VH having the amino acid sequence of SEQ ID NO:17; (8) a VL comprising VL CDR1, CDR2, and CDR3 from a VL having the amino acid sequence of SEQ ID NO:8, and/or a VH comprising VH CDR1, CDR2, and CDR3 from a VH having the amino acid sequence of SEQ ID NO:18; (9) a VL comprising VL CDR1, CDR2, and CDR3 from a VL having the amino acid sequence of SEQ ID NO:9, and/or a VH comprising VH CDR1, CDR2, and CDR3 from a VH having the amino acid sequence of SEQ ID NO:19; (10) a VL comprising VL CDR1, CDR2, and CDR3 from a VL having the amino acid sequence of SEQ ID NO:10, and/or a VH comprising VH CDR1, CDR2, and CDR3 from a VH having the amino acid sequence of SEQ ID NO:20; (11) a VL comprising VL CDR1, CDR2, and CDR3 from a VL having the amino acid sequence of SEQ ID NO:180, and/or a VH comprising VH CDR1, CDR2, and CDR3 from a VH having the amino acid sequence of SEQ ID NO:189; (12) a VL comprising VL CDR1, CDR2, and CDR3 from a VL having the amino acid sequence of SEQ ID NO:181, and/or a VH comprising VH CDR1, CDR2, and CDR3 from a VH having the amino acid sequence of SEQ ID NO:190; (13) a VL comprising VL CDR1, CDR2, and CDR3 from a VL having the amino acid sequence of SEQ ID NO:182, and/or a VH comprising VH CDR1, CDR2, and CDR3 from a VH having the amino acid sequence of SEQ ID NO:191; (14) a VL comprising VL CDR1, CDR2, and CDR3 from a VL having the amino acid sequence of SEQ ID NO:183, and/or a VH comprising VH CDR1, CDR2, and CDR3 from a VH having the amino acid sequence of SEQ ID NO:192; (15) a VL comprising VL CDR1, CDR2, and CDR3 from a VL having the amino acid sequence of SEQ ID NO:184, and/or a VH comprising VH CDR1, CDR2, and CDR3 from a VH having the amino acid sequence of SEQ ID NO:193; (16) a VL comprising VL CDR1, CDR2, and CDR3 from a VL having the amino acid sequence of SEQ ID NO:185, and/or a VH comprising VH CDR1, CDR2, and CDR3 from a VH having the amino acid sequence of SEQ ID NO:194; (17) a VL comprising VL CDR1, CDR2, and CDR3 from a VL having the amino acid sequence of SEQ ID NO:186, and/or a VH comprising VH CDR1, CDR2, and CDR3 from a VH having the amino acid sequence of SEQ ID NO:195; (18) a VL comprising VL CDR1, CDR2, and CDR3 from a VL having the amino acid sequence of SEQ ID NO:187, and/or a VH comprising VH CDR1, CDR2, and CDR3 from a VH having the amino acid sequence of SEQ ID NO:196; or (19) a VL comprising VL CDR1, CDR2, and CDR3 from a VL having the amino acid sequence of SEQ ID NO:188, and/or a VH comprising VH CDR1, CDR2, and CDR3 from a VH having the amino acid sequence of SEQ ID NO:197.

In some embodiments, provided herein are antibodies or antigen-binding fragments thereof that specifically bind human TIM-3 comprising a VL and a VH, wherein the VL comprises VL CDR1, CDR2, and CDR3 from a VL having an amino acid sequence selected from the group consisting of SEQ ID NOs:1, 21, and 207-215, and the VH comprises VH CDR1, CDR2, and CDR3 from a VH having an amino acid sequence selected from the group consisting of SEQ ID NO:11 and 22-29.

In some embodiments, provided herein are antibodies or antigen-binding fragments thereof that compete with any anti-TIM-3 antibody or antigen-binding fragment disclosed herein for binding to human TIM-3.

In some embodiments, provided herein are antibodies or antigen-binding fragments thereof that specifically bind human TIM-3, wherein the antibodies or antigen-binding fragments specifically bind to an epitope that comprises at least one of amino acids 71-82 of human TIM-3. In some embodiments, the antibodies or antigen-binding fragments disclosed herein specifically bind to at least one of the following amino acid residues of human TIM-3: D71, R73, D74, V75, N76, W78, T79, and Y82. In some embodiments, the antibodies or antigen-binding fragments disclosed herein specifically bind to at least two, at least three, at least four, at least five, at least six, at least seven or eight of the following residues of human TIM-3: D71, R73, D74, V75, N76, W78, T79, and Y82. In some embodiments, the antibodies or antigen-binding fragments disclosed herein specifically bind to at least D71, N76, or Y82 of human TIM-3. In some embodiments, the antibodies or antigen-binding fragments disclosed herein do not specifically bind to an epitope outside amino acids 71-82 of human TIM-3.

In some embodiments, the anti-TIM-3 antibodies or antigen-binding fragments provided herein bind human TIM-3 with a KD that is $5\times10^{-8}$ M or less. In some embodiments, the anti-TIM-3 antibodies or antigen-binding fragments provided herein bind human TIM-3 with a KD that ranges from $10^{-11}$ M to $5\times10^{-9}$ M.

In some embodiments, the anti-TIM-3 antibodies or antigen-binding fragments provided herein block the interaction between TIM-3 and a TIM-3 ligand. In some embodiments, the TIM-3 ligand is phosphatidylserine, CEACAM1, HMGB1, or any combination thereof.

In some embodiments, the anti-TIM-3 antibodies or antigen-binding fragments provided herein (1) inhibit TIM-3 mediated T cell suppression. (2) inhibit TIM-3 mediated myeloid cell suppression, (3) inhibit TIM-3 mediated suppression of inflammasome activation, or any combination thereof.

In some embodiments, the anti-TIM-3 antibody or antigen-binding fragment provided herein is a monoclonal antibody or antigen-binding fragment. In some embodiments, the anti-TIM-3 antibody or antigen-binding fragment provided herein is selected from the group consisting of an IgG1 antibody, an IgG2 antibody, an IgG3 antibody, and an IgG4 antibody. In some embodiments, the anti-TIM-3 antibody or antigen-binding fragment provided herein is an IgG1 antibody. In some embodiments, the anti-TIM-3 antibody or antigen-binding fragment provided herein is selected from the group consisting of a Fab, a Fab', a F(ab')2, a Fv, a scFv, a (scFv)2, a single domain antibody (sdAb), and a heavy chain antibody (HCAb).

In some embodiments, the anti-TIM-3 antibody or antigen-binding fragment provided herein is a chimeric antibody or antigen-binding fragment, a humanized antibody or antigen-binding fragment, or a human antibody or antigen-binding fragment. In some embodiments, the anti-TIM-3 antibody or antigen-binding fragment provided herein is a humanized antibody or antigen-binding fragment.

In some embodiments, the anti-TIM-3 antibody or antigen-binding fragment provided herein is a bispecific antibody or a multispecific antibody. In some embodiments, the anti-TIM-3 antibody or antigen-binding fragment is a bispecific antibody that further specifically binds PD-1, PD-L1, CEACAM1, or CEACAM5.

In some embodiments, provided herein are polynucleotides encoding an anti-TIM-3 antibody or antigen-binding fragment provided herein. In some embodiments, provided herein are vectors comprising a polynucleotide provided herein. In some embodiments, provided herein are host cells comprising a polynucleotide provided herein, or a vector provided herein.

In some embodiments, provided herein are pharmaceutical compositions comprising a therapeutically effective amount of an anti-TIM-3 antibody or antigen-binding fragment provided herein, and a pharmaceutically acceptable carrier.

In some embodiments, provided herein are methods of inducing or stimulating immune cell activation and/or proliferation, comprising contacting an immune cell with an effective amount of an anti-TIM-3 antibody or antigen-binding fragment provided herein. In some embodiments, provided herein are methods of reducing TIM-3-mediated suppression of an immune cell comprising contacting the immune cell with an effective amount of an anti-TIM-3 antibody or antigen-binding fragment provided herein. In some embodiments, the immune cell is a T cell, an NK cell, an NKT cell, or a myeloid cell. In some embodiments, the immune cell is a T cell. In some embodiments, the immune cell is an NK cell. In some embodiments, the immune cell is a myeloid cell, wherein the myeloid cell is a macrophage or a dendritic cell.

In some embodiments, provided herein are methods of stimulating anti-tumor immunity in a subject in need thereof, comprising administering to the subject a therapeutically effective amount of an anti-TIM-3 antibody or antigen-binding fragment provided herein or a pharmaceutical composition provided herein. In some embodiments, provided herein are methods of inhibiting tumor cell growth in a subject in need thereof, comprising administering to the subject a therapeutically effective amount of an anti-TIM-3 antibody or antigen-binding fragment provided herein or a pharmaceutical composition provided herein.

In some embodiments, provided herein are methods of treating cancer in a subject in need thereof, comprising administering to the subject a therapeutically effective amount of an anti-TIM-3 antibody or antigen-binding fragment provided herein or a pharmaceutical composition provided herein.

In some embodiments, the methods provided herein further comprise administering an additional therapy to the subject. In some embodiments, the additional therapy comprises an antibody that specifically binds PD-L1, PD-1, CEACAM1, CTLA4, CEACAM5, latent TGF-β, TGF-β receptor, CD70, B7H4, or B7H3. In some embodiments, the additional therapy comprises irradiation or chemotherapy.

In some embodiments of the methods provided herein, the subject is a human.

In some embodiments, provided herein are use of an anti-TIM-3 antibody or antigen-binding fragment provided herein in cancer treatment. In some embodiments, provided herein are uses of an anti-TIM-3 antibody or antigen-binding fragment for the preparation of a medicament for the treatment of cancer.

In some embodiments, the cancer is a hematological cancer. In some embodiments, the hematological cancer is acute myelogenous leukemia (AML) or myelodysplastic syndromes (MDS).

In some embodiments, the cancer is a solid tumor. In some embodiments, the cancer is melanoma, lung cancer, head and neck cancer, colorectal cancer, pancreatic cancer, gastric cancer, kidney cancer, bladder cancer, prostate cancer, breast cancer, ovarian cancer, uterine/cervical cancer, testicular cancer, thyroid cancer, esophageal cancer, soft tissue sarcoma, liver cancer, gallbladder cancer, cervical cancer, duodenal cancer, bone cancer, neuroendocrine cancer, intestinal cancer, skin cancer, or germ cell cancer. In some embodiments, the cancer is selected from the group consisting of renal cell carcinoma (RCC), non-small cell lung carcinoma (NSCLC), squamous cell carcinoma of the head and neck (SCCHN), triple negative breast cancer (TNBC), gastric/stomach adenocarcinoma (STAD), pancreatic adenocarcinoma (PAAD), colon adenocarcinoma (COAD), or rectum adenocarcinoma (READ). In some embodiments, the cancer has a high degree of microsatellite instability. In some embodiments, the cancer is a metastatic cancer, refractory cancer, or recurrent cancer.

5. BRIEF DESCRIPTION OF DRAWINGS

Figure 1B:
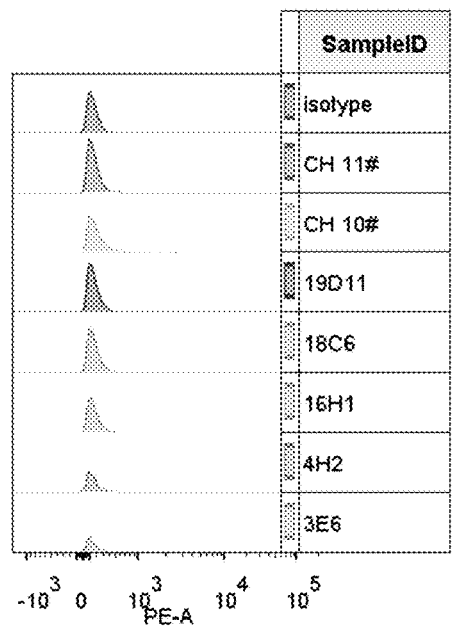

FIG. 1A provide flow cytometry data showing the cross-reaction of various anti-TIM-3 antibodies with cynomolgus TIM-3. FIG. 1B provides flow cytometry data showing that none of the tested anti-TIM-3 antibodies cross-reacted with mouse TIM-3.

Figure 2:
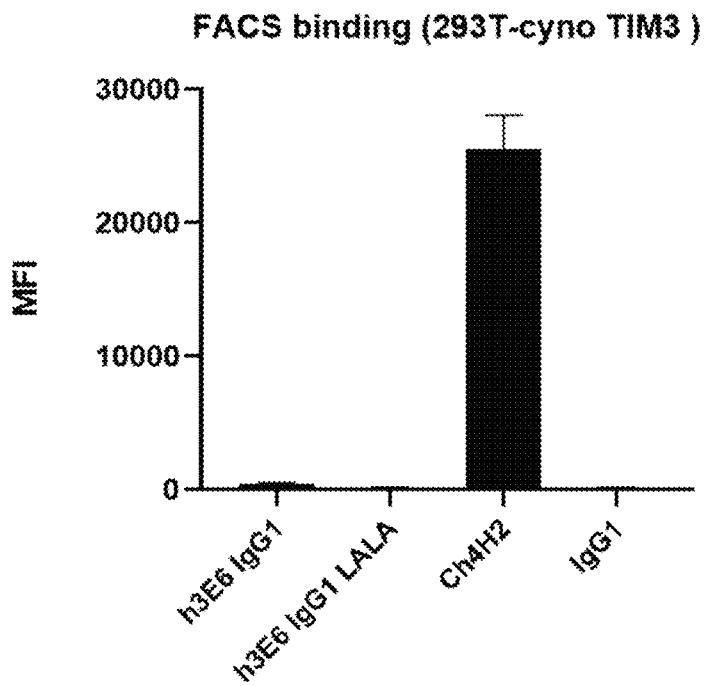

FIG. 2 provide flow cytometry data showing that some humanized anti-TIM-3 antibodies did not cross-react with cynomolgus TIM-3.

Figure 3:
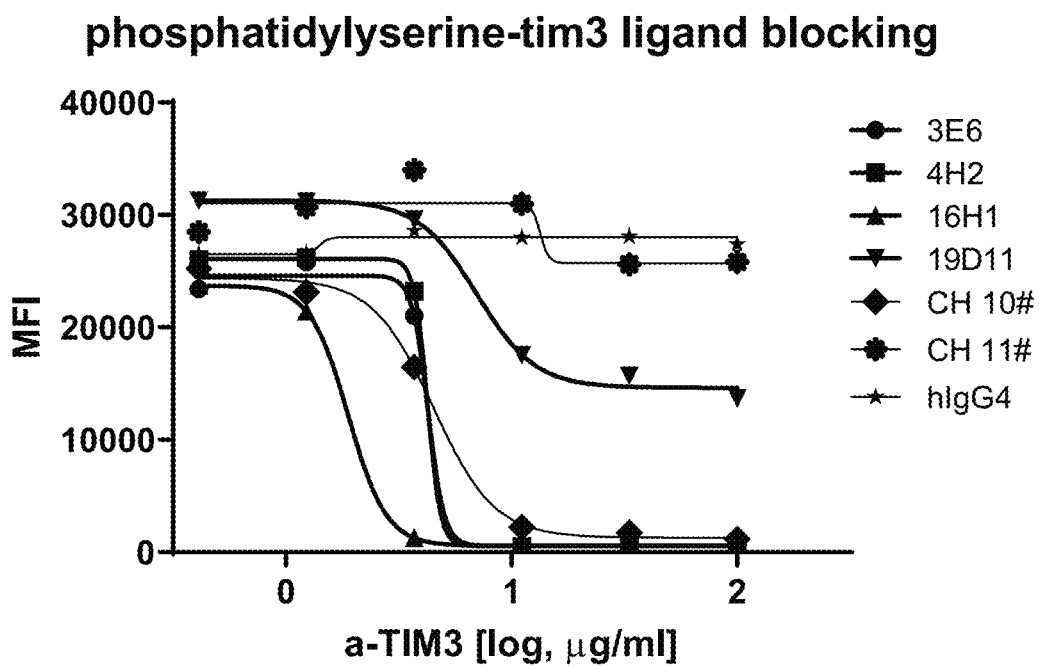

FIG. 3 provides flow cytometry data showing that certain anti-TIM-3 antibodies blocked TIM-3 binding to phosphatidylserine on apoptotic cells.

Figure 4:
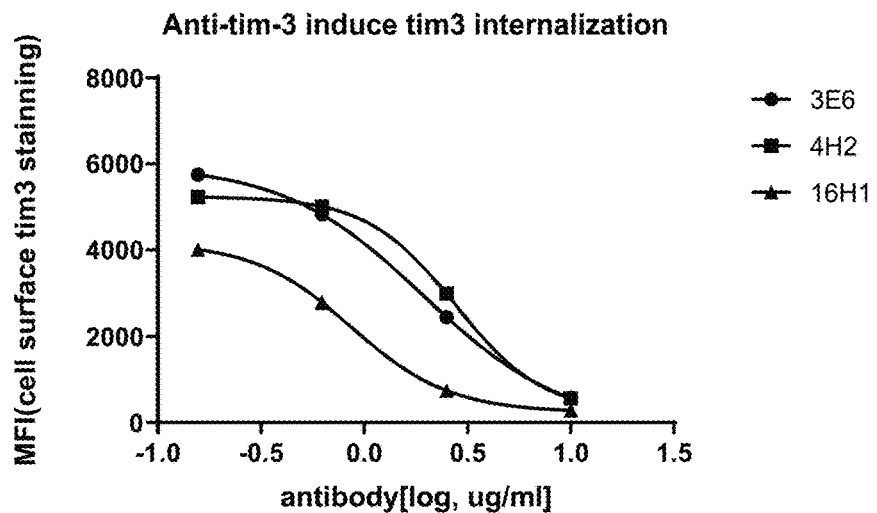

FIG. 4 provides flow cytometry data showing that certain anti-TIM-3 antibodies induced internalization of TIM-3.

Figure 5A:
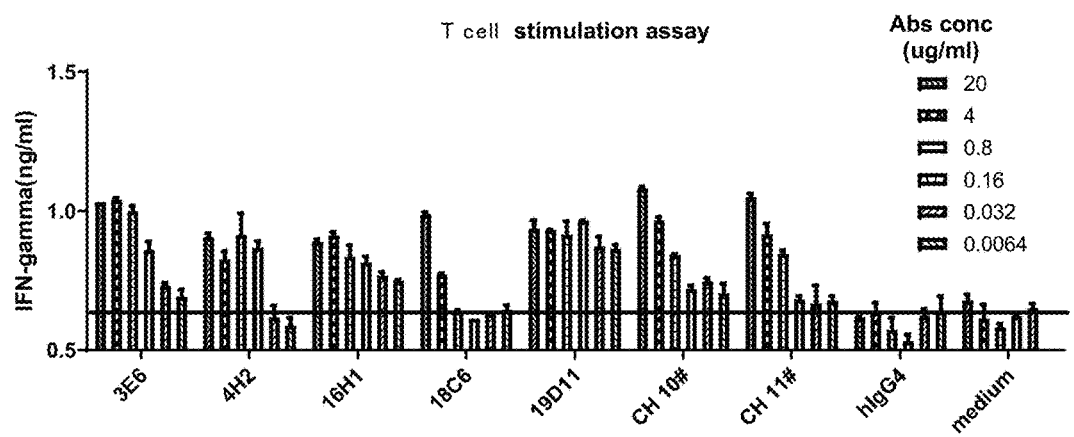
Figure 5A:
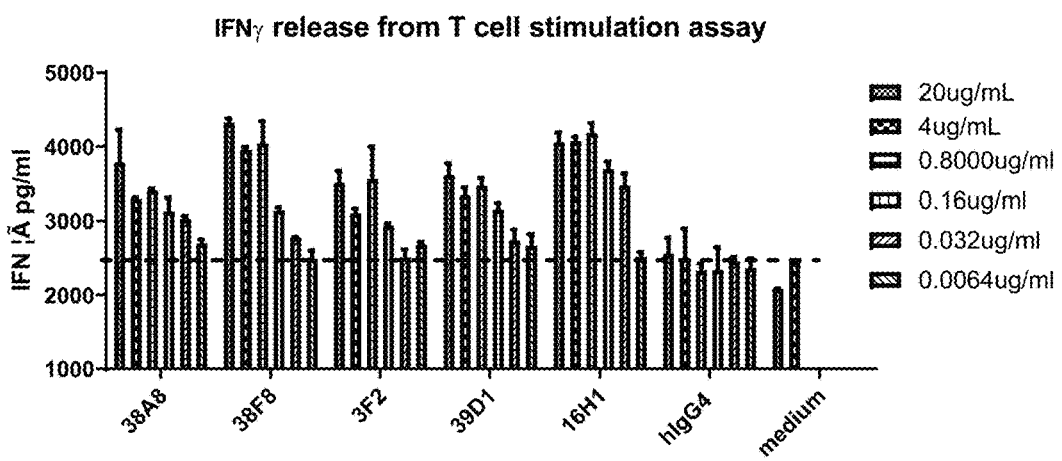
Figure 5B:
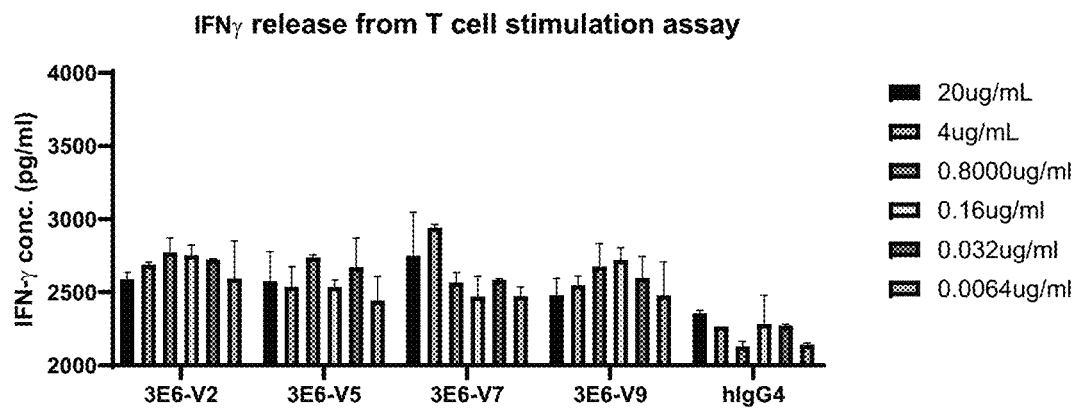

FIG. 5A provides ELISA data showing that anti-TIM-3 antibodies increased IFN-γ secretion in the co-culture of 293T/OS8 target cells and effector cells in a dose-dependent manner. FIG. 5B provides results of the same assay for affinity matured 3E6 antibodies.

Figure 6:
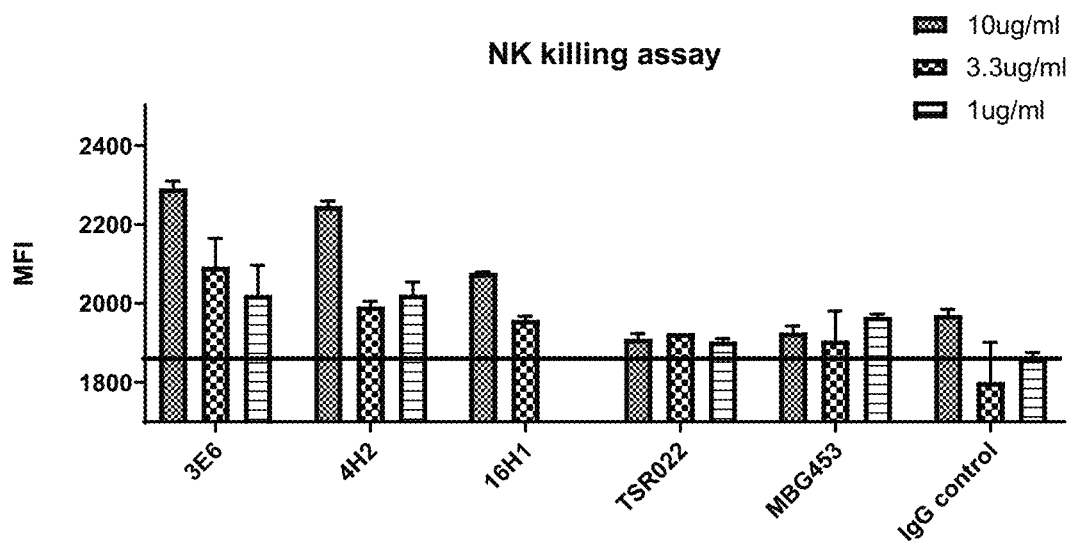

FIG. 6 provides flow cytometry data showing that certain anti-TIM-3 antibodies increased CD107a expression in NK cells in a dose-dependent manner.

Figure 7A:
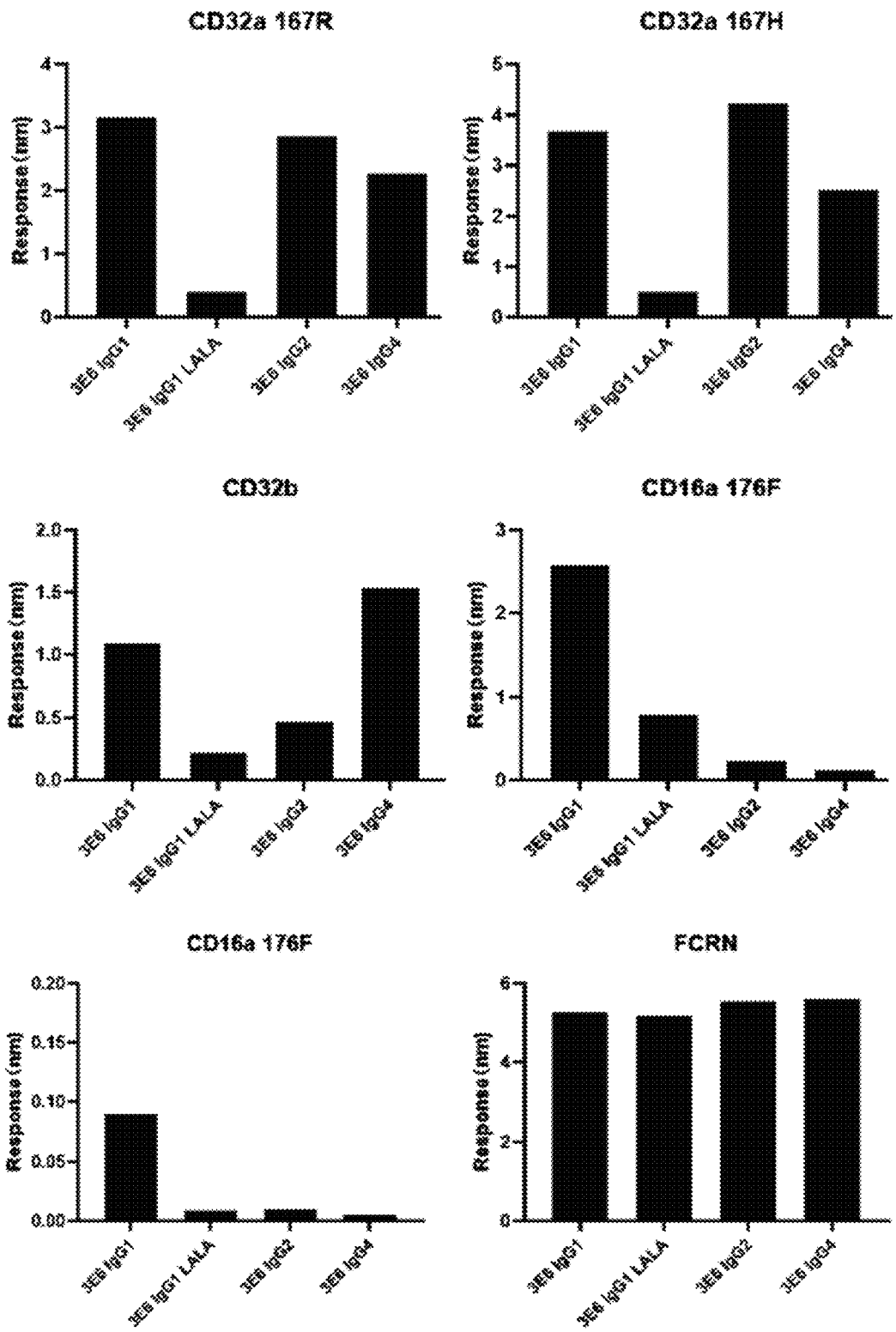
Figure 7B:
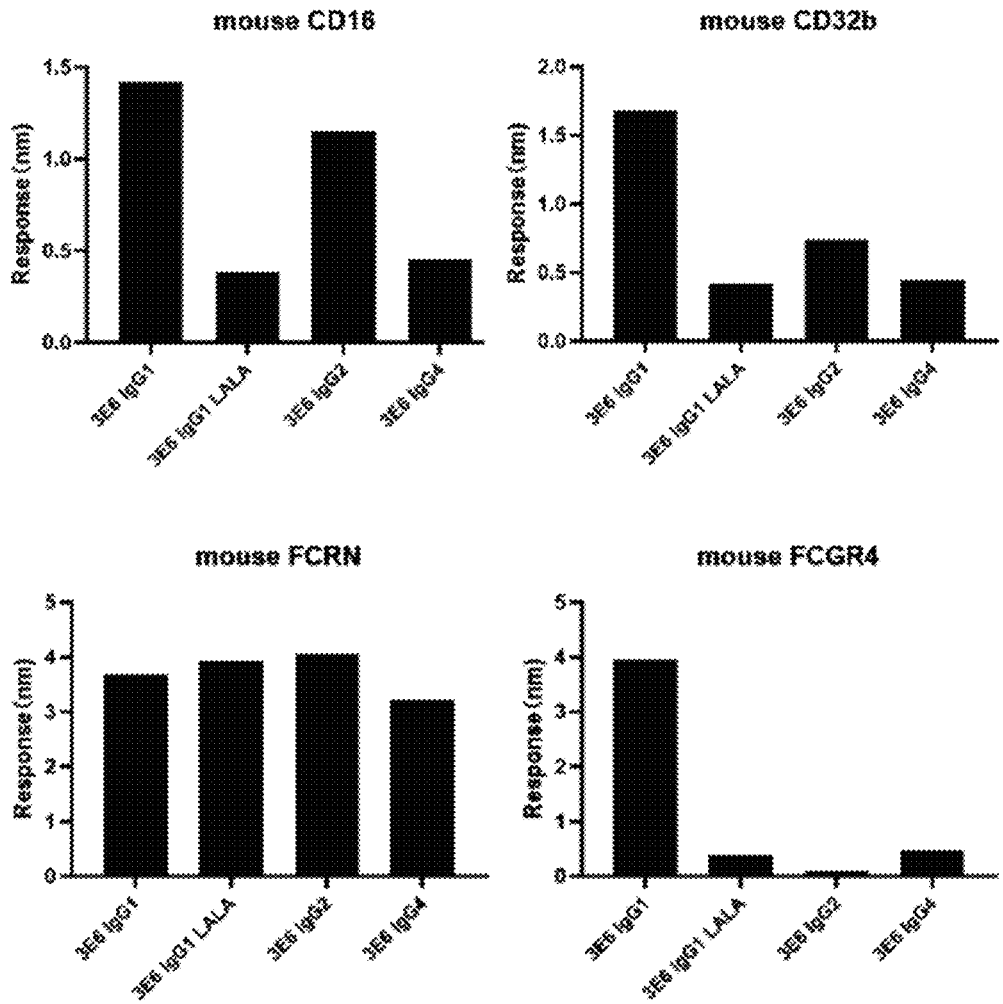

FIGS. 7A-7B provide data from the biomolecular interaction system Gator (Probe Life) measuring the binding between humanized anti-TIM-3 antibody 3E6 of different isotypes (IgG1, IgG1 LALA, IgG2, and IgG4) to different Fc receptors. FIG. 7A (human Fc receptors): CD32a H167, CD32a R167, CD32b, Cd16a 176F, Cd16a 176V, and FCRN; FIG. 7B (mouse Fc receptors): CD16, CD32B, FCRN, or FCGR4. IgG1 LALA: IgG1 with L234A and L235A mutations.

Figure 8:
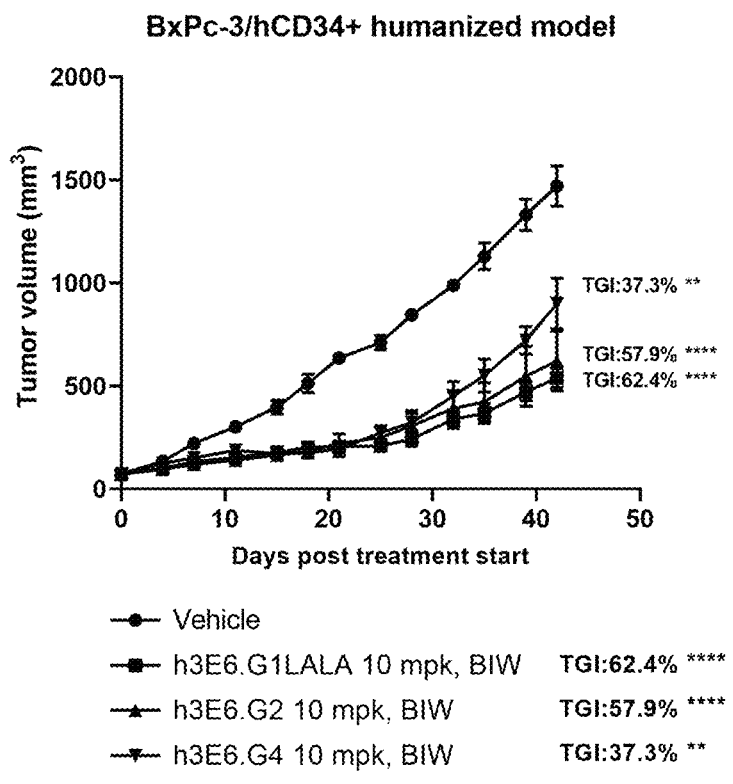

FIG. 8 provides BxPC-3/hCD34+ humanized mouse model results showing that humanized anti-TIM-3 antibody 3E6 of different isotypes (IgG1 LALA, IgG2, and IgG4) effectively inhibited tumor growth.

Figure 9:
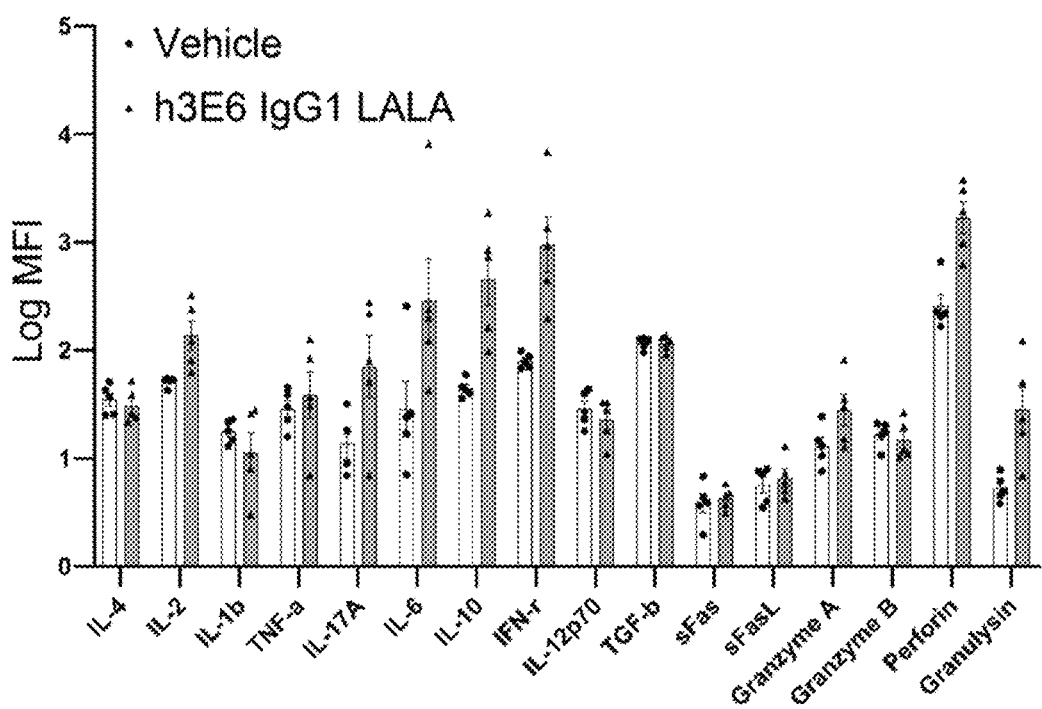

FIG. 9 provides the levels of cytokines (LEGENDplex™ Human Essential Immune Response Panel) detected in the endpoint serum samples in the BxPC-3/hCD34+ humanized mouse model, showing that humanized anti-TIM-3 antibody (h3E6 IgG1 LALA) enhanced serum levels of a number of cytokines in the mouse model.

Figure 10:
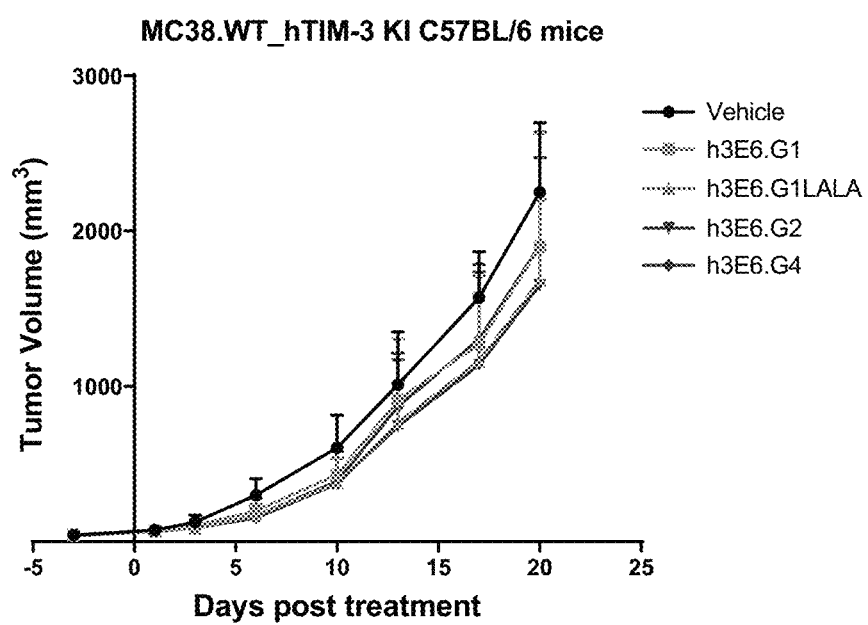

FIG. 10 provides MC38/TIM3-humanized C57BL/6 mouse model results showing that humanized anti-TIM-3 antibodies of different isotypes (IgG1, IgG1 LALA, IgG2, and IgG4) effectively inhibited tumor growth.

Figure 11A:
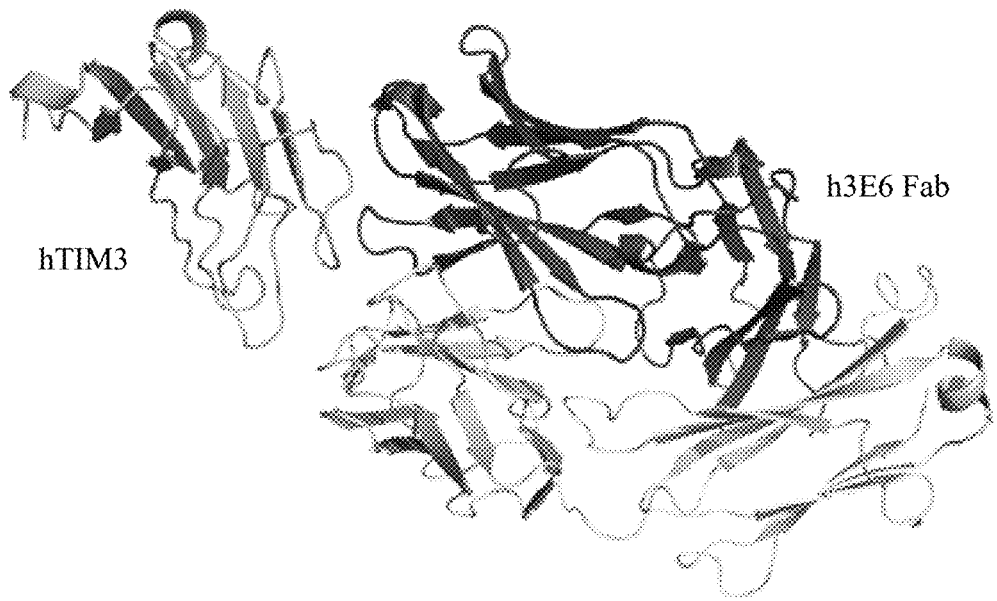
Figure 11B:
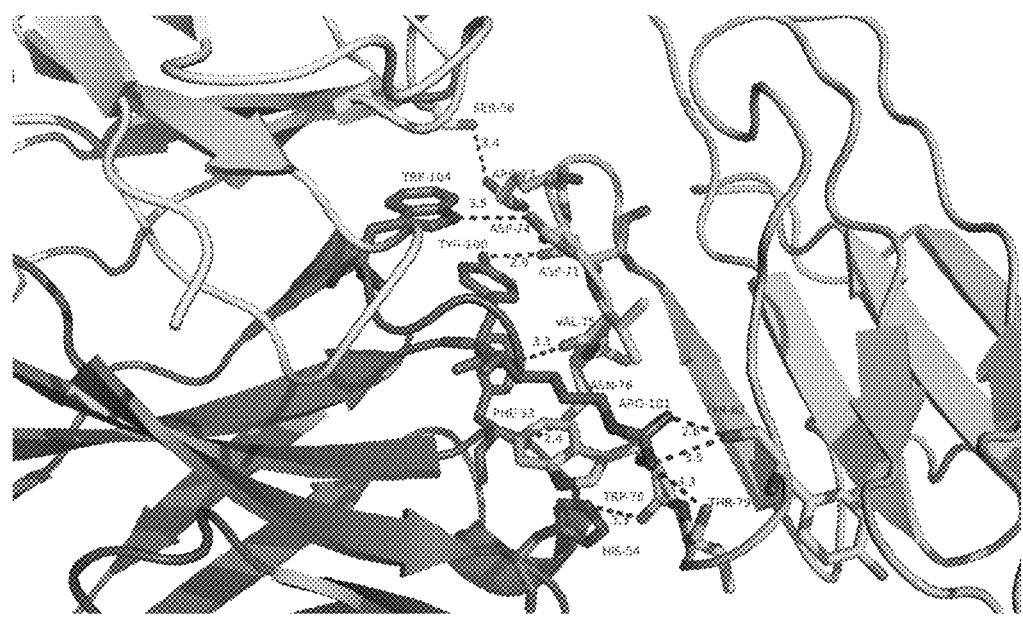

FIG. 11A provides the crystal structure of humanized 3E6 Fab bound to human TIM-3 (left: hTIM-3; right: humanized 3E6 Fab (upper: VH; lower: VL)). FIG. 11B shows interactions between specific residues of the TIM-3 antigen and those of the VH CDRs and VL CDRs.

Figure 12A:
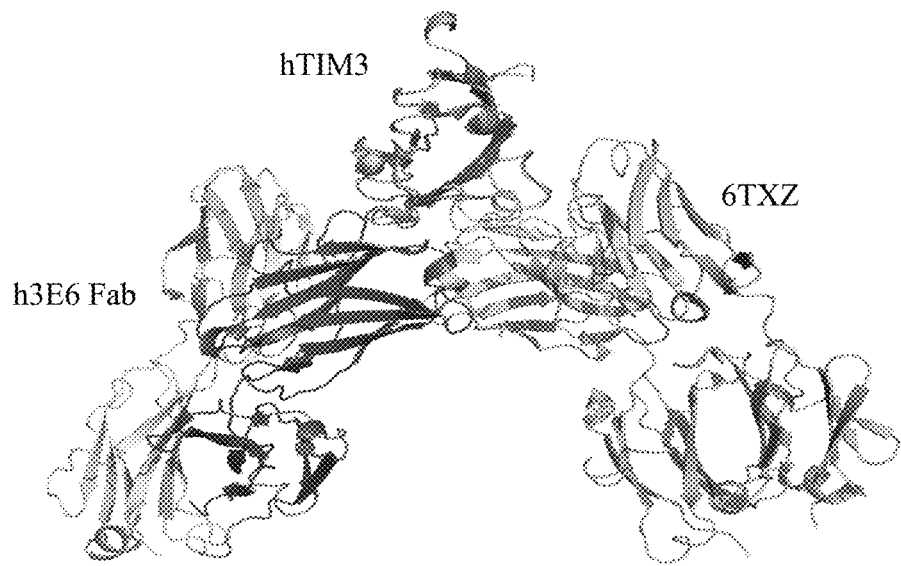
Figure 12B:
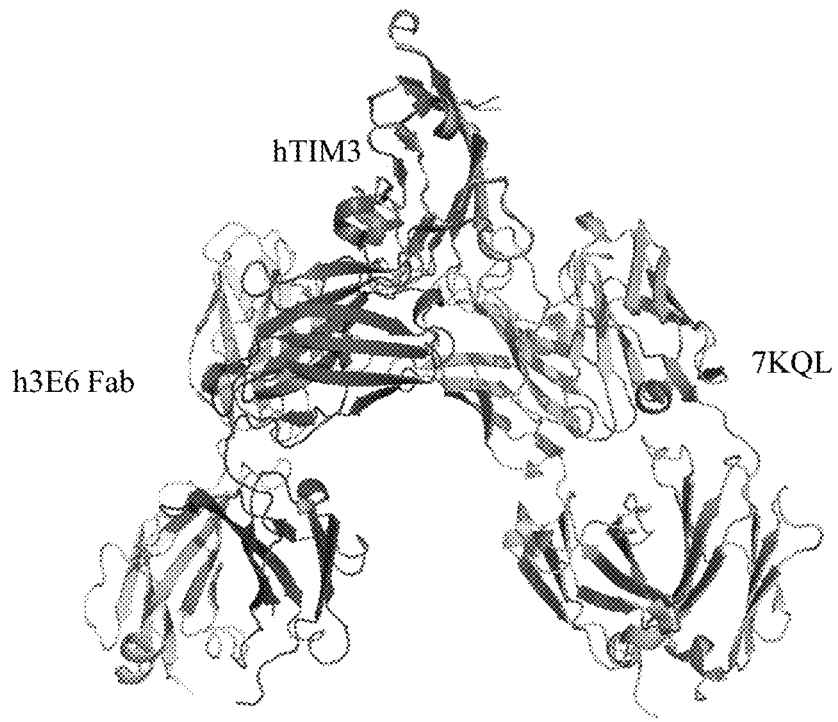

FIGS. 12A-12B provide the crystal structures of complexes formed by human TIM-3 simultaneously bound with humanized 3E6 Fab and another anti-TIM-3 antibody (FIG. 12A: 6TXZ; FIG. 12B: 7KQL)

6. DETAILED DESCRIPTION

Before the present disclosure is further described, it is to be understood that the disclosure is not limited to the particular embodiments set forth herein, and it is also to be understood that the terminology used herein is for the purpose of describing particular embodiments, and is not intended to be limiting.

The present disclosure provides novel antibodies, including antigen-binding fragments that specifically bind TIM-3 (e.g., human TIM-3). In some embodiments, the anti-TIM-3 antibodies or antigen-binding fragments disclosed herein bind to novel epitopes of human TIM-3, and are capable of inhibiting tumor growth by reducing or inhibiting the TIM-3 mediated suppression of both the innate immune response and the acquired immune response. Pharmaceutical compositions comprising a therapeutically effective amount of such antibodies or antigen-binding fragments are also disclosed herein. Also disclosed herein are uses of such pharmaceutical compositions for treating cancer (e.g., TIM-3-expressing cancer) and methods of cancer treatment.

T Cell Immunoglobulin and Mucin Domain-3 (TIM-3), also known as Hepatitis A Virus Cellular Receptor 2 (HAVCR2) is an immune checkpoint protein. First identified as a molecule selectively expressed on IFN-g-producing CD4+ T helper 1 (Th1) and CD8+ T cytotoxic 1 (Tc1) T cells (Monney et al. (2002), *Nature*, 415(6871):536-41), TIM-3 is also expressed on the surface of many immune cell types, including certain subsets of T cells such as FOXP3$^+$CD4$^+$ T regulatory cells (Tregs), natural killer (NK) cells, NKT cells, monocytes, and tumor-associated dendritic cells (TADCs) (Clayton et al. (2014) J. Immunol., 192(2):782-791; Anderson et al. (2007) *Science* 318(5853): 1141-1143; Baitsch et al. (2012) Plos One 7(2):e30852; Ndhlovu et al. (2012) Blood 119(16):3734-3743).

T-cell immunoglobulin and mucin-domain containing-3 (TIM-3), also known as hepatitis A virus cellular receptor 2 (HAVCR2), TIM-3, TIMD3, TIMD-3. Kidney Injury Molecule-3. KIM-3, and CD366. TIM-3 is a type-I transmembrane protein that functions as a key regulator of immune responses. TIM-3 was initially identified on activated IFN-γ-producing T cells (e.g., type 1 helper CD4+ T cells and cytotoxic CD8-T cells) and shown to induce T cell death or exhaustion after binding to galectin-9 (Monney et ah, 2002). More recent studies have indicated that TIM-3 expression is also important in regulating the activities of many innate immune cells (e.g., macrophages, monocytes, dendritic cells, mast cells, and natural killer cells) (Han et ak, 2013).

Ligands of TIM-3 (TIM-3 L) that have been reported include phosphatidylserine ("PtdSer"; Nakayama et al., (2009) *Blood* 113(16):3821-30), galectin-9 (Gal-9) (Zhu et al. (2005) *Nat Immunol* 6(12): 1245-52), high-mobility group protein 1 (HMGB1) (Chiba et al. (2012) *Nat Immunol*

13(9):832-42), carcinoembryonic antigen cell adhesion molecule 1 (CEACAM1) (Huang et al. (2015) *Nature* 517 (7534):386-90), Semaphorin-4A, and ILT-4. PtdSer is an important cell membrane component and is normally localized to the inner leaflet of cell membranes. But as a cell undergoes apoptosis, PtdSer is redistributed and exposed to the outer membrane. This redistribution is also observed in many tumor cell lines. Binding of TIM-3 to PtdSer can be critical for phagocytosis and cross-presentation (Nakayama 2009, supra).

TIM-3 regulates various aspects of the immune response. The interaction of TIM-3 and its ligand galectin-9 (Gal-9) induces cell death. The in vivo blockade of this interaction exacerbated autoimmunity and abrogated tolerance in experimental models, indicating that TIM-3/Gal-9 interaction negatively regulates immune responses (Zhu et al. (2005), supra, Kanzaki et al. (2012) *Endocrinology* 153(2): 612-620). The inhibition of TIM-3 also enhanced the pathological severit in in vivo experimental autoimmune encephalomyelitis (Monney et al. (2002) *Nature* 415:536-541: Das, et al. (2017) *Immunol Rev* 276(1):97-111). In studies using materials from human patients with multiple sclerosis (Koguchi et al. (2006) *J Exp Med* 203(6): 1413-1418), Crohn's disease (CD) (Morimoto et al. (2011) *Scand J Gastroenterol* 46(6):701-709) and rheumatoid arthritis (RA) (Liu et al. (2010) *Clin Immunol* 137(2):288-295; Li et al. (2014) *PLoS ONE* 9(2):e85784), the observation that TIM-3 expression level on T cells is inversely correlated with autoimmune disease progression demonstrates an immunosuppressive role of Tim-3 on T-cells.

TIM-3 is considered a promising candidate for cancer immunotherapy, in part, because it is upregulated in tumor-infiltrating lymphocytes including Foxp3+CD4+ Treg and exhausted CD8+ T cells, two key immune cell populations that constitute immunosuppression in tumor environment of many human cancers (McMahan et al. (2010) *J. Clin. Invest.* 120(12):4546-4557: Jin et al. (2010) *Proc Natl Acad Sci USA* 107(33): 14733-8; Zhou et al. (2011) *Blood* 117(17): 4501-4510; Yan, et a). (2013) *PLoS ONE* 8(3):e58006). The interaction of TIM-3 on CD8+ T cells and its ligand galectin-9 on tumor cells is reported to result in the phosphorylation of the TIM-3 cytoplasmic tail at tyrosines 256 and 263, leading to the release of HLA-B-associated transcript 3 (Bat3) and catalytically active lymphocyte-specific protein tyrosine kinase (Lck) from the TIM-3 cytoplasmic tail. The dissociation of Bat3 and Lck from TIM-3 leads to the accumulation of inactive phosphorylated Lck, which can account for the observed T cell dysfunction (Rangachari, et al. (2012) *Nat. Med* 18(9): 1394-400).

Further, intratumoral TIM-3$^+$FoxP3$^+$ Treg cells are reported to express high amounts of Treg effector molecules (IL-10, perforin, and granzymes). TIM-3+ Tregs are reported to promote the development of a dysfunctional phenotype in CD8+ tumor infiltrating lymphocytes (TILs) in tumor environment (Sakuishi, et al. (2013) *Oncoimmunology* 2(4):e23849). TIM-3 has also been reported to have effects in the myeloid compartment. T-cell expression of TIM-3 has been shown to promote CD11b+Gr-1+ myeloid-derived suppressor cells (MDSC) in a galectin-9-dependent manner (Dardalhon, et al. (2010) *J Immunol* 185(3): 1383-92). Furthermore, TIM-3 is specifically upregulated on tumor-associated dendritic cells (TADC), and can interfere with the sensing of DNA released by cells undergoing necrotic cell death. TIM-3 binds to high mobility group protein 1 (HMGB1), thereby prevents HMGB1 from binding to DNA released from dying cells and mediating delivery to innate cells via receptor for advanced glycation end (RAGE) products and/or Toll-like receptors (TLR) 2 and 4 pathways. TIM-3 binding to HMGB 1 dampens activation of the innate immune response in tumor tissue (Chiba, et al. (2012), supra). TIM-3 also potentially plays a gatekeeper role for inflammation and restrains anti-tumor immunity by regulating inflammasome activation (Gayden et al., *Nature Genetics* 50.12 (2018): 1650-1657; Dixon et al., *Nature* 595.7865 (2021): 101-106). Taken together, these observations show that TIM-3 can further suppress antitumor T-cell responses by T-cell extrinsic mechanisms involving myeloid cells and different TIM-3/ligand interactions.

Like many inhibitory receptors (e.g., PD-1 and CTLA-4), TIM-3 expression has been associated with many types of chronic diseases, including cancer. TIM-3-T cells have been detected in patients with advanced melanoma, non-small cell lung cancer, or follicular B-cell non-Hodgkin lymphoma. And the presence of TIM-3' regulatory T cells have been described as an effective indicator of lung cancer progression (Anderson (2014), *Cancer Immunol. Res.* 2, 393-98). Studies have shown a close relationship between TIM-3 and the inhibitory receptor PD-1. For example, many tumor-specific T cells express both PD-1 and TIM-3, and these T cells have been shown to be more dysfunctional compared to T cells that express only PD-1 or TIM-3 (Fourcade et al., 2010, *J. Exp. Med.* 207, 2175-2186).

The term "TIM-3" includes any variants or isoforms of TIM-3 which are naturally expressed by cells. Some antibodies described herein can cross-react with TIM-3 from certain species other than human (e.g., cynomolgus TIM-3), but not some other species, such as mouse TIM-3. Some antibodies described herein (e.g., humanized 3E6) do not cross-react with TIM-3 from species other than human, including cynomolgus TIM-3 and mouse TIM-3. TIM-3 or any variants and isoforms thereof, can either be isolated from cells or tissues which naturally express them or be recombinantly produced using well-known techniques in the art and/or those described herein.

Two isoforms of human TIM-3 have been identified. Isoform 1 (NCBI Reference Sequence: NP_116171.3: SEQ ID NO:84) consists of 301 amino acids and represents the canonical sequence. The extracellular region of human TIM-3 includes amino acid residues 22-202 of SEQ ID NO:84. The transmembrane domain of human TIM-3 includes amino acid residues 203-223 of SEQ ID NO:84. The cytoplasmic domain of human TIM-3 includes amino acid residues 224-301 of SEQ ID NO:84.

```
                                                    (SEQ ID NO: 84)
  1  MFSHLPFDCV  LLLLLLLLTR  SSEVEYRAEV  GQNAYLPCFY
     TPAAPGNLVP  VCWGKGACPV

61  FECGNVVLRT  DERDVNYWTS  RYWLNGDFRK  GDVSLTIENV
     TLADSGIYCC  RIQIPGIMND

121  EKFNLKLVIK  PAKVTPAPTR  QRDFTAAFPR  MLTTRGHGPA
     ETQTLGSLPD  INLTQISTLA

181  NELRDSRLAN  DLRDSGATIR  IGIYIGAGIC  AGLALALIFG
     ALIFKWYSHS  KEKIQNLSLI

241  SLANLPPSGL  ANAVAEGIRS  EENIYTIEEN  VYEVEEPNEY
     YCYVSSRQQP  SQPLGCRFAM

301  P
```

Isoform 2 (Accession No. AAH20843; SEQ ID NO:85) of human TIM-3 consists of 142 amino acids and is soluble. It lacks amino acid residues 143-301 of Isoform 1, which encode the transmembrane domain, the cytoplasmic domain, and part of the extracellular domain of TIM-3. The amino acid residues 132-142 also differ from the canonical sequence described above.

```
                                          (SEQ ID NO: 85)
  1  MFSHLPFDCV  LLLLLLLLTR  SSEVEYRAEV  GQNAYLPCFY
     TPAAPGNLVP  VCWGKGACPV

61  FECGNVVLRT  DERDVNYWTS  RYWLNGDFRK  GDVSLTIENV
     TLADSGIYCC  RIQIPGIMND

121  EKFNLKLVIK  PGEWTFACHL  YE
```

6.1 Definitions

Unless otherwise defined herein, scientific and technical terms used in the present disclosures shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well-known and commonly used in the art.

The term "a" or "an" entity refers to one or more of that entity; for example, "an antibody, is understood to represent one or more antibodies.

The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and B" (alone). Likewise, the term "and/or" as used in a phrase such as "A, B, and/or C" is intended to encompass each of the following aspects; A, B, and C; A, B, or C; A or C; A or B; B or C; A and C: A and B; B and C; A (alone); B (alone); and C (alone).

The term "antibody," and its grammatical equivalents as used herein refer to an immunoglobulin molecule that recognizes and specifically binds a target, such as a protein, polypeptide, peptide, carbohydrate, polynucleotide, lipid, or a combination of any of the foregoing, through at least one antigen-binding site wherein the antigen-binding site is usually within the variable region of the immunoglobulin molecule. As used herein, the term encompasses intact polyclonal antibodies, intact monoclonal antibodies, single-domain antibodies (sdAbs; e.g., camelid antibodies, alpaca antibodies), single-chain Fv (scFv) antibodies, heavy chain antibodies (HCAbs), light chain antibodies (LCAbs), multispecific antibodies, bispecific antibodies, monospecific antibodies, monovalent antibodies, and any other modified immunoglobulin molecule comprising an antigen-binding site (e.g., dual variable domain immunoglobulin molecules) as long as the antibodies exhibit the desired biological activity. Antibodies also include, but are not limited to, mouse antibodies, camel antibodies, chimeric antibodies, humanized antibodies, and human antibodies. An antibody can be any of the five major classes of immunoglobulins: IgA, IgD, IgE, IgG, and IgM, or subclasses (isotypes) thereof (e.g., IgG1, IgG2, IgG3, IgG4, IgA1 and IgA2), based on the identity of their heavy-chain constant domains referred to as alpha, delta, epsilon, gamma, and mu, respectively. Unless expressly indicated otherwise, the term "antibody" as used herein include "antigen-binding fragment" of intact antibodies. The term "antigen-binding fragment" as used herein refers to a portion or fragment of an intact antibody that is the antigenic determining variable region of an intact antibody. Examples of antigen-binding fragments include, but are not limited to, Fab, Fab', F(ab')2, Fv, linear antibodies, single chain antibody molecules (e.g., scFv), heavy chain antibodies (HCAbs), light chain antibodies (LCAbs), disulfide-linked scFv (dsscFv), diabodies, tribodies, tetrabodies, minibodies, dual variable domain antibodies (DVD), single variable domain antibodies (sdAbs; e.g., camelid antibodies, alpaca antibodies), and single variable domain of heavy chain antibodies (VHH), and bispecific or multispecific antibodies formed from antibody fragments. A "bispecific" antibody is an artificial hybrid antibody having two different antigen binding sites, which recognize and specifically bind two different targets. Bispecific antibodies can be produced by a variety of methods including fusion of hybridomas or linking of Fab' fragments. See, e.g., Song-sivilai & Lachmann, *Clin. Exp. Immunol.* 79:315-321 (1990) Kostelny et al., *J. Immunol.* 148, 1547-1553 (1992).

The term "humanized antibody" as used herein refers to forms of non-human (e.g., murine) antibodies that are specific immunoglobulin chains, chimeric immunoglobulins, or fragments thereof that contain minimal non-human sequences. Typically, humanized antibodies are human immunoglobulin. In some instances, the Fv framework region residues of a human immunoglobulin are replaced with the corresponding residues in an antibody from a non-human species. In some instances, residues of the CDRs are replaced by residues from the CDRs of a non-human species (e.g., mouse, rat, hamster, camel) that have the desired specificity, affinity, and/or binding capability. The humanized antibody can be further modified by the substitution of additional residues either in the Fv framework region and/or within the replaced non-human residues to refine and optimize antibody specificity, affinity, and/or binding capability. The term "human antibody" as used herein refers to an antibody produced by a human or an antibody having an amino acid sequence corresponding to an antibody produced by a human made using any of the techniques known in the art.

The term "heavy chain" when used in reference to an antibody refers to a polypeptide chain of about 50-70 kDa, wherein the amino-terminal portion includes a variable region of about 120 to 130 or more amino acids and a carboxy-terminal portion that includes a constant region. The constant region can be one of five distinct types, referred to as alpha (a), delta (δ), epsilon (ε), gamma (γ) and mu (μ), based on the amino acid sequence of the heavy chain constant region. The distinct heavy chains differ in size: α, δ and γ contain approximately 450 amino acids, while μ and ε contain approximately 550 amino acids. When combined with a light chain, these distinct types of heavy chains give rise to five well known classes of antibodies, IgA, IgD, IgE, IgG and IgM, respectively including four subclasses of IgG, namely IgG1, IgG2, IgG3 and IgG4. A heavy chain can be a human heavy chain.

The term "light chain" when used in reference to an antibody refers to a polypeptide chain of about 25 kDa, wherein the amino-terminal portion includes a variable region of about 100 to about 110 or more amino acids and a carboxy-terminal portion that includes a constant region. The approximate length of a light chain is 211 to 217 amino acids. There are two distinct types, referred to as kappa (κ) of lambda (λ) based on the amino acid sequence of the constant domains. Light chain amino acid sequences are well known in the art. A light chain can be a human light chain.

The term "variable domain" or "variable region" refers to a portion of the light or heavy chains of an antibody that is generally located at the amino-terminal of the light or heavy chain and has a length of about 120 to 130 amino acids in the heavy chain and about 100 to 110 amino acids in the light chain, and are used in the binding and specificity of each particular antibody for its particular antigen. The variable domains differ extensively in sequence between different antibodies. The variability in sequence is concentrated in the CDRs while the less variable portions in the variable domain are referred to as framework regions (FR). The CDRs of the light and heavy chains are primarily responsible for the interaction of the antibody with antigen. Numbering of amino acid positions used herein is according to the EU Index, as in Kabat et al. (1991) Sequences of proteins of immunological interest. (U.S. Department of Health and Human Services, Washington, D.C.) 5th ed. A variable region can be a human variable region.

A CDR refers to one of three hypervariable regions (H1, H2 or H3) within the non-framework region of the immunoglobulin (Ig or antibody) VH-sheet framework, or one of three hypervariable regions (L1, L2 or L3) within the non-framework region of the antibody VL β-sheet framework. Accordingly, CDRs are variable region sequences interspersed within the framework region sequences. CDR regions are well known to those skilled in the art and have been defined by a variety of methods/systems. These systems and/or definitions have been developed and refined over years and include Kabat, Chothia, IMGT, AbM, and Contact. For example, Kabat defines the regions of most hypervariability within the antibody variable (V) domains (Kabat et al. *J Biol. Chem.* 252:6609-6616 (1977); Kabat, *Adv. Prot. Chem.* 32: 1-75 (1978)). The Chothia definition is based on the location of the structural loop regions, which defines CDR region sequences as those residues that are not part of the conserved 1-sheet framework, and thus are able to adapt different conformations (Chothia and Lesk, *J. Mol. Biol.* 196:901-917 (1987)). Both terminologies are well recognized in the art. Additionally, the IMGT system is based on sequence variability and location within the structure of the variable regions. The AbM definition is a compromise between Kabat and Chothia. The Contact definition is based on analyses of the available antibody crystal structures. Software programs (e.g., abYsis) are available and known to those of skill in the art for analysis of antibody sequence and determination of CDRs. The positions of CDRs within a canonical antibody variable domain have been determined by comparison of numerous structures (Al-Lazikani et al, *J. Mol. Biol.* 273:927-948 (1997); Morea et al, *Methods* 20:267-279 (2000)). Because the number of residues within a hypervariable region varies in different antibodies, additional residues relative to the canonical positions are conventionally numbered with a, b, c and so forth next to the residue number in the canonical variable domain numbering scheme (Al-Lazikani et al., supra (1997)). Such nomenclature is similarly well known to those skilled in the art.

For example, CDRs defined according to either the Kabat (hypervariable) or Chothia (structural) designations, are set forth in the table below.

|        | Kabat[1] | Chothia[2] | Loop Location |
|--------|----------|------------|---------------|
| VHCDR1 | 31-35    | 26-32      | linking B and C strands |
| VHCDR2 | 50-65    | 53-55      | linking C' and C" strands |
| VHCDR3 | 95-102   | 96-101     | linking F and G strands |

-continued

|        | Kabat[1] | Chothia[2] | Loop Location |
|--------|----------|------------|---------------|
| VLCDR1 | 24-34    | 26-32      | linking B and C strands |
| VLCDR2 | 50-56    | 50-52      | linking C' and C" strands |
| VLCDR3 | 89-97    | 91-96      | linking F and G strands |

[1]Residue numbering follows the nomenclature of Kabat et al., supra
[2]Residue numbering follows the nomenclature of Chothia et al., supra One or more CDRs also can be incorporated into a molecule either covalently or noncovalently to make it an immunoadhesin. An immunoadhesin can incorporate the CDR(s) as part of a larger polypeptide chain, can covalently link the CDR(s) to another polypeptide chain, or can incorporate the CDR(s) noncovalently. The CDRs permit the immunoadhesin to bind to a particular antigen of interest. The CDR regions can be analyzed by, for example, abysis website (http://abysis.org/).

The terms "epitope" and "antigenic determinant" are used interchangeably herein an refer to the site on the surface of a target molecule to which an antibody or antigen-binding fragment binds, such as a localized region on the surface of an antigen. The target molecule can comprise, a protein, a peptide, a nucleic acid, a carbohydrate, or a lipid. An epitope having immunogenic activity is a portion of a target molecule that elicits an immune response in an animal. An epitope of a target molecule having antigenic activity is a portion of the target molecule to which an antibody binds, as determined by any method well known in the art, including, for example, by an immunoassay. Antigenic epitopes need not necessarily be immunogenic. Epitopes often consist of chemically active surface groupings of molecules such as amino acids or sugar side chains and have specific three dimensional structural characteristics as well as specific charge characteristics. The term, "epitope" includes linear epitopes and conformational epitopes. A region of a target molecule (e.g., a polypeptide) contributing to an epitope can be contiguous amino acids of the polypeptide or the epitope can come together from two or more non-contiguous regions of the target molecule. The epitope may or may not be a three-dimensional surface feature of the target molecule. Epitopes formed from contiguous amino acids (also referred to as linear epitopes) are typically retained upon protein denaturing, whereas epitopes formed by tertiary folding (also referred to as conformational epitopes) are typically lost upon protein denaturing. An epitope typically includes at least 3, and more usually, at least 5, 6, 7, or 8-10 amino acids in a unique spatial conformation.

The term "specifically binds," as used herein, means that a polypeptide or molecule interacts more frequently, more rapidly, with greater duration, with greater affinity, or with some combination of the above to the epitope, protein, or target molecule than with alternative substances, including related and unrelated proteins. A binding moiety (e.g., antibody) that specifically binds a target molecule (e.g. antigen) can be identified, for example, by immunoassays, ELISAs, Bio-Layer Interferometry ("BLI"), SPR (e.g., Biacore), or other techniques known to those of skill in the art. Typically, a specific reaction will be at least twice background signal or noise and can be more than 10 times background. See, e.g., Paul, ed., 1989, *Fundamental Immunology* Second Edition, Raven Press, New York at pages 332-336 for a discussion regarding antibody specificity. A binding moiety that specifically binds a target molecule can bind the target molecule at a higher affinity than its affinity for a different molecule. In some embodiments, a binding moiety that specifically binds a target molecule can bind the target molecule with an affinity that is at least 20 times greater, at least 30 times greater, at least 40 times greater, at least 50 times greater, at least 60 times greater, at least 70 times greater, at least 80 times greater, at least 90 times greater, or at least 100 times greater, than its affinity for a different molecule. In some embodiments, a binding moiety that specifically binds a particular target molecule binds a different molecule at such a low affinity that binding cannot be detected using an assay described herein or otherwise known in the art. In some embodiments, "specifically binds" means, for instance, that a binding moiety binds a molecule target with a $K_D$ of about 0.1 mM or less. In some embodiments, "specifically binds" means that a polypeptide or molecule binds a target with a $K_D$ of at about 10 µM or less or about 1 µM or less. In some embodiments, "specifically binds" means that a polypeptide or molecule binds a target with a $K_D$ of at about 0.1 µM or less, about 0.01 µM or less, or about 1 µM or less. Because of the sequence identity between homologous proteins in different species, specific binding can include a polypeptide or molecule that recognizes a protein or target in more than one species. Likewise, because of homology within certain regions of polypeptide sequences of different proteins, specific binding can include a polypeptide or molecule that recognizes more than one protein or target. It is understood that, in some embodiments, a binding moiety (e.g. antibody) that specifically binds a first target may or may not specifically bind a second target. As such, "specific binding" does not necessarily require (although it can include) exclusive binding, i.e., binding to a single target. Thus, a binding moiety (e.g., antibody) can, in some embodiments, specifically bind more than one target. For example, an antibody can, in certain instances, comprise two identical antigen-binding sites, each of which specifically binds the same epitope on two or more proteins. In certain alternative embodiments, an antibody can be bispecific and comprise at least two antigen-binding sites with differing specificities.

The term "binding affinity" as used herein generally refers to the strength of the sum total of noncovalent interactions between a binding moiety and a target molecule (e.g., antigen). The binding of a binding moiety and a target molecule is a reversible process, and the affinity of the binding is typically reported as an equilibrium dissociation constant ($K_D$). $K_D$ is the ratio of a dissociation rate ($k_{off}$ or $k_d$) to the association rate ($k_{on}$ or $k_a$). The lower the $K_D$ of a binding pair, the higher the affinity. A variety of methods of measuring binding affinity are known in the art, any of which can be used for purposes of the present disclosure. Specific illustrative embodiments include the following. In some embodiments, the "$K_D$" or "$K_D$ value" can be measured by assays known in the art, for example by a binding assay. The $K_D$ may be measured in a radiolabeled antigen binding assay (RIA) (Chen, et al., (1999)*J. Mol Biol* 293: 865-881). The $K_D$ or $K_D$ value can also be measured by using biolayer interferometry (BLI) using, for example, the Gator system (Probe Life), or the Octet-96 system (Sartorius AG). The $K_D$ or $K_D$ value can also be measured by using surface plasmon resonance assays by Biacore, using, for example, a BIAcore™-2000 or a BIAcore™-3000 BIAcore, Inc., Piscataway. NJ).

The term "variant" as used herein in relation to a protein or a polypeptide with particular sequence features (the "reference protein" or "reference polypeptide") refers to a different protein or polypeptide having one or more (such as, for example, about 1 to about 25, about 1 to about 20, about 1 to about 15, about 1 to about 10, or about 1 to about 5) amino acid substitutions, deletions, and/or additions as compared to the reference protein or reference polypeptide. The changes to an amino acid sequence can be amino acid substitutions. The changes to an amino acid sequence can be conservative amino acid substitutions. A functional fragment or a functional variant of a protein or polypeptide maintains the basic structural and functional properties of the reference protein or polypeptide.

The terms "polypeptide," "peptide," "protein," and their grammatical equivalents as used interchangeably herein refer to polymers of amino acids of any length, which can be linear or branched. It can include unnatural or modified amino acids or be interrupted by non-amino acids. A polypeptide, peptide, or protein can also be modified with, for example, disulfide bond formation, glycosylation, lipidation, acetylation, phosphorylation, or any other manipulation or modification.

The terms "polynucleotide," "nucleic acid," and their grammatical equivalents as used interchangeably herein mean polymers of nucleotides of any length and include DNA and RNA. The nucleotides can be deoxyribonucleotides, ribonucleotides, modified nucleotides or bases, and/or their analogs, or any substrate that can be incorporated into a polymer by DNA or RNA polymerase.

The terms "identical," percent "identity," and their grammatical equivalents as used herein in the context of two or more polynucleotides or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software that can be used to obtain alignments of amino acid or nucleotide sequences are well-known in the art. These include, but are not limited to, BLAST, ALIGN, Megalign, BestFit, GCG Wisconsin Package, and variants thereof. In some embodiments, two polynucleotides or polypeptides provided herein are substantially identical, meaning they have at least 70%, at least 75%, at least 80%, at least 85%, at least 90%, and in some embodiments at least 95%, at least 96%, at least 97%, at least 98%, or at least 99% nucleotide or amino acid residue identity, when compared and aligned for maximum correspondence, as measured using a sequence comparison algorithm or by visual inspection. In some embodiments, identity exists over a region of the amino acid sequences that is at least about 10 residues, at least about 20 residues, at least about 40-60 residues, at least about 60-80 residues in length or any integral value there between. In some embodiments, identity exists over a longer region than 60-80 residues, such as at least about 80-100 residues, and in some embodiments the sequences are substantially identical over the full length of the sequences being compared, such as the coding region of a target protein or an antibody. In some embodiments, identity exists over a region of the nucleotide sequences that is at least about 10 bases, at least about 20 bases, at least about 40-60 bases, at least about 60-80 bases in length or any integral value there between. In some embodiments, identity exists over a longer region than 60-80 bases, such as at least about 80-1000 bases or more, and in some embodiments the sequences are substantially identical over the full length of the sequences being compared, such as a nucleotide sequence encoding a protein of interest.

The term "vector," and its grammatical equivalents as used herein refer to a vehicle that is used to carry genetic material (e.g. a polynucleotide sequence), which can be introduced into a host cell, where it can be replicated and/or expressed. Vectors applicable for use include, for example, expression vectors, plasmids, phage vectors, viral vectors, episomes and artificial chromosomes, which can include selection sequences or markers operable for stable integration into a host cell's chromosome. Additionally, the vectors can include one or more selectable marker genes and appropriate expression control sequences. Selectable marker genes that can be included, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more polynucleotides are to be co-expressed, both polynucleotides can be inserted, for example, into a single expression vector or in separate expression vectors. For single vector expression, the encoding polynucleotides can be operationally linked to one common expression control sequence or linked to different expression control sequences, such as one inducible promoter and one constitutive promoter. The introduction of polynucleotides into a host cell can be confirmed using methods well known in the art. It is understood by those skilled in the art that the polynucleotides are expressed in a sufficient amount to produce a desired product (e.g., an anti-TIM-3 antibody or antigen-binding fragment as described herein), and it is further understood that expression levels can be optimized to obtain sufficient expression using methods well known in the art.

As used herein, the term "encode" and its grammatical equivalents refer to the inherent property of specific sequences of nucleotides in a polynucleotide or a nucleic acid, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein. Unless otherwise specified, a "nucleotide sequence encoding an amino acid sequence" includes all nucleotide sequences that are degenerate versions of each other and that encode the same amino acid sequence. Nucleotide sequences that encode proteins and RNA can include introns.

A polypeptide, peptide, protein, antibody, polynucleotide, vector, cell, or composition which is "isolated" is a polypeptide, peptide, protein, antibody, polynucleotide, vector, cell, or composition which is in a form not found in nature. Isolated polypeptides, peptides, proteins, antibodies, polynucleotides, vectors, cells, or compositions include those which have been purified to a degree that they are no longer in a form in which they are found in nature. In some embodiments, a polypeptide, peptide, protein, antibody, polynucleotide, vector, cell, or composition which is isolated is substantially pure.

The term "treat" and its grammatical equivalents as used herein in connection with a disease or a condition, or a subject having a disease or a condition refer to an action that suppresses, eliminates, reduces, and/or ameliorates a symptom, the severity of the symptom, and/or the frequency of the symptom associated with the disease or disorder being treated. For example, when used in reference to a cancer or tumor, the term "treat" and its grammatical equivalents refer to an action that reduces the severity of the cancer or tumor, or retards or slows the progression of the cancer or tumor, including (a) inhibiting the growth, or arresting development of the cancer or tumor, (b) causing regression of the cancer or tumor, or (c) delaying, ameliorating or minimizing one or more symptoms associated with the presence of the cancer or tumor.

The term "administer" and its grammatical equivalents as used herein refer to the act of delivering, or causing to be delivered, a therapeutic or a pharmaceutical composition to the body of a subject by a method described herein or otherwise known in the art. The therapeutic can be a compound, a polypeptide, an antibody, a cell, or a population of cells. Administering a therapeutic or a pharmaceutical composition includes prescribing a therapeutic or a pharmaceutical composition to be delivered into the body of a subject. Exemplary forms of administration include oral dosage forms, such as tablets, capsules, syrups, suspensions; injectable dosage forms, such as intravenous (IV), intramuscular (IM), or intraperitoneal (IP); transdermal dosage forms, including creams, jellies, powders, or patches; buccal dosage forms; inhalation powders, sprays, suspensions, and rectal suppositories.

The terms "effective amount," "therapeutically effective amount," and their grammatical equivalents as used herein refer to the administration of an agent to a subject, either alone or as a part of a pharmaceutical composition and either in a single dose or as part of a series of doses, in an amount that is capable of having any detectable, positive effect on any symptom, aspect, or characteristics of a disease, disorder or condition when administered to the subject. The therapeutically effective amount can be ascertained by measuring relevant physiological effects. The exact amount required vary from subject to subject, depending on the age, weight, and general condition of the subject, the severity of the condition being treated, the judgment of the clinician, and the like. An appropriate "effective amount" in any individual case can be determined by one of ordinary skill in the art using routine experimentation.

The term "pharmaceutically acceptable carrier" or "pharmaceutically acceptable excipient" refers to a material that is suitable for drug administration to an individual along with an active agent without causing undesirable biological effects or interacting in a deleterious manner with any of the other components of the pharmaceutical composition.

The term "subject" as used herein refers to any animal (e.g., a mammal), including, but not limited to, humans, non-human primates, canines, felines, rodents, and the like, which is to be the recipient of a particular treatment. A subject can be a human. A subject can have a particular disease or condition.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Exemplary genes and polypeptides are described herein with reference to GenBank numbers, GI numbers and/or SEQ ID NOS. It is understood that one skilled in the art can readily identify homologous sequences by reference to sequence sources, including but not limited to GenBank (ncbi.nlm.nih.gov/genbank/) and EMBL (embl.org/).

6.2 Anti-TIM-3 Antibodies and Antigen-Binding Fragments

Provided herein are antibodies or antigen-binding fragments thereof that specifically bind TIM-3 (e.g., human TIM-3). In some embodiments, provided herein are anti-TIM-3 antibodies. In some embodiments, the antibody is an IgA, IgD, IgE. IgG, or IgM antibody. In some embodiments, the antibody is an IgA antibody. In some embodiments, the antibody is an IgD antibody. In some embodiments, the antibody is an IgE antibody. In some embodiments, the antibody is an IgG antibody. In some embodiments, the antibody is an IgM antibody. In some embodiments, the antibodies provided herein can be an IgG1 antibody, an IgG2 antibody, an IgG3 antibody, or an IgG4 antibody. In some embodiments, the antibody is an IgG1 antibody. In some embodiments, the antibody is an IgG2 antibody. In some embodiments, the antibody is an IgG3 antibody. In some embodiments, the antibody is an IgG4 antibody.

In some embodiments, provided herein are antigen-binding fragments of an anti-TIM-3 antibody. In some embodiments, antigen-binding fragments provided herein can be a single domain antibody (sdAb), a heavy chain antibody (HCAb), a Fab, a Fab', a F(ab')$_2$, a Fv, a single-chain variable fragment (scFv), or a (scFv)$_2$. In some embodiments, the antigen-binding fragment of an anti-TIM-3 antibody is a single domain antibody (sdAb). In some embodiments, the antigen-binding fragment of an anti-TIM-3 antibody is a heavy chain antibody (HCAb). In some embodiments, the antigen-binding fragment of an anti-TIM-3 antibody is a Fab. In some embodiments, the antigen-binding fragment of an anti-TIM-3 antibody is a Fab'. In some embodiments, the antigen-binding fragment of an anti-TIM-3 antibody is a F(ab')$_2$. In some embodiments, the antigen-binding fragment of an anti-TIM-3 antibody is a Fv. In some embodiments, the antigen-binding fragment of an anti-TIM-3 antibody is a scFv. In some embodiments, the antigen-binding fragment of an anti-TIM-3 antibody is a disulfide-linked scFv [(scFv)$_2$]. In some embodiments, the antigen-binding fragment of an anti-TIM-3 antibody is a diabody (dAb).

In some embodiments, the anti-TIM-3 antibodies or antigen-binding fragments provided herein comprise recombinant antibodies or antigen-binding fragments. In some embodiments, the anti-TIM-3 antibodies or antigen-binding fragments provided herein comprise monoclonal antibodies or antigen-binding fragments. In some embodiments, the anti-TIM-3 antibodies or antigen-binding fragments provided herein comprise polyclonal antibodies or antigen-binding fragments. In some embodiments, the anti-TIM-3 antibodies or antigen-binding fragments provided herein comprise camelid (e.g., camels, dromedary and llamas) antibodies or antigen-binding fragments. In some embodiments, the anti-TIM-3 antibodies or antigen-binding fragments provided herein comprise chimeric antibodies or antigen-binding fragments. In some embodiments, the anti-TIM-3 antibodies or antigen-binding fragments provided herein comprise humanized antibodies or antigen-binding fragments. In some embodiments, the anti-TIM-3 antibodies or antigen-binding fragments provided herein comprise human antibodies or antigen-binding fragments. In some embodiments, provided herein are anti-TIM-3 human scFvs.

In some embodiments, the anti-TIM-3 antibodies or antigen-binding fragments provided herein are isolated. In some embodiments, the anti-TIM-3 antibodies or antigen-binding fragments provided herein are substantially pure.

In some embodiments, the anti-TIM-3 antibody or antigen-binding fragment provided herein comprises a multi-specific antibody or antigen-binding fragment. In some embodiments, the anti-TIM-3 antibody or antigen-binding fragment provided herein comprises a bispecific antibody or antigen-binding fragment. In some embodiments, provided herein is a Bi-specific T-cell engager (BiTE). BiTEs are bispecific antibodies that bind to a T cell antigen (e.g., CD3) and a tumor antigen. BiTEs have been shown to induce directed lysis of target tumor cells and thus provide great potential therapies for cancers and other disorders. In some embodiments, provided herein are BiTEs that specifically bind CD3 and TIM-3. In some embodiments, the BiTEs comprises an anti-TIM-3 antibody or antigen-binding fragment provided herein. In some embodiments, the BiTEs comprises an anti-TIM-3 scFv provided herein.

In some embodiments, the anti-TIM-3 antibody or antigen-binding fragment provided herein comprises a monovalent antigen-binding site. In some embodiments, an anti-TIM-3 antibody or antigen-binding fragment comprises a monospecific binding site. In some embodiments, an anti-TIM-3 antibody or antigen-binding fragment comprises a bivalent binding site.

In some embodiments, an anti-TIM-3 antibody or antigen-binding fragment is a monoclonal antibody or antigen-binding fragment. Monoclonal antibodies can be prepared by any method known to those of skill in the art. One exemplary approach is screening protein expression libraries, e.g., phage or ribosome display libraries. Phage display is described, for example, in Ladner et al., U.S. Pat. No. 5,223,409; Smith (1985) Science 228:1315-1317; and WO 92/18619. In some embodiments, recombinant monoclonal antibodies are isolated from phage display libraries expressing variable regions or CDRs of a desired species. Screening of phage libraries can be accomplished by various techniques known in the art.

In some embodiments, monoclonal antibodies are prepared using hybridoma methods known to one of skill in the art. For example, using a hybridoma method, a mouse, rat, rabbit, hamster, or other appropriate host animal, is immunized as described above. In some embodiments, lymphocytes are immunized in vitro. In some embodiments, the immunizing antigen is a human protein or a fragment thereof. In some embodiments, the immunizing antigen is a human protein or a fragment thereof.

Following immunization, lymphocytes are isolated and fused with a suitable myeloma cell line using, for example, polyethylene glycol. The hybridoma cells are selected using specialized media as known in the art and unfused lymphocytes and myeloma cells do not survive the selection process. Hybridomas that produce monoclonal antibodies directed to a chosen antigen can be identified by a variety of methods including, but not limited to, immunoprecipitation, immunoblotting, and in vitro binding assays (e.g., flow cytometry, FACS, ELISA, BLI, SPR (e.g., Biacore), and radioimmunoassay). Once hybridoma cells that produce antibodies of the desired specificity, affinity, and/or activity are identified, the clones may be subcloned by limiting dilution or other techniques. The hybridomas can be propagated either in in vitro culture using standard methods or in vivo as ascites tumors in an animal. The monoclonal antibodies can be purified from the culture medium or ascites fluid according to standard methods in the art including, but not limited to, affinity chromatography, ion-exchange chromatography, gel electrophoresis, and dialysis.

In some embodiments, monoclonal antibodies are made using recombinant DNA techniques as known to one skilled in the art. For example, the polynucleotides encoding an antibody are isolated from mature B-cells or hybridoma cells, such as by RT-PCR using oligonucleotide primers that specifically amplify, the genes encoding the heavy and light chains of the antibody, and their sequence is determined using standard techniques. The isolated polynucleotides encoding the heavy and light chains are then cloned into suitable expression vectors which produce the monoclonal antibodies when transfected into host cells such as E. coli, simian COS cells, Chinese hamster ovary (CHO) cells, or myeloma cells that do not otherwise produce immunoglobulin proteins.

In some embodiments, a monoclonal antibody is modified by using recombinant DNA technology to generate alternative antibodies. In some embodiments, the constant domains of the light chain and heavy chain of a mouse monoclonal antibody are replaced with the constant regions of a human antibody to generate a chimeric antibody. In some embodiments, the constant regions are truncated or removed to generate a desired antibody fragment of a monoclonal antibody. In some embodiments, site-directed or high-density mutagenesis of the variable region(s) is used to optimize specificity and/or affinity of a monoclonal antibody.

In some embodiments, an anti-TIM-3 antibody or antigen-binding fragment is a humanized antibody or antigen-binding fragment. Various methods for generating humanized antibodies are known in the art. Methods are known in the art for achieving high affinity binding with humanized antibodies. A non-limiting example of such a method is hypermutation of the variable region and selection of the cells expressing such high affinity antibodies (affinity maturation). In addition to the use of display libraries, the specified antigen (e.g., recombinant TIM-3 or an epitope thereof) can be used to immunize a non-human animal, e.g., a rodent. In certain embodiments, rodent antigen-binding fragments (e.g., mouse antigen-binding fragments) can be generated and isolated using methods known in the art and/or disclosed herein. In some embodiments, a mouse can be immunized with an antigen (e.g., recombinant TIM-3 or an epitope thereof).

In some embodiments, an anti-TIM-3 antibody or antigen-binding fragment is a human antibody or antigen-binding fragment. Human antibodies can be prepared using various techniques known in the art. In some embodiments, human antibodies are generated from immortalized human B lymphocytes immunized in vitro. In some embodiments, human antibodies are generated from lymphocytes isolated from an immunized individual. In any case, cells that produce an antibody directed against a target antigen can be generated and isolated. In some embodiments, a human antibody is selected from a phage library, where that phage library expresses human antibodies. Alternatively, phage display technology can be used to produce human antibodies and antibody fragments in vitro, from immunoglobulin variable region gene repertoires from unimmunized donors. Techniques for the generation and use of antibody phage libraries are well-known in the art. Once antibodies are identified, affinity maturation strategies known in the art, including but not limited to, chain shuffling and site-directed mutagenesis, can be employed to generate higher affinity human antibodies. In some embodiments, human antibodies are produced in transgenic mice that contain human immunoglobulin loci. Upon immunization these mice are capable of producing the full repertoire of human antibodies in the absence of endogenous immunoglobulin production.

The specific CDR sequences defined herein are generally based on a combination of Kabat and Chothia definitions. However, it is understood that reference to a heavy chain CDR or CDRs and/or a light chain CDR or CDRs of a specific antibody encompass all CDR definitions as known to those of skill in the art.

Anti-TIM-3 antibodies or antigen-binding fragments provided herein include the followings clones: 3E6, 4H2, 16H1, 18C6, 19D11, CH 5 #, CH 8 #, CH 9 #, CH 10 #, CH11 #, 3F2, 36A2, 36B11, 38F8, 38A8, 40F11, 50H9, 84G10, and 39D1. The sequence features are described below. In some embodiments, anti-TIM-3 antibodies or antigen-binding fragments provided herein comprise one, two, three, four, five, and/or six CDRs of any one of the antibodies described herein. In some embodiments, anti-TIM-3 antibodies or antigen-binding fragments provided herein comprise one, two, three, four, five, and/or six CDRs of 3E6, 4H2, 16H1, 18C6, 19D11, CH 5 #, CH 8 #, CH 9 #, CH 10 #, CH 11 #, 3F2, 36A2, 36B11, 38F8, 38A8, 40F11, 50H9, 84G10, or 39D1. In some embodiments, anti-TIM-3 antibodies or antigen-binding fragments provided herein comprise a VL comprising one, two, and/or three, VL CDRs from Tables 1a-1c. In some embodiments, anti-TIM-3 antibodies or antigen-binding fragments provided herein comprise a VH comprising one, two, and/or three VH CDRs from Tables 2a-2b. In some embodiments, anti-TIM-3 antibodies or antigen-binding fragments provided herein comprise one, two, and/or three VL CDRs from Table 1 and one, two, and/or three VH CDRs from Tables 2a-2b.

TABLE 1a

Amino acid sequences of light chain variable region CDRs (VL CDRs; Kabat designation) of anti-TIM-3 Abs

| Antibody | VL CDR1 | VL CDR2 | VL CDR3 |
| --- | --- | --- | --- |
| 3E6 | KASQNVGANVA (SEQ ID NO: 86) | SASYRYS (SEQ ID NO: 94) | QQYNSYPT (SEQ ID NO: 47) |
| 4H2 | KASQDINKYIA (SEQ ID NO: 87) | YTSTLQP (SEQ ID NO: 95) | LQYDNLLFT (SEQ ID NO: 48) |
| 16H1 | KASQDVSAAVA (SEQ ID NO: 88) | STFYRYI (SEQ ID NO: 96) | QQHYSVPWT (SEQ ID NO: 49) |
| 18C6 | RSSQSLVHSNGNTYLH (SEQ ID NO: 89) | KVSNRFS (SEQ ID NO: 97) | CQSTHVPPLT (SEQ ID NO: 50) |
| 19D11 | KASQNVGTNVA (SEQ ID NO: 90) | SASYRYS (SEQ ID NO: 94) | QQYNSYPLVT (SEQ ID NO: 51) |

TABLE 1a-continued

Amino acid sequences of light chain variable region CDRs (VL CDRs; Kabat designation) of anti-TIM-3 Abs

| Antibody | VL CDR1 | VL CDR2 | VL CDR3 |
|---|---|---|---|
| CH 5# | RASESVEYYGTSLMQ (SEQ ID NO: 91) | AASNVES (SEQ ID NO: 98) | QQSRKVPIT (SEQ ID NO: 52) |
| CH 8# | RASESVEYYGTSLMQ (SEQ ID NO: 91) | AASNVES (SEQ ID NO: 98) | QPSRKVPYT (SEQ ID NO: 53) |
| CH 9# | RASSSVSYMH (SEQ ID NO: 92) | ATSNLAS (SEQ ID NO: 99) | QQWSSNPLT (SEQ ID NO: 54) |
| CH 10# | SASSSVSSSYLH (SEQ ID NO: 93) | STSNLAS (SEQ ID NO: 100) | QQWSSYPLT SEQ ID NO: 55) |
| CH 11# | RASESVEYYGTSLMQ (SEQ ID NO: 91) | AASNVES (SEQ ID NO: 98) | QQSRKVPIT (SEQ ID NO: 52) |
| 3F2 | KSSQSVLYSSNQKNYLA (SEQ ID NO: 129) | WASFRES (SEQ ID NO: 138) | HQSLSSYT (SEQ ID NO: 145) |
| 36A2 | KSSQSVLHSSNQKNFLA (SEQ ID NO: 130) | WASTRES (SEQ ID NO: 139) | HQYLSSLT (SEQ ID NO: 146) |
| 36B11 | SASSGISSSYLY (SEQ ID NO: 131) | GTSNLAS (SEQ ID NO: 140) | HQWSNYPYT (SEQ ID NO: 147) |
| 38F8 | RASQDISNYLN (SEQ ID NO: 132) | HTSRLYS (SEQ ID NO: 141) | QQGNTLPLT (SEQ ID NO: 148) |
| 38A8 | KSSQSLLNSRTRKNYLA (SEQ ID NO: 133) | WASTRES (SEQ ID NO: 139) | KQSYSLLT (SEQ ID NO: 149) |
| 40F11 | RASSIVSSSYLH (SEQ ID NO: 134) | STSNLPS (SEQ ID NO: 142) | QQYSGYPYT (SEQ ID NO: 150) |
| 50H9 | QASQGSSVNLN (SEQ ID NO: 135) | GSNILED (SEQ ID NO: 143) | LQHSYLPYT (SEQ ID NO: 151) |
| 84G10 | RASENINSYLA (SEQ ID NO: 136) | HAKTLAS (SEQ ID NO: 144) | QHHYGTPLT (SEQ ID NO: 152) |
| 39D1 | SASSSVRFMH (SEQ ID NO: 137) | STSNLAS (SEQ ID NO: 100) | QQRSSYPPT (SEQ ID NO: 153) |

TABLE 1b

Amino acid sequences of VL CDRs (alternative designation) of anti-TIM-3 Abs

| Antibody | VL CDR1 | VL CDR2 | VL CDR3 |
|---|---|---|---|
| 3E6 | KASQNVGANVAWY (SEQ ID NO: 31) | ALIYSASYRYS (SEQ ID NO: 39) | QQYNSYPT (SEQ ID NO: 47) |
| 4H2 | KASQDINKYIAWY (SEQ ID NO: 32) | LLIHYTSTLQP (SEQ ID NO: 40) | LQYDNLLFT (SEQ ID NO: 48) |
| 16H1 | KASQDVSAAVAWY (SEQ ID NO: 33) | LLIYSTFYRYI (SEQ ID NO: 41) | QQHYSVPWT (SEQ ID NO: 49) |
| 18C6 | RSSQSLVHSNGNTYLHWF (SEQ ID NO: 34) | LLIYKVSNRFS (SEQ ID NO: 42) | CQSTHVPPLT (SEQ ID NO: 50) |
| 19D11 | KASQNVGTNVAWY (SEQ ID NO: 35) | TLIYSASYRYS (SEQ ID NO: 43) | QQYNSYPLVT (SEQ ID NO: 51) |
| CH 5# | RASESVEYYGTSLMQWY (SEQ ID NO: 36) | LLIYAASNVES (SEQ ID NO: 44) | QQSRKVPIT (SEQ ID NO: 52) |
| CH 8# | RASESVEYYGTSLMQWY (SEQ ID NO: 36) | LLIYAASNVES (SEQ ID NO: 44) | QPSRKVPYT (SEQ ID NO: 53) |

TABLE 1b-continued

Amino acid sequences of VL CDRs (alternative designation) of anti-TIM-3 Abs

| Antibody | VL CDR1 | VL CDR2 | VL CDR3 |
|---|---|---|---|
| CH 9# | RASSSVSYMHWY (SEQ ID NO: 37) | PWIYATSNLAS (SEQ ID NO: 45) | QQWSSNPLT (SEQ ID NO: 54) |
| CH 10# | SASSSVSSSYLHWY (SEQ ID NO: 38) | LWIYSTSNLAS (SEQ ID NO: 46) | QQWSSYPLT (SEQ ID NO: 55) |
| CH 11# | RASESVEYYGTSLMQWY (SEQ ID NO: 36) | LLIYAASNVES (SEQ ID NO: 44) | QQSRKVPIT (SEQ ID NO: 52) |

TABLE 1c

Amino acid sequences of 3E6 VL CDRs (affinity maturated)

| Antibody | VL CDR1 | VL CDR2 | VL CDR3 |
|---|---|---|---|
| 3E6 VL0-v1 | KASQNVGANVA (SEQ ID NO: 86) | SASYRYS (SEQ ID NO: 94) | SQVNSYNT (SEQ ID NO: 198) |
| 3E6 VL0-v2 | KASQNVGANVA (SEQ ID NO: 86) | SASYRYS (SEQ ID NO: 94) | EQVNSYPT (SEQ ID NO: 199) |
| 3E6 VL0-v3 | KASQNVGANVA (SEQ ID NO: 86) | SASYRYS (SEQ ID NO: 94) | SQYNPYNT (SEQ ID NO: 200) |
| 3E6 VL0-v4 | KASQNVGANVA (SEQ ID NO: 86) | SASYRYS (SEQ ID NO: 94) | SQVNPYNT (SEQ ID NO: 201) |
| 3E6 VL0-v5 | KASQNVGANVA (SEQ ID NO: 86) | SASYRYS (SEQ ID NO: 94) | EQVNPYPT (SEQ ID NO: 202) |
| 3E6 VL0-v6 | KASQNVGANVA (SEQ ID NO: 86) | SASYRYS (SEQ ID NO: 94) | QQVNPYPT (SEQ ID NO: 203) |
| 3E6 VL0-v7 | KASQNVGANVA (SEQ ID NO: 86) | SASYRYS (SEQ ID NO: 94) | EQYNPYPT (SEQ ID NO: 204) |
| 3E6 VL0-v8 | KASQNVGANVA (SEQ ID NO: 86) | SASYRYS (SEQ ID NO: 94) | SQVNSYPT (SEQ ID NO: 205) |
| 3E6-VL0-v9 | KASQNVGANVA (SEQ ID NO: 86) | SASYRYS (SEQ ID NO: 94) | EQVQSYPT (SEQ ID NO: 206) |

TABLE 2a

Amino acid sequences of heavy chain variable region CDRs (VH CDRs; Kabat designation) of anti-TIM-3 Abs

| Antibody | VH CDR1 | VH CDR2 | VH CDR3 |
|---|---|---|---|
| 3E6 | SGFAWN (SEQ ID NO: 101) | YISHSGSTSYNPSLKS (SEQ ID NO: 109) | GYRSPWFAY (SEQ ID NO: 119) |
| 4H2 | SGYWN (SEQ ID NO: 102) | YINYSGSTYYNPSLKS (SEQ ID NO: 110) | GNHFDY (SEQ ID NO: 120) |
| 16H1 | SYLMH (SEQ ID NO: 103) | SIDPSDSEISLNQKFMD (SEQ ID NO: 111) | DFGYVAWFVY (SEQ ID NO: 121) |
| 18C6 | DFLMH (SEQ ID NO: 104) | AIDTSDSYASYNQKFKG SEQ ID NO: 112) | EAMDY (SEQ ID NO: 122) |
| 19D11 | SGYSWH (SEQ ID NO: 105) | YIYFSGSTNYNPSLKS (SEQ ID NO: 113) | GYRSAWFAY (SEQ ID NO: 123) |
| CH 5# | GYYMH (SEQ ID NO: 106) | RVPNNGGTDYDQKFKG (SEQ ID NO: 114) | EGEYFDYYAMDY (SEQ ID NO: 124) |
| CH 8# | GYYMH (SEQ ID NO: 106) | RVYPNNGGTSYNQKFKG (SEQ ID NO: 115) | EGEYFDYFAMDY (SEQ ID NO: 125) |

TABLE 2a-continued

Amino acid sequences of heavy chain variable region CDRs (VH CDRs; Kabat designation) of anti-TIM-3 Abs

| Antibody | VH CDR1 | VH CDR2 | VH CDR3 |
|---|---|---|---|
| CH 9# | GYGVH (SEQ ID NO: 107) | MIWGDGSTDYNSALKS (SEQ ID NO: 116) | DRGNHWYFDV (SEQ ID NO: 126) |
| CH 10# | SYWIE (SEQ ID NO: 108) | EISPGRGSTNYNEKFKG (SEQ ID NO: 117) | DYYGSIFDV (SEQ ID NO: 127) |
| CH 11# | GYYMH (SEQ ID NO: 106) | RVNPNNGGTTYKQKFKG (SEQ ID NO: 118) | EGEYFDYYTMDY (SEQ ID NO: 128) |
| 3F2 | GYYMH (SEQ ID NO: 106) | YISCYNGATNYNQKFKG (SEQ ID NO: 162) | DYYLSVMDY (SEQ ID NO: 171) |
| 36A2 | SFEMH (SEQ ID NO: 154) | YISGGSTTIYYADTMKG (SEQ ID NO: 163) | SYYGLLDY (SEQ ID NO: 172) |
| 36B11 | TSGMGVG (SEQ ID NO: 155) | HIWWDDVKRYNPALKS (SEQ ID NO: 164) | TFITTTTMDY (SEQ ID NO: 173) |
| 38F8 | DYSMD (SEQ ID NO: 156) | DINPNYDSLSYNQKFKG (SEQ ID NO: 165) | RGYGKDYFDF (SEQ ID NO: 174) |
| 38A8 | TYNMH (SEQ ID NO: 157) | GIYPGNGDTSYNQKFKG (SEQ ID NO: 166) | SYYTFDAMDC (SEQ ID NO: 175) |
| 40F11 | TAEMQ (SEQ ID NO: 158) | WINTRSGVPKYAEDFKG (SEQ ID NO: 167) | GTYAMDY (SEQ ID NO: 176) |
| 50H9 | TNGMS (SEQ ID NO: 159) | TISSGGSNTYYPDSVKG (SEQ ID NO: 168) | RSELGPFAY (SEQ ID NO: 177) |
| 84G10 | SYWMN (SEQ ID NO: 160) | QIYPGEGDTNYNGKFKG (SEQ ID NO: 169) | GHFYGSSYDWFAY (SEQ ID NO: 178) |
| 39D1 | SSYWIE (SEQ ID NO: 161) | EILPGSGSINYNEKFKG (SEQ ID NO: 170) | SYYYVMDY (SEQ ID NO: 179) |

TABLE 2b

Amino acid sequences of VH CDRs (alternative designation) of anti-TIM-3 Abs

| Antibody | VH CDR1 | VH CDR2 | VH CDR3 |
|---|---|---|---|
| 3E6 | GYSITSGFAWN (SEQ ID NO: 56) | WMGYISHSGSTSYNPSLKS (SEQ ID NO: 64) | ARGYRSPWFAY (SEQ ID NO: 74) |
| 4H2 | GDSITSGYWN (SEQ ID NO: 57) | YMGYINYSGSTYYNPSLKS (SEQ ID NO: 65) | ATGNHFDY (SEQ ID NO: 75) |
| 16H1 | GYSFTSYLMH (SEQ ID NO: 58) | WIGSIDPSDSEISLNQKFMD (SEQ ID NO: 66) | ARDFGYVAWFVY (SEQ ID NO: 76) |
| 18C6 | GYKFTDFLMH (SEQ ID NO: 59) | WIGAIDTSDSYASYNOKFKG (SEQ ID NO: 67) | SREAMDY (SEQ ID NO: 77) |
| 19D11 | GYSITSGYSWH (SEQ ID NO: 60) | WMGYIYFSGSTNYNPSLKS (SEQ ID NO: 68) | ARGYRSAWFAY (SEQ ID NO: 78) |
| CH 5# | GYSFTGYYMH (SEQ ID NO: 61) | WIGRVNPNNGGTDYDQKFKG (SEQ ID NO: 69) | AREGEYFDYYAMDY (SEQ ID NO: 79) |
| CH 8# | GYSFTGYYMH (SEQ ID NO: 61) | WIGR VYPNNGGTSYNQKFKG (SEQ ID NO: 70) | AREGEYFDYFAMDY (SEQ ID NO: 80) |
| CH 9# | GFSLTGYGVH (SEQ ID NO: 62) | WLGMIWGDGSTDYNSALKS (SEQ ID NO: 71) | ARDRGNHWYFDV (SEQ ID NO: 81) |
| CH 10# | GYTFSSYWIE (SEQ ID NO: 63) | WIGEISPGRGSTNYNEKFKG (SEQ ID NO: 72) | ARDYYGSIFDV (SEQ ID NO: 82) |

TABLE 2b-continued

Amino acid sequences of VH CDRs (alternative designation) of anti-TIM-3 Abs

| Antibody | VH CDR1 | VH CDR2 | VH CDR3 |
|---|---|---|---|
| CH 11# | GYSFTGYYMH (SEQ ID NO: 61) | WIGRVNPNNGGTTYKQKFKG (SEQ ID NO: 73) | AREGEYFDYYTMDY (SEQ ID NO: 83) |

In some embodiments, an anti-TIM-3 antibody, or antigen-binding fragment thereof comprises a humanized antibody or antigen-binding fragment. In some embodiments, an anti-TIM-3 antibody or antigen-binding fragment thereof comprises a VL CDR1, VL CDR2, VL CDR3, VH CDR1, VH CDR2, and/or VH CDR3 from an antibody or antigen-binding fragment described herein. In some embodiments, an anti-TIM-3 antibody or antigen-binding fragment thereof comprises a variant of an anti-TIM-3 antibody or antigen-binding fragment described herein. In some embodiments, a variant of an anti-TIM-3 antibody or antigen-binding fragment comprises one to 30 amino acid substitutions, additions, and/or deletions in the anti-TIM-3 antibody or antigen-binding fragment. In some embodiments, a variant of an anti-TIM-3 antibody or antigen-binding fragment comprises one to 25 amino acid substitutions, additions, and/or deletions in the anti-TIM-3 antibody or antigen-binding fragment. In some embodiments, a variant of an anti-TIM-3 antibody or antigen-binding fragment comprises one to 20 substitutions, additions, and/or deletions in the anti-TIM-3 antibody or antigen-binding fragment. In some embodiments, a variant of an anti-TIM-3 antibody or antigen-binding fragment comprises one to 15 substitutions, additions, and/or deletions in the anti-TIM-3 antibody or antigen-binding fragment. In some embodiments, a variant of an anti-TIM-3 antibody or antigen-binding fragment comprises one to 10 substitutions, additions, and/or deletions in the anti-TIM-3 antibody or antigen-binding fragment. In some embodiments, a variant of an anti-TIM-3 antibody or antigen-binding fragment comprises one to five conservative amino acid substitutions, additions, and/or deletions in the anti-TIM-3 antibody or antigen-binding fragment. In some embodiments, a variant of an anti-TIM-3 antibody or antigen-binding fragment comprises one to three amino acid substitutions, additions, and/or deletions in the anti-TIM-3 antibody or antigen-binding fragment. In some embodiments, the amino acid substitutions, additions, and/or deletions are conservative amino acid substitutions. In some embodiments, the conservative amino acid substitution(s) is in a CDR of the antibody or antigen-binding fragment. In some embodiments, the conservative amino acid substitution(s) is not in a CDR of the antibody or antigen-binding fragment. In some embodiments, the conservative amino acid substitution(s) is in a framework region of the antibody or antigen-binding fragment.

In some embodiments, provided herein are antibodies or antigen-binding fragments thereof that specifically bind TIM-3, comprising a light chain variable region (VL) comprising (1) a light chain CDR1 (VL CDR1) having an amino acid sequence selected from the group consisting of SEQ ID NOs:86-93; (2) a light chain CDR2 (VL CDR2) having an amino acid sequence selected from the group consisting of SEQ ID NOs:94-100; or (3) a light chain CDR3 (VL CDR3) having an amino acid sequence selected from the group consisting of SEQ ID NOs:47-55 and 198-206; or a variant thereof having up to about 3, about 5, about 8, about 10, about 12, or about 15 amino acid substitutions, additions, and/or deletions in the VL CDRs. In some embodiments, the variant has about 5 amino acid substitutions, additions, and/or deletions in the VL CDRs. In some embodiments, the antibodies or antigen-binding fragments comprise all three VL CDRs.

In some embodiments, provided herein are antibodies or antigen-binding fragments thereof that specifically bind TIM-3 comprising a heavy chain variable region (VH) comprising (1) a heavy chain CDR1 (VH CDR1) having an amino acid sequence selected from the group consisting of SEQ ID NOs:101-108; (2) a heavy chain CDR2 (VH CDR2) having an amino acid sequence selected from the group consisting of SEQ ID NOs:109-118; or (3) a heavy chain CDR3 (VH CDR3) having an amino acid sequence selected from the group consisting of SEQ ID NOs:119-128; or a variant thereof having up to about 3, about 5, about 8, about 10, about 12, or about 15 amino acid substitutions, additions, and/or deletions in the VH CDRs. In some embodiments, the variant has up about 5 amino acid substitutions, additions, and/or deletions in the VH CDRs. In some embodiments, the antibodies or antigen-binding fragments comprise all three VH CDRs.

In some embodiments, provided herein are antibodies or antigen-binding fragments thereof that specifically bind TIM-3, comprising (a) a VL comprising (1) a VL CDR1 having an amino acid sequence selected from the group consisting of SEQ ID NOs:86-93; (2) a VL CDR2 having an amino acid sequence selected from the group consisting of SEQ ID NOs:94-100; and (3) a VL CDR3 having an amino acid sequence selected from the group consisting of SEQ ID NOs:47-55 and 198-206; or a variant thereof having up to about 5 amino acid substitutions, additions, and/or deletions in the VL CDRs; and (b) a VH comprising (1) a VH CDR1 having an amino acid sequence selected from the group consisting of SEQ ID NOs:101-108; (2) a VH CDR2 having an amino acid sequence selected from the group consisting of SEQ ID NOs:109-118; and (3) a VH CDR3 having an amino acid sequence selected from the group consisting of SEQ ID NOs:119-128; or a variant thereof having up to about 5 amino acid substitutions, additions, and/or deletions in the VH CDRs.

In some embodiments, provided herein are antibodies or antigen-binding fragments thereof that specifically bind TIM-3 having a VL, wherein the VL comprises VL CDR1, CDR2 and CDR3 having specific sequences. The VL CDR1, CDR2 and CDR3 can have (1) the amino acid sequences of SEQ ID NOs:86, 94, and 47, respectively. The VL CDR1, CDR2 and CDR3 can have (2) the amino acid sequences of SEQ ID NOs:87, 95, and 48, respectively. The VL CDR1, CDR2 and CDR3 can have (3) the amino acid sequences of SEQ ID NOs:88, %, and 49, respectively. The VL CDR1, CDR2 and CDR3 can have (4) the amino acid sequences of SEQ ID NOs:89, 97, and 50, respectively. The VL CDR1, CDR2 and CDR3 can have (5) the amino acid sequences of SEQ ID NOs:90, 94, and 51, respectively. The VL CDR1, CDR2 and CDR3 can have (6) the amino acid sequences of SEQ ID NOs:91, 98, and 52, respectively. The VL CDR1, CDR2 and CDR3 can have (7) the amino acid sequences of SEQ ID NOs:91, 98, and 53, respectively. The VL CDR1, CDR2 and CDR3 can have (8) the amino acid sequences of SEQ ID NOs:92, 99, and 54, respectively. The VL CDR1, CDR2 and CDR3 can have (9) the amino acid sequences of SEQ ID NOs:93, 100, and 55, respectively. The VL CDR1, CDR2 and CDR3 can have (10) the amino acid sequences of SEQ ID NOs:129, 138, and 145, respectively. The VL CDR1, CDR2 and CDR3 can have (11) the amino acid sequences of SEQ ID NOs:130, 139, and 146, respectively. The VL CDR1, CDR2 and CDR3 can have (12) the amino acid sequences of SEQ ID NOs:131, 140, and 147, respectively. The VL CDR1, CDR2 and CDR3 can have (13) the amino acid sequences of SEQ ID NOs:132, 141, and 148, respectively. The VL CDR1, CDR2 and CDR3 can have (14) the amino acid sequences of SEQ ID NOs:133, 139, and 149, respectively. The VL CDR1, CDR2 and CDR3 can have (15) the amino acid sequences of SEQ ID NOs:134, 142, and 150, respectively. The VL CDR1, CDR2 and CDR3 can have (16) the amino acid sequences of SEQ ID NOs: 135, 143, and 151, respectively. The VL CDR1, CDR2 and CDR3 can have (17) the amino acid sequences of SEQ ID NOs:136, 144, and 152, respectively. The VL CDR1, CDR2 and CDR3 can have (18) the amino acid sequences of SEQ ID NOs:137, 100, and 153, respectively. The VL CDR1, CDR2 and CDR3 can have (19) the amino acid sequences of SEQ ID NOs:86, 94, and 198, respectively. The VL CDR1, CDR2 and CDR3 can have (20) the amino acid sequences of SEQ ID NOs:86, 94, and 199, respectively. The VL CDR1, CDR2 and CDR3 can have (21) the amino acid sequences of SEQ ID NOs:86, 94, and 200, respectively. The VL CDR1, CDR2 and CDR3 can have (22) the amino acid sequences of SEQ ID NOs:86, 94, and 201, respectively. The VL CDR1, CDR2 and CDR3 can have (23) the amino acid sequences of SEQ ID NOs:86, 94, and 202, respectively. The VL CDR1, CDR2 and CDR3 can have (24) the amino acid sequences of SEQ ID NOs:86, 94, and 203, respectively. The VL CDR1, CDR2 and CDR3 can have (25) the amino acid sequences of SEQ ID NOs:86, 94, and 204, respectively. The VL CDR1, CDR2 and CDR3 can have (26) the amino acid sequences of SEQ ID NOs:86, 94, and 205, respectively. The VL CDR1, CDR2 and CDR3 can have (27) the amino acid sequences of SEQ ID NOs:86, 94, and 206, respectively. The VL can be a variant of the VL described above having up to about 3, about 5, about 8, about 10, about 12, or about 15 amino acid substitutions, additions, and/or deletions in the VL CDRs. In some embodiments, the variant has up about 5 amino acid substitutions, additions, and/or deletions in the VL CDRs.

In some embodiments, provided herein are antibodies or antigen-binding fragments thereof that specifically bind TIM-3 having a VH, wherein the VH comprises VH CDR1, CDR2 and CDR3 having specific sequences. The VH CDR1, CDR2 and CDR3 can have (1) the amino acid sequences of SEQ ID NOs:101, 109, and 119, respectively. The VH CDR1, CDR2 and CDR3 can have (2) the amino acid sequences of SEQ ID NOs:102, 110, and 120, respectively. The VH CDR1, CDR2 and CDR3 can have (3) the amino acid sequences of SEQ ID NOs:103, 111, and 121, respectively. The VH CDR1, CDR2 and CDR3 can have (4) the amino acid sequences of SEQ ID NOs:104, 112, and 122, respectively. The VH CDR1. CDR2 and CDR3 can have (5) the amino acid sequences of SEQ ID NOs:105, 113, and 123, respectively. The VH CDR1. CDR2 and CDR3 can have (6) the amino acid sequences of SEQ ID NOs:106, 114, and 124, respectively. The VH CDR1. CDR2 and CDR3 can have (7) the amino acid sequences of SEQ ID NOs:106, 115, and 125, respectively. The VH CDR1, CDR2 and CDR3 can have (8) the amino acid sequences of SEQ ID NOs:107, 116, and 126, respectively. The VH CDR1, CDR2 and CDR3 can have (9) the amino acid sequences of SEQ ID NOs:108, 117, and 127, respectively. The VH CDR1, CDR2 and CDR3 can have (10) the amino acid sequences of SEQ ID NOs:106, 118, and 128, respectively. The VH CDR1. CDR2 and CDR3 can have (11) the amino acid sequences of SEQ ID NOs:106, 162, and 171, respectively. The VH CDR1, CDR2 and CDR3 can have (12) the amino acid sequences of SEQ ID NOs:154, 163, and 172, respectively. The VH CDR1, CDR2 and CDR3 can have (13) the amino acid sequences of SEQ ID NOs:155, 164, and 173, respectively. The VH CDR1, CDR2 and CDR3 can have (14) the amino acid sequences of SEQ ID NOs:156, 165, and 174, respectively. The VH CDR1, CDR2 and CDR3 can have (15) the amino acid sequences of SEQ ID NOs:157, 166, and 175, respectively. The VH CDR1, CDR2 and CDR3 can have (16) the amino acid sequences of SEQ ID NOs:158, 167, and 176, respectively. The VH CDR1, CDR2 and CDR3 can have (17) the amino acid sequences of SEQ ID NOs:159, 168, and 177, respectively. The VH CDR1, CDR2 and CDR3 can have (18) the amino acid sequences of SEQ ID NOs:160, 169, and 178, respectively. The VH CDR1, CDR2 and CDR3 can have (19) the amino acid sequences of SEQ ID NOs:161, 170, and 179, respectively. The VH can be a variant of the VH described above having up to about 3, about 5, about 8, about 10, about 12, or about 15 amino acid substitutions, additions, and/or deletions in the VH CDRs. In some embodiments, the variant has up about 5 amino acid substitutions, additions, and/or deletions in the VH CDRs.

In some embodiments, provided herein are antibodies or antigen-binding fragments thereof that specifically bind TIM-3 having a VL and a VH. In some embodiments, the VL and VH are connected by a linker. In some embodiments, the linker has the amino acid sequence of (GGGGS)n, n=1, 2, 3, 4, or 5 (SEQ ID NO:216). In some embodiments, the linker has the amino acid sequence of (EAAAK)n, n=1, 2, 3, 4, or 5 (SEQ ID NO:217). In some embodiments, the linker has the amino acid sequence of GGGGSGGGGSGGGGS (SEQ ID NO:30).

In some embodiments, provided herein are antibodies or antigen-binding fragments thereof that specifically bind TIM-3 having a VL and a VH, wherein (a) the VL comprises VL CDR1, CDR2 and CDR3 having the amino acid sequences of (1) SEQ ID NOs:86, 94, and 47, respectively; (2) SEQ ID NOs:87, 95, and 48, respectively; (3) SEQ ID NOs:88, 96, and 49, respectively; (4) SEQ ID NOs:89, 97, and 50, respectively; (5) SEQ ID NOs:90, 94, and 51, respectively; (6) SEQ ID NOs:91, 98, and 52, respectively; (7) SEQ ID NOs:91, 98, and 53, respectively; (8) SEQ ID NOs:92, 99, and 54, respectively; (9) SEQ ID NOs:93, 100, and 55, respectively; (10) SEQ ID NOs:129, 138, and 145, respectively; (11) SEQ ID NOs:130, 139, and 146, respectively; (12) SEQ ID NOs:131, 140, and 147, respectively; (13) SEQ ID NOs:132, 141, and 148, respectively; (14) SEQ ID NOs:133, 139, and 149, respectively; (15) SEQ ID NOs:134, 142, and 150, respectively; (16) SEQ ID NOs:135, 143, and 151, respectively; (17) SEQ ID NOs:136, 144, and 152, respectively; (18) SEQ ID NOs:137, 100, and 153, respectively; (19) SEQ ID NOs:86, 94, and 198, respectively; (20) SEQ ID NOs:86, 94, and 199, respectively; (21) SEQ ID NOs:86, 94, and 200, respectively; (22) SEQ ID NOs:86, 94, and 201, respectively; (23) SEQ ID NOs:86, 94, and 202, respectively; (24) SEQ ID NOs:86, 94, and 203, respectively; (25) SEQ ID NOs:86, 94, and 204, respectively; (26) SEQ ID NOs:86, 94, and 205, respectively; or (27) SEQ ID NOs:86, 94, and 206, respectively; or a variant thereof having up to about 3 amino acid substitutions, additions, and/or deletions in the VL CDRs; and/or (b) the VH CDR1, CDR2 and CDR3 have the amino acid sequences of (1) SEQ ID NOs:101, 109, and 119, respectively. (2) SEQ ID NOs:102, 110, and 120, respectively; (3) SEQ ID NOs:103, 111, and 121, respectively; (4) SEQ ID NOs:104, 112, and 122, respectively; (5) SEQ ID NOs:105, 113, and 123, respectively; (6) SEQ ID NOs:106, 114, and 124, respectively; (7) SEQ ID NOs:106, 115, and 125, respectively; (8) SEQ ID NOs:107, 116, and 126, respectively; (9) SEQ ID NOs:108, 117, and 127, respectively; (10) SEQ ID NOs:106, 118, and 128, respectively; (11) SEQ ID NOs:106, 162, and 171, respectively; (12) SEQ ID NOs:154, 163, and 172, respectively; (13) SEQ ID NOs:155, 164, and 173, respectively; (14) SEQ ID NOs:156, 165, and 174, respectively; (15) SEQ ID NOs:157, 166, and 175, respectively; (16) SEQ ID NOs:158, 167, and 176, respectively; (17) SEQ ID NOs:159, 168, and 177, respectively; (18) SEQ ID NOs:160, 169, and 178, respectively; or (19) SEQ ID NOs:161, 170, and 179, respectively, or a variant thereof having up to about 5 amino acid substitutions, additions, and/or deletions in the VH CDRs.

In some embodiments, provided herein are antibodies or antigen-binding fragments thereof that specifically bind TIM-3 having a VL and a VH, wherein the VL comprises VL CDR1, CDR2 and CDR3 and the VH comprises VH CDR1, CDR2 and CDR3, and wherein the VL CDR1, VL CDR2, VL CDR3, VH CDR1, VH CDR2 and VH CDR3 have specific sequences. The VL CDR1, VL CDR2, VL CDR3, VH CDR1, VH CDR2 and VH CDR3 can have (1) the amino acid sequences of SEQ ID NOs:86, 94, 47, 101, 109, and 119, respectively. The VL CDR1, VL CDR2, VL CDR3, VH CDR1, VH CDR2 and VH CDR3 can have (2) the amino acid sequences of SEQ ID NOs:87, 95, 48, 102, 110, and 120, respectively. The VL CDR1, VL CDR2, VL CDR3, VH CDR1, VH CDR2 and VH CDR3 can have (3) the amino acid sequences of SEQ ID NOs:88, %, 49, 103, 111, and 121, respectively. The VL CDR1, VL CDR2, VL CDR3, VH CDR1, VH CDR2 and VH CDR3 can have (4) the amino acid sequences of SEQ ID NOs:89, 97, 50, 104, 112, and 122, respectively. The VL CDR1, VL CDR2, VL CDR3, VH CDR1, VH CDR2 and VH CDR3 can have (5) the amino acid sequences of SEQ ID NOs:90, 94, 51, 105, 113, and 123, respectively. The VL CDR1, VL CDR2, VL CDR3, VH CDR1, VH CDR2 and VH CDR3 can have (6) the amino acid sequences of SEQ ID NOs:91, 98, 52, 106, 114, and 124, respectively. The VL CDR1, VL CDR2, VL CDR3, VH CDR1, VH CDR2 and VH CDR3 can have (7) the amino acid sequences of SEQ ID NOs:91, 98, 53, 106, 115, and 125, respectively. The VL CDR1, VL CDR2, VL CDR3, VH CDR1, VH CDR2 and VH CDR3 can have (8) the amino acid sequences of SEQ ID NOs:92, 99, 54, 107, 116, and 126, respectively. The VL CDR1, VL CDR2, VL CDR3, VH CDR1, VH CDR2 and VH CDR3 can have (9) the amino acid sequences of SEQ ID NOs:93, 100, 55, 108, 117, and 127, respectively. The VL CDR1, VL CDR2, VL CDR3, VH CDR1. VH CDR2 and VH CDR3 can have (10) the amino acid sequences of SEQ ID NOs:91, 98, 52, 106, 118, and 128, respectively. The VL CDR1, VL CDR2, VL CDR3, VH CDR1, VH CDR2 and VH CDR3 can have (11) the amino acid sequences of SEQ ID NOs:129, 138, 145, 106, 162, and 171, respectively. The VL CDR1, VL CDR2, VL CDR3, VH CDR1, VH CDR2 and VH CDR3 can have (12) the amino acid sequences of SEQ ID NOs:130, 139, 146, 154, 163, and 172, respectively. The VL CDR1, VL CDR2, VL CDR3, VH CDR1, VH CDR2 and VH CDR3 can have (13) the amino acid sequences of SEQ ID NOs:131, 140, 147, 155, 164, and 173, respectively. The VL CDR1, VL CDR2, VL CDR3, VH CDR1, VH CDR2 and VH CDR3 can have (14) the amino acid sequences of SEQ ID NOs:132, 141, 148, 156, 165, and 174, respectively. The VL CDR1, VL CDR2, VL CDR3, VH CDR1, VH CDR2 and VH CDR3 can have (15) the amino acid sequences of SEQ ID NOs: 133, 139, 149, 157, 166, and 175, respectively. The VL CDR1, VL CDR2, VL CDR3, VH CDR1, VH CDR2 and VH CDR3 can have (16) the amino acid sequences of SEQ ID NOs:134, 142, 150, 158, 167, and 176, respectively. The VL CDR1, VL CDR2, VL CDR3, VH CDR1, VH CDR2 and VH CDR3 can have (17) the amino acid sequences of SEQ ID NOs:135, 143, 151, 159, 168, and 177, respectively. The VL CDR1, VL CDR2, VL CDR3, VH CDR1, VH CDR2 and VH CDR3 can have (18) the amino acid sequences of SEQ ID NOs: 136, 144, 152, 160, 169, and 178, respectively. The VL CDR1, VL CDR2, VL CDR3, VH CDR1, VH CDR2 and VH CDR3 can have (19) the amino acid sequences of SEQ ID NOs:137, 100, 153, 161, 170, and 179, respectively. The VL CDR1, VL CDR2, VL CDR3, VH CDR1, VH CDR2 and VH CDR3 can have (20) the amino acid sequences of SEQ ID NOs:86, 94, 198, 101, 109, and 119, respectively. The VL CDR1, VL CDR2, VL CDR3, VH CDR1, VH CDR2 and VH CDR3 can have (21) the amino acid sequences of SEQ ID NOs:86, 94, 199, 101, 109, and 119, respectively. The VL CDR1, VL CDR2, VL CDR3, VH CDR1, VH CDR2 and VH CDR3 can have (22) the amino acid sequences of SEQ ID NOs:86, 94, 200, 101, 109, and 119, respectively. The VL CDR1, VL CDR2, VL CDR3, VH CDR1, VH CDR2 and VH CDR3 can have (23) the amino acid sequences of SEQ ID NOs:86, 94, 201, 101, 109, and 119, respectively. The VL CDR1, VL CDR2, VL CDR3, VH CDR1, VH CDR2 and VH CDR3 can have (24) the amino acid sequences of SEQ ID NOs:86, 94, 202, 101, 109, and 119, respectively. The VL CDR1. VL CDR2, VL CDR3, VH CDR1, VH CDR2 and VH CDR3 can have (25) the amino acid sequences of SEQ ID NOs:86, 94, 203, 101, 109, and 119, respectively. The VL CDR1, VL CDR2, VL CDR3, VH CDR1, VH CDR2 and VH CDR3 can have (26) the amino acid sequences of SEQ ID NOs:86, 94, 204, 101, 109, and 119, respectively. The VL CDR1, VL CDR2, VL CDR3, VH CDR1, VH CDR2 and VH CDR3 can have (27) the amino acid sequences of SEQ ID NOs:86, 94, 205, 101, 109, and 119, respectively. The VL CDR1, VL CDR2, VL CDR3, VH CDR1, VH CDR2 and VH CDR3 can have (28) the amino acid sequences of SEQ ID NOs:86, 94, 206, 101, 109, and 119, respectively. The antibody or antigen-binding fragment can be a variant of the antibodies or antigen-binding fragments described above having up to about 5 amino acid substitutions, additions, and/or deletions in the CDRs.

In some embodiments, provided herein are antibodies or antigen-binding fragments thereof that specifically bind TIM-3, comprising a VL comprising (1) a VL CDR1 having an amino acid sequence selected from the group consisting of SEQ ID NOs:31-38; (2) a VL CDR2 having an amino acid sequence selected from the group consisting of SEQ ID NOs:39-46; or (3) a VL CDR3 having an amino acid sequence selected from the group consisting of SEQ ID NOs:47-55; or a variant thereof having up to about 3, about 5, about 8, about 10, about 12, or about 15 amino acid substitutions, additions, and/or deletions in the VL CDRs. In some embodiments, the variant has about 5 amino acid substitutions, additions, and/or deletions in the VL CDRs. In some embodiments, the antibodies or antigen-binding fragments comprise all three VL CDRs.

In some embodiments, provided herein are antibodies or antigen-binding fragments thereof that specifically bind TIM-3 comprising a VH comprising (1) a VH CDR1 having an amino acid sequence selected from the group consisting of SEQ ID NOs:56-63; (2) a VH CDR2 having an amino acid sequence selected from the group consisting of SEQ ID NOs:64-73; or (3) a VH CDR3 having an amino acid sequence selected from the group consisting of SEQ ID NOs:74-83; or a variant thereof having up to about 3, about 5, about 8, about 10, about 12, or about 15 amino acid substitutions, additions, and/or deletions in the VH CDRs. In some embodiments, the variant has up about 5 amino acid substitutions, additions, and/or deletions in the VH CDRs. In some embodiments, the antibodies or antigen-binding fragments comprise all three VH CDRs.

In some embodiments, provided herein are antibodies or antigen-binding fragments thereof that specifically bind TIM-3, comprising (a) a VL comprising (1) a VL CDR1 having an amino acid sequence selected from the group consisting of SEQ ID NOs:31-38; (2) a VL CDR2 having an amino acid sequence selected from the group consisting of SEQ ID NOs:39-46; and (3) a VL CDR3 having an amino acid sequence selected from the group consisting of SEQ ID NOs:47-55; or a variant thereof having up to about 5 amino acid substitutions, additions, and/or deletions in the VL CDRs; and (b) a VH comprising (1) a VH CDR1 having an amino acid sequence selected from the group consisting of SEQ ID NOs:56-63; (2) a VH CDR2 having an amino acid sequence selected from the group consisting of SEQ ID NOs:64-73; and (3) a VH CDR3 having an amino acid sequence selected from the group consisting of SEQ ID NOs:74-83; or a variant thereof having up to about 5 amino acid substitutions, additions, and/or deletions in the VH CDRs.

In some embodiments, provided herein are antibodies or antigen-binding fragments thereof that specifically bind TIM-3 having a VL, wherein the VL comprises VL CDR1, CDR2 and CDR3 having specific sequences. The VL CDR1, CDR2 and CDR3 can have the amino acid sequences of (1) SEQ ID NOs:31, 39, and 47, respectively. The VL CDR1, CDR2 and CDR3 can have the amino acid sequences of (2) SEQ ID NOs:32, 40, and 48, respectively. The VL CDR1, CDR2 and CDR3 can have the amino acid sequences of (3) SEQ ID NOs:33, 41, and 49, respectively. The VL CDR1, CDR2 and CDR3 can have the amino acid sequences of (4) SEQ ID NOs:34, 42, and 50, respectively. The VL CDR1, CDR2 and CDR3 can have the amino acid sequences of (5) SEQ ID NOs:35, 43, and 51, respectively. The VL CDR1, CDR2 and CDR3 can have the amino acid sequences of (6) SEQ ID NOs:36, 44, and 52, respectively. The VL CDR1, CDR2 and CDR3 can have the amino acid sequences of (7) SEQ ID NOs:36, 44, and 53, respectively. The VL CDR1, CDR2 and CDR3 can have the amino acid sequences of (8) SEQ ID NOs:37, 45, and 54, respectively. The VL CDR1, CDR2 and CDR3 can have the amino acid sequences of (9) SEQ ID NOs:38, 46 and 55, respectively. The VL can be a variant of the VL described above having up to about 3, about 5, about 8, about 10, about 12, or about 15 amino acid substitutions, additions, and/or deletions in the VL CDRs. In some embodiments, the variant has up about 5 amino acid substitutions, additions, and/or deletions in the VL CDRs.

In some embodiments, provided herein are antibodies or antigen-binding fragments thereof that specifically bind TIM-3 having a VH, wherein the VH comprises VH CDR1, CDR2 and CDR3 having the amino acid sequences of (1) SEQ ID NOs:56, 64, and 74, respectively. The VH CDR1, CDR2 and CDR3 can have (2) SEQ ID NOs:57, 65, and 75, respectively. The VH CDR1, CDR2 and CDR3 can have (3) SEQ ID NOs:58, 66, and 76, respectively. The VH CDR1, CDR2 and CDR3 can have (4) SEQ ID NOs:59, 67 and 77, respectively. The VH CDR1, CDR2 and CDR3 can have (5) SEQ ID NOs:60, 68, and 78, respectively. The VH CDR1, CDR2 and CDR3 can have (6) SEQ ID NOs:61, 69, and 79, respectively. The VH CDR1, CDR2 and CDR3 can have (7) SEQ ID NOs:61, 70, and 80, respectively. The VH CDR1, CDR2 and CDR3 can have (8) SEQ ID NOs:62, 71, and 81, respectively. The VH CDR1, CDR2 and CDR3 can have (9) SEQ ID NOs:63, 72, and 82, respectively. The VH CDR1, CDR2 and CDR3 can have (10) SEQ ID NOs:61, 73, and 83, respectively. In some embodiments, the VH can be a variant of the VH described above having up to about 3, about 5, about 8, about 10, about 12, or about 15 amino acid substitutions, additions, and/or deletions in the VH CDRs. In some embodiments, the variant has up about 5 amino acid substitutions, additions, and/or deletions in the VH CDRs.

In some embodiments, provided herein are antibodies or antigen-binding fragments thereof that specifically bind TIM-3 having a VL and a VH. In some embodiments, the VL and VH are connected by a linker. In some embodiments, the linker has the amino acid sequence of (GGGGS)n, n=1, 2, 3, 4, or 5 (SEQ ID NO:216). In some embodiments, the linker has the amino acid sequence of (EAAAK)n, n=1, 2, 3, 4, or 5 (SEQ ID NO:217). In some embodiments, the linker has the amino acid sequence of GGGGSGGGGSGGGGS (SEQ ID NO:30).

In some embodiments, provided herein are antibodies or antigen-binding fragments thereof that specifically bind TIM-3 having a VL and a VH, wherein (a) the VL comprises VL CDR1, CDR2 and CDR3 having the amino acid sequences of (1) SEQ ID NOs:31, 39, and 47, respectively; (2) SEQ ID NOs:32, 40, and 48, respectively; (3) SEQ ID NOs:33, 41, and 49, respectively; (4) SEQ ID NOs:34, 42, and 50, respectively; (5) SEQ ID NOs:35, 43, and 51, respectively; (6) SEQ ID NOs:36, 44, and 52, respectively; (7) SEQ ID NOs:36, 44, and 53, respectively; (8) SEQ ID NOs:37, 45, and 54, respectively; or (9) SEQ ID NOs:38, 46 and 55, respectively; or a variant thereof having up to about 5 amino acid substitutions, additions, and/or deletions in the VL CDRs; and (b) the VH comprises VH CDR1, CDR2 and CDR3 having the amino acid sequences of (1) SEQ ID NOs:56, 64, and 74, respectively; (2) SEQ ID NOs:57, 65, and 75, respectively; (3) SEQ ID NOs:58, 66, and 76, respectively; (4) SEQ ID NOs:59, 67 and 77, respectively; or (5) SEQ ID NOs:60, 68, and 78, respectively; (6) SEQ ID NOs:61, 69, and 79, respectively; (7) SEQ ID NOs:61, 70, and 80, respectively; (8) SEQ ID NOs:62, 71, and 81, respectively; (9) SEQ ID NOs:63, 72, and 82, respectively; or (10) SEQ ID NOs:61, 73, and 83, respectively; or a variant thereof having up to about 5 amino acid substitutions, additions, and/or deletions in the VH CDRs.

In some embodiments, provided herein are antibodies or antigen-binding fragments thereof that specifically bind TIM-3 having a VL and a VH, wherein the VL comprises VL CDR1, CDR2 and CDR3 and the VH comprises VH CDR1, CDR2 and CDR3, and wherein the VL CDR1. VL CDR2, VL CDR3, VH CDR1, VH CDR2 and VH CDR3 have the amino acid sequences of (1) SEQ ID NOs:31, 39, 47, 56, 64, and 74, respectively. The VL CDR1, VL CDR2, VL CDR3, VH CDR1, VH CDR2 and VH CDR3 have the amino acid sequences of (2) SEQ ID NOs:32, 40, 48, 57, 65, and 75, respectively. The VL CDR1, VL CDR2, VL CDR3, VH CDR1, VH CDR2 and VH CDR3 have the amino acid sequences of (3) SEQ ID NOs:33, 41, 49, 58, 66, and 76, respectively. The VL CDR1. VL CDR2, VL CDR3, VH CDR1, VH CDR2 and VH CDR3 have the amino acid sequences of (4) SEQ ID NOs:34, 42, 50, 59, 67 and 77, respectively. The VL CDR1, VL CDR2, VL CDR3, VH CDR1, VH CDR2 and VH CDR3 have the amino acid sequences of (5) SEQ ID NOs:35, 43, 51, 60, 68, and 78, respectively. The VL CDR1, VL CDR2, VL CDR3, VH CDR1, VH CDR2 and VH CDR3 have the amino acid sequences of (6) SEQ ID NOs:36, 44, 52, 61, 69, and 79, respectively. The VL CDR1, VL CDR2. VL CDR3, VH CDR1, VH CDR2 and VH CDR3 have the amino acid sequences of (7) SEQ ID NOs:36, 44, 53, 61, 70, and 80, respectively. The VL CDR1, VL CDR2, VL CDR3, VH CDR1, VH CDR2 and VH CDR3 have the amino acid sequences of (8) SEQ ID NOs:37, 45, 54, 62, 71, and 81, respectively. The VL CDR1, VL CDR2, VL CDR3, VH CDR1, VH CDR2 and VH CDR3 have the amino acid sequences of (9) SEQ ID NOs:38, 46, 55, 63, 72, and 82, respectively. The VL CDR1, VL CDR2, VL CDR3, VH CDR1, VH CDR2 and VH CDR3 have the amino acid sequences of (10) SEQ ID NOs:36, 44, 52, 61, 73, and 83, respectively. The antibody or antigen-binding fragment can be a variant of the antibodies or antigen-binding fragments described above having up to about 5 amino acid substitutions, additions, and/or deletions in the CDRs.

In some embodiments, anti-TIM-3 antibodies or antigen-binding fragments provided herein comprise the VL and/or the VH of any one of the antibodies described herein. In some embodiments, anti-TIM-3 antibodies or antigen-binding fragments provided herein comprise the VL and/or the VH of 3E6, 4H2, 16H1, 18C6, 19D11, CH 5 #, CH 8 #, CH 9 #, CH 10 #, CH 11 #. 3F2, 36A2, 36B11, 38F8, 38A8, 40F11, 50H9, 84G10, or 39D1.

TABLE 3

Amino acid sequences of light chain variable regions (VLs) and heavy chain variable region (VHs) of anti-TIM-3 antibodies

| Antibody | VL | VH |
|---|---|---|
| 3E6 | DIIMTQSQKFMSTSVGDRVSVTCKASQN VGANVAWYQQKPRQSPKALIYSASYRY SGVPDRFTGSGSGTDFTLTISNVQSEDLA EYFCQQYNSYPTFGGGTKLEIK (SEQ ID NO: 1) | DVQLQEAGPGLVKPSQSLSLNCTVTGYS ITSGFAWNWIRQFPGNKLEWMGYISHSG STSYNPSLKSRISITRDTSKNQFFLQLNSV TTEDTATYYCARGYRSPWFAYWGQGTL VTVSA (SEQ ID NO: 11) |
| 4H2 | DIQMTQSPSSLSASLGGKVTITCKASQDI NKYIAWYQHKPGKGPRLLIHYTSTLQPG IPSRFSGSGSGTDYSFSISNLEPEDFATYY CLQYDNLLFTFGSGTKLEIK (SEQ ID NO: 2) | EVQLQESGPSLVKPSQTLSLTCSVTGDSI TSGYWNWIRKFPGNKLEYMGYINYSGS TYYNPSLKSRISITRDTSKNQYYLQLNSV TTEDTATYYCATGNHFDYWGQGTTLTV SS (SEQ ID NO: 12) |
| 16H1 | DIVMTQSHKFMSTSIEDRVSITCKASQDV SAAVAWYQQKPGQTPKLLIYSTFYRYIG VPDRFTGSGSGTDFTFTITSVQAEDLAVY FCQQHYSVPWTFGGGTKLEIK (SEQ ID NO: 3) | QVQLQQSGPQLVRPGSSVQISCKTSGYSF TSYLMHWVRORPGQGLEWIGSIDPSDSE ISLNQKFMDKATLTVDKSSSTANMQFSS PTSEDSAVYFCARDFGYVAWFVYWGQG TLVTVSA (SEQ ID NO: 13) |
| 18C6 | DVVMTQTPLSLPVSLGDQASISCRSSQSL VHSNGNTYLHWFLQKPGQSPKLLIYKVS NRFSGVPDRFSGSGSGTDFTLKISRVEAE DLGVYFCCQSTHVPPLIFGAGTKLELK (SEQ ID NO: 4) | QVQLQQPGAEIVMPGASVKMSCKASGY KFTDFLMHWVKQRPGQGLEWIGAIDTS DSYASYNQKFKGKATLTLDESSSTAYM QLSSLTSEDSAVYYCSREAMDYWGQGT SVTVSS (SEQ ID NO: 14) |
| 19D11 | DIVMTQSQKFMSTSVGDRVSVTCKASQ NVGTNVAWYQQKPGQSPKTLIYSASYR YSGVPDRFTGSGSGTDFTLTISNVQSEDL AEYFCQQYNSYPLVTFGTGTKLELK (SEQ ID NO: 5) | DVQLQESGPDLVKPSQSLSLTCTVTGYSI TSGYSWHWIRQFPGNKLEWMGYIYFSG STNYNPSLKSRISITRDTSKNQFFLQLNSV TTEDTATYYCARGYRSAWFAYWGQGT LVTVSA (SEQ ID NO: 15) |
| CH 5# | DIELTQSPASLAVSLGQRATISCRASESV EYYGTSLMQWYQQKPGQPPKLLIYAAS NVESGVPARFSGSVSGTDFSLNIHPVEED DIAMYFCQQSRKVPITFGSGTKLEIK (SEQ ID NO: 6) | QVQLQQSGPDLVKPGASVKISCKASGYS FTGYYMHWVKQSHGKSLEWIGRVNPN NGGTDYDQKFKGKAILSVDKSSNTAYM ELRSLTSEDSAVYYCAREGEYFDYYAM DYWGQGTTVTVSS (SEQ ID NO: 16) |
| CH 8# | DIELTQSPASLAVSLGQRATISCRASESV EYYGTSLMQWYQQKPGQPPKLLIYAAS NVESGVAARFSGSGSGTDFSLNIHPVEED DIAMYFCQPSRKVPYTFGGGTKLEIK (SEQ ID NO: 7) | QVKLQQSGPDLVKPGASVKISCKASGYS FTGYYMHWVKQSHGKSLEWIGRVYPN NGGTSYNQKFKGKAILTVDKSSSTAYME LRSLTSEDSAVYYCAREGEYFDYFAMD YWGQGTTVTVSS (SEQ ID NO: 17) |
| CH9# | DIELTQSPAILSASPGEKVTMTCRASSSV SYMHWYQQKPGSSPKPWIYATSNLASG VPARFSGSGSGTSYSLTISRVEAEDAATY YCQQWSSNPLTFGAGTKLEIK (SEQ ID NO: 8) | QVKLQESGPGLVAPSQSLSITCTVSGFSL TGYGVHWVRQPPGKGLEWLGMIWGDG STDYNSALKSRLSISKDNSKSQVFLKMN SLQTDDTARYYCARDRGNHWYFDVWG QGTTVTVSS (SEQ ID NO: 18) |
| CH 10# | DIELTQSPALMAASPGEKVTITCSASSSV SSSYLHWYQQKPGSSPKLWIYSTSNLAS GVPARFSGSGSGTSYSLTISSMEAEDAAT YYCQQWSSYPLTFGAGTKLEIK (SEQ ID NO: 9) | QVQLQQSGAELMKPGASVKISCKAIGYT FSSYWIEWVKQRPGHGLEWIGEISPGRG STNYNEKFKGKATFTADTSSNTAYMQLS SLTSEDSAVYYCARDYYGSIFDVWGQG TTVTVSS (SEQ ID NO: 19) |

TABLE 3-continued

Amino acid sequences of light chain variable regions (VLs) and heavy chain variable region (VHs) of anti-TIM-3 antibodies

| Antibody | VL | VH |
| --- | --- | --- |
| CH 11# | DIELTQSPASLAVSLGQRATISCRASESV EYYGTSLMQWYQQKPGQPPKLLIYAAS NVESGVPARFSGSVSGTDFSLNIHIPVEED DIAVYFCQQSRKVPITFGSGTKLELK (SEQ ID NO: 10) | QVKLQQSGPDLVKPGASVKISCKASGYS FTGYYMHWVKQSHGKSLEWIGRVNPN NGGTTYKQKFKGKVILTVDKSSSTAYM ELRSLTSEDSAVYYCAREGEYFDYYTM DYWGQGTTVTVSS (SEQ ID NO: 20) |
| 3F2 | NIMMTQSPSSLAVSAGEKVTMSCKSSQS VLYSSNQKNYLAWYQQKPGQSPKLLIY WASFRESGVPDRFTGSGSGTDFTLTISSV QAEDLAVYYCHQSLSSYTFGGGTKLEIK (SEQ ID NO: 180) | EVQLQQSGPELVKTGSSVKISCKASGYSF TGYYMHWVRQSPGKSLEWIGYISCYNG ATNYNQKFKGKATFTVDTYSSTAYMQF DSLASEDSAVYYCVRDYYLSVMDYWG QGTSVTVSS (SEQ ID NO: 189) |
| 36A2 | NIMMTQSPSSLSVSTGEKVTMSCKSSQS VLHSSNQKNFLAWFQQKPGQSPKLLIY WASTRESGVPDRFTGSGSGTDFTLTINN VQPEDLAVYYCHQYLSSLTFGAGTKLEL K (SEQ ID NO: 181) | DVQLVESGGGLVQPGGSRKLSCAASGFT FSSFEMHWVRQAPETGLEWVAYISGGST TIYYADTMKGRFTISRDNPENTLFLQMT SLRSEDTAIYYCVRSYYGLLDYWGQGTT LTVSS (SEQ ID NO: 190) |
| 36B11 | QIVLTQSPTIMSASPGEKVTLTCSASSGIS SSYLYWYQQKPGSSPKLWIYGTSNLASG VPARFSGSGSGTSYSLTISSLEAEDAASY FCHQWSNYPYTFGGGTKLEIK (SEQ ID NO: 182) | QVTLKESGPGILQPSQTLSLTCSFSGFSLS TSGMGVGWIRQPSGKGLEWLAHIWWD DVKRYNPALKSRLTISKDTSSSQVFLKIA SVDTADTATYYCVRTFITTTTMDYWGQ GTSVTVSS (SEQ ID NO: 191) |
| 38F8 | TWGMTQTTSSLSASLGDRVTISCRASQDI SNYLNWYQQKPDGTVKLLIYHTSRLYS GVPSRFTGSGSGTDYSLTISNLEQEDIAT YFCQQGNTLPLTFGAGTKLELK (SEQ ID NO: 183) | EVQLQQLGAELVKPGASVKISCKASGYI FTDYSMDWVKQSHGESLEWIGDINPNY DSLSYNQKFKGKATLTVDKSSSTAYMEL RSLTSEDTAVYYCARRGYGKDYFDFWG QGTSLTVSS (SEQ ID NO: 192) |
| 38A8 | DIVMSQSPSSLAVSAGEKVTMSCKSSOS LLNSRTRKNYLAWYQQKPGRSPKLLIY WASTRESGVPDRFTGGSGTDFTLTISSV QAEDLAVYYCKQSYSLLTFGAGTKLEL K (SEQ ID NO: 184) | QVQLQQPGAELVKPGASVKMSCKASGY TFTTYNMHWVKQTPGQGLEWIGGIYPG NGDTSYNQKFKGKATLTADKSSSTAYM QLSSLTSEDSAVYYCARSYYTFDAMDC WGQGTSVTVSS (SEQ ID NO: 193) |
| 40F11 | ENVLTQSPAIMSASPGEKVTMTCRASSIV SSSYLHWYQQKSGASPKLWIYSTSNLPS GVPARFSGSGSGTFYSLTVSSVESEDAAT YYCQQYSGYPYTFGGGTKLEIK (SEQ ID NO: 185) | QIQLVQSGPELKKPGETVRISCKASGYTF RTAEMQWVQKMPGRGLKWIGWINTRS GVPKYAEDFKGRFALSLETSATTAYLOIS NLKNEDTATYFCTRGTYAMDYWGQGT SVTVSS (SEQ ID NO: 194) |
| 50H9 | DVQMIQSPSSLSASLGDIVTMTCQASQG SSVNLNWFQQKPGKSPKLLIHGSNILED GVPSRFSGSRYGTDFTLTISSLENEDMAT YFCLQHSYLPYTFGGGTKLEIK (SEQ ID NO: 186) | EVQLVESGGDLVKPGGSLKLSCAASGFT FSTNGMSWVRQIPDKRLEWVATISSGGS NTYYPDSVKGRFTISRDNAKNTLYLQMS SLKSEDTAMYYCARRSELGPFAYWGQG TLVTVSA (SEQ ID NO: 195) |
| 84G10 | DIQMTQSPASLSASVGETVTITCRASENI NSYLAWYQQKOGKSPOLLVYHAKTLAS GVPSRFSGSGSGTQFSLKINSLQPEDFGS YYCQHHYGTPLTFGAGARLELK (SEQ ID NO: 187) | QVQLQQSGGELVRPGSSVKISCKASGYA FSSYWMNWVKQRPGQGLEWIGQIYPGE GDTNYNGKFKGKATLTADKSSSTAYMQ LSSLTSEDSAVYFCARGHFYGSSYDWFA YWGQGTLVTVSA (SEQ ID NO: 196) |
| 39D1 | QIVLTQSPAIMSASPGEMLTITCSASSSVR FMHWFQQKPGTSPKLWIYSTSNLASGVP ARFSGSGSGTSYSLTVSRMEAEDAATYY CQQRSSYPPTFGGGTKLEIK (SEQ ID NO: 188) | QVQLQQSGAELMKPGASVKISCKATGY TFSSSYWIEWVKQRPGHGLEWIGEILPGS GSINYNEKFKGKATFTADTSSNTVYMQL SSLTSDDSAVYYCARSYYYVMDYWGQ GTSVTVSS (SEQ ID NO: 197) |

In some embodiments, the anti-TIM-3 antibody or antigen-binding fragment thereof provided herein is a humanized version of any one of the antibodies described herein. In some embodiments, the anti-TIM-3 antibody or antigen-binding fragment thereof provided herein is a humanized version of 3E6, 4H2, 16H1, 18C6, 19D11, CH 5 #, CH 8 #, CH 9 #, CH 10 #, CH 11 #, 3F2, 36A2, 36B11, 381F8, 38A8, 40F11, 50H9, 84G10, or 391D1, Exemplary sequences are provided below.

TABLE 4a

Amino acid sequences of VLs and VHs of humanized anti-TIM-3 antibodies

| | SEQUENCES |
|---|---|
| 3E6 VL0 | DIQMTQSPSSLSASVGDRVTITCKASQNVGANVAWYQQKPGKAPKSLIYSASYRYSGV PSRFSGSGSGTDFTLTISSLQPEDFATYYCQQYNSYPTFGGGTKVEIK (SEQ ID NO: 21) |
| 3E6VH0 | QVQLQESGPGLVKPSQTLSLTCTVSGYSITSGFAWNWIRQPPGKGLEWIGYISHSGSTSY NPSLKSRVTISVDTSKNQFSLKLSSVTAADTAVYYCARGYRSPWFAYWGQGTTVTSS (SEQ ID NO: 22) |
| 3E6 VH1 | QVQLQESGPGLVKPSQTLSLTCTVSGYSITSGFAWNWIRQFPGNGLEWMGYISHSGSTS YNPSLKSRVTISVDTSKNQFSLKLSSVTAADTAVYYCARGYRSPWFAYWGQGTTVTVS S (SEQ ID NO: 23) |
| 3E6 VH2 | QVQLQESGPGLVKPSQTLSLTCTVSGYSITSGFAWNWIRQPPGKGLEWMGYISHSGSTS YNPSLKSRVTISVDTSKNQFSLKLSSVTAADTAVYYCARGYRSPWFAYWGQGTTVTVS S (SEQ ID NO: 24) |
| 3E6 VH3 | QVQLQESGPGLVKPSQTLSLTCTVSGYSITSGFAWNWIRQPPGNGLEWIGYISHSGSTSY NPSLKSRVTISVDTSKNQFSLKLSSVTAADTAVYYCARGYRSPWFAYWGQGTTVTVSS (SEQ ID NO: 25) |
| 3E6 VH4 | QVQLQESGPGLVKPSQTLSLTCTVSGYSITSGFAWNWIRQPPGNGLEWIGYISHSGSTSY NPSLKSRITISVDTSKNQFSLKLSSVTAADTAVYYCARGYRSPWFAYWGQGTTVTVSS (SEQ ID NO: 26) |
| 3E6 VH5 | QVQLQESGPGLVKPSQTLSLTCTVSGYSITSGFAWNWIRQPPGNGLEWIGYISHSGSTSY NPSLKSRITISRDTSKNQFSLKLSSVTAADTAVYYCARGYRSPWFAYWGQGTTVTVSS (SEQ ID NO: 27) |
| 3E6 VH6 | QVQLQESGPGLVKPSQTLSLTCTVSGYSITSGFAWNWIRQPPGKGLEWMGYISHSGSTS YNPSLKSRITISVDTSKNQFSLKLSSVTAADTAVYYCARGYRSPWFAYWGQGTTVTVS S (SEQ ID NO: 28) |
| 3E6 VH7 | QVQLQESGPGLVKPSQTLSLTCTVSGYSITSGFAWNWIRQPPGKGLEWMGYISHSGSTS YNPSLKSRITISRDTSKNQFSLKLSSVTAADTAVYYCARGYRSPWFAYWGQGTTVTVSS (SEQ ID NO: 29) |

TABLE 4b

Amino acid sequences of affinity matured 3E6 VL0s

| | SEQUENCES |
|---|---|
| 3E6 VL0-v1 | DIQMTQSPSSLSASVGDRVTITCKASQNVGANVAWYQQKPGKAPKSLIYSASYRYSGV PSRFSGSGSGTDFTLTISSLQPEDFATYYCSQVNSYNTFGGGTKVEIK (SEQ ID NO: 207) |
| 3E6 VL0-v2 | DIQMTQSPSSLSASVGDRVTITCKASQNVGANVAWYQQKPGKAPKSLIYSASYRYSGV PSRFSGSGSGTDFTLTISSLQPEDFATYYCEQVNSYPTFGGGTKVEIK (SEQ ID NO: 208) |
| 3E6 VL0-v3 | DIQMTQSPSSLSASVGDRVTITCKASQNVGANVAWYQQKPGKAPKSLIYSASYRYSGV PSRFSGSGSGTDFTLTISSLQPEDFATYYCSQYNPYNTFGGGTKVEIK (SEQ ID NO: 209) |
| 3E6 VL0-v4 | DIQMTQSPSSLSASVGDRVTITCKASQNVGANVAWYQQKPGKAPKSLIYSASYRYSGV PSRFSGSGSGTDFTLTISSLQPEDFATYYCSQVNPYNTFGGGTKVEIK (SEQ ID NO: 210) |
| 3E6 VL0-v5 | DIQMTQSPSSLSASVGDRVTITCKASQNVGANVAWYQQKPGKAPKSLIYSASYRYSGV PSRFSGSGSGTDFTLTISSLQPEDFATYYCEQVNPYPTFGGGTKVEIK (SEQ ID NO: 211) |
| 3E6 VL0-v6 | DIQMTQSPSSLSASVGDRVTITCKASQNVGANVAWYQQKPGKAPKSLIYSASYRYSGV PSRFSGSGSGTDFTLTISSLQPEDFATYYCQQVNPYPTFGGGTKVEIK (SEQ ID NO: 212) |

TABLE 4b-continued

Amino acid sequences of affinity matured 3E6 VL0s

SEQUENCES

3E6 VL0-v7  DIQMTQSPSSLSASVGDRVTITCKASQNVGANVAWYQQKPGKAPKSLIYSASYRYSGV
            PSRFSGSGSGTDFTLTISSLQPEDFATYYCEQYNPYPTFGGGTKVEIK (SEQ ID NO: 213)

3E6 VL0-v8  DIQMTQSPSSLSASVGDRVTITCKASQNVGANVAWYQQKPGKAPKSLIYSASYRYSGV
            PSRFSGSGSGTDFTLTISSLQPEDFATYYCSQVNSYPTFGGGTKVEIK (SEQ ID NO: 214)

3E6 VL0-v9  DIQMTQSPSSLSASVGDRVTITCKASQNVGANVAWYQQKPGKAPKSLIYSASYRYSGV
            PSRFSGSGSGTDFTLTISSLQPEDFATYYCEQVQSYPIFGGGTKVEIK (SEQ ID NO: 215)

In some embodiments, provided herein are antibodies or antigen-binding fragments thereof that specifically bind TIM-3 comprising a VL having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to an amino acid sequence selected from the group consisting of SEQ ID NOs:1-10 and 180-188. In some embodiments, provided herein are antibodies or antigen-binding fragments thereof that specifically bind TIM-3 comprising a VH having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to an amino acid sequence selected from the group consisting of SEQ ID NOs:11-20 and 189-197. In some embodiments, the antibodies or antigen-binding fragments comprise both the VL and the VH.

The anti-TIM-3 antibodies or antigen-binding fragments thereof can comprise a combination of any VL disclosed herein and any VH disclosed herein. In some embodiments, the VL and VH are connected by a linker. In some embodiments, the linker has the amino acid sequence of (GGGGS)n, n=1, 2, 3, 4, or 5 (SEQ ID NO:216). In some embodiments, the linker has the amino acid sequence of (EAAAK)n, n=1, 2, 3, 4, or 5 (SEQ ID NO:217). In some embodiments, the linker has the amino acid sequence of GGGGSGGGGSGGGGS (SEQ ID NO:30).

In some embodiments, provided herein are antibodies or antigen-binding fragments thereof that specifically bind TIM-3 comprising a VL and a VH, wherein the VH has an amino acid sequence selected from the group consisting of SEQ ID NOs:11-20 and 189-197, and the VL has a specific sequence selected from the group consisting of SEQ ID NOs:1-10 and 180-188. The VL can have the amino acid sequence of SEQ ID NO:1. The VL can have the amino acid sequence of SEQ ID N0:2. The VL can have the amino acid sequence of SEQ ID NO:3. The VL can have the amino acid sequence of SEQ ID NO:4 The VL can have the amino acid sequence of SEQ ID NO:5. The VL can have the amino acid sequence of SEQ ID NO:6. The VL can have the amino acid sequence of SEQ ID NO:7. The VL can have the amino acid sequence of SEQ ID NO:8. The VL can have the amino acid sequence of SEQ ID NO:9. The VL can have the amino acid sequence of SEQ ID NO:10. The VL can have the amino acid sequence of SEQ ID NO: 180. The VL can have the amino acid sequence of SEQ ID NO:181. The VL can have the amino acid sequence of SEQ ID NO:182. The VL can have the amino acid sequence of SEQ ID NO:183. The VL can have the amino acid sequence of SEQ ID NO:184. The VL can have the amino acid sequence of SEQ ID NO:185. The VL can have the amino acid sequence of SEQ ID NO:186. The VL can have the amino acid sequence of SEQ ID NO: 187. The VL can have the amino acid sequence of SEQ ID NO:188.

In some embodiments, provided herein are antibodies or antigen-binding fragments thereof that specifically bind TIM-3 comprising a VL and a VH, wherein the VL has an amino acid sequence selected from the group consisting of SEQ ID NOs:1-10 and 180-188, and the VH has a specific sequence selected from the group consisting of SEQ ID NOs:11-20 and 189-197. The VH can have the amino acid sequence of SEQ ID NO:11. The VH can have the amino acid sequence of SEQ ID NO:12. The VH can have the amino acid sequence of SEQ ID NO: 13. The VH can have the amino acid sequence of SEQ ID NO:14. The VH can have the amino acid sequence of SEQ ID NO:15. The VH can have the amino acid sequence of SEQ ID NO:16. The VH can have the amino acid sequence of SEQ ID NO:17. The VH can have the amino acid sequence of SEQ ID NO:18. The VH can have the amino acid sequence of SEQ ID NO:19. The VH can have the amino acid sequence of SEQ ID NO:20. The VH can have the amino acid sequence of SEQ ID NO: 189. The VH can have the amino acid sequence of SEQ ID NO:190. The VH can have the amino acid sequence of SEQ ID NO:191. The VH can have the amino acid sequence of SEQ ID NO:192. The VH can have the amino acid sequence of SEQ ID NO:193. The VH can have the amino acid sequence of SEQ ID NO: 194. The VH can have the amino acid sequence of SEQ ID NO:195. The VH can have the amino acid sequence of SEQ ID NO:196. The VH can have the amino acid sequence of SEQ ID NO:197.

In some embodiments, provided herein are antibodies or antigen-binding fragments thereof that specifically bind TIM-3 comprising a VL, wherein the VL has at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to SEQ ID NO:1. The VL can have at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO:2. The VL can have at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO:3. The VL can have at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO:4. The VL can have at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO:5. The VL can have at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO:6. The VL can have at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO:7. The VL can have at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO:8. The VL can have at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO:9. The VL can have at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO:10. The VL can have at least 80%, at least 850% at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO:180. The VL can have at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO:181. The VL can have at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO:182. The VL can have at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO:183. The VL can have at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 184. The VL can have at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO:185. The VL can have at least 80%, at least 85%, at least 86%, at least 87%, at least 88%, at least 89%, at least 900%, at least 91%, at least 92%, at least 93%, at least 94%, at least 95%, at least 96%, at least 97%, at least 98%, at least 99%, or 100% sequence identity to SEQ ID NO:186. The VL can have at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 187. The VL can have at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO:188.

In some embodiments, provided herein are antibodies or antigen-binding fragments thereof that specifically bind TIM-3 comprising a VH, wherein the VH has at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO:11. The VH can have at least 80%, at least 85%, at least 86%, at least 87%, at least 88%, at least 89%, at least 90%, at least 91%, at least 92%, at least 93%, at least 94%, at least 95%, at least 9%%, at least 97%, at least 98%, at least 99%, or 100% sequence identity to SEQ ID NO:12. The VH can have at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO:13. The VH can have at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO:14. The VH can have at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO:15. The VH can have at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO:16. The VH can have at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO:17. The VH can have at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO:18. The VH can have at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO:19. The VH can have at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO:20. The VH can have at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO:189. The VH can have at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO:190. The VH can have at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO:191. The VH can have at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 192. The VH can have at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO:193. The VH can have at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO:194. The VH can have at least 80%, at least 85%, at least 86%, at least 87%, at least 88%, at least 89%, at least 90%, at least 91%, at least 92%, at least 93%, at least 94%, at least 95%, at least %*%, at least 97%, at least 98%, at least 99%, or 100% sequence identity to SEQ ID NO: 195. The VH can have at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO:196. The VH can have at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO:197.

In some embodiments, provided herein are antibodies or antigen-binding fragments thereof that specifically bind TIM-3 comprising a VL and a VH, wherein the VL and VH have the amino acid sequences of SEQ ID NO:1 and 11, respectively. In some embodiments, the VL and VH have the amino acid sequences of SEQ ID NO:2 and 12, respectively. In some embodiments, the VL and VH have the amino acid sequences of SEQ ID NO:3 and 13, respectively. In some embodiments, the VL and VH have the amino acid sequences of SEQ ID NOs:4 and 14, respectively. In some embodiments, the VL and VH have the amino acid sequences of SEQ ID NOs:5 and 15, respectively. In some embodiments, the VL and VH have the amino acid sequences of SEQ ID NOs:6 and 16, respectively. In some embodiments, the VL and VH have the amino acid sequences of SEQ ID NOs:7 and 17, respectively. In some embodiments, the VL and VH have the amino acid sequences of SEQ ID NOs:8 and 18, respectively. In some embodiments, the VL and VH have the amino acid sequences of SEQ ID NOs:9 and 19, respectively. In some embodiments, the VL and VH have the amino acid sequences of SEQ ID NOs:10 and 20, respectively. In some embodiments, the VL and VH have the amino acid sequences of SEQ ID NOs:180 and 189, respectively. In some embodiments, the VL and VH have the amino acid sequences of SEQ ID NOs:181 and 190, respectively. In some embodiments, the VL and VH have the amino acid sequences of SEQ ID NOs:182 and 191, respectively. In some embodiments, the VL and VH have the amino acid sequences of SEQ ID NOs:183 and 192, respectively. In some embodiments, the VL and VH have the amino acid sequences of SEQ ID NOs:184 and 193, respectively. In some embodiments, the VL and VH have the amino acid sequences of SEQ ID NOs:185 and 194, respectively. In some embodiments, the VL and VH have the amino acid sequences of SEQ ID NOs:186 and 195, respectively. In some embodiments, the VL and VH have the amino acid sequences of SEQ ID NOs:187 and 196, respectively. In some embodiments, the VL and VH have the amino acid sequences of SEQ ID NOs:188 and 197, respectively.

In some embodiments, provided herein are humanized antibodies or antigen-binding fragments thereof that specifically bind TIM-3 comprising a VL having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to an amino acid sequence selected from the group consisting of SEQ ID NOs:21 and 207-215. In some embodiments, provided herein are antibodies or antigen-binding fragments thereof that specifically bind TIM-3 comprising a VH having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to an amino acid sequence selected from the group consisting of SEQ ID NOs:22-29. In some embodiments, the humanized antibodies or antigen-binding fragments comprise both the VL and the VH.

The anti-TIM-3 antibodies or antigen-binding fragments thereof can comprise a combination of any VL disclosed herein and any VH disclosed herein. In some embodiments, the VL and VH are connected by a linker. In some embodiments, the linker has the amino acid sequence of (GGGGS)n, n=1, 2, 3, 4, or 5 (SEQ ID NO:216). In some embodiments, the linker has the amino acid sequence of (EAAAK)n, n=1, 2, 3, 4, or 5 (SEQ ID NO:217). In some embodiments, the linker has the amino acid sequence of GGGGSGGGGSGGGGS (SEQ ID NO:30).

In some embodiments, provided herein are antibodies or antigen-binding fragments thereof that specifically bind TIM-3 comprising a VL, wherein the VL has at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to SEQ ID NO:21. The VL can have at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to SEQ ID NO:207. The VL can have at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to SEQ ID NO:208. The VL can have at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to SEQ ID NO:209. The VL can have at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to SEQ ID NO:210. The VL can have at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to SEQ ID NO:211. The VL can have at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to SEQ ID NO:212. The VL can have at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to SEQ ID NO:213. The VL can have at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to SEQ ID NO:214. The VL can have at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to SEQ ID NO:215.

In some embodiments, provided herein are antibodies or antigen-binding fragments thereof that specifically bind TIM-3 comprising a VH wherein the VH has at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to SEQ ID NO:22. The VH can have at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to SEQ ID NO:23. The VH can have at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to SEQ ID NO:24. The VH can have at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to SEQ ID NO:25. The VH can have at least 80%, at least 85%, at least 86%, at least 87%, at least 88%, at least 89%, at least 90%, at least 91%, at least 92%, at least 93%, at least 94%, at least 95%, at least 96%, at least 97%, at least 98/6, at least 99% or 100% sequence identity to SEQ ID NO:26. The VH can have at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to SEQ ID NO:27. The VH can have at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to SEQ ID NO:28. The VH can have at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to SEQ ID NO:29.

In some embodiments, provided herein are antibodies or antigen-binding fragments thereof that specifically bind TIM-3 comprising a VL and a VH, wherein the VL and VH have the amino acid sequences of SEQ ID NOs:21 and 22, respectively. The VL and VH can have the amino acid sequences of SEQ ID NOs:21 and 23, respectively. The VL and VH can have the amino acid sequences of SEQ ID NOs:21 and 24, respectively. The VL and VH can have the amino acid sequences of SEQ ID NOs:21 and 25, respectively. The VL and VH can have the amino acid sequences of SEQ ID NOs:21 and 26, respectively. The VL and VH can have the amino acid sequences of SEQ ID NOs:21 and 27, respectively. The VL and VH can have the amino acid sequences of SEQ ID NOs:21 and 28, respectively. The VL and VH can have the amino acid sequences of SEQ ID NOs:21 and 29, respectively. The VL and VH can have the amino acid sequences of SEQ ID NOs:207 and 22, respectively. The VL and VH can have the amino acid sequences of SEQ ID NOs:207 and 23, respectively. The VL and VH can have the amino acid sequences of SEQ ID NOs:207 and 24, respectively. The VL and VH can have the amino acid sequences of SEQ ID NOs:207 and 25, respectively. The VL and VH can have the amino acid sequences of SEQ ID NOs:207 and 26, respectively. The VL and VH can have the amino acid sequences of SEQ ID NOs:207 and 27, respectively. The VL and VH can have the amino acid sequences of SEQ ID NOs:207 and 28, respectively. The VL and VH can have the amino acid sequences of SEQ ID NOs:207 and 29, respectively. The VL and VH can have the amino acid sequences of SEQ ID NOs:208 and 22, respectively. The VL and VH can have the amino acid sequences of SEQ ID NOs:208 and 23, respectively. The VL and VH can have the amino acid sequences of SEQ ID NOs:208 and 24, respectively. The VL and VH can have the amino acid sequences of SEQ ID NOs:208 and 25, respectively. The VL and VH can have the amino acid sequences of SEQ ID NOs:208 and 26, respectively. The VL and VH can have the amino acid sequences of SEQ ID NOs:208 and 27, respectively. The VL and VH can have the amino acid sequences of SEQ ID NOs:208 and 28, respectively. The VL and VH can have the amino acid sequences of SEQ ID NOs:208 and 29, respectively. The VL and VH can have the amino acid sequences of SEQ ID NOs:209 and 23, respectively. The VL and VH can have the amino acid sequences of SEQ ID NOs:209 and 23, respectively. The VL and VH can have the amino acid sequences of SEQ ID NOs:209 and 24, respectively. The VL and VH can have the amino acid sequences of SEQ ID NOs:209 and 25, respectively. The VL and VH can have the amino acid sequences of SEQ ID NOs:209 and 26, respectively. The VL and VH can have the amino acid sequences of SEQ ID NOs:209 and 27, respectively. The VL and VH can have the amino acid sequences of SEQ ID NOs:209 and 28, respectively. The VL and VH can have the amino acid sequences of SEQ ID NOs:209 and 29, respectively. The VL and VH can have the amino acid sequences of SEQ ID NOs:210 and 22, respectively. The VL and VH can have the amino acid sequences of SEQ ID NOs:210 and 23, respectively. The VL and VH can have the amino acid sequences of SEQ ID NOs:210 and 24, respectively. The VL and VH can have the amino acid sequences of SEQ ID NOs:210 and 25, respectively. The VL and VH can have the amino acid sequences of SEQ ID NOs:210 and 26, respectively. The VL and VH can have the amino acid sequences of SEQ ID NOs:210 and 27, respectively. The VL and VH can have the amino acid sequences of SEQ ID NOs:210 and 28, respectively. The VL and VH can have the amino acid sequences of SEQ ID NOs:210 and 29, respectively. The VL and VH can have the amino acid sequences of SEQ ID NOs:211 and 22, respectively. The VL and VH can have the amino acid sequences of SEQ ID NOs:211 and 23, respectively. The VL and VH can have the amino acid sequences of SEQ ID NOs:211 and 24, respectively. The VL and VH can have the amino acid sequences of SEQ ID NOs:211 and 25, respectively. The VL and VH can have the amino acid sequences of SEQ ID NOs:211 and 26, respectively. The VL and VH can have the amino acid sequences of SEQ ID NOs:211 and 27, respectively. The VL and VH can have the amino acid sequences of SEQ ID NOs:211 and 28, respectively. The VL and VH can have the amino acid sequences of SEQ ID NOs:211 and 29, respectively. The VL and VH can have the amino acid sequences of SEQ ID NOs:212 and 22, respectively. The VL and VH can have the amino acid sequences of SEQ ID NOs:212 and 23, respectively. The VL and VH can have the amino acid sequences of SEQ ID NOs:212 and 24, respectively. The VL and VH can have the amino acid sequences of SEQ ID NOs:212 and 25, respectively. The VL and VH can have the amino acid sequences of SEQ ID NOs:212 and 26, respectively. The VL and VH can have the amino acid sequences of SEQ ID NOs:212 and 27, respectively. The VL and VH can have the amino acid sequences of SEQ ID NOs:212 and 28, respectively. The VL and VH can have the amino acid sequences of SEQ ID NOs:212 and 29, respectively. The VL and VH can have the amino acid sequences of SEQ ID NOs:213 and 22, respectively. The VL and VH can have the amino acid sequences of SEQ ID NOs:213 and 23, respectively. The VL and VH can have the amino acid sequences of SEQ ID NOs:213 and 24, respectively. The VL and VH can have the amino acid sequences of SEQ ID NOs:213 and 25, respectively. The VL and VH can have the amino acid sequences of SEQ ID NOs:213 and 26, respectively. The VL and VH can have the amino acid sequences of SEQ ID NOs:213 and 27, respectively. The VL and VH can have the amino acid sequences of SEQ ID NOs:213 and 28, respectively. The VL and VH can have the amino acid sequences of SEQ ID NOs:213 and 29, respectively. The VL and VH can have the amino acid sequences of SEQ ID NOs:214 and 22, respectively. The VL and VH can have the amino acid sequences of SEQ ID NOs:214 and 23, respectively. The VL and VH can have the amino acid sequences of SEQ ID NOs:214 and 24, respectively. The VL and VH can have the amino acid sequences of SEQ ID NOs:214 and 25, respectively. The VL and VH can have the amino acid sequences of SEQ ID NOs:214 and 26, respectively. The VL and VH can have the amino acid sequences of SEQ ID NOs:214 and 27, respectively. The VL and VH can have the amino acid sequences of SEQ ID NOs:214 and 28, respectively. The VL and VH can have the amino acid sequences of SEQ ID NOs:214 and 29, respectively. The VL and VH can have the amino acid sequences of SEQ ID NOs:215 and 22, respectively. The VL and VH can have the amino acid sequences of SEQ ID NOs:215 and 23, respectively. The VL and VH can have the amino acid sequences of SEQ ID NOs:215 and 24, respectively. The VL and VH can have the amino acid sequences of SEQ ID NOs:215 and 25, respectively. The VL and VH can have the amino acid sequences of SEQ ID NOs:215 and 26, respectively. The VL and VH can have the amino acid sequences of SEQ ID NOs:215 and 27, respectively. The VL and VH can have the amino acid sequences of SEQ ID NOs:215 and 28, respectively. The VL and VH can have the amino acid sequences of SEQ ID NOs:215 and 29, respectively.

In some embodiments, provided herein are antibodies or antigen-binding fragments thereof that specifically bind TIM-3 comprising (a) a VL comprising VL CDRs 1, 2, and 3 from a VL having an amino acid sequence selected from the group consisting of SEQ ID NOs:1-10 and 180-188; and/or (b) a VH comprising VH CDRs 1, 2, and 3 from a VH having an amino acid sequence selected from the group consisting of SEQ ID NOs:11-20 and 189-197. In some embodiments, provided herein are antibodies or antigen-binding fragments thereof that specifically bind TIM-3 comprising (a) a VL comprising VL CDRs 1, 2, and 3 from a VL having an amino acid sequence selected from the group consisting of SEQ ID NOs:21 and 207-215; and/or (b) a VH comprising VH CDRs 1, 2, and 3 from a VH having an amino acid sequence selected from the group consisting of SEQ ID NOs:22-29.

In some embodiments, provided herein are antibodies or antigen-binding fragments thereof that specifically bind TIM-3 comprising a VL, wherein the VL comprises VL CDRs 1, 2, and 3 from a VL having the amino acid sequence of SEQ ID NO:1. The VL can comprise VL CDRs 1, 2, and 3 from a VL having the amino acid sequence of SEQ ID NO:2. The VL can comprise VL CDRs 1, 2, and 3 from a VL having the amino acid sequence of SEQ ID NO:3. The VL can comprise VL CDRs 1, 2, and 3 from a VL having the amino acid sequence of SEQ ID NO:4 The VL can comprise VL CDRs 1, 2, and 3 from a VL having the amino acid sequence of SEQ ID NO:5. The VL can comprise VL CDRs 1, 2, and 3 from a VL having the amino acid sequence of SEQ ID NO:6. The VL can comprise VL CDRs 1, 2, and 3 from a VL having the amino acid sequence of SEQ ID NO:7. The VL can comprise VL CDRs 1, 2, and 3 from a VL having the amino acid sequence of SEQ ID NO:8. The VL can comprise VL CDRs 1, 2, and 3 from a VL having the amino acid sequence of SEQ ID NO:9. The VL can comprise VL CDRs 1, 2, and 3 from a VL having the amino acid sequence of SEQ ID NO:10. The VL can comprise VL CDRs 1, 2, and 3 from a VL having the amino acid sequence of SEQ ID NO:180. The VL can comprise VL CDRs 1, 2, and 3 from a VL having the amino acid sequence of SEQ ID NO:181. The VL can comprise VL CDRs 1, 2, and 3 from a VL having the amino acid sequence of SEQ ID NO:182. The VL can comprise VL CDRs 1, 2, and 3 from a VL having the amino acid sequence of SEQ ID NO:183. The VL can comprise VL CDRs 1, 2, and 3 from a VL having the amino acid sequence of SEQ ID NO:184. The VL can comprise VL CDRs 1, 2, and 3 from a VL having the amino acid sequence of SEQ ID NO:185. The VL can comprise VL CDRs 1, 2, and 3 from a VL having the amino acid sequence of SEQ ID NO:186. The VL can comprise VL CDRs 1, 2, and 3 from a VL having the amino acid sequence of SEQ ID NO:187. The VL can comprise VL CDRs 1, 2, and 3 from a VL having the amino acid sequence of SEQ ID NO:188. The VL can comprise VL CDRs 1, 2, and 3 from a VL having the amino acid sequence of SEQ ID NO:21. The VL can comprise VL CDRs 1, 2, and 3 from a VL having the amino acid sequence of SEQ ID NO:207. The VL can comprise VL CDRs 1, 2, and 3 from a VL having the amino acid sequence of SEQ ID NO:208. The VL can comprise VL CDRs 1, 2, and 3 from a VL having the amino acid sequence of SEQ ID NO:209. The VL can comprise VL CDRs 1, 2, and 3 from a VL having the amino acid sequence of SEQ ID NO:210. The VL can comprise VL CDRs 1, 2, and 3 from a VL having the amino acid sequence of SEQ ID NO:211. The VL can comprise VL CDRs 1, 2, and 3 from a VL having the amino acid sequence of SEQ ID NO:212. The VL can comprise VL CDRs 1, 2, and 3 from a VL having the amino acid sequence of SEQ ID NO:213. The VL can comprise VL CDRs 1, 2, and 3 from a VL having the amino acid sequence of SEQ ID NO:214. The VL can comprise VL CDRs 1, 2, and 3 from a VL having the amino acid sequence of SEQ ID NO:215.

In some embodiments, provided herein are antibodies or antigen-binding fragments thereof that specifically bind TIM-3 comprising a VH, wherein the VH comprises VH CDRs 1, 2, and 3 from a VH having the amino acid sequence of SEQ ID NO:11. The VH can comprise VH CDRs 1, 2, and 3 from a VH having the amino acid sequence of SEQ ID NO:12. The VH can comprise VH CDRs 1, 2, and 3 from a VH having the amino acid sequence of SEQ ID NO:13. The VH can comprise VH CDRs 1, 2, and 3 from a VH having the amino acid sequence of SEQ ID NO:14. The VH can comprise VH CDRs 1, 2, and 3 from a VH having the amino acid sequence of SEQ ID NO:15. The VH can comprise VH CDRs 1, 2, and 3 from a VH having the amino acid sequence of SEQ ID NO:16. The VH can comprise VH CDRs 1, 2, and 3 from a VH having the amino acid sequence of SEQ ID NO:17. The VH can comprise VH CDRs 1, 2, and 3 from a VH having the amino acid sequence of SEQ ID NO:18. The VH can comprise VH CDRs 1, 2, and 3 from a VH having the amino acid sequence of SEQ ID NO:19. The VH can comprise VH CDRs 1, 2, and 3 from a VH having the amino acid sequence of SEQ ID NO:20. The VH can comprise VH CDRs 1, 2, and 3 from a VH having the amino acid sequence of SEQ ID NO:189. The VH can comprise VH CDRs 1, 2, and 3 from a VH having the amino acid sequence of SEQ ID NO:190. The VH can comprise VH CDRs 1, 2, and 3 from a VH having the amino acid sequence of SEQ ID NO:191. The VH can comprise VH CDRs 1, 2, and 3 from a VH having the amino acid sequence of SEQ ID NO:192. The VH can comprise VH CDRs 1, 2, and 3 from a VH having the amino acid sequence of SEQ ID NO:193. The VH can comprise VH CDRs 1, 2, and 3 from a VH having the amino acid sequence of SEQ ID NO:194. The VH can comprise VH CDRs 1, 2, and 3 from a VH having the amino acid sequence of SEQ ID NO:195. The VH can comprise VH CDRs 1, 2, and 3 from a VH having the amino acid sequence of SEQ ID NO:196. The VH can comprise VH CDRs 1, 2, and 3 from a VH having the amino acid sequence of SEQ ID NO:197. The VH can comprise VH CDRs 1, 2, and 3 from a VH having the amino acid sequence of SEQ ID NO:22. The VH can comprise VH CDRs 1, 2, and 3 from a VH having the amino acid sequence of SEQ ID NO:23. The VH can comprise VH CDRs 1, 2, and 3 from a VH having the amino acid sequence of SEQ ID NO:24. The VH can comprise VH CDRs 1, 2, and 3 from a VH having the amino acid sequence of SEQ ID NO:25. The VH can comprise VH CDRs 1, 2, and 3 from a VH having the amino acid sequence of SEQ ID NO:26. The VH can comprise VH CDRs 1, 2, and 3 from a VH having the amino acid sequence of SEQ ID NO:27. The VH can comprise VH CDRs 1, 2, and 3 from a VH having the amino acid sequence of SEQ ID NO:28. The VH can comprise VH CDRs 1, 2, and 3 from a VH having the amino acid sequence of SEQ ID NO:29.

In some embodiments, provided herein are antibodies or antigen-binding fragments thereof that specifically bind TIM-3 comprising a VL and a VH, wherein the VL comprises VL CDR1, CDR2, and CDR3 from a VL of a specific sequence, and the VH comprises VH CDR1, CDR2, and CDR3 from a VH of a specific sequence. In some embodiments, the VL CDRs and VH CDRs are derived from VL and VH having the amino acid sequences of SEQ ID NOs:1 and 11, respectively. The VL CDRs and VH CDRs can be derived from VL and VH having the amino acid sequences of SEQ ID NOs:2 and 12, respectively. The VL CDRs and VH CDRs can be derived from VL and VH having the amino acid sequences of SEQ ID NOs:3 and 13, respectively. The VL CDRs and VH CDRs can be derived from VL and VH having the amino acid sequences of SEQ ID NOs 4 and 14, respectively. The VL CDRs and VH CDRs can be derived from VL and VH having the amino acid sequences of SEQ ID NOs:5 and 15, respectively. The VL CDRs and VH CDRs can be derived from VL and VH having the amino acid sequences of SEQ ID NOs:6 and 16, respectively. The VL CDRs and VH CDRs can be derived from VL and VH having the amino acid sequences of SEQ ID NOs:7 and 17, respectively. The VL CDRs and VH CDRs can be derived from VL and VH having the amino acid sequences of SEQ ID NOs:8 and 18, respectively. The VL CDRs and VH CDRs can be derived from VL and VH having the amino acid sequences of SEQ ID NOs:9 and 19, respectively. The VL CDRs and VH CDRs can be derived from VL and VH having the amino acid sequences of SEQ ID NOs:10 and 20, respectively. The VL CDRs and VH CDRs can be derived from VL and VH having the amino acid sequences of SEQ ID NOs:180 and 189, respectively. The VL CDRs and VH CDRs can be derived from VL and VH having the amino acid sequences of SEQ ID NOs:181 and 190, respectively. The VL CDRs and VH CDRs can be derived from VL and VH having the amino acid sequences of SEQ ID NOs:182 and 191, respectively. The VL CDRs and VH CDRs can be derived from VL and VH having the amino acid sequences of SEQ ID NOs:183 and 192, respectively. The VL CDRs and VH CDRs can be derived from VL and VH having the amino acid sequences of SEQ ID NOs:184 and 193, respectively. The VL CDRs and VH CDRs can be derived from VL and VH having the amino acid sequences of SEQ ID NOs:185 and 194, respectively. The VL CDRs and VH CDRs can be derived from VL and VH having the amino acid sequences of SEQ ID NOs:186 and 195, respectively. The VL CDRs and VH CDRs can be derived from VL and VH having the amino acid sequences of SEQ ID NOs:187 and 196, respectively. The VL CDRs and VH CDRs can be derived from VL and VH having the amino acid sequences of SEQ ID NOs:188 and 197, respectively.

In some embodiments, provided herein are antibodies or antigen-binding fragments thereof that specifically bind TIM-3 comprising a VL and a VH, wherein the VL comprises VL CDR1, CDR2, and CDR3 from a VL having an amino acid sequence selected from the group consisting of SEQ ID NOs:21 and 207-215, and the VH comprises VH CDR1, CDR2, and CDR3 from a VH having an amino acid sequence selected from the group consisting of SEQ ID NOs:22-29. The VL CDRs can be derived from the VL having the amino acid sequences of SEQ ID NO:21 and the VH CDRs can be derived from a VH having an amino acid sequence selected from the group consisting of SEQ ID NOs:22-29 (e.g., SEQ ID NO:22), respectively. The VL CDRs can be derived from the VL having the amino acid sequences of SEQ ID NO:207 and the VH CDRs can be derived from a VH having an amino acid sequence selected from the group consisting of SEQ ID NOs:22-29 (e.g., SEQ ID NO:22), respectively. The VL CDRs can be derived from the VL having the amino acid sequences of SEQ ID NO:208 and the VH CDRs can be derived from a VH having an amino acid sequence selected from the group consisting of SEQ ID NOs:22-29 (e.g., SEQ ID NO:22), respectively. The VL CDRs can be derived from the VL having the amino acid sequences of SEQ ID NO:209 and the VH CDRs can be derived from a VH having an amino acid sequence selected from the group consisting of SEQ ID NOs:22-29 (e.g., SEQ ID NO:22), respectively. The VL CDRs can be derived from the VL having the amino acid sequences of SEQ ID NO:210 and the VH CDRs can be derived from a VH having an amino acid sequence selected from the group consisting of SEQ ID NOs:22-29 (e.g., SEQ ID NO:22), respectively. The VL CDRs can be derived from the VL having the amino acid sequences of SEQ ID NO:211 and the VH CDRs can be derived from a VH having an amino acid sequence selected from the group consisting of SEQ ID NOs:22-29 (e.g., SEQ ID NO:22), respectively. The VL CDRs can be derived from the VL having the amino acid sequences of SEQ ID NO:212 and the VH CDRs can be derived from a VH having an amino acid sequence selected from the group consisting of SEQ ID NOs:22-29 (e.g., SEQ ID NO:22), respectively. The VL CDRs can be derived from the VL having the amino acid sequences of SEQ ID NO:213 and the VH CDRs can be derived from a VH having an amino acid sequence selected from the group consisting of SEQ ID NOs:22-29 (e.g., SEQ ID NO:22), respectively. The VL CDRs can be derived from the VL having the amino acid sequences of SEQ ID NO:214 and the VH CDRs can be derived from a VH having an amino acid sequence selected from the group consisting of SEQ ID NOs:22-29 (e.g., SEQ ID NO:22), respectively. The VL CDRs can be derived from the VL having the amino acid sequences of SEQ ID NO:215 and the VH CDRs can be derived from a VH having an amino acid sequence selected from the group consisting of SEQ ID NOs:22-29 (e.g., SEQ ID NO:22), respectively.

In some embodiments, the anti-TIM-3 antibody or antigen-binding fragment thereof provided herein is the antibody designated as 3E6. In some embodiments, the anti-TIM-3 antibody or antigen-binding fragment thereof provided herein has a VL from 3E6 (SEQ ID NO:1). In some embodiments, the anti-TIM-3 antibody or antigen-binding fragment thereof provided herein has a VH from 3E6 (SEQ ID NO:11). The anti-TIM-3 antibody or antigen-binding fragment thereof provided herein can have both a VL and a VH from 3E6. In some embodiments, the anti-TIM-3 antibody or antigen-binding fragment thereof provided herein has a VL that comprises VL CDRs 1, 2, and 3 from the VL from 3E6 (SEQ ID NO:1). In some embodiments, the anti-TIM-3 antibody or antigen-binding fragment thereof provided herein has a VH that comprises VH CDRs 1, 2, and 3 from the VH from 3E6 (SEQ ID NO:11). The anti-TIM-3 antibody or antigen-binding fragment thereof provided herein can have a VL comprising VL CDRs 1, 2, and 3 and a VH comprising VH CDRs 1, 2, and 3 from the VL and VH of 3E6, respectively. In some embodiments, the anti-TIM-3 antibody or antigen-binding fragment thereof provided herein is a variant of 3E6. The 3E6 variant can have a VL that is a variant of the VL of 3E6 having up to about 5 amino acid substitutions, additions, and/or deletions in SEQ ID NO:1. The 3E6 variant can have a VH that is a variant of the VH of 3E6 having up to about 5 amino acid substitutions, additions, and/or deletions in SEQ ID NO:11. The amino acid substitutions, additions, and/or deletions can be in the VH CDRs or VL CDRs. In some embodiments, the amino acid substitutions, additions, and/or deletions are not in the CDRs. In some embodiments, the variant of 3E6 has up to about 5 conservative amino acid substitutions. In some embodiments, the variant of 3E6 has up to 3 conservative amino acid substitutions. In some embodiments, the anti-TIM-3 antibody or antigen-binding fragment thereof provided herein is a humanized antibody or antigen-binding fragment derived from 3E6. In some embodiments, the anti-TIM-3 antibody or antigen-binding fragment thereof provided herein is a human antibody or antigen-binding fragment derived from 3E6. In some embodiments, provided herein are affinity matured variants of 3E6 with one, two, or three mutations in the VL CDR3 region as shown in Table 1c.

As provided below, epitope mapping revealed that 3E6 binds to amino acids 71-82 of human TIM-3, a fragment within the extracellular domain of human TIM-3. Isoform 1 (SEQ ID NO:84) and Isoform 2 of human TIM-3 (SEQ ID NO:85) share identical amino acids 1-131. As such, 3E6 binds to the same epitope on both isoforms. As used herein, an antibody or antigen-binding fragment that specific binds to one or more amino acid residues with amino acids 1-131, or amino acids 71-82 of human TIM-3, means that the antibody or antigen-binding fragment binds to the recited amino acid residue(s) on both Isoform 1 and Isoform 2 of human TIM-3.

Specifically, 3E6 binds human TIM-3 via CDR1-3 of the VH and CDR2 of the VL. As shown in FIG. 11B and Table 9 below: the F residue of VH CDR1 (amino acid 3 of SEQ ID NO:101) binds to N76 of human TIM-3; the H residue of VH CDR2 (amino acid 4 of SEQ ID NO:109) binds to W78 of human TIM-3; the S reside of VH CDR2 (amino acid 5 of SEQ ID NO:109) binds to W78 of human TIM-3: the Y residue of VH CDR3 (amino acid 2 of SEQ ID NO:119) binds to D71 of human TIM-3; the R residue of VH CDR3 (amino acid 3 of SEQ ID NO:119) binds to V75, T79 and Y82 of human TIM-3; the S residue of VH CDR3 (amino acid 4 of SEQ ID NO: 119) binds to D74 of human TIM-3: the W residue of VH CDR3 (amino acid 6 of SEQ ID NO:119) binds to D74 of human TIM-3; the S residue of VL CDR2 (amino acid 7 of SEQ ID NO:94) binds to R73 of human TIM-3.

As such, in some embodiments, provided herein are variants of 3E6 having up to about 3 amino acid substitutions, additions, and/or deletions in the VL CDRs and up to about 3 amino acid substitutions, additions, and/or deletions in the VH CDRs. In some embodiments, provided herein are variants of affinity-matured 3E6 having up to about 3 amino acid substitutions, additions, and/or deletions in the VL CDRs and up to about 3 amino acid substitutions, additions, and/or deletions in the VH CDRs. In some embodiments, provided herein are anti-TIM-3 antibodies or antigen-binding fragments comprising a VL CDR1, a VL CDR2, a VH CDR1, a VH CDR2 and a VH CDR3 having the amino acid sequences of SEQ ID NOs:86, 94, 101, 109, and 119, respectively, and a VL CDR3 having an amino acid sequence selected from the group consisting of SEQ ID NOs:47 and 198-206; or a variant thereof having up to about 3 amino acid substitutions, additions, and/or deletions in the VL CDRs and up to about 3 amino acid substitutions, additions, and/or deletions in the VH CDRs.

In some embodiments of the antibodies or antigen-binding fragments provided herein, the F residue of VH CDR1 (amino acid 3 of SEQ ID NO:101), H and S resides of VH CDR2 (amino acids 4 and 5 of SEQ ID NO:109), Y, R, S and W residues of VH CDR3 (amino acids 2, 3, 4, and 6 of SEQ ID NO:119), and S residue of VL CDR2 (amino acid 7 of SEQ ID NO:94) are not mutated. In some embodiments, the 3E6 variants do not have mutation in at least one of the following sites: the F residue of VH CDR1 (amino acid 3 of SEQ ID NO:101), H and S resides of VH CDR2 (amino acids 4 and 5 of SEQ ID NO:109), Y, R, S and W residues of VH CDR3 (amino acids 2, 3, 4, and 6 of SEQ ID NO: 119), and S residue of VL CDR2 (amino acid 7 of SEQ ID N0:94). In some embodiments, the 3E6 variants do not have mutation in at least two, at least three, at least four, at least five, at least six, at least seven or all eight of the following sites: the F residue of VH CDR1 (amino acid 3 of SEQ ID NO:101), H and S resides of VH CDR2 (amino acids 4 and 5 of SEQ ID NO:109), Y, R, S and W residues of VH CDR3 (amino acids 2, 3, 4, and 6 of SEQ ID NO:119), and S residue of VL CDR2 (amino acid 7 of SEQ ID NO:94). In some embodiments, the 3E6 variants do not have mutation in the R residue of VH CDR3 (amino acid 3 of SEQ ID NO: 119).

In some embodiments, provided herein are humanized 3E6 and affinity matured humanized 3E6. In some embodiments, the humanized anti-TIM-3 antibody or antigen-binding fragment thereof provided herein comprises a VL having an amino acid sequence selected from the group consisting of SEQ ID NOs:21 and 207-215. In some embodiments, the humanized anti-TIM-3 antibody or antigen-binding fragment thereof provided herein comprises a VH having an amino acid sequence selected from SEQ ID NOs:22-29. In some embodiments, the humanized anti-TIM-3 antibody or antigen-binding fragment thereof provided herein comprises a VL having an amino acid sequence selected from the group consisting of SEQ ID NOs:21 and 207-215 and a VH having an amino acid sequence selected from SEQ ID NO:22-29. In some embodiments, the anti-TIM-3 antibody or antigen-binding fragment thereof provided herein is a variant of a humanized 3E6 provided herein. The variant can have a VL that is a variant of the VL of a humanized 3E6 having up to about 5 amino acid substitutions, additions, and/or deletions in an amino acid sequence selected from the group consisting of SEQ ID NOs:21 and 207-215. The variant can have a VH that is a variant of the VH of a humanized 3E6 having up to about 5 amino acid substitutions, additions, and/or deletions in an amino acid sequence selected from the group consisting of SEQ ID NOs:22-29. In some embodiments, the variant of a humanized 3E6 has up to about 5 conservative amino acid substitutions.

In some embodiments, the variant of a humanized 3E6 has up to 3 conservative amino acid substitutions. In some embodiments, provided herein are IgG1 antibodies having VH and VL derived from 3E6 or a 3E6 variant. In some embodiments, the IgG1 heavy chain constant region comprises the amino acid substitutions of L234A and L235A, per EU numbering. In some embodiments, provided herein are IgG2 antibodies having VH and VL derived from 3E6 or a 3E6 variant. In some embodiments, provided herein are IgG4 antibodies having VH and VL derived from 3E6 or a 3E6 variant. For illustrative purposes, in some embodiments, provided herein are 3E6 variants comprising VL0 (SEQ ID NO:21) and VH6 (SEQ ID NO:28) described herein. In some embodiments, provided herein are 3E6 variants comprising VL0-v5 (SEQ ID NO:211) and VH6 (SEQ ID NO:28) described herein In some embodiments, the anti-TIM-3 antibody or antigen-binding fragment thereof provided herein is the antibody designated as 4H2. In some embodiments, the anti-TIM-3 antibody or antigen-binding fragment thereof provided herein has a VL from 4H2 (SEQ ID NO:2). In some embodiments, the anti-TIM-3 antibody or antigen-binding fragment thereof provided herein has a VH from 4H2 (SEQ ID NO: 12). The anti-TIM-3 antibody or antigen-binding fragment thereof provided herein can have both a VL and a VH from 4H2. In some embodiments, the anti-TIM-3 antibody or antigen-binding fragment thereof provided herein has a VL that comprises VL CDRs 1, 2, and 3 from the VL from 4H2 (SEQ ID NO:2). In some embodiments, the anti-TIM-3 antibody or antigen-binding fragment thereof provided herein has a VH that comprises VH CDRs 1, 2, and 3 from the VH from 4H2 (SEQ ID NO:12). The anti-TIM-3 antibody or antigen-binding fragment thereof provided herein can have a VL comprising VL CDRs 1, 2, and 3 and a VH comprising VH CDRs 1, 2, and 3 from the VL and VH of 4H2, respectively. In some embodiments, the anti-TIM-3 antibody or antigen-binding fragment thereof provided herein is a variant of 4H2. The 4H2 variant can have a VL that is a variant of the VL of 4H2 having up to about 5 amino acid substitutions, additions, and/or deletions in SEQ ID NO:2. The 4H2 variant can have a VH that is a variant of the VH of 4H2 having up to about 5 amino acid substitutions, additions, and/or deletions in SEQ ID NO:12. The amino acid substitutions, additions, and/or deletions can be in the VH CDRs or VL CDRs. In some embodiments, the amino acid substitutions, additions, and/or deletions are not in the CDRs. In some embodiments, the variant of 4H2 has up to about 5 conservative amino acid substitutions. In some embodiments, the variant of 4H2 has up to 3 conservative amino acid substitutions. In some embodiments, the anti-TIM-3 antibody or antigen-binding fragment thereof provided herein is a humanized antibody or antigen-binding fragment derived from 4H2. In some embodiments, the anti-TIM-3 antibody or antigen-binding fragment thereof provided herein is a human antibody or antigen-binding fragment derived from 4H2.

In some embodiments, the anti-TIM-3 antibody or antigen-binding fragment thereof provided herein is the antibody designated as 16H1. In some embodiments, the anti-TIM-3 antibody or antigen-binding fragment thereof provided herein has a VL from 16H1 (SEQ ID NO:3). In some embodiments, the anti-TIM-3 antibody or antigen-binding fragment thereof provided herein has a VH from 16H1 (SEQ ID NO: 13). The anti-TIM-3 antibody or antigen-binding fragment thereof provided herein can have both a VL and a VH from 16H1. In some embodiments, the anti-TIM-3 antibody or antigen-binding fragment thereof provided herein has a VL that comprises VL CDRs 1, 2, and 3 from the VL from 16H1 (SEQ ID NO:3). In some embodiments, the anti-TIM-3 antibody or antigen-binding fragment thereof provided herein has a VH that comprises VH CDRs 1, 2, and 3 from the VH from 16H1 (SEQ ID NO:13). The anti-TIM-3 antibody or antigen-binding fragment thereof provided herein can have a VL comprising VL CDRs 1, 2, and 3 and a VH comprising VH CDRs 1, 2, and 3 from the VL and VH of 16H1, respectively. In some embodiments, the anti-TIM-3 antibody or antigen-binding fragment thereof provided herein is a variant of 16H1. The 16H1 variant can have a VL that is a variant of the VL of 16H1 having up to about 5 amino acid substitutions, additions, and/or deletions in SEQ ID NO:3. The 16H1 variant can have a VH that is a variant of the VH of 16H1 having up to about 5 amino acid substitutions, additions, and/or deletions in SEQ ID NO:13. The amino acid substitutions, additions, and/or deletions can be in the VH CDRs or VL CDRs. In some embodiments, the amino acid substitutions, additions, and/or deletions are not in the CDRs. In some embodiments, the variant of 16H1 has up to about 5 conservative amino acid substitutions. In some embodiments, the variant of 16H1 has up to 3 conservative amino acid substitutions. In some embodiments, the anti-TIM-3 antibody or antigen-binding fragment thereof provided herein is a humanized antibody or antigen-binding fragment derived from 16H1. In some embodiments, the anti-TIM-3 antibody or antigen-binding fragment thereof provided herein is a human antibody or antigen-binding fragment derived from 16H1.

In some embodiments, the anti-TIM-3 antibody or antigen-binding fragment thereof provided herein is the antibody designated as 18C6. In some embodiments, the anti-TIM-3 antibody or antigen-binding fragment thereof provided herein has a VL from 18C6 (SEQ ID NO:4). In some embodiments, the anti-TIM-3 antibody or antigen-binding fragment thereof provided herein has a VH from 18C6 (SEQ ID NO:14). The anti-TIM-3 antibody or antigen-binding fragment thereof provided herein can have both a VL and a VH from 18C6. In some embodiments, the anti-TIM-3 antibody or antigen-binding fragment thereof provided herein has a VL that comprises VL CDRs 1, 2, and 3 from the VL from 18C6 (SEQ ID NO:4). In some embodiments, the anti-TIM-3 antibody or antigen-binding fragment thereof provided herein has a VH that comprises VH CDRs 1, 2, and 3 from the VH from 18C6 (SEQ ID NO:14). The anti-TIM-3 antibody or antigen-binding fragment thereof provided herein can have a VL comprising VL CDRs 1, 2, and 3 and a VH comprising VH CDRs 1, 2, and 3 from the VL and VH of 18C6, respectively. In some embodiments, the anti-TIM-3 antibody or antigen-binding fragment thereof provided herein is a variant of 18C6. The 18C6 variant can have a VL that is a variant of the VL of 18C6 having up to about 5 amino acid substitutions, additions, and/or deletions in SEQ ID NO:4. The 18C6 variant can have a VH that is a variant of the VH of 18C6 having up to about 5 amino acid substitutions, additions, and/or deletions in SEQ ID NO:14. The amino acid substitutions, additions, and/or deletions can be in the VH CDRs or VL CDRs. In some embodiments, the amino acid substitutions, additions, and/or deletions are not in the CDRs. In some embodiments, the variant of 18C6 has up to about 5 conservative amino acid substitutions. In some embodiments, the variant of 18C6 has up to 3 conservative amino acid substitutions. In some embodiments, the anti-TIM-3 antibody or antigen-binding fragment thereof provided herein is a humanized antibody or antigen-binding fragment derived from 18C6. In some embodiments, the anti-TIM-3 antibody or antigen-binding fragment thereof provided herein is a human antibody or antigen-binding fragment derived from 18C6.

In some embodiments, the anti-TIM-3 antibody or antigen-binding fragment thereof provided herein is the antibody designated as 19D11. In some embodiments, the anti-TIM-3 antibody or antigen-binding fragment thereof provided herein has a VL from 19D11 (SEQ ID NO:5). In some embodiments, the anti-TIM-3 antibody or antigen-binding fragment thereof provided herein has a VH from 19D11 (SEQ ID NO: 15). The anti-TIM-3 antibody or antigen-binding fragment thereof provided herein can have both a VL and a VH from 19D11. In some embodiments, the anti-TIM-3 antibody or antigen-binding fragment thereof provided herein has a VL that comprises VL CDRs 1, 2, and 3 from the VL from 19D11 (SEQ ID NO:5). In some embodiments, the anti-TIM-3 antibody or antigen-binding fragment thereof provided herein has a VH that comprises VH CDRs 1, 2, and 3 from the VH from 19D11 (SEQ ID NO:15). The anti-TIM-3 antibody or antigen-binding fragment thereof provided herein can have a VL comprising VL CDRs 1, 2, and 3 and a VH comprising VH CDRs 1, 2, and 3 from the VL and VH of 19D11, respectively. In some embodiments, the anti-TIM-3 antibody or antigen-binding fragment thereof provided herein is a variant of 19D11. The 19D11 variant can have a VL that is a variant of the VL of 19D111 having up to about 5 amino acid substitutions, additions, and/or deletions in SEQ ID NO:5. The 19D11 variant can have a VH that is a variant of the VH of 19D11 having up to about 5 amino acid substitutions, additions, and/or deletions in SEQ ID NO:15. The amino acid substitutions, additions, and/or deletions can be in the VH CDRs or VL CDRs. In some embodiments, the amino acid substitutions, additions, and/or deletions are not in the CDRs. In some embodiments, the variant of 19D11 has up to about 5 conservative amino acid substitutions. In some embodiments, the variant of 19D11 has up to 3 conservative amino acid substitutions. In some embodiments, the anti-TIM-3 antibody or antigen-binding fragment thereof provided herein is a humanized antibody or antigen-binding fragment derived from 19D11. In some embodiments, the anti-TIM-3 antibody or antigen-binding fragment thereof provided herein is a human antibody or antigen-binding fragment derived from 19D11.

In some embodiments, the anti-TIM-3 antibody or antigen-binding fragment thereof provided herein is the antibody designated as CH 5 #. In some embodiments, the anti-TIM-3 antibody or antigen-binding fragment thereof provided herein has a VL from CH 5 #(SEQ ID NO:6). In some embodiments, the anti-TIM-3 antibody or antigen-binding fragment thereof provided herein has a VH from CH 5 #(SEQ ID NO:16). The anti-TIM-3 antibody or antigen-binding fragment thereof provided herein can have both a VL and a VH from CH 5 #. In some embodiments, the anti-TIM-3 antibody or antigen-binding fragment thereof provided herein has a VL that comprises VL CDRs 1, 2, and 3 from the VL from CH 5 #(SEQ ID NO:6). In some embodiments, the anti-TIM-3 antibody or antigen-binding fragment thereof provided herein has a VH that comprises VH CDRs 1, 2, and 3 from the VH from CH 5 #(SEQ ID NO:16). The anti-TIM-3 antibody or antigen-binding fragment thereof provided herein can have a VL comprising VL CDRs 1, 2, and 3 and a VH comprising VH CDRs 1, 2, and 3 from the VL and VH of CH 5 #, respectively. In some embodiments, the anti-TIM-3 antibody or antigen-binding fragment thereof provided herein is a variant of CH 5 #. The CH 5 # variant can have a VL that is a variant of the VL of CH 5 # having up to about 5 amino acid substitutions, additions, and/or deletions in SEQ ID NO:6. The CH 5 # variant can have a VH that is a variant of the VH of CH 5 # having up to about 5 amino acid substitutions, additions, and/or deletions in SEQ ID NO: 16. The amino acid substitutions, additions, and/or deletions can be in the VH CDRs or VL CDRs. In some embodiments, the amino acid substitutions, additions, and/or deletions are not in the CDRs. In some embodiments, the variant of CH 5 # has up to about 5 conservative amino acid substitutions. In some embodiments, the variant of CH 5 # has up to 3 conservative amino acid substitutions. In some embodiments, the anti-TIM-3 antibody or antigen-binding fragment thereof provided herein is a humanized antibody or antigen-binding fragment derived from CH 5 #. In some embodiments, the anti-TIM-3 antibody or antigen-binding fragment thereof provided herein is a human antibody or antigen-binding fragment derived from CH 5 #.

In some embodiments, the anti-TIM-3 antibody or antigen-binding fragment thereof provided herein is the antibody designated as CH 8 #. In some embodiments, the anti-TIM-3 antibody or antigen-binding fragment thereof provided herein has a VL from CH 8 #(SEQ ID NO:7). In some embodiments, the anti-TIM-3 antibody or antigen-binding fragment thereof provided herein has a VH from CH 8 #(SEQ ID NO:17). The anti-TIM-3 antibody or antigen-binding fragment thereof provided herein can have both a VL and a VH from CH 8 #. In some embodiments, the anti-TIM-3 antibody or antigen-binding fragment thereof provided herein has a VL that comprises VL CDRs 1, 2, and 3 from the VL from CH 8 #(SEQ ID NO:7). In some embodiments, the anti-TIM-3 antibody or antigen-binding fragment thereof provided herein has a VH that comprises VH CDRs 1, 2, and 3 from the VH from CH 8 #(SEQ ID NO:17). The anti-TIM-3 antibody or antigen-binding fragment thereof provided herein can have a VL comprising VL CDRs 1, 2, and 3 and a VH comprising VH CDRs 1, 2, and 3 from the VL and VH of CH 8 #, respectively. In some embodiments, the anti-TIM-3 antibody or antigen-binding fragment thereof provided herein is a variant of CH 8 #. The CH 8 # variant can have a VL that is a variant of the VL of CH 8 # having up to about 5 amino acid substitutions, additions, and/or deletions in SEQ ID NO:7. The CH 8 # variant can have a VH that is a variant of the VH of CH 8 # having up to about 5 amino acid substitutions, additions, and/or deletions in SEQ ID NO:17. The amino acid substitutions, additions, and/or deletions can be in the VH CDRs or VL CDRs. In some embodiments, the amino acid substitutions, additions, and/or deletions are not in the CDRs. In some embodiments, the variant of CH 8 # has up to about 5 conservative amino acid substitutions. In some embodiments, the variant of CH 8 # has up to 3 conservative amino acid substitutions. In some embodiments, the anti-TIM-3 antibody or antigen-binding fragment thereof provided herein is a humanized antibody or antigen-binding fragment derived from CH 8 #. In some embodiments, the anti-TIM-3 antibody or antigen-binding fragment thereof provided herein is a human antibody or antigen-binding fragment derived from CH 8 #.

In some embodiments, the anti-TIM-3 antibody or antigen-binding fragment thereof provided herein is the antibody designated as CH 9 #. In some embodiments, the anti-TIM-3 antibody or antigen-binding fragment thereof provided herein has a VL from CH 9 #(SEQ ID NO:8). In some embodiments, the anti-TIM-3 antibody or antigen-binding fragment thereof provided herein has a VH from CH 9 #(SEQ ID NO:18). The anti-TIM-3 antibody or antigen-binding fragment thereof provided herein can have both a VL and a VH from CH 9 #. In some embodiments, the anti-TIM-3 antibody or antigen-binding fragment thereof provided herein has a VL that comprises VL CDRs 1, 2, and 3 from the VL from CH 9 #(SEQ ID NO:8). In some embodiments, the anti-TIM-3 antibody or antigen-binding fragment thereof provided herein has a VH that comprises VH CDRs 1, 2, and 3 from the VH from CH 9 #(SEQ ID NO:18). The anti-TIM-3 antibody or antigen-binding fragment thereof provided herein can have a VL comprising VL CDRs 1, 2, and 3 and a VH comprising VH CDRs 1, 2, and 3 from the VL and VH of CH 9 #, respectively. In some embodiments, the anti-TIM-3 antibody or antigen-binding fragment thereof provided herein is a variant of CH 9 #. The CH 9 # variant can have a VL that is a variant of the VL of CH 9 # having up to about 5 amino acid substitutions, additions, and/or deletions in SEQ ID NO:8. The CH 9 # variant can have a VH that is a variant of the VH of CH 9 # having up to about 5 amino acid substitutions, additions, and/or deletions in SEQ ID NO:18. The amino acid substitutions, additions, and/or deletions can be in the VH CDRs or VL CDRs. In some embodiments, the amino acid substitutions, additions, and/or deletions are not in the CDRs. In some embodiments, the variant of CH 9 # has up to about 5 conservative amino acid substitutions. In some embodiments, the variant of CH 9 # has up to 3 conservative amino acid substitutions. In some embodiments, the anti-TIM-3 antibody or antigen-binding fragment thereof provided herein is a humanized antibody or antigen-binding fragment derived from CH 9 #. In some embodiments, the anti-TIM-3 antibody or antigen-binding fragment thereof provided herein is a human antibody or antigen-binding fragment derived from CH 9 #.

In some embodiments, the anti-TIM-3 antibody or antigen-binding fragment thereof provided herein is the antibody designated as CH 10 #. In some embodiments, the anti-TIM-3 antibody or antigen-binding fragment thereof provided herein has a VL from CH 10 #(SEQ ID NO:9). In some embodiments, the anti-TIM-3 antibody or antigen-binding fragment thereof provided herein has a VH from CH 10 #(SEQ ID NO:19). The anti-TIM-3 antibody or antigen-binding fragment thereof provided herein can have both a VL and a VH from CH 10 #. In some embodiments, the anti-TIM-3 antibody or antigen-binding fragment thereof provided herein has a VL that comprises VL CDRs 1, 2, and 3 from the VL from CH 10 #(SEQ ID NO:9). In some embodiments, the anti-TIM-3 antibody or antigen-binding fragment thereof provided herein has a VH that comprises VH CDRs 1, 2, and 3 from the VH from CH 10 #(SEQ ID NO:19). The anti-TIM-3 antibody or antigen-binding fragment thereof provided herein can have a VL comprising VL CDRs 1, 2, and 3 and a VH comprising VH CDRs 1, 2, and 3 from the VL and VH of CH 10 #, respectively. In some embodiments, the anti-TIM-3 antibody or antigen-binding fragment thereof provided herein is a variant of CH 10 #. The CH 10 # variant can have a VL that is a variant of the VL of CH 10 # having up to about 5 amino acid substitutions, additions, and/or deletions in SEQ ID NO:9. The CH 10 # variant can have a VH that is a variant of the VH of CH 10 # having up to about 5 amino acid substitutions, additions, and/or deletions in SEQ ID NO:19. The amino acid substitutions, additions, and/or deletions can be in the VH CDRs or VL CDRs. In some embodiments, the amino acid substitutions, additions, and/or deletions are not in the CDRs. In some embodiments, the variant of CH 10 # has up to about 5 conservative amino acid substitutions. In some embodiments, the variant of CH 10 # has up to 3 conservative amino acid substitutions. In some embodiments, the anti-TIM-3 antibody or antigen-binding fragment thereof provided herein is a humanized antibody or antigen-binding fragment derived from CH 10 #. In some embodiments, the anti-TIM-3 antibody or antigen-binding fragment thereof provided herein is a human antibody or antigen-binding fragment derived from CH 10 #.

In some embodiments, the anti-TIM-3 antibody or antigen-binding fragment thereof provided herein is the antibody designated as CH 11 #. In some embodiments, the anti-TIM-3 antibody or antigen-binding fragment thereof provided herein has a VL from CH 11 #(SEQ ID NO:10). In some embodiments, the anti-TIM-3 antibody or antigen-binding fragment thereof provided herein has a VH from CH 11 #(SEQ ID NO:20). The anti-TIM-3 antibody or antigen-binding fragment thereof provided herein can have both a VL and a VH from CH 11 #. In some embodiments, the anti-TIM-3 antibody or antigen-binding fragment thereof provided herein has a VL that comprises VL CDRs 1, 2, and 3 from the VL from CH 11 #(SEQ ID NO:10). In some embodiments, the anti-TIM-3 antibody or antigen-binding fragment thereof provided herein has a VH that comprises VH CDRs 1, 2, and 3 from the VH from CH 11 #(SEQ ID NO:20). The anti-TIM-3 antibody or antigen-binding fragment thereof provided herein can have a VL comprising VL CDRs 1, 2, and 3 and a VH comprising VH CDRs 1, 2, and 3 from the VL and VH of CH 11 #, respectively.

In some embodiments, the anti-TIM-3 antibody or antigen-binding fragment thereof provided herein is a variant of CH 11 #. The CH 11 # variant can have a VL that is a variant of the VL of CH 11 # having up to about 5 amino acid substitutions, additions, and/or deletions in SEQ ID NO:10. The CH 11 # variant can have a VH that is a variant of the VH of CH 11 # having up to about 5 amino acid substitutions, additions, and/or deletions in SEQ ID NO:20. The amino acid substitutions, additions, and/or deletions can be in the VH CDRs or VL CDRs. In some embodiments, the amino acid substitutions, additions, and/or deletions are not in the CDRs. In some embodiments, the variant of CH 11 # has up to about 5 conservative amino acid substitutions. In some embodiments, the variant of CH 11 # has up to 3 conservative amino acid substitutions. In some embodiments, the anti-TIM-3 antibody or antigen-binding fragment thereof provided herein is a humanized antibody or antigen-binding fragment derived from CH 11 #. In some embodiments, the anti-TIM-3 antibody or antigen-binding fragment thereof provided herein is a human antibody or antigen-binding fragment derived from CH 11 #.

In some embodiments, the anti-TIM-3 antibody or antigen-binding fragment thereof provided herein is the antibody designated as 3F2. In some embodiments, the anti-TIM-3 antibody or antigen-binding fragment thereof provided herein has a VL from 3F2 (SEQ ID NO:180). In some embodiments, the anti-TIM-3 antibody or antigen-binding fragment thereof provided herein has a VH from 3F2 (SEQ ID NO:189). The anti-TIM-3 antibody or antigen-binding fragment thereof provided herein can have both a VL and a VH from 3F2. In some embodiments, the anti-TIM-3 antibody or antigen-binding fragment thereof provided herein has a VL that comprises VL CDRs 1, 2, and 3 from the VL from 3F2 (SEQ ID NO:180). In some embodiments, the anti-TIM-3 antibody or antigen-binding fragment thereof provided herein has a VH that comprises VH CDRs 1, 2, and 3 from the VH from 3F2 (SEQ ID NO:189). The anti-TIM-3 antibody or antigen-binding fragment thereof provided herein can have a VL comprising VL CDRs 1, 2, and 3 and a VH comprising VH CDRs 1, 2, and 3 from the VL and VH of 3F2, respectively. In some embodiments, the anti-TIM-3 antibody or antigen-binding fragment thereof provided herein is a variant of 3F2. The 3F2 variant can have a VL that is a variant of the VL of 3F2 having up to about 5 amino acid substitutions, additions, and/or deletions in SEQ ID NO:180. The 3F2 variant can have a VH that is a variant of the VH of 3F2 having up to about 5 amino acid substitutions, additions, and/or deletions in SEQ ID NO:189. The amino acid substitutions, additions, and/or deletions can be in the VH CDRs or VL CDRs. In some embodiments, the amino acid substitutions, additions, and/or deletions are not in the CDRs. In some embodiments, the variant of 3F2 has up to about 5 conservative amino acid substitutions. In some embodiments, the variant of 3F2 has up to 3 conservative amino acid substitutions. In some embodiments, the anti-TIM-3 antibody or antigen-binding fragment thereof provided herein is a humanized antibody or antigen-binding fragment derived from 3F2. In some embodiments, the anti-TIM-3 antibody or antigen-binding fragment thereof provided herein is a human antibody or antigen-binding fragment derived from 3F2.

In some embodiments, the anti-TIM-3 antibody or antigen-binding fragment thereof provided herein is the antibody designated as 36A2. In some embodiments, the anti-TIM-3 antibody or antigen-binding fragment thereof provided herein has a VL from 36A2 (SEQ ID NO:181). In some embodiments, the anti-TIM-3 antibody or antigen-binding fragment thereof provided herein has a VH from 36A2 (SEQ ID NO:190). The anti-TIM-3 antibody or antigen-binding fragment thereof provided herein can have both a VL and a VH from 36A2. In some embodiments, the anti-TIM-3 antibody or antigen-binding fragment thereof provided herein has a VL that comprises VL CDRs 1, 2, and 3 from the VL from 36A2 (SEQ ID NO:181). In some embodiments, the anti-TIM-3 antibody or antigen-binding fragment thereof provided herein has a VH that comprises VH CDRs 1, 2, and 3 from the VH from 36A2 (SEQ ID NO:190). The anti-TIM-3 antibody or antigen-binding fragment thereof provided herein can have a VL comprising VL CDRs 1, 2, and 3 and a VH comprising VH CDRs 1, 2, and 3 from the VL and VH of 36A2, respectively. In some embodiments, the anti-TIM-3 antibody or antigen-binding fragment thereof provided herein is a variant of 36A2. The 36A2 variant can have a VL that is a variant of the VL of 36A2 having up to about 5 amino acid substitutions, additions, and/or deletions in SEQ ID NO:181. The 36A2 variant can have a VH that is a variant of the VH of 36A2 having up to about 5 amino acid substitutions, additions, and/or deletions in SEQ ID NO:190. The amino acid substitutions, additions, and/or deletions can be in the VH CDRs or VL CDRs. In some embodiments, the amino acid substitutions, additions, and/or deletions are not in the CDRs. In some embodiments, the variant of 36A2 has up to about 5 conservative amino acid substitutions. In some embodiments, the variant of 36A2 has up to 3 conservative amino acid substitutions. In some embodiments, the anti-TIM-3 antibody or antigen-binding fragment thereof provided herein is a humanized antibody or antigen-binding fragment derived from 36A2. In some embodiments, the anti-TIM-3 antibody or antigen-binding fragment thereof provided herein is a human antibody or antigen-binding fragment derived from 36A2.

In some embodiments, the anti-TIM-3 antibody or antigen-binding fragment thereof provided herein is the antibody designated as 36B11. In some embodiments, the anti-TIM-3 antibody or antigen-binding fragment thereof provided herein has a VL from 36B11 (SEQ ID NO:182). In some embodiments, the anti-TIM-3 antibody or antigen-binding fragment thereof provided herein has a VH from 36B11 (SEQ ID NO:191). The anti-TIM-3 antibody or antigen-binding fragment thereof provided herein can have both a VL and a VH from 36B11. In some embodiments, the anti-TIM-3 antibody or antigen-binding fragment thereof provided herein has a VL that comprises VL CDRs 1, 2, and 3 from the VL from 36B11 (SEQ ID NO:182). In some embodiments, the anti-TIM-3 antibody or antigen-binding fragment thereof provided herein has a VH that comprises VH CDRs 1, 2, and 3 from the VH from 36B11 (SEQ ID NO:191). The anti-TIM-3 antibody or antigen-binding fragment thereof provided herein can have a VL comprising VL CDRs 1, 2, and 3 and a VH comprising VH CDRs 1, 2, and 3 from the VL and VH of 36B11, respectively. In some embodiments, the anti-TIM-3 antibody or antigen-binding fragment thereof provided herein is a variant of 36B11. The 36B11 variant can have a VL that is a variant of the VL of 36B11 having up to about 5 amino acid substitutions, additions, and/or deletions in SEQ ID NO:182. The 36B11 variant can have a VH that is a variant of the VH of 36B11 having up to about 5 amino acid substitutions, additions, and/or deletions in SEQ ID NO:191. The amino acid substitutions, additions, and/or deletions can be in the VH CDRs or VL CDRs. In some embodiments, the amino acid substitutions, additions, and/or deletions are not in the CDRs. In some embodiments, the variant of 36B11 has up to about 5 conservative amino acid substitutions. In some embodiments, the variant of 36B11 has up to 3 conservative amino acid substitutions. In some embodiments, the anti-TIM-3 antibody or antigen-binding fragment thereof provided herein is a humanized antibody or antigen-binding fragment derived from 36B11. In some embodiments, the anti-TIM-3 antibody or antigen-binding fragment thereof provided herein is a human antibody or antigen-binding fragment derived from 36B11.

In some embodiments, the anti-TIM-3 antibody or antigen-binding fragment thereof provided herein is the antibody designated as 38F8. In some embodiments, the anti-TIM-3 antibody or antigen-binding fragment thereof provided herein has a VL from 38F8 (SEQ ID NO:183). In some embodiments, the anti-TIM-3 antibody or antigen-binding fragment thereof provided herein has a VH from 38F8 (SEQ ID NO:192). The anti-TIM-3 antibody or antigen-binding fragment thereof provided herein can have both a VL and a VH from 38F8. In some embodiments, the anti-TIM-3 antibody or antigen-binding fragment thereof provided herein has a VL that comprises VL CDRs 1, 2, and 3 from the VL from 38F8 (SEQ ID NO:183). In some embodiments, the anti-TIM-3 antibody or antigen-binding fragment thereof provided herein has a VH that comprises VH CDRs 1, 2, and 3 from the VH from 38F8 (SEQ ID NO:192). The anti-TIM-3 antibody or antigen-binding fragment thereof provided herein can have a VL comprising VL CDRs 1, 2, and 3 and a VH comprising VH CDRs 1, 2, and 3 from the VL and VH of 38F8, respectively. In some embodiments, the anti-TIM-3 antibody or antigen-binding fragment thereof provided herein is a variant of 38F8. The 38F8 variant can have a VL that is a variant of the VL of 38F8 having up to about 5 amino acid substitutions, additions, and/or deletions in SEQ ID NO:183. The 38F8 variant can have a VH that is a variant of the VH of 38F8 having up to about 5 amino acid substitutions, additions, and/or deletions in SEQ ID NO:192. The amino acid substitutions, additions, and/or deletions can be in the VH CDRs or VL CDRs. In some embodiments, the amino acid substitutions, additions, and/or deletions are not in the CDRs. In some embodiments, the variant of 38F8 has up to about 5 conservative amino acid substitutions. In some embodiments, the variant of 38F8 has up to 3 conservative amino acid substitutions. In some embodiments, the anti-TIM-3 antibody or antigen-binding fragment thereof provided herein is a humanized antibody or antigen-binding fragment derived from 38F8. In some embodiments, the anti-TIM-3 antibody or antigen-binding fragment thereof provided herein is a human antibody or antigen-binding fragment derived from 38F8.

In some embodiments, the anti-TIM-3 antibody or antigen-binding fragment thereof provided herein is the antibody designated as 38A8. In some embodiments, the anti-TIM-3 antibody or antigen-binding fragment thereof provided herein has a VL from 38A8 (SEQ ID NO:184). In some embodiments, the anti-TIM-3 antibody or antigen-binding fragment thereof provided herein has a VH from 38A8 (SEQ ID NO:193). The anti-TIM-3 antibody or antigen-binding fragment thereof provided herein can have both a VL and a VH from 38A8. In some embodiments, the anti-TIM-3 antibody or antigen-binding fragment thereof provided herein has a VL that comprises VL CDRs 1, 2, and 3 from the VL from 38A8 (SEQ ID NO:184). In some embodiments, the anti-TIM-3 antibody or antigen-binding fragment thereof provided herein has a VH that comprises VH CDRs 1, 2, and 3 from the VH from 38A8 (SEQ ID NO:193). The anti-TIM-3 antibody or antigen-binding fragment thereof provided herein can have a VL comprising VL CDRs 1, 2, and 3 and a VH comprising VH CDRs 1, 2, and 3 from the VL and VH of 38A8, respectively. In some embodiments, the anti-TIM-3 antibody or antigen-binding fragment thereof provided herein is a variant of 38A8. The 38A8 variant can have a VL that is a variant of the VL of 38A8 having up to about 5 amino acid substitutions, additions, and/or deletions in SEQ ID NO:184. The 38A8 variant can have a VH that is a variant of the VH of 38A8 having up to about 5 amino acid substitutions, additions, and/or deletions in SEQ ID NO:193. The amino acid substitutions, additions, and/or deletions can be in the VH CDRs or VL CDRs. In some embodiments, the amino acid substitutions, additions, and/or deletions are not in the CDRs. In some embodiments, the variant of 38A8 has up to about 5 conservative amino acid substitutions. In some embodiments, the variant of 38A8 has up to 3 conservative amino acid substitutions. In some embodiments, the anti-TIM-3 antibody or antigen-binding fragment thereof provided herein is a humanized antibody or antigen-binding fragment derived from 38A8. In some embodiments, the anti-TIM-3 antibody or antigen-binding fragment thereof provided herein is a human antibody or antigen-binding fragment derived from 38A8.

In some embodiments, the anti-TIM-3 antibody or antigen-binding fragment thereof provided herein is the antibody designated as 40F11. In some embodiments, the anti-TIM-3 antibody or antigen-binding fragment thereof provided herein has a VL from 40F11 (SEQ ID NO:185). In some embodiments, the anti-TIM-3 antibody or antigen-binding fragment thereof provided herein has a VH from 40F11 (SEQ ID NO:194). The anti-TIM-3 antibody or antigen-binding fragment thereof provided herein can have both a VL and a VH from 40F11. In some embodiments, the anti-TIM-3 antibody or antigen-binding fragment thereof provided herein has a VL that comprises VL CDRs 1, 2, and 3 from the VL from 40F11 (SEQ ID NO:185). In some embodiments, the anti-TIM-3 antibody or antigen-binding fragment thereof provided herein has a VH that comprises VH CDRs 1, 2, and 3 from the VH from 40F11 (SEQ ID NO:194). The anti-TIM-3 antibody or antigen-binding fragment thereof provided herein can have a VL comprising VL CDRs 1, 2, and 3 and a VH comprising VH CDRs 1, 2, and 3 from the VL and VH of 40F1, respectively. In some embodiments, the anti-TIM-3 antibody or antigen-binding fragment thereof provided herein is a variant of 40F11. The 40F11 variant can have a VL that is a variant of the VL of 40F11 having up to about 5 amino acid substitutions, additions, and/or deletions in SEQ ID NO:185. The 40F11 variant can have a VH that is a variant of the VH of 40F11 having up to about 5 amino acid substitutions, additions, and/or deletions in SEQ ID NO:194. The amino acid substitutions, additions, and/or deletions can be in the VH CDRs or VL CDRs. In some embodiments, the amino acid substitutions, additions, and/or deletions are not in the CDRs. In some embodiments, the variant of 40F11 has up to about 5 conservative amino acid substitutions. In some embodiments, the variant of 40F11 has up to 3 conservative amino acid substitutions. In some embodiments, the anti-TIM-3 antibody or antigen-binding fragment thereof provided herein is a humanized antibody or antigen-binding fragment derived from 40F11. In some embodiments, the anti-TIM-3 antibody or antigen-binding fragment thereof provided herein is a human antibody or antigen-binding fragment derived from 40F11.

In some embodiments, the anti-TIM-3 antibody or antigen-binding fragment thereof provided herein is the antibody designated as 50H9. In some embodiments, the anti-TIM-3 antibody or antigen-binding fragment thereof provided herein has a VL from 50H9 (SEQ ID NO:186). In some embodiments, the anti-TIM-3 antibody or antigen-binding fragment thereof provided herein has a VH from 50H9 (SEQ ID NO:195). The anti-TIM-3 antibody or antigen-binding fragment thereof provided herein can have both a VL and a VH from 50H9. In some embodiments, the anti-TIM-3 antibody or antigen-binding fragment thereof provided herein has a VL that comprises VL CDRs 1, 2, and 3 from the VL from 50H9 (SEQ ID NO:186). In some embodiments, the anti-TIM-3 antibody or antigen-binding fragment thereof provided herein has a VH that comprises VH CDRs 1, 2, and 3 from the VH from 50H9 (SEQ ID NO:195). The anti-TIM-3 antibody or antigen-binding fragment thereof provided herein can have a VL comprising VL CDRs 1, 2, and 3 and a VH comprising VH CDRs 1, 2, and 3 from the VL and VH of 50H9, respectively. In some embodiments, the anti-TIM-3 antibody or antigen-binding fragment thereof provided herein is a variant of 50H9. The 50H9 variant can have a VL that is a variant of the VL of 50H9 having up to about 5 amino acid substitutions, additions, and/or deletions in SEQ ID NO:186. The 50H9 variant can have a VH that is a variant of the VH of 50H9 having up to about 5 amino acid substitutions, additions, and/or deletions in SEQ ID NO:195. The amino acid substitutions, additions, and/or deletions can be in the VH CDRs or VL CDRs. In some embodiments, the amino acid substitutions, additions, and/or deletions are not in the CDRs. In some embodiments, the variant of 50H9 has up to about 5 conservative amino acid substitutions. In some embodiments, the variant of 50H9 has up to 3 conservative amino acid substitutions. In some embodiments, the anti-TIM-3 antibody or antigen-binding fragment thereof provided herein is a humanized antibody or antigen-binding fragment derived from 50H9. In some embodiments, the anti-TIM-3 antibody or antigen-binding fragment thereof provided herein is a human antibody or antigen-binding fragment derived from 50H9.

In some embodiments, the anti-TIM-3 antibody or antigen-binding fragment thereof provided herein is the antibody designated as 84G10. In some embodiments, the anti-TIM-3 antibody or antigen-binding fragment thereof provided herein has a VL from 84G10 (SEQ ID NO:187). In some embodiments, the anti-TIM-3 antibody or antigen-binding fragment thereof provided herein has a VH from 84G10 (SEQ ID NO:196). The anti-TIM-3 antibody or antigen-binding fragment thereof provided herein can have both a VL and a VH from 84G10. In some embodiments, the anti-TIM-3 antibody or antigen-binding fragment thereof provided herein has a VL that comprises VL CDRs 1, 2, and 3 from the VL from 84G10 (SEQ ID NO:187). In some embodiments, the anti-TIM-3 antibody or antigen-binding fragment thereof provided herein has a VH that comprises VH CDRs 1, 2, and 3 from the VH from 84G10 (SEQ ID NO:196). The anti-TIM-3 antibody or antigen-binding fragment thereof provided herein can have a VL comprising VL CDRs 1, 2, and 3 and a VH comprising VH CDRs 1, 2, and 3 from the VL and VH of 84G10, respectively. In some embodiments, the anti-TIM-3 antibody or antigen-binding fragment thereof provided herein is a variant of 84G10. The 84G10 variant can have a VL that is a variant of the VL of 84G10 having up to about 5 amino acid substitutions, additions, and/or deletions in SEQ ID NO: 187. The 84G10 variant can have a VH that is a variant of the VH of 84G10 having up to about 5 amino acid substitutions, additions, and/or deletions in SEQ ID NO:%19. The amino acid substitutions, additions, and/or deletions can be in the VH CDRs or VL CDRs. In some embodiments, the amino acid substitutions, additions, and/or deletions are not in the CDRs. In some embodiments, the variant of 84G10 has up to about 5 conservative amino acid substitutions. In some embodiments, the variant of 84G10 has up to 3 conservative amino acid substitutions. In some embodiments, the anti-TIM-3 antibody or antigen-binding fragment thereof provided herein is a humanized antibody or antigen-binding fragment derived from 84G10. In some embodiments, the anti-TIM-3 antibody or antigen-binding fragment thereof provided herein is a human antibody or antigen-binding fragment derived from 84G10.

In some embodiments, the anti-TIM-3 antibody or antigen-binding fragment thereof provided herein is the antibody designated as 39D1. In some embodiments, the anti-TIM-3 antibody or antigen-binding fragment thereof provided herein has a VL from 39D1 (SEQ ID NO:188). In some embodiments, the anti-TIM-3 antibody or antigen-binding fragment thereof provided herein has a VH from 39D1 (SEQ ID NO:197). The anti-TIM-3 antibody or antigen-binding fragment thereof provided herein can have both a VL and a VH from 39D1. In some embodiments, the anti-TIM-3 antibody or antigen-binding fragment thereof provided herein has a VL that comprises VL CDRs 1, 2, and 3 from the VL from 39D1 (SEQ ID NO:188). In some embodiments, the anti-TIM-3 antibody or antigen-binding fragment thereof provided herein has a VH that comprises VH CDRs 1, 2, and 3 from the VH from 39D1 (SEQ ID NO:197). The anti-TIM-3 antibody or antigen-binding fragment thereof provided herein can have a VL comprising VL CDRs 1, 2, and 3 and a VH comprising VH CDRs 1, 2, and 3 from the VL and VH of 39D1, respectively. In some embodiments, the anti-TIM-3 antibody or antigen-binding fragment thereof provided herein is a variant of 39D1. The 39D1 variant can have a VL that is a variant of the VL of 39D1 having up to about 5 amino acid substitutions, additions, and/or deletions in SEQ ID NO:188. The 39D1 variant can have a VH that is a variant of the VH of 39D1 having up to about 5 amino acid substitutions, additions, and/or deletions in SEQ ID NO:197. The amino acid substitutions, additions, and/or deletions can be in the VH CDRs or VL CDRs. In some embodiments, the amino acid substitutions, additions, and/or deletions are not in the CDRs. In some embodiments, the variant of 39D1 has up to about 5 conservative amino acid substitutions. In some embodiments, the variant of 39D1 has up to 3 conservative amino acid substitutions. In some embodiments, the anti-TIM-3 antibody or antigen-binding fragment thereof provided herein is a humanized antibody or antigen-binding fragment derived from 39D1. In some embodiments, the anti-TIM-3 antibody or antigen-binding fragment thereof provided herein is a human antibody or antigen-binding fragment derived from 39D1.

In some embodiments, provided herein are also antibodies or antigen-binding fragments that compete with an antibody or antigen-binding fragment provided above for binding to TIM-3 (e.g., human TIM-3). Antibodies that "compete with another antibody for binding to a target" refer to antibodies that inhibit (partially or completely) the binding of the other antibody to the target. Whether two antibodies compete with each other for binding to a target, i.e., whether and to what extent one antibody inhibits the binding of the other antibody to a target, can be determined using known competition experiments. e.g., BLI analysis, or BIACORE® surface plasmon resonance (SPR) analysis. In some embodiments, an anti-TIM-3 antibody or antigen-binding fragment competes with, and inhibits binding of another antibody or antigen-binding fragment to TIM-3 (e.g., human TIM-3) by at least 50%, 60%, 70%, 80%, 90% or 100%. The level of inhibition or competition can be different depending on which antibody is the "blocking antibody" (i.e., the cold antibody that is incubated first with the target). Competition assays can be conducted as described, for example, in Ed Harlow and David Lane, *Cold Spring Harb Protoc;* 2006; doi: 10.1101/pdb.prot 4277 or in Chapter 11 of USING ANTIBODIES by Ed Harlow and David Lane, Cold Spring Harbor Laboratory Press, Cold Spring Harbor, NY, USA 1999. Two antibodies "cross-compete" if antibodies block each other both ways by at least 50%, i.e., regardless of whether one or the other antibody is contacted first with the antigen in the competition experiment.

Competitive binding assays for determining whether two antibodies compete or cross-compete for binding include: competition for binding to T cells expressing TIM-3, e.g., by flow cytometry, such as described in the Examples. Other methods include, biolayer interferometry (BLI), SPR (e.g., BIACORE®), solid phase direct or indirect radioimmunoassay (RIA), solid phase direct or indirect enzyme immunoassay (EIA), sandwich competition assay (see Stahli et al., *Methods in Enzymology* 9:242 (1983)); solid phase direct biotin-avidin EIA (see Kirkland et al., *J. Immunol.* 137:3614 (1986)); solid phase direct labeled assay, solid phase direct labeled sandwich assay (see Harlow and Lane, ANTIBODIES: A LABORATORY MANUAL, Cold Spring Harbor Press (1988)); solid phase direct label RIA using 1-125 label (see Morel et al., *Mol. Immunol.* 25(1):7 (1988)); solid phase direct biotin-avidin EIA (Cheung et al., *Virology* 176:546 (1990)); and direct labeled RIA. (Moldenhauer et al., *Scand. J. Immunol.* 32:77 (1990)).

In some embodiments, provided herein are antibodies or antigen-binding fragments that compete with 3E6 for binding to TIM-3 (e.g., human TIM-3). In some embodiments, provided herein are antibodies or antigen-binding fragments that compete with 4H2 for binding to TIM-3 (e.g., human TIM-3). In some embodiments, provided herein are antibodies or antigen-binding fragments that compete with 16H1 for binding to TIM-3 (e.g., human TIM-3). In some embodiments, provided herein are antibodies or antigen-binding fragments that compete with 18C6 for binding to TIM-3 (e.g., human TIM-3). In some embodiments, provided herein are antibodies or antigen-binding fragments that compete with 19D11 for binding to TIM-3 (e.g., human TIM-3). In some embodiments, provided herein are antibodies or antigen-binding fragments that compete with CH 5 # for binding to TIM-3 (e.g., human TIM-3). In some embodiments, provided herein are antibodies or antigen-binding fragments that compete with CH 8 # for binding to TIM-3 (e.g., human TIM-3). In some embodiments, provided herein are antibodies or antigen-binding fragments that compete with CH 9 # for binding to TIM-3 (e.g., human TIM-3). In some embodiments, provided herein are antibodies or antigen-binding fragments that compete with CH 10 # for binding to TIM-3 (e.g., human TIM-3). In some embodiments, provided herein are antibodies or antigen-binding fragments that compete with CH 11 # for binding to TIM-3 (e.g., human TIM-3). In some embodiments, provided herein are antibodies or antigen-binding fragments that compete with 3F2 for binding to TIM-3 (e.g., human TIM-3). In some embodiments, provided herein are antibodies or antigen-binding fragments that compete with 36A2 for binding to TIM-3 (e.g., human TIM-3). In some embodiments, provided herein are antibodies or antigen-binding fragments that compete with 36B11 for binding to TIM-3 (e.g., human TIM-3). In some embodiments, provided herein are antibodies or antigen-binding fragments that compete with 38F8 for binding to TIM-3 (e.g., human TIM-3). In some embodiments, provided herein are antibodies or antigen-binding fragments that compete with 38A8 for binding to TIM-3 (e.g., human TIM-3). In some embodiments, provided herein are antibodies or antigen-binding fragments that compete with 40F11 for binding to TIM-3 (e.g., human TIM-3). In some embodiments, provided herein are antibodies or antigen-binding fragments that compete with 50H9 for binding to TIM-3 (e.g., human TIM-3). In some embodiments, provided herein are antibodies or antigen-binding fragments that compete with 84G10 for binding to TIM-3 (e.g., human TIM-3). In some embodiments, provided herein are antibodies or antigen-binding fragments that compete with 39D1 for binding to TIM-3 (e.g., human TIM-3).

In some embodiments, provided herein are antibodies or antigen-binding fragments that compete with a humanized 3E6 for binding to TIM-3 (e.g., human TIM-3). In some embodiments, provided herein are antibodies or antigen-binding fragments that compete with a humanized 4H2 for binding to TIM-3 (e.g., human TIM-3). In some embodiments, provided herein are antibodies or antigen-binding fragments that compete with a humanized 16H1 for binding to TIM-3 (e.g., human TIM-3). In some embodiments, provided herein are antibodies or antigen-binding fragments that compete with a humanized 18C6 for binding to TIM-3 (e.g., human TIM-3). In some embodiments, provided herein are antibodies or antigen-binding fragments that compete with a humanized 19D11 for binding to TIM-3 (e.g., human TIM-3). In some embodiments, provided herein are antibodies or antigen-binding fragments that compete with a humanized CH 5 # for binding to TIM-3 (e.g., human TIM-3). In some embodiments, provided herein are antibodies or antigen-binding fragments that compete with a humanized CH 8 # for binding to TIM-3 (e.g., human TIM-3). In some embodiments, provided herein are antibodies or antigen-binding fragments that compete with a humanized CH 9 # for binding to TIM-3 (e.g., human TIM-3). In some embodiments, provided herein are antibodies or antigen-binding fragments that compete with a humanized CH 10 # for binding to TIM-3 (e.g., human TIM-3). In some embodiments, provided herein are antibodies or antigen-binding fragments that compete with a humanized CH 11 # for binding to TIM-3 (e.g., human TIM-3). In some embodiments, provided herein are antibodies or antigen-binding fragments that compete with a humanized 3F2 for binding to TIM-3 (e.g., human TIM-3). In some embodiments, provided herein are antibodies or antigen-binding fragments that compete with a humanized 36A2 for binding to TIM-3 (e.g., human TIM-3). In some embodiments, provided herein are antibodies or antigen-binding fragments that compete with a humanized 36B11 for binding to TIM-3 (e.g., human TIM-3). In some embodiments, provided herein are antibodies or antigen-binding fragments that compete with a humanized 38F8 for binding to TIM-3 (e.g., human TIM-3). In some embodiments, provided herein are antibodies or antigen-binding fragments that compete with a humanized 38A8 for binding to TIM-3 (e.g., human TIM-3). In some embodiments, provided herein are antibodies or antigen-binding fragments that compete with a humanized 40F11 for binding to TIM-3 (e.g., human TIM-3). In some embodiments, provided herein are antibodies or antigen-binding fragments that compete with a humanized 50H9 for binding to TIM-3 (e.g., human TIM-3). In some embodiments, provided herein are antibodies or antigen-binding fragments that compete with a humanized 84G10 for binding to TIM-3 (e.g., human TIM-3). In some embodiments, provided herein are antibodies or antigen-binding fragments that compete with a humanized 39D1 for binding to TIM-3 (e.g., human TIM-3).

In some embodiments, provided herein are also antibodies or antigen-binding fragments that bind to the same epitope on TIM-3 (e.g., human TIM-3) as does an antibody or antigen-binding fragment provided above. In some embodiments, provided herein are antibodies or antigen-binding fragments that bind to the same epitope on TIM-3 (e.g., human TIM-3) as does 3E6, or a humanized 3E6. In some embodiments, provided herein are antibodies or antigen-binding fragments that bind to the same epitope on TIM-3 (e.g., human TIM-3) as does 4H2, or a humanized 4H2. In some embodiments, provided herein are antibodies or antigen-binding fragments that bind to the same epitope on TIM-3 (e.g., human TIM-3) as does 16H1, or a humanized 16H1. In some embodiments, provided herein are antibodies or antigen-binding fragments that bind to the same epitope on TIM-3 (e.g., human TIM-3) as does 18C6, or a humanized 18C6. In some embodiments, provided herein are antibodies or antigen-binding fragments that bind to the same epitope on TIM-3 (e.g., human TIM-3) as does 19D11, or a humanized 19D11. In some embodiments, provided herein are antibodies or antigen-binding fragments that bind to the same epitope on TIM-3 (e.g., human TIM-3) as does CH 5 #, or a humanized CH 5 #. In some embodiments, provided herein are antibodies or antigen-binding fragments that bind to the same epitope on TIM-3 (e.g., human TIM-3) as does CH 8 #, or a humanized CH 8 #. In some embodiments, provided herein are antibodies or antigen-binding fragments that bind to the same epitope on TIM-3 (e.g., human TIM-3) as does CH 9 #, or a humanized CH 9 #. In some embodiments, provided herein are antibodies or antigen-binding fragments that bind to the same epitope on TIM-3 (e.g., human TIM-3) as does CH 10 #, or a humanized CH 10 #. In some embodiments, provided herein are antibodies or antigen-binding fragments that bind to the same epitope on TIM-3 (e.g., human TIM-3) as does CH 11 #, or a humanized CH 11 #. In some embodiments, provided herein are antibodies or antigen-binding fragments that bind to the same epitope on TIM-3 (e.g., human TIM-3) as does 3F2, or a humanized 3F2. In some embodiments, provided herein are antibodies or antigen-binding fragments that bind to the same epitope on TIM-3 (e.g., human TIM-3) as does 36A2, or a humanized 36A2. In some embodiments, provided herein are antibodies or antigen-binding fragments that bind to the same epitope on TIM-3 (e.g., human TIM-3) as does 36B11, or a humanized 36B11. In some embodiments, provided herein are antibodies or antigen-binding fragments that bind to the same epitope on TIM-3 (e.g., human TIM-3) as does 38F8, or a humanized 38F8. In some embodiments, provided herein are antibodies or antigen-binding fragments that bind to the same epitope on TIM-3 (e.g., human TIM-3) as does 38A8, or a humanized 38A8. In some embodiments, provided herein are antibodies or antigen-binding fragments that bind to the same epitope on TIM-3 (e.g., human TIM-3) as does 40F11, or a humanized 40F11. In some embodiments, provided herein are antibodies or antigen-binding fragments that bind to the same epitope on TIM-3 (e.g., human TIM-3) as does 50H9, or a humanized 50H9. In some embodiments, provided herein are antibodies or antigen-binding fragments that bind to the same epitope on TIM-3 (e.g., human TIM-3) as does 84G10, or a humanized 84G10. In some embodiments, provided herein are antibodies or antigen-binding fragments that bind to the same epitope on TIM-3 (e.g., human TIM-3) as does 39D1, or a humanized 39D1.

The present disclosure further contemplates additional variants and equivalents that are substantially homologous to the recombinant, monoclonal, chimeric, humanized, and human antibodies, or antibody fragments thereof, described herein. In some embodiments, it is desirable to improve the binding affinity of the antibody. In some embodiments, it is desirable to modulate biological properties of the antibody, including but not limited to, specificity, thermostability, expression level, effector function(s), glycosylation, immunogenicity, and/or solubility. Those skilled in the art will appreciate that amino acid changes may alter post-translational processes of an antibody, such as changing the number or position of glycosylation sites or altering membrane anchoring characteristics.

Variations can be a substitution, deletion, or insertion of one or more nucleotides encoding the antibody or polypeptide that results in a change in the amino acid sequence as compared with the native antibody or polypeptide sequence. In some embodiments, amino acid substitutions are the result of replacing one amino acid with another amino acid having similar structural and/or chemical properties, such as the replacement of a leucine with a serine, e.g., conservative amino acid replacements. Insertions or deletions can be in the range of about 1 to 5 amino acids. In some embodiments, the substitution, deletion, or insertion includes less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the parent molecule. In some embodiments, variations in the amino acid sequence that are biologically useful and/or relevant can be determined by systematically making insertions, deletions, or substitutions in the sequence and testing the resulting variant proteins for activity as compared to the parent protein.

It is known in the art that the constant region(s) of an antibody mediates several effector function and these effector functions can vary depending on the isotype of the antibody. For example, binding of the C1 component of complement to the Fc region of IgG or IgM antibodies (bound to antigen) activates the complement system. Activation of complement is important in the opsonization and lysis of cell pathogens. The activation of complement also stimulates the inflammatory response and can be involved in autoimmune hypersensitivity. In addition, the Fc region of an antibody can bind a cell expressing a Fc receptor (FcR). There are a number of Fc receptors which are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell cytotoxicity or ADCC), antibody-dependent cellular phagocytosis (ADCP), release of inflammatory mediators, placental transfer, and control of immunoglobulin production. In some embodiments, anti-TIM-3 antibody or antigen-binding fragment described herein comprise at least one constant region of a human IgA antibody. In some embodiments, anti-TIM-3 antibody or antigen-binding fragment described herein comprise at least one constant region of a human IgD antibody. In some embodiments, anti-TIM-3 antibody or antigen-binding fragment described herein comprise at least one constant region of a human IgE antibody. In some embodiments, anti-TIM-3 antibody or antigen-binding fragment described herein comprise at least one constant region of a human IgG antibody. In some embodiments, anti-TIM-3 antibody or antigen-binding fragment described herein comprise at least one constant region of a human IgM antibody. In some embodiments, anti-TIM-3 antibody or antigen-binding fragment described herein comprise at least one constant region of a human IgG1 antibody. In some embodiments, anti-TIM-3 antibody or antigen-binding fragment described herein comprise at least one constant region of a human IgG2 antibody. In some embodiments, anti-TIM-3 antibody or antigen-binding fragment described herein comprise at least one constant region of a human IgG3 antibody. In some embodiments, anti-TIM-3 antibody or antigen-binding fragment described herein comprise at least one constant region of a human IgG4 antibody.

Also provided are engineered and modified antibodies that can be prepared using an antibody having one or more of the VH and/or VL sequences disclosed herein as starting material to engineer a modified antibody, which modified antibody can have altered properties from the starting antibody. An antibody can be engineered by modifying one or more residues within one or both variable regions (i.e., VH and/or VL), for example within one or more CDR regions and/or within one or more framework regions. Additionally or alternatively, an antibody can be engineered by modifying residues within the constant region(s), for example to alter the effector function(s) of the antibody. One type of variable region engineering that can be performed is CDR grafting. Antibodies interact with target antigens predominantly through amino acid residues that are located in the six CDRs. Because CDR sequences are responsible for most antibody-antigen interactions, recombinant antibodies that mimic the properties of specific naturally-occurring antibodies can be expressed by constructing expression vectors that include CDR sequences from the specific naturally-occurring antibody grafted onto framework sequences from a different antibody with different properties (see, e.g., Riechmann, L. et al. (1998) Nature 332:323-327; Jones, P. el al. (1986) Nature 321:522-525; Queen, C. et al (1989) Proc. Natl. Acad Sci. U.S.A. 86: 10029-10033; U.S. Pat. No. 5,225,539 to Winter, and U.S. Pat. Nos. 5,530,101; 5,585,089; 5,693,762 and 6,180,370 to Queen et al.).

Accordingly, some embodiments described herein pertain to an isolated monoclonal antibody, or antigen binding portion thereof, comprising a light chain variable region comprising CDR1, CDR2, and CDR3 sequences and comprising an amino acid sequence selected from the group consisting of SEQ ID NOs:1-10, 21, 180-188, and 207-215; respectively, and a heavy chain variable region comprising CDR1. CDR2, and CDR3 sequences and comprising an amino acid sequence selected from the group consisting of SEQ ID NOs:11-20, 22-29 and 189-197; respectively. Thus, such antibodies contain the VH and VL CDR sequences of monoclonal antibodies 3E6, 4H2, 16H1, 18C6, 19D11, CH 5 #, CH 8 #, CH 9 #, CH 10 #, CH 11 #, 3F2, 36A2, 36B11, 38F8, 38A8, 40F11, 50H9, 84G10, or 39D1, yet can contain different framework sequences from these antibodies.

Such framework sequences can be obtained from public DNA databases or published references that include germline antibody gene sequences. For example, germline DNA sequences for human heavy and light chain variable region genes can be found in the "Vbase" human germline sequence database (available on the Internet at www.mrc-cpe.cam.ac.uk/vbase), as well as in Kabat, E. A., et al. (1991) SEQUENCES OF PROTEINS OF IMMUNOLOGICAL INTEREST, Fifth Edition, U.S. Department of Health and Human Services, NIH Publication No. 91-3242; Tomlinson. I. M. et al. (1992) Mol. Biol. 227:776-798; and Cox, J. P. L. et al. (1994), Eur. J. Immunol. 24:827-836; the contents of each of which are expressly incorporated herein by reference.

In some embodiments, the framework sequences for use in the anti-TIM-3 antibodies or antigen-binding fragments described herein are those that are structurally similar to the framework sequences used by the anti-TIM-3 antibodies described herein. The VH CDR1, 2 and 3 sequences, and the VL CDR1, 2 and 3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see, e.g., U.S. Pat. Nos. 5,530,101; 5,585,089; 5,693,762; and 6,180, 370 to Queen et al.).

Engineered anti-TIM-3 antibodies or antigen-binding fragments described herein include those in which modifications have been made to framework residues within VH and/or VL, e.g., to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation can contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis or PCR-mediated mutagenesis. Such "backmutated" antibodies are also intended to be encompassed. Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U S. Patent Publication No. 20030153043 by Carr et al.

Another type of variable region modification is to mutate amino acid residues within the VH and/or VL CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. In some embodiments, conservative modifications (as discussed above) are introduced. The mutations can be amino acid substitutions, additions or deletions. Moreover, typically no more than one, two, three, four or five residues within a CDR region are altered.

Methionine residues in CDRs of antibodies can be oxidized, resulting in potential chemical degradation and consequent reduction in potency of the antibody. Accordingly, also provided are anti-TIM-3 antibodies or antigen-binding fragments which have one or more methionine residues in the heavy and/or light chain CDRs replaced with amino acid residues which do not undergo oxidative degradation. In some embodiments, the methionine residues in the CDRs of antibodies 3E6, 4H2, 16H1, 18C6, 19D11, CH 5 #, CH 8 #, CH 9 #, CH 10 #, CH 11 #, 3F2, 36A2, 36B11, 38F8, 38A8, 40F11, 50H9, 84G10, or 39D1, are replaced with amino acid residues which do not undergo oxidative degradation. Similarly, deamidation sites can be removed from anti-TIM-3 antibodies or antigen-binding fragments, particularly in the CDRs.

Anti-TIM-3 variable regions described herein can be linked (e.g., covalently linked or fused) to an Fc, e.g., an IgG1, IgG2, IgG3 or IgG4 Fc, which can be of any allotype or isoallotype, e.g., for IgG1:G1m, G1m1(a), G1m2(x), G1m3(f), G1m17(z); for IgG2:G2m, G2m23(n); for IgG3: G3n, G3m21(g1), G3m28(g5), G3m11(b0), G3m5(b1), G3m13(b3), G3m14(b4), G3m10(b5), G3m15(s), G3m16

(t), G3m6(c3), G3m24(c5), G3m26(u), G3m27(v); and for K: Km, Km1, Km2, Km3 (see, e.g., Jefferies et al. (2009) mAbs 1:1).

In some embodiments, anti-TIM-3 variable regions described herein are linked to an effectorless or mostly effectorless Fc, e.g., IgG4.

Generally, variable regions described herein can be linked to an Fc comprising one or more modification, typically to alter one or more functional properties of the antibody, such as serum half-life, complement fixation, Fc receptor binding, and/or antigen-dependent cellular cytotoxicity. Furthermore, an antibody described herein can be chemically modified (e.g., one or more chemical moieties can be attached to the antibody) or be modified to alter its glycosylation, to alter one or more functional properties of the antibody. Each of these embodiments is described in further detail below. The numbering of residues in the Fc region is that of the EU index of Kabat.

The Fc region encompasses domains derived from the constant region of an immunoglobulin, including a fragment, analog, variant, mutant or derivative of the constant region. Suitable immunoglobulins include IgG1, IgG2, IgG3, IgG4, and other classes such as IgA, IgD, IgE and IgM. The constant region of an immunoglobulin is defined as a naturally-occurring or synthetically-produced polypeptide homologous to the immunoglobulin C-terminal region, and can include a CH1 domain, a hinge, a CH2 domain, a CH3 domain, or a CH4 domain, separately or in combination. In some embodiments, at least one or more of the constant regions has been modified or deleted in the anti-TIM-3 antibody or antigen-binding fragment described herein. In some embodiments, the antibodies comprise modifications to one or more of the three heavy chain constant regions (CH1, CH2 or CH3) and/or to the light chain constant region (CL). In some embodiments, the heavy chain constant region of the modified antibodies comprises at least one human constant region. In some embodiments, the heavy chain constant region of the modified antibodies comprises more than one human constant region. In some embodiments, modifications to the constant region comprise additions, deletions, or substitutions of one or more amino acids in one or more regions. In some embodiments, one or more regions are partially or entirely deleted from the constant regions of the modified antibodies. In some embodiments, the entire CH2 domain has been removed from an antibody (ΔCH2 constructs). In some embodiments, a deleted constant region is replaced by a short amino acid spacer that provides some of the molecular flexibility typically imparted by the absent constant region. In some embodiments, a modified antibody comprises a CH3 domain directly fused to the hinge region of the antibody. In some embodiments, a modified antibody comprises a peptide spacer inserted between the hinge region and modified CH2 and/or CH3 domains.

Ig molecules interact with multiple classes of cellular receptors. For example, IgG molecules interact with three classes of Fcγ receptors (FcγR) specific for the IgG class of antibody, namely FcγRI, FcγRII, and FcγRIII. The important sequences for the binding of IgG to the FcγR receptors have been reported to be located in the CH2 and CH3 domains. The serum half-life of an antibody is influenced by the ability of that antibody to bind to an Fc receptor (FcR). In some embodiments, an anti-TIM-3 antibody or antigen-binding fragment comprises a Fc region. In some embodiments, the Fc region is fused via a hinge. The hinge can be an IgG1 hinge, an IgG2 hinge, or an IgG3 hinge. The amino acid sequences of the Fc region of human IgG1, IgG2, IgG3, and IgG4 are known to those of ordinary skill in the art. In some cases, Fc regions with amino acid variations have been identified in native antibodies. In some embodiments, the modified antibodies (e.g., modified Fc region) provide for altered effector functions that, in turn, affect the biological profile of the antibody. For example, in some embodiments, the deletion or inactivation (through point mutations or other means) of a constant region reduces Fc receptor binding of the modified antibody as it circulates. In some embodiments, the constant region modifications reduce the immunogenicity of the antibody. In some embodiments, the constant region modifications increase the serum half-life of the antibody. In some embodiments, the constant region modifications reduce the serum half-life of the antibody. In some embodiments, the constant region modifications decrease or remove ADCC, ADCP, and/or complement dependent cytotoxicity (CDC) of the antibody. In some embodiments, specific amino acid substitutions in a human IgG1 Fc region with corresponding IgG2 or IgG4 residues reduce effector functions (e.g., ADCC, ADCP and CDC) in the modified antibody. In some embodiments, an antibody does not have one or more effector functions (e.g., "effectorless" antibodies). In some embodiments, the antibody has no ADCC activity and/or no CDC activity. In some embodiments, the antibody does not bind an Fc receptor and/or complement factors. In some embodiments, the antibody has no effector function(s). In some embodiments, the constant region modifications increase or enhance ADCC, ADCP, and/or CDC of the antibody. In some embodiments, the constant region is modified to eliminate disulfide linkages or oligosaccharide moieties. In some embodiments, the constant region is modified to add/substitute one or more amino acids to provide one or more cytotoxin, oligosaccharide, or carbohydrate attachment sites. In some embodiments, an anti-TIM-3 antibody or antigen-binding fragment comprises a variant Fc region that is engineered with substitutions at specific amino acid positions as compared to a native Fc region.

In some embodiments, the Fc region is a variant Fc region, e.g., an Fc sequence that has been modified (e.g., by amino acid substitution, deletion and/or insertion) relative to a parent Fc sequence (e.g., an unmodified Fc polypeptide that is subsequently modified to generate a variant), to provide desirable structural features and/or biological activity. Generally, variants of the constant region or portions thereof, e.g., CH1, CL, hinge, CH2 or CH3 domains can comprise 1, 2, 3, 4, 5, 6, 7, 8, 9, 10 or more mutations, and/or at most 10, 9, 8, 7, 6, 5, 4, 3, 2 or 1 mutation, or 1-10 or 1-5 mutations, or comprise an amino acid sequence that is at least about 75%, 80%, 85%, 90%, 95%, 96%, 97%, 98%, or 99% identical to that of the corresponding wild-type region or domain (CH1, CL, hinge, CH2, or CH3 domain, respectively), provided that the heavy chain constant region comprising the specific variant retains the necessary biological activity.

For example, one can make modifications in the Fc region in order to generate an Fc variant that (a) has increased or decreased antibody-dependent cell-mediated cytotoxicity (ADCC), (b) increased or decreased antibody-dependent cell-mediated phagocytosis (ACDP), (c) increased or decreased complement mediated cytotoxicity (CDC), (d) has increased or decreased affinity for C1q and/or (e) has increased or decreased affinity for a Fc receptor relative to the parent Fc. Such Fc region variants will generally comprise at least one amino acid modification in the Fc region. Combining amino acid modifications is thought to be particularly desirable. For example, the variant Fc region can include two, three, four, five, etc. substitutions therein, e.g., of the specific Fc region positions identified herein.

A variant Fc region can also comprise a sequence alteration wherein amino acids involved in disulfide bond formation are removed or replaced with other amino acids. Such removal can avoid reaction with other cysteine-containing proteins present in the host cell used to produce the anti-TIM-3 antibodies or antigen-binding fragments described herein. Even when cysteine residues are removed, single chain Fc domains can still form a dimeric Fc domain that is held together non-covalently. In some embodiments, the Fc region can be modified to make it more compatible with a selected host cell. For example, one can remove the PA sequence near the N-terminus of a typical native Fc region, which can be recognized by a digestive enzyme in *E. coli* such as proline iminopeptidase. In some embodiments, one or more glycosylation sites within the Fc domain can be removed. Residues that are typically glycosylated (e.g., asparagine) can confer cytolytic response. Such residues can be deleted or substituted with unglycosylated residues (e.g., alanine). In some embodiments, sites involved in interaction with complement, such as the C1q binding site, can be removed from the Fc region. For example, one can delete or substitute the EKK sequence of human IgG1. In some embodiments, sites that affect binding to Fc receptors can be removed, preferably sites other than salvage receptor binding sites. In some embodiments, an Fc region can be modified to remove an ADCC site. In some embodiments, an Fc region can be modified to remove an ADCP site. ADCC and ADCP sites are known in the art; see, for example, *Molec. Immunol.* 29 (5): 633-9 (1992) with regard to ADCC sites in IgG1, Herbrand, U. (2016). *BioProcessing*, 15(1), 1538-8786 with regard to ADCP sites in IgG1. Specific examples of variant Fc domains are disclosed for example, in WO 97/34631 and WO 96/32478.

In some embodiments, the hinge region of Fc is modified such that the number of cysteine residues in the hinge region is altered, e.g., increased or decreased. This approach is described further in U.S. Pat. No. 5,677,425 by Bodmer el al. The number of cysteine residues in the hinge region of Fc is altered to, for example, facilitate assembly of the light and heavy chains or to increase or decrease the stability of the antibody. In some embodiments, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In some embodiments, the Fc region is altered by replacing at least one amino acid residue with a different amino acid residue to alter the effector function(s) of the antibody. For example, one or more amino acids selected from amino acid residues 234, 235, 236, 237, 297, 318, 320, 322, 330, and/or 331 can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et at.

In another example, one or more amino acids selected from amino acid residues 329, 331 and 322 can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another example, one or more amino acid residues within amino acid positions 231 and 239 are altered to thereby alter the ability of the antibody to fix complement. This approach is described further in PCT Publication WO 94/29351 by Bodmer et at.

In some embodiments, an anti-TIM-3 antibody or antigen-binding fragment described herein comprises an IgG1 heavy chain constant region that comprises one or more amino acid substitutions selected from the group consisting of K214R, L234A, L235E, G237A, D356E, and L358M, per EU numbering. In some embodiments, the IgG1 heavy chain constant region comprises one or more amino acid substitutions selected from the group consisting of K214R, L234A, L234F, L235A, L235E, G236R, G237A, D265A, N297A, N297Q, N297G, E318A, L328R, P329G, A330S, P331S, D356E, and L358M, per EU numbering. In some embodiments, the IgG1 heavy chain constant region comprises one or more amino acid substitutions selected from the group consisting of K214R, C226S, C229S, and P238S, per EU numbering. In some embodiments, the IgG1 heavy chain constant region comprises one or more amino acid substitutions selected from the group consisting of K214R, D356E, and L358M, per EU numbering. In some embodiments, the IgG1 heavy chain constant region comprises one or more amino acid substitutions selected from the group consisting of S131C, K133R, G137E, G138S, Q196K, I199T, N203D, K214R, C226S, C229S, and P238S, per EU numbering. In some embodiments, the IgG1 heavy chain constant region comprises an amino acid substitution selected from the group consisting of N297A, N297Q and N297G, per EU numbering. In some embodiments, the IgG1 heavy chain constant region comprises the amino acid substitutions of L234A and L235A, per EU numbering. In some embodiments, the IgG1 heavy chain constant region comprises the amino acid substitutions of G236R and L328R, per EU numbering. In some embodiments, the IgG1 heavy chain constant region comprises the amino acid substitutions of L234F, L235E, and P331S per EU numbering. In some embodiments, the IgG1 heavy chain constant region comprises the amino acid substitutions of L234A, L235A, and P329G, per EU numbering. In some embodiments, the IgG1 heavy chain constant region comprises the amino acid substitutions of L234F, L235E, and D265A per EU numbering.

In some embodiments, the Fc region can be modified to decrease ADCC, ADCP, and/or to decrease the affinity for an Fcγ receptor by modifying one or more amino acids at the following positions: 234, 235, 236, 237, 238, 239, 240, 241, 243, 244, 245, 247, 248, 249, 252, 254, 255, 256, 258, 262, 263, 264, 265, 267, 268, 269, 270, 272, 276, 278, 280, 283, 285, 286, 289, 290, 292, 293, 294, 295, 296, 297, 298, 299, 301, 303, 305, 307, 309, 312, 313, 315, 318, 320, 322, 324, 325, 326, 327, 328, 329, 330, 331, 332, 333, 334, 335, 337, 338, 340, 360, 373, 376, 378, 382, 388, 389, 398, 414, 416, 419, 430, 433, 434, 435, 436, 437, 438 or 439. Exemplary substitutions include 234A, 235A, 236A, 239D, 239E, 268D, 267E, 268E, 268F, 324T, 332D, 332E, and any combination thereof. Exemplary variants include 234A/235A, 239D/332E, 236A/332E, 236A/239D/332E, 268F/324T, 267E/268F, 267E1324T, and 267E/268F7324T. Other modifications for enhancing FcγR and complement interactions include but are not limited to substitutions 298A, 333A, 334A, 326A, 2471, 339D, 339Q, 280H, 2905, 298D, 298V, 243L, 292P, 300L, 3% L, 305I, and 3% L. These and other modifications are reviewed in Strohl, 2009, *Current Opinion in Biotechnology* 20:685-691.

Fc modifications that increase binding to an Fc receptor include amino acid modifications at any one or more of amino acid positions 238, 239, 248, 249, 252, 254, 255, 256, 258, 265, 267, 268, 269, 270, 272, 279, 280, 283, 285, 298, 289, 290, 292, 293, 294, 295, 296, 298, 301, 303, 305, 307, 312, 315, 324, 327, 329, 330, 335, 337, 338, 340, 360, 373, 376, 379, 382, 388, 389, 398, 414, 416, 419, 430, 434, 435, 437, 438 or 439 of the Fc region, wherein the numbering of the residues in the Fc region is that of the EU index as in abat (WO00/42072).

Other Fc modifications that can be made to Fcs are those for reducing or ablating binding to FcγR and/or complement proteins, thereby reducing or ablating Fc-mediated effector functions such as ADCC, ADCP, and CDC. Exemplary modifications include but are not limited substitutions, insertions, and deletions at positions 234, 235, 236, 237, 267, 269, 325, 328, 330, and/or 331 (e.g., 330 and 331), wherein numbering is according to the EU index. Exemplary substitutions include but are not limited to 234A, 235E, 236R, 237A, 267R, 269R, 325L, 328R, 330S, and 331S (e.g., 330S, and 331S), wherein numbering is according to the EU index. An Fc variant can comprise 236R/328R. Other modifications for reducing FcγR and complement interactions include substitutions 297A, 234A, 235A, 237A, 318A, 228P, 236E, 268Q, 309L, 330S, 331S, 220S, 226S, 229S, 238S, 233P, and 234V, as well as removal of the glycosylation at position 297 by mutational or enzymatic means or by production in organisms such as bacteria that do not glycosylate proteins. These and other modifications are reviewed in Strohl, 2009, *Current Opinion in Biotechnology* 20:685-691.

Optionally, the Fc region can comprise a non-naturally-occurring amino acid residue at additional and/or alternative positions known to one skilled in the art (see, e.g., U.S. Pat. Nos. 5,624,821; 6,277,375; 6,737,056; 6,194,551; 7,317,091; 8,101,720; PCT Patent Publications WO 00/42072: WO 01/58957; WO 02/06919; WO 04/016750; WO 04/029207: WO 04/035752; WO 04/074455; WO 04/099249; WO 04/063351; WO 05/070963; WO 05/040217, WO 05/092925 and WO 06/020114).

Fc variants that enhance affinity for an inhibitory receptor FcγRIIb can also be used. Such variants can provide an Fc fusion protein with immunomodulatory activities related to FcγRIIb cells, including for example B cells and monocytes. In some embodiments, the Fc variants provide selectively enhanced affinity to FcγRIIb relative to one or more activating receptors. Modifications for altering binding to FcγRIIb include one or more modifications at a position selected from the group consisting of 234, 235, 236, 237, 239, 266, 267, 268, 325, 326, 327, 328, 330, 331, and 332, according to the EU index. Exemplary substitutions for enhancing FcγRIIb affinity include but are not limited to 234A, 234D, 234E, 234F, 234W, 235A, 235D, 235E, 235F, 235R, 235Y, 236D, 236N, 237A, 237D, 237N, 239D, 239E, 266M, 267D, 267E, 268D, 268E, 327D, 327E, 328F, 328W, 328 Y, 330S, 331S, and 332E. Exemplary substitutions include 235Y, 236D, 239D, 266M, 267E, 268D, 268E, 328F, 328W, and 328Y. Other Fc variants for enhancing binding to FcγRIIb include 235Y/267E, 236D/267E, 239D/268D, 239D/267E, 267E/268D, 267E/268E, and 267E/328F.

The affinities and binding properties of an Fc region for its ligand can be determined by a variety of in vitro assay methods (biochemical or immunological based assays) known in the art including but not limited to, equilibrium methods (e.g., enzyme-linked immunosorbent assay (ELISA), biolayer interferometry (BLI), or radioimmunoassay (RIA)), or kinetics (e.g., BIACORE analysis), and other methods such as indirect binding assays, competitive inhibition assays, fluorescence resonance energy transfer (FRET), gel electrophoresis and chromatography (e.g., gel filtration). These and other methods can utilize a label on one or more of the components being examined and/or employ a variety of detection methods including but not limited to chromogenic, fluorescent, luminescent, or isotopic labels. A detailed description of binding affinities and kinetics can be found in Paul, W. E., ed., FUNDAMENTAL IMMUNOLOGY, 4th Ed., Lippincott-Raven, Philadelphia (1999), which focuses on antibody-immunogen interactions.

In some embodiments, the antibody is modified to increase its biological half-life. Various approaches are possible. For example, this can be done by increasing the binding affinity of the Fc region for FcRn. For example, one or more of more of following residues can be mutated; 252, 254, 256, 433, 435, 436, as described in U.S. Pat. No. 6,277,375. Specific exemplary substitutions include one or more of the following: T252L, T254S, and/or T256F. Alternatively, to increase the biological half-life, the antibody can be altered within the CH or CL region to contain a salvage receptor binding epitope taken from two loops of a CH2 domain of an Fc region of an IgG, as described in U.S. Pat. Nos. 5,869,046 and 6,121,022 by Presta et al. Other exemplary variants that increase binding to FcRn and/or improve pharmacokinetic properties include substitutions at positions 259, 308, 428, and 434, including for example 259I, 308F, 428L, 428M, 434S, 434I, 434F, 434Y, and 434X1. Other variants that increase Fc binding to FcRn include: 250E, 250Q, 428 L, 428F, 250Q/428L (Hinton et al. 2004, *J. Biol. Chem.* 279(8): 6213-6216, Hinton et al. 2006. *Journal of Immunology* 176:346-356), 256A, 272A, 286A, 305A, 307A, 307Q, 311A, 312A, 376A, 378Q, 380A, 382A, 434A (Shields et al., *Journal of Biological Chemistry*, 2001, 276(9):6591-6604), 252F, 252T, 252Y, 252W, 254T, 256S, 256R, 256Q, 256E, 256D, 256T, 309P, 311 S, 433R, 433S, 433I, 433P, 433Q, 434H, 434F, 434Y, 252Y/254T/256E, 433K/434F/436H, 308T/309P/311S (Dall Acqua et al., *Journal of Immunology*, 2002, 169:5171-5180, Dall Acqua et al., 2006, *Journal of Biological Chemistry* 281:23514-23524). Other modifications for modulating FcRn binding are described in Yeung et al., 2010, *J Immunol*, 182:7663-7671.

In some embodiments, hybrid IgG isotypes with particular biological characteristics can be used. For example, an IgG1/IgG3 hybrid variant can be constructed by substituting IgG1 positions in the CH2 and/or CH3 region with the amino acids from IgG3 at positions where the two isotypes differ. Thus, a hybrid variant IgG antibody can be constructed that comprises one or more substitutions, e.g., 274Q, 276K, 300F, 339T, 356E, 358M, 384S, 392N, 397M, 422I, 435R, and 436F. In some embodiments described herein, an IgG1/IgG2 hybrid variant can be constructed by substituting IgG2 positions in the CH2 and/or CH3 region with amino acids from IgG1 at positions where the two isotypes differ. Thus, a hybrid variant IgG antibody can be constructed that comprises one or more substitutions, e.g., one or more of the following amino acid substitutions: 233E, 234L, 235L, -236G (referring to an insertion of a glycine at position 236), and 327A.

Moreover, the binding sites on human IgG1 for FcγRI. FcγRII, FcγRIII and FcRn have been mapped and variants with improved binding have been described (see Shields, R. L. et al. (2001) *J Biol. Chem.* 276:6591-6604). Specific mutations at positions 256, 290, 298, 333, 334 and 339 were shown to improve binding to FcγRIII. Additionally, the following combination mutants were shown to improve FcγRIII binding: T256A/S298A, S298A/E333A, S298/K224A and S298A/E333A/K334A, which has been shown to exhibit enhanced FcγRIIIa binding and ADCC activity (Shields et al., 2001). Other IgG1 variants with strongly enhanced binding to FcγRIIa have been identified, including variants with S239D/I332E and S239D/I332E/A330L mutations which showed the greatest increase in affinity for FcγRIIIa, a decrease in FcγRIIb binding, and strong cytotoxic activity in cynomolgus monkeys (Lazar et al., 2006). Introduction of the triple mutations into antibodies such as alemtuzumab (CD52-specific), trastuzumab (HER2/neu-specific), rituximab (CD20-specific), and cetuximab (EGFR-specific) translated into greatly enhanced ADCC activity in vitro, and the S239D/I332E variant showed an enhanced capacity to deplete B cells in monkeys (Lazar et al., 2006). In addition, IgG1 mutants containing L235 V, F243L, R292P, Y300L and P396L mutations which exhibited enhanced binding to FcγRIIIa and concomitantly enhanced ADCC activity in transgenic mice expressing human FcγRIIIa in models of B cell malignancies and breast cancer have been identified (Stavenhagen et al. 2007; Nordstrom et al. 2011). Other Fc mutants that can be used include: S298A/E333A/L334A, S239D/I332E, S239D/I332E/A330L, L235V/F243L/R292P/Y300L/P396L, and M4281/N434S.

In some embodiments, an Fc is chosen that has reduced binding to FcγRs. An exemplary Fc, e.g., IgG1 Fc, with reduced FcγR binding comprises the following three amino acid substitutions: L234A, L235E and G237A.

In some embodiments, an Fc is chosen that has reduced complement fixation. An exemplary Fc, e.g., IgG1 Fc, with reduced complement fixation has the following two amino acid substitutions: A330S and P331S.

In some embodiments, an Fc is chosen that has essentially no effector function, i.e., it has reduced binding to FcγRs and reduced complement fixation. An exemplary Fc, e.g., IgG1 Fc, that is effectorless comprises the following five mutations: L234A, L235E, G237A, A330S and P331S.

When using an IgG4 constant domain, it can include the substitution S228P, which mimics the hinge sequence in IgG1 and thereby stabilizes IgG4 molecules. In some embodiments, the IgG4 constant domain includes the substitutions S228P and L235E.

In some embodiments, the glycosylation of an antibody is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation can increase the affinity of the antibody for antigen. Such an approach is described in further detail in U.S. Pat. Nos. 5,714,350 and 6,350,861 by Co et al.

Glycosylation of the constant region on N297 can be prevented by mutating the N297 residue to another residue, e.g., N297A, and/or by mutating an adjacent amino acid, e.g., 298 to thereby reduce glycosylation on N297.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC and/or ADCP ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant anti-TIM-3 antibodies or antigen-binding fragments described herein to thereby produce an antibody with altered glycosylation. For example, EP 1,176.195 by Hanai et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, Led 3 cells, with reduced ability to attach fucose to Asn (297)-linked carbohydrates, also resulting in hypofucosylation of antibodies expressed in that host cell (see also Shields, R. L. et al. (2002) *J. Biol. Chem.* 277:26733-26740). PCT Publication WO 99/54342 by Umana et al. describes cell lines engineered to express glycoprotein-modifying glycosyl transferases (e.g., beta(1,4)-N-acetylglucosaminyltransferase III (GnTIII)) such that antibodies expressed in the engineered cell lines exhibit increased bisecting GlcNac structures which results in increased ADCC activity of the antibodies (see also Umana et al. (1999) *Nat. Biotech.* 17: 176-180).

Another modification of the anti-TIM-3 antibodies or antigen-binding fragments described herein is pegylation. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. In some embodiments, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (CI-CIO) alkoxy- or arylox-polyethylene glycol or polyethylene glycol-maleimide. In some embodiments, the antibody to be pegylated is an aglycosylated antibody. Methods for pegylating proteins are known in the art and can be applied to the anti-TIM-3 antibodies or antigen-binding fragments described herein. See, for example, EP 0 154 316 by Nishimura et al, and EP 0 401 384 by Ishikawa et al.

In some embodiments, variants can include addition of amino acid residues at the amino- and/or carboxyl-terminal end of the antibody or polypeptide. The length of additional amino acids residues can range from one residue to a hundred or more residues. In some embodiments, a variant comprises an N-terminal methionyl residue. In some embodiments, the variant comprises an additional polypeptide/protein (e.g., Fc region) to create a fusion protein. In some embodiments, a variant is engineered to be detectable and may comprise a detectable label and/or protein (e.g., a fluorescent tag or an enzyme).

The variant antibodies or antigen-binding fragments described herein can be generated using methods known in the art, including but not limited to, site-directed mutagenesis, alanine scanning mutagenesis, and PCR mutagenesis.

In some embodiments, a variant of an anti-TIM-3 antibody or antigen-binding fragment disclosed herein can retain the ability to bind TIM-3 to a similar extent, the same extent, or to a higher extent, as the parent antibody or antigen-binding fragment. In some embodiments, the variant can be at least about 80%, about 85%, about 90%, about 91%, about 92%, about 93%, about 94%, about 95%, about 96%, about 97%, about 98%, about 99% or more identical in amino acid sequence to the parent antibody or antigen-binding fragment. In certain embodiments, a variant of an anti-TIM-3 antibody or antigen-binding fragment comprises the amino acid sequence of the parent anti-TIM-3 antibody or antigen-binding fragment with one or more conservative amino acid substitution. Conservative amino acid substitutions are known in the art and include amino acid substitutions in which one amino acid having certain physical and/or chemical properties is exchanged for another amino acid that has the same or similar chemical or physical properties.

In some embodiments, a variant of an anti-TIM-3 antibody or antigen-binding fragment comprises the amino acid sequence of the parent antibody or antigen-binding fragment with one or more non-conservative amino acid substitutions. In some embodiments, a variant of an anti-TIM-3 antibody or antigen-binding fragment comprises the amino acid sequence of the parent binding antibody or antigen-binding fragment with one or more non-conservative amino acid substitution, wherein the one or more non-conservative amino acid substitutions do not interfere with or inhibit one or more biological activities of the variant (e.g., TIM-3 binding). In certain embodiments, the one or more conservative amino acid substitutions and/or the one or more non-conservative amino acid substitutions can enhance a biological activity of the variant, such that the biological activity of the functional variant is increased as compared to the parent antibody or antigen-binding fragment.

In some embodiments, the variant can have 1, 2, 3, 4, or 5 amino acid substitutions in the CDRs (e.g., VH CDR1, VH CDR2, VH CDR3, VL CDR1, VL CDR2 and VL CDR3) of the antibody or antigen-binding fragment.

Described herein are antibodies, e.g., humanized antibodies, which are characterized by particular functional features or properties. For example, the antibodies specifically bind human TIM-3, and more specifically, a particular domain (e.g., a functional domain) within the extracellular domain of human TIM-3. In some embodiments, the antibodies are antagonist antibodies, i.e., they inhibit or suppress the inhibitory activity of TIM-3 on cells, e.g., T cells or myeloid cells. In some embodiments, anti-TIM-3 antibodies provided herein do not cross-react with TIM-3 from other species, such as cynomolgus TIM-3 or mouse TIM-3. In some embodiments, the antibodies specifically bind to the extracellular region of human TIM-3. In some embodiments, the antibodies bind to human TIM-3 with high affinity.

Anti-TIM-3 antibodies or antigen-binding fragments described herein exhibit one or more of the following binding properties: (1) blocking or inhibiting the binding of human TIM-3 to a TIM-3 ligand (e.g., PtdSer), as determined, e.g., in the assay described herein; (2) internalizing or downregulating surface TIM-3 when binding to TIM-3 on immune cells, e.g., CD4$^+$, CD8$^+$ T cells, Th1 cells. NK cells, NKT cells, myeloid cells (e.g., dendritic cells, macrophages, monocytes, or tumor cells), or TILs; (3) inducing or stimulating an acquired immune response; (4) inducing or stimulating an innate immune response; (5) inducing or stimulating immune cell activation, e.g., CD4$^+$, CD8$^+$ T cells, Th1 cells, NK cells, NKT cells, myeloid cells (e.g., dendritic cells, macrophages, monocytes, or tumor cells), or TILs; (6) inducing or stimulating immune cell proliferation, e.g., CD4$^+$, CD8$^+$ T cells, Th cells, NK cells, NKT cells, myeloid cells (e.g., dendritic cells, macrophages, monocytes, or tumor cells), or TILs, in, e.g., a coculture assay; (7) inducing or stimulating cytokine (e.g., IFN-γ) production by T cells, e.g., Th1 cells or TILs, such as TILs from human renal, lung, pancreatic, or breast cancer tumors; (8) inducing or stimulating the production of inflammasome-activated cytokines (e.g., IL-18, soluble CD25), inflammatory cytokines produced by monocyte/macrophage activation (e.g., human IL-1D, IL-18, IL-6, TNFα, or granulysin), and/or Treg effector molecules (e.g., IL-10, perforin); (9) reducing or inhibiting TIM-3-mediated suppression of an immune cell, e.g., CD4$^+$, CD8$^+$ T cells, Th1 cells, NK cells, NKT cells, myeloid cells (e.g., dendritic cells, macrophages, monocytes, or tumor cells), or TILs; (10) reducing or inhibiting TIM-3-mediated suppression of inflammasome activation, as determined, e.g., using the methods and assays described in Gayden 2018 and Dixon 2021, supra.

Anti-TIM-3 antibodies or antigen-binding fragments described herein exhibit one or more of the following binding properties: (1) specifically binding to soluble and/or membrane bound human TIM-3; (2) not cross-reacting with cynomolgus TIM-3 or mouse TIM-3; and (4) competing with, or cross-blocking, the binding to human TIM-3 of an antibody binding to TIM-3 described herein (e.g., 3E6, 4H2, 16H1, 18C6, 19D11, CH 5 #, CH 8 #, CH 9 #, CH 10 #, CH 11 #, 3F2, 36A2, 36B11, 38F8, 38A8, 40F111, 50H9, 84G10, or 39D1), as determined. e.g., in the assay described in the Examples.

Epitope mapping is a method of identifying the binding site, region, or epitope on a target protein where an antibody binds. A variety of methods are known in the art for mapping epitopes on target proteins. These methods include mutagenesis, including but not limited to, shotgun mutagenesis, site-directed mutagenesis, and alanine scanning; domain or fragment scanning; peptide scanning (e.g., Pepscan technology); display methods (e.g., phage display, microbial display, and ribosome/mRNA display); methods involving proteolysis and mass spectroscopy; and structural determination (e.g., X-ray crystallography and NMR). In some embodiments, anti-TIM-3 antibodies or antigen-binding fragments described herein are characterized by assays including, but not limited to, N-terminal sequencing, amino acid analysis, HPLC, mass spectrometry, ion exchange chromatography, and papain digestion. In some embodiments, anti-TIM-3 antibodies or antigen-binding fragments described herein bind to the epitope on human-TIM-3 that is recognized by MBG453 (an anti-TIM-3 antibody developed by Novartis; see e.g., Borate et al. *Blood* (2019): 570-570.). In some embodiments, anti-TIM-3 antibodies or antigen-binding fragments described herein bind to the epitope on human-TIM-3 that is recognized by TSR022 (an anti-TIM-3 antibody developed by Tesaro/GSK, see e.g., Pollyea and Craig, *Blood* 129.12 (2017): 1627-1635.). In some embodiments, anti-TIM-3 antibodies or antigen-binding fragments described herein bind to the epitope on human-TIM-3 that is recognized by both MBG453 and TSR022. In some embodiments, anti-TIM-3 antibodies or antigen-binding fragments described herein do not bind to the epitope on human-TIM-3 that is recognized by MBG453. In some embodiments, anti-TIM-3 antibodies or antigen-binding fragments described herein do not bind to the epitope on human-TIM-3 that is recognized by TSR022. In some embodiments, anti-TIM-3 antibodies or antigen-binding fragments described herein do not bind to the epitope on human-TIM-3 that is recognized by MBG453 or TSR022. In some embodiments, anti-TIM-3 antibodies or antigen-binding fragments described herein bind to an epitope on human-TIM-3 that is not recognized by MBG453. In some embodiments, anti-TIM-3 antibodies or antigen-binding fragments described herein bind to an epitope on human-TIM-3 that is not recognized by TSR022. In some embodiments, anti-TIM-3 antibodies or antigen-binding fragments described herein bind to an epitope on human-TIM-3 that is not recognized by MBG453 or TSR022. In some embodiments, the anti-TIM-3 antibodies or antigen-binding fragments described herein bind to an epitope on human-TIM-3 that is recognized by MBG453, and an epitope on human-TIM-3 that is not recognized by MBG453. In some embodiments, anti-TIM-3 antibodies or antigen-binding fragments described herein bind to an epitope on human-TIM-3 that is recognized by TSR022, and an epitope on human-TIM-3 that is not recognized by TSR022.

In some embodiments, anti-TIM-3 antibodies or antigen-binding fragments described herein do not compete with either Fab 6TXZ or Fab 7KQL for binding to human TIM-3. In some embodiments, anti-TIM-3 antibodies or antigen-binding fragments described herein bind to an epitope on human TIM-3 that is distinct from the epitope recognized by either Fab 6TXZ or Fab 7KQL. In some embodiments, anti-TIM-3 antibodies or antigen-binding fragments described herein do not bind to the epitope on human-TIM-3 that is recognized by Fab 6TXZ. In some embodiments, anti-TIM-3 antibodies or antigen-binding fragments described herein do not bind to the epitope on human-TIM-3 that is recognized by Fab 7KQL. In some embodiments, anti-TIM-3 antibodies or antigen-binding fragments described herein bind to an epitope on human-TIM-3 that is not recognized by Fab 6TXZ. In some embodiments, anti-TIM-3 antibodies or antigen-binding fragments described herein bind to an epitope on human-TIM-3 that is not recognized by Fab 7KQL.

As provided in Experimental sections below, the epitope of 3E6 was mapped to the following residues of human TIM-3: D71, R73, D74, V75, N76, W78, T79, and Y82. In some embodiments, provided herein are antibodies or antigen-binding fragments thereof that specifically bind human TIM-3 at an epitope that comprises at least one of amino acids 71-82 of human TIM-3. In some embodiments, the epitope of the antibodies or antigen-binding fragments provided herein can comprise at least two, at least three, at least four, at least five, at least six, at least seven, or all eight of the following residues of human TIM-3: D71, R73, D74, V75, N76, W78, T79, and Y82. In some embodiments, anti-TIM-3 antibodies or antigen-binding fragments described herein specifically bind to at least one of the following residues of human TIM-3: D71, R73, D74, V75, N76, W78, T79, and Y82. In some embodiments, the anti-TIM-3 antibodies or antigen-binding fragments described herein specifically bind to D71 of human TIM-3. In some embodiments, the anti-TIM-3 antibodies or antigen-binding fragments described herein specifically bind to R73 of human TIM-3. In some embodiments, the anti-TIM-3 antibodies or antigen-binding fragments described herein specifically bind to D74 of human TIM-3. In some embodiments, the anti-TIM-3 antibodies or antigen-binding fragments described herein specifically bind to V75 of human TIM-3 In some embodiments, the anti-TIM-3 antibodies or antigen-binding fragments described herein specifically bind to N76 of human TIM-3. In some embodiments, the anti-TIM-3 antibodies or antigen-binding fragments described herein specifically bind to W78 of human TIM-3. In some embodiments, the anti-TIM-3 antibodies or antigen-binding fragments described herein specifically bind to T79 of human TIM-3. In some embodiments, the anti-TIM-3 antibodies or antigen-binding fragments described herein specifically bind to Y82 of human TIM-3. In some embodiments, the anti-TIM-3 antibodies or antigen-binding fragments described herein specifically bind to at least two of the following residues of human TIM-3: D71, R73, D74, V75, N76, W78, T79, and Y82. In some embodiments, the anti-TIM-3 antibodies or antigen-binding fragments described herein specifically bind to at least three of the following residues of human TIM-3: D71, R73, D74, V75, N76, W78, T79, and Y82. In some embodiments, the anti-TIM-3 antibodies or antigen-binding fragments described herein specifically bind to at least four of the following residues of human TIM-3: D71, R73, D74, V75, N76, W78, T79, and Y82. In some embodiments, the anti-TIM-3 antibodies or antigen-binding fragments described herein specifically bind to at least five of the following residues of human TIM-3: D71, R73, D74, V75, N76, W78, T79, and Y82. In some embodiments, the anti-TIM-3 antibodies or antigen-binding fragments described herein specifically bind to at least six of the following residues of human TIM-3: D71, R73, D74, V75, N76, W78, T79, and Y82. In some embodiments, the anti-TIM-3 antibodies or antigen-binding fragments described herein specifically bind to at least seven of the following residues of human TIM-3: D71, R73, D74, V75, N76, W78, T79, and Y82. In some embodiments, the anti-TIM-3 antibodies or antigen-binding fragments described herein bind to all of the following residues of human TIM-3: D71, R73, D74, V75, N76, W78, T79, and Y82.

In some embodiments, provided herein are also anti-TIM-3 antibodies or antigen-binding fragments that would compete for binding to amino acids 71-82 of human TIM-3 with an anti-TIM-3 antibody described herein (e.g., 3E6). In some embodiments, the anti-TIM-3 antibodies or antigen-binding fragments described herein would compete for binding to at least one of the following residues of human TIM-3: D71, R73, D74, V75, N76, W78, T79, and Y82. In some embodiments, the anti-TIM-3 antibodies or antigen-binding fragments described herein would compete for binding to at least two, at least three, at least four, at least five, at least six, at least seven, or all eight of the following residues of human TIM-3: D71, R73, D74, V75, N76, W78, T79, and Y82.

Without being bound by theory, in addition to promoting acquired immunity, the anti-TIM-3 antibodies or antigen-binding fragments described herein can also promote innate immune activity by reducing or inhibiting the TIM-3-mediated suppression of inflammasome activation. In some embodiments, the anti-TIM-3 antibodies or antigen-binding fragments described herein can also reduce or inhibit the TIM-3-mediated suppression of myeloid cells such as dendritic cells, macrophages, or monocytes. In some embodiments, the anti-TIM-3 antibodies or antigen-binding fragments described herein promote inflammasome activation or myeloid activation at least in part by specifically binding to D71, N76, or Y82 of human TIM-3, or any combination thereof. Mutations in some of these residues are known to result in persistent immune activation and increased production of cytokines (Gayden, 2018).

In some embodiments, the anti-TIM-3 antibodies or antigen-binding fragments described herein specifically bind to D71, N76, or Y82 of human TIM-3. In some embodiments, provided herein are also anti-TIM-3 antibodies or antigen-binding fragments that which would compete for binding to D71, N76, or Y82 of human TIM-3 with an anti-TIM-3 antibody described herein. In some embodiments, the anti-TIM-3 antibodies or antigen-binding fragments described herein do not bind a variant of human TIM-3 that has an amino acid mutation at D71, N76, or Y82. In some embodiments, the anti-TIM-3 antibodies or antigen-binding fragments described herein do not bind a variant of human TIM-3 that has an amino acid substitution at D71, N76, or Y82. In some embodiments, the anti-TIM-3 antibodies or antigen-binding fragments described herein do not bind a variant of human TIM-3 that has N D71, N76, or Y82 deleted.

In some embodiments, the anti-TIM-3 antibodies or antigen-binding fragments described herein specifically bind to Y82 of human TIM-3. In some embodiments, provided herein are also anti-TIM-3 antibodies or antigen-binding fragments that which would compete for binding to Y82 of human TIM-3 with an anti-TIM-3 antibody described herein. In some embodiments, the anti-TIM-3 antibodies or antigen-binding fragments described herein do not bind a variant of human TIM-3 that has an amino acid mutation at Y82. In some embodiments, the anti-TIM-3 antibodies or antigen-binding fragments described herein do not bind a variant of human TIM-3 that has an amino acid substitution at Y82. In some embodiments, the anti-TIM-3 antibodies or antigen-binding fragments described herein do not bind a variant of human TIM-3 that has Y82 deleted. In some embodiments, the anti-TIM-3 antibodies or antigen-binding fragments described herein specifically bind to D71 of human TIM-3. In some embodiments, provided herein are also anti-TIM-3 antibodies or antigen-binding fragments that which would compete for binding to D71 of human TIM-3 with an anti-TIM-3 antibody described herein. In some embodiments, the anti-TIM-3 antibodies or antigen-binding fragments described herein do not bind a variant of human TIM-3 that has an amino acid mutation at D71. In some embodiments, the anti-TIM-3 antibodies or antigen-binding fragments described herein do not bind a variant of human TIM-3 that has an amino acid substitution at D71. In some embodiments, the anti-TIM-3 antibodies or antigen-binding fragments described herein do not bind a variant of human TIM-3 that has D71 deleted. In some embodiments, the anti-TIM-3 antibodies or antigen-binding fragments described herein specifically bind to N76 of human TIM-3. In some embodiments, provided herein are also anti-TIM-3 antibodies or antigen-binding fragments that which would compete for binding to N76 of human TIM-3 with an anti-TIM-3 antibody described herein. In some embodiments, the anti-TIM-3 antibodies or antigen-binding fragments described herein do not bind a variant of human TIM-3 that has an amino acid mutation at N76. In some embodiments, the anti-TIM-3 antibodies or antigen-binding fragments described herein do not bind a variant of human TIM-3 that has an amino acid substitution at N76. In some embodiments, the anti-TIM-3 antibodies or antigen-binding fragments described herein do not bind a variant of human TIM-3 that has N76 deleted. In some embodiments, the anti-TIM-3 antibodies or antigen-binding fragments described herein specifically bind to D71, N76, and Y82 of human TIM-3. In some embodiments, provided herein are also anti-TIM-3 antibodies or antigen-binding fragments that which would compete for binding to D71, N76, and Y82 of human TIM-3 with an anti-TIM-3 antibody described herein. In some embodiments, the anti-TIM-3 antibodies or antigen-binding fragments described herein do not bind a variant of human TIM-3 that has amino acid mutations at D71, N76, and Y82.

In some embodiments, anti-TIM-3 antibodies or antigen-binding fragments described herein bind to human TIM-3 with high affinity, for example, with a $K_D$ of $10^{-7}$ M or less, $10^{-8}$ or less, $5\times10^{-9}$ M or less, $10^{-9}$ M or less, $5\times10^{-10}$ M or less, $10^{-10}$ M or less, $5\times10^{-11}$ M or less, $10^{-11}$ M or less, $5\times10^{-12}$ M or less, $10^{-12}$ M or less, $10^{-12}$ M to $10^{-7}$ M, $10^{-10}$ M to $10^{-7}$ M, $10^{-9}$ M to $10^{-7}$ M, $10^{-8}$ M to $10^{-7}$ M, $10^{-8}$ M to $10^{-7}$ M, $10^{-10}$ M to $10^{-8}$ M, $10^{-9}$ M to $10^{-8}$ M, $10^{-11}$ M to $10^{-9}$ M, or $10^{-10}$ M to $10^{-9}$ M. In some embodiments, anti-TIM-3 antibodies or antigen-binding fragments described herein bind to human TIM-3 with a $K_D$ of $10^{-11}$ M to $5\times10^{-9}$ M. In some embodiments, anti-TIM-3 antibodies or antigen-binding fragments described herein bind to soluble human TIM-3 with high affinity, e.g., as determined by BLI, with a $K_D$ of $10^{-7}$ M or less, $10^{-8}$M or less, $5\times10^{-9}$ M or less, $10^{-9}$ M or less, $5\times10^{-10}$ M or less, $10^{-10}$ M or less, $5\times10^{-11}$ M or less, $10^{-11}$ M or less, $5\times10^{-12}$ M or less, $10^{-12}$ M or less, $10^{-12}$ M to $10^{-7}$ M, $10^{-11}$ M to $10^{-7}$ M, $10^{-0}$ M to $10^{-7}$ M, $10^{-9}$ M to $10^{-7}$ M, $10^{-8}$ M to $10^{-7}$, $10^{-10}$ M to $10^{-8}$ M, $10^{-9}$ M to $10^{-8}$ M, $10^{-11}$ M to $10^{-9}$ M, or $10^{-10}$ M to $10^{-9}$ M. In some embodiments, anti-TIM-3 antibodies or antigen-binding fragments described herein bind to soluble human TIM-3 with a $K_D$ of $10^{-11}$ M to $5\times10^{-9}$ M. In some embodiments, anti-TIM-3 antibodies or antigen-binding fragments described herein bind to bound (e.g., cell membrane bound) human TIM-3, such as on activated human T cells, e.g., as determined by flow cytometry and Scatchard plot, with a $K_D$ of $10^{-7}$ M or less, $10^{-8}$ M or less, $5\times10^{-9}$ M or less, $10^{-9}$ M or less, $5\times10^{-10}$ M or less, $10^{-10}$ M or less, $5\times10^{-11}$ M or less, $10^{-11}$ M or less, $5\times10^{-12}$ M or less, $10^{-12}$ M or less, $10^{-12}$ M to $10^{-7}$ M, $10^{-11}$ M to $10^{-7}$ M, $10^{-10}$ M to $10^{-7}$ M, $10^{-9}$ M to $10^{-7}$ M, $10^{-8}$ M to $10^{-7}$, $10^{-10}$ M to $10^{-8}$ M, $10^{-9}$ M to $10^{-8}$ M, $10^{-11}$ M to $10^{-9}$ M, or $10^{-10}$ M to $10^{-9}$ M. In some embodiments, an anti-TIM-3 antibody or antigen-binding fragment binds to bound (e.g., cell membrane bound) human TIM-3, such as on activated human T cells, e.g., as determined by flow cytometry, with an $EC_{50}$ of 10 μg/mL or less, 5 μg/mL or less, 1 μg/mL or less, 0.9 μg/mL or less, 0.8 μg/mL or less, 0.7 μg/mL or less, 0.6 μg/mL or less, 0.5 μg/mL or less, 0.4 μg/mL or less, 0.3 μg/mL or less, 0.2 μg/mL or less, 0.1 μg/mL or less, 0.05 μg/mL or less, or 0.01 μg/mL or less.

In some embodiments, anti-TIM-3 antibodies or antigen-binding fragments described herein bind to cynomolgus TIM-3, for example, with a $K_D$ of $10^{-7}$ M or less, $10^{-8}$ M or less, $5\times10^{-9}$ M or less, $10^{-9}$ M or less, $5\times10^{-10}$ M or less, $10^{-10}$ M or less, $5\times10^{-11}$ M or less, $10^{-11}$ M or less, $5\times10^{-12}$ M or less, $10^{-12}$ M or less, $10^{-12}$ M to $10^{-7}$ M, $10^{-11}$ M to $10^{-7}$ M, $10^{-10}$ M to $10^{-7}$ M, $10^{-9}$ M to $10^{-7}$ M, $10^{-8}$ M to $10^{-7}$, $10^{-10}$ M to $10^{-8}$ M, $10^{-9}$ M to $10^{-8}$ M, $10^{-11}$ M to $10^{-9}$ M, or $10^{-10}$ M to $10^{-9}$ M. In some embodiments, an anti-TIM-3 antibody or antigen-binding fragment binds to soluble cynomolgus TIM-3, e.g., as determined by BLI (e.g., as described in the Examples), with a $K_D$ of $10^{-7}$ M or less, $10^{-8}$ M or less, $5\times10^{-9}$ M or less, $10^{-9}$ M or less, $5\times10^{-10}$ M or less, $10^{-10}$ M or less, $5\times10^{-11}$ M or less, $10^{-11}$ M or less, $5\times10^{-12}$ M or less, $10^{-12}$ M or less, $10^{-12}$ M to $10^{-7}$ M, $10^{-11}$ M to $10^{-7}$ M, $10^{-10}$ M to $10^{-7}$M, $10^{-9}$ M to $10^{-7}$ M, $10^{-8}$ M to $10^{-7}$, $10^{-10}$ M to $10^{-8}$ M, $10^{-9}$ M to $10^{-8}$ M $10^{-11}$ M to $10^{-9}$ M, or $10^{-10}$ M to $10^{-9}$ M. Anti-TIM-3 antibodies or antigen-binding fragments can bind to membrane bound cynomolgus TIM-3, e.g., with an $EC_{50}$ of 100 nM or less, 10 nM or less, 100 nM to 0.01 nM, 100 nM to 0.1 nM, 100 nM to 1 nM, or 10 nM to 1 nM, e.g., as measured by flow cytometry (e.g., as described in the Examples). In some embodiments, an anti-TIM-3 antibody or antigen-binding fragment binds to bound (e.g., cell membrane bound) cynomolgus TIM-3, such as on activated human T cells, e.g., as determined by flow cytometry and Scatchard plot, with a $K_D$ of $10^{-7}$ M or less, $10^{-8}$ M or less, $5\times10^{-9}$ M or less, $10^{-9}$ M or less, $5\times10^{-10}$ M or less, $10^{-10}$ M or less, $5\times10{-11}$ M or less, $10^{-11}$ M or less, $5\times10^{-12}$ M or less, $10^{-12}$ M or less, $10^{-12}$ M to $10^{-7}$ M, $10^{-11}$ M to $10^{-7}$ M, $10^{-10}$ M to $10^{-7}$ M, $10^{-9}$ M to $10^{-7}$ M, $10^{-8}$ M to $10^{-7}$, $10^{-10}$ M to $10^{-8}$ M, $10^{-9}$ M to $10^{-8}$ M, $10^{-11}$ M to $10^{-9}$ M, or $10^{-10}$ M to $10^{-9}$ M.

In some embodiments, anti-TIM-3 antibodies or antigen-binding fragments described herein do not detectably bind to cynomolgus TIM-3.

In some embodiments, anti-TIM-3 antibodies or antigen-binding fragments described herein stimulate or enhance an acquired immune response. In some embodiments, anti-TIM-3 antibodies or antigen-binding fragments described herein stimulate or enhance an immune response, e.g., by activating T cells, e.g., in the tumor. For example, the anti-TIM-3 antibodies or antigen-binding fragments can activate or costimulate cells, as evidenced, e.g., by enhanced cytokine (e.g., IFN-γ) secretion and/or enhanced proliferation, which can result from the inhibition of TIM-3 mediated T cell inhibitory activity. In some embodiments, T cell activation or co-stimulation by a TIM-3 antibody or antigen-binding fragment occurs in the presence of CD3 stimulation. In some embodiments, an anti-TIM-3 antibody increases IFN-γ secretion by a factor of 50%, 100% (i.e., 2 fold), 3 fold, 4 fold, 5 fold or more, optionally with a maximum of up to 10 fold, 30 fold, 100 fold, as measured, e.g., on primary human T cells and/or T cells expressing human TIM-3, such as TILs. In some embodiments, anti-TIM-3 antibodies or antigen-binding fragments described herein block or reduce the inhibitory effects of TIM-3. In some embodiments, anti-TIM-3 antibodies or antigen-binding fragments described herein increased IFN-γ production in TIM-3-expressing T cells (e.g., Th1 cells or TILs). In some embodiments, anti-TIM-3 antibodies or antigen-binding fragments described herein enhance proliferation of TIM-3 expressing T cells (e.g., Th1 cells or TILs). In some embodiments, anti-TIM-3 antibodies or antigen-binding fragments described herein stimulate T cell proliferation in a mixed lymphocyte reaction (MLR) assay.

In some embodiments, anti-TIM-3 antibodies or antigen-binding fragments described herein stimulate or enhance an innate immune response. In some embodiments, anti-TIM-3 antibodies or antigen-binding fragments described herein induce or stimulate activation of myeloid cells such as dendritic cells, macrophages, or monocytes. In some embodiments, anti-TIM-3 antibodies or antigen-binding fragments described herein reduce or inhibit TIM-3-mediated suppression of myeloid cells such as dendritic cells, macrophages, or monocytes. In some embodiments, anti-TIM-3 antibodies or antigen-binding fragments described herein reduce or inhibit TIM-3-mediated regulation or suppression of inflammasome activation. In some embodiments, anti-TIM-3 antibodies or antigen-binding fragments described herein induce or stimulate the production of inflammasome-activated cytokines such as IL-18 and soluble CD25. In some embodiments, anti-TIM-3 antibodies or antigen-binding fragments described herein induce or stimulate the production of inflammatory cytokines produced by monocyte/macrophage activation, such as human IL-10, IL-18, IL-6, TNFα, or granulysin. In some embodiments, anti-TIM-3 antibodies or antigen-binding fragments described herein induce or stimulate the production of Treg effector molecules, such as IL-10 and perforin.

In some embodiments, anti-TIM-3 antibodies or antigen-binding fragments described herein internalize or downregulate cell surface TIM-3 when binding to TIM-3 on cells. In some embodiments, anti-TIM-3 antibodies or antigen-binding fragments described herein internalize or downregulate cell surface TIM-3 when binding to TIM-3 on immune cells, e.g., CD4$^+$, CD8$^+$ T cells, Th1 cells, NK cells, NKT cells, myeloid cells (e.g., dendritic cells, macrophages, or monocytes), or TILs. In some embodiments, anti-TIM-3 antibodies or antigen-binding fragments described herein internalize or downregulate cell surface TIM-3 when binding to TIM-3 on T cells. In some embodiments, anti-TIM-3 antibodies or antigen-binding fragments described herein internalize or downregulate cell surface TIM-3 when binding to TIM-3 on NK cells. In some embodiments, anti-TIM-3 antibodies or antigen-binding fragments described herein internalize or downregulate cell surface TIM-3 when binding to TIM-3 on tumor cells. In some embodiments, anti-TIM-3 antibodies or antigen-binding fragments described herein do not internalize or downregulate cell surface TIM-3 when binding to TIM-3 on tumor cells.

In some embodiments, the antibodies or antigen-binding fragments provided herein bind to the site on TIM-3 to which a TIM-3 ligand binds. In some embodiments, the antibodies or antigen-binding fragments provided herein blocks the interaction between TIM-3 and a TIM-3 ligand wherein the TIM-3 ligand is PtdSer, HMGB1, CEACAM-1, or any combination thereof. In some embodiments, the TIM-3 ligand is PtdSer, and the antibodies or antigen-binding fragments provided herein bind to the site on TIM-3 to which PtdSer binds. In some embodiments, the antibodies or antigen-binding fragments provided herein block the interaction of PtdSer to TIM-3. In some embodiments, the TIM-3 ligand is CEACAM-1, and the antibodies or antigen-binding fragments provided herein bind to the site on TIM-3 to which CEACAM-1 binds. In some embodiments, the antibodies or antigen-binding fragments provided herein block the interaction of CEACAM-1 to TIM-3. In some embodiments, the TIM-3 ligand is HMGB1, and the antibodies or antigen-binding fragments provided herein bind to the site on TIM-3 to which HMGB1 binds. In some embodiments, the antibodies or antigen-binding fragments provided herein block the interaction of HMGB1 to TIM-3. In some embodiments, an antibody or antigen-binding fragment provided herein that inhibits the binding of TIM-3 to its ligand, e.g., PtdSer, e.g., in binding assays using CHO cells transfected with human TIM-3 or TIM-3 expressing activated T cells, with an EC50 of about 1 μg/mL or less, such as about 0.9 pg/mL or less, about 0.85 pg/mL or less, about 0.8 pg/mL or less, about 0.75 pg/mL or less, about 0.7 pg/mL or less, about 0.65 pg/mL or less, about 0.6 pg/mL or less, about 0.55 pg/mL or less, about 0.5 pg/mL or less, about 0.45 pg/mL or less, about 0.4 pg/mL or less, about 0.35 pg/mL or less, about 0.3 pg/mL or less, about 0.25 pg/mL or less, about 0.2 pg/mL or less, about 0.15 pg/mL or less, about 0.1 pg/mL or less, or about 0.05 pg/mL or less, in art-recognized methods, e.g., FACS-based binding assays.

In some embodiments, anti-TIM-3 antibodies or antigen-binding fragments described herein inhibit the binding of phosphatidylserine to TIM-3, e.g., as measured by PS-hTIM-3 "in-tandem" blocking assay. In some embodiments, anti-TIM-3 antibodies or antigen-binding fragments inhibit binding of PtdSer to human TIM-3 on cells, e.g., CHO cells or activated T cells expressing human TIM-3, e.g., with an $EC_{50}$ of 10 pg/mL or less, 1 pg/mL or less, 0.01 pg/mL to 10 pg/mL, 0.1 pg/mL to 10 pg/mL, or 0.1 pg/mL to 1 pg/mL.

Accordingly, an anti-TIM-3 antibody or antigen-binding fragment that exhibits one or more of these functional properties (e.g., biochemical, immunochemical, cellular, physiological or other biological activities, or the like) as determined according to methodologies known to the art and described herein, will be understood to exhibit a statistically significant difference in the particular activity relative to that seen in the absence of the antibody (e.g., or when a control antibody of irrelevant specificity is present). In some embodiments, anti-TIM-3 antibody or antigen-binding fragment-induced increases in a measured parameter (e.g., T cell proliferation, cytokine production) in a given assay effects a statistically significant increase by at least 10% of the measured parameter, e.g., by at least 20%, 30%, 40%, 50%, 60%, 70%, 80%, 90%, 95%, 100% (i.e., 2 fold), 3 fold, 5 fold or 10 fold, and in some embodiments, an antibody described herein can increase the measured parameter, e.g., by greater than 92%, 94%, 95%, 97%, 98%, 99%, 100% (i.e., 2 fold), 3 fold, 5 fold or 10 fold, relative to the same assay conducted in the absence of the antibody. Conversely, anti-TIM-3 antibody-induced decreases in a measured parameter (e.g., tumor volume, TIM-3 ligand binding to human TIM-3) in a given assay effects a statistically significant decrease by at least 10% of the measured parameter, e.g., by at least 20%, 30%, 40%, 50%, 60%, 70%, 80% or 90%, and in some embodiments, an antibody described herein can decrease the measured parameter, e.g., by greater than 92%, 94%, 95%, 97%, 98% or 99%, relative to the same assay conducted in the absence of the antibody.

In some embodiments, anti-TIM-3 antibodies do not have agonist activity, as determined, e.g., in cross-linking of anti-TIM-3 antibodies in CHO-OKT3-CD32:T cell co-culture experiments, in which such antibodies do not enhance activity beyond anti-TIM-3 alone. In some embodiments, anti-TIM-3 antibodies block the interaction of TIM-3 with its ligand without promoting agonist activity.

In some embodiments, anti-TIM-3 antibodies enhance IL-12 production from monocytes or dendritic cells treated with lipopolysaccharide (LPS).

In some embodiments, anti-TIM-3 antibodies revive tumor infiltrating $CD8^+$ T cells that co-express PD-1 and TIM-3 by combined treatment, hence avoiding depletion of $CD8^+$ T cells.

The anti-TIM-3 antibodies or antigen-binding fragments can be analyzed for their physical, chemical and/or biological properties by various methods known in the art. In some embodiments, an anti-TIM-3 antibody is tested for its ability to bind TIM-3 (e.g., human TIM-3). Binding assays include, but are not limited to, BLI, SPR (e.g., Biacore), ELISA, FACS, Western blots, and RIAs. In addition, antibodies can be evaluated for solubility, stability, thermostability, viscosity, expression levels, expression quality, and/or purification efficiency. Assays to evaluate the effects of the antibodies on functional properties of TIM-3 (e.g., ligand binding, T cell proliferation, cytokine production) are described in further detail below and in the Examples.

In some embodiments, anti-TIM-3 antibodies are not native antibodies or are not naturally-occurring antibodies. For example, anti-TIM-3 antibodies have post-translational modifications that are different from those of antibodies that are naturally-occurring, such as by having more, less or a different type of post-translational modification.

In some embodiments, anti-TIM-3 antibodies or antigen-binding fragments described herein are chemically modified naturally or by intervention. In some embodiments, the anti-TIM-3 antibodies or antigen-binding fragments have been chemically modified by glycosylation, acetylation, pegylation, phosphorylation, amidation, derivatization by known protecting/blocking groups, proteolytic cleavage, and/or linkage to a cellular ligand or other protein. Any of numerous chemical modifications can be carried out by known techniques. The anti-TIM-3 antibodies or antigen-binding fragments can comprise one or more analogs of an amino acid (including, for example, unnatural amino acids), as well as other modifications known in the art.

In some embodiments, an anti-TIM-3 antibody or antigen-binding fragment is conjugated to a cytotoxic agent or moiety. In some embodiments, an anti-TIM-3 antibody or antigen-binding fragment is conjugated to a cytotoxic agent to form an ADC (antibody-drug conjugate). In some embodiments, the cytotoxic moiety is a chemotherapeutic agent including, but not limited to, methotrexate, adriamycin/doxorubicin, melphalan, mitomycin C, chlorambucil, duocarmycin, daunorubicin, pyrrolobenzodiazepines (PBDs), or other intercalating agents. In some embodiments, the cytotoxic moiety is a microtubule inhibitor including, but not limited to, auristatins, maytansinoids (e.g., DM1 and DM4), and tubulysins. In some embodiments, the cytotoxic moiety is an enzymatically active toxin of bacterial, fungal, plant, or animal origin, or fragments thereof, including, but not limited to, diphtheria A chain, non-binding active fragments of diphtheria toxin, exotoxin A chain, ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. In some embodiments, an antibody is conjugated to one or more small molecule toxins, such as calicheamicins, maytansinoids, trichothenes, and CC1065.

In some embodiments, an anti-TIM-3 antibody or antigen-binding fragment described herein is conjugated to a detectable substance or molecule that allows the agent to be used for diagnosis and/or detection. A detectable substance can include, but is not limited to, enzymes, such as horseradish peroxidase, alkaline phosphatase, beta-galactosidase, and acetylcholinesterase; prosthetic groups, such as biotin and flavine(s); fluorescent materials, such as, umbelliferone, fluorescein, fluorescein isothiocyanate (FITC), rhodamine, tetramethylrhodamine isothiocyanate (TRITC), dichlorotriazinylamine fluorescein, dansyl chloride, cyanine (Cy3), and phycoerythrin; bioluminescent materials, such as luciferase; radioactive materials, such as $^{212}Bi$, $^{14}C$, $^{57}Co$, $^{51}Cr$, $^{67}Cu$, $^{18}F$, $^{68}Ga$, $^{67}Ga$, $^{153}Gd$, $^{159}Gd$, $^{68}Ge$, $^{3}H$, $^{166}Ho$, $^{131}I$, $^{125}I$, $^{123}I$, $^{121}I$, $^{115}In$, $^{113}In$, $^{112}In$, $^{111}In$, $^{140}La$, $^{177}Lu$, $^{54}Mn$, $^{99}Mo$, $^{32}P$, $^{103}Pd$, $^{149}Pm$, $^{142}Pr$, $^{186}Re$, $^{188}Re$, $^{105}Rh$, $^{97}Ru$, $^{35}S$, $^{47}Sc$, $^{75}Se$, $^{153}Sm$, $^{113}Sn$, $^{117}Sn$, $^{85}Sr$, $^{99m}Tc$, $^{201}Ti$, $^{133}Xe$, $^{90}Y$, $^{69}Yb$, $^{175}Yb$, $^{65}Zn$; positron emitting metals; and magnetic metal ions positron emitting metals; and magnetic metal ions.

In some embodiments, anti-TIM-3 antibodies or antigen-binding fragments described herein can be bispecific molecules or multi-specific molecules such as bispecific antibodies or multi-specific antibodies. A monospecific anti-TIM-3 antibody, or antigen binding portion thereof, can be derivatized or linked to another binding moiety, e.g., another peptide or protein (e.g., another antibody or ligand for a receptor) to generate a bispecific molecule that binds to at least two different binding sites or target molecules. For example, an anti-TIM-3 antibody or antigen-binding fragment can be linked to an antibody or scFv that binds specifically to any protein that can be used as potential targets for combination treatments, such as the proteins described herein. The second target can be PD-1, PD-L1, CEACAM1, CEACAM5, GITR, or LAG-3. The antibodies and antigen-binding fragments described herein can in fact be derived or linked to more than one other functional molecule to generate multispecific molecules that have more than two different binding sites and bind to more than two target molecules. To create a bispecific molecule (e.g., a bispecific antibody) described herein, an antibody described herein can be functionally linked (e.g., by chemical coupling, genetic fusion, noncovalent association or otherwise) to one or more other binding molecules, such as another antibody, antigen-binding fragment, peptide or binding mimetic, such that a bispecific molecule results.

Accordingly, provided herein are bispecific molecules (e.g., bispecific antibodies) comprising at least a first binding specificity for TIM-3 and a second binding specificity for a second target antigen. In some embodiments, provided herein are multispecific molecules (e.g., multispecific antibodies), which can further include a third binding specificity.

In some embodiments, the bispecific molecules described herein comprise as a binding specificity at least one antibody, or an antibody fragment thereof, including, e.g., an Fab, Fab', F(ab')2, Fv, or a single chain Fv (scFv). The antibody can also be a light chain or heavy chain dimer, or any minimal fragment thereof such as a Fv or a single chain construct as described in U.S. Pat. No. 4,946,778.

While human or humanized monoclonal antibodies are preferred, other antibodies which can be employed in the bispecific molecules described herein are murine and chimeric monoclonal antibodies.

The bispecific molecules described herein can be prepared by conjugating the constituent binding specificities using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl) cyclohaxane-1-carboxylate (sulfo-SMCC) (see e.g., Karpovsky et al. (1984) $J.\ Exp.\ Med$ 160: 1686: Liu. M A et al. (1985) $Proc.\ Natl.\ Acad.\ \&\ J.\ USA$ 82:8648). Other methods include those described in Paulus (1985) $Behring\ Ins.\ Mitt.\ No.$ 78, 118-132; Brennan et al. (1985) $Science$ 229:81-83), and Glennie et al. (1987), $J.\ Immunol.$ 139: 2367-2375). Some conjugating agents are SATA and sulfo-SMCC, both available from Pierce Chemical Co. (Rockford, IL).

When the binding specificities are antibodies, they can be conjugated via sulfhydryl bonding of the C-terminus hinge regions of the two heavy chains. In some embodiments, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific molecule is a mAb×mAb, mAb×Fab, mAb×(scFv, Fab×F(ab')₂ or ligand×Fab fusion protein. A bispecific antibody can comprise an antibody comprising an scFv at the C-terminus of each heavy chain. A bispecific molecule described herein can be a single chain molecule comprising one single chain antibody and a binding determinant, or a single chain bispecific molecule comprising two binding determinants. Bispecific molecules can comprise at least two single chain molecules. Methods for preparing bispecific molecules are described for example in U.S. Pat. Nos. 5,260,203; 5,455,030; 4,881,175; 5,132,405; 5,091,513; 5,476,786; 5,013,653; 5,258,498; and 5,482,858.

Binding of the bispecific molecules to their specific targets can be confirmed using art-recognized methods, such as enzyme-linked immunosorbent assay (ELISA), radioimmunoassay (RIA). FACS analysis, bioassay (e.g., growth inhibition), or Western Blot assay. Each of these assays generally detects the presence of protein-antibody complexes of particular interest by employing a labeled reagent (e.g., an antibody) specific for the complex of interest.

An anti-TIM-3 antibody or antigen-binding fragment described herein can be attached to a solid support. Such solid supports include, but are not limited to, glass, cellulose, polyacrylamide, nylon, polystyrene, polyvinyl chloride, or polypropylene. In some embodiments, an immobilized anti-TIM-3 antibody or antigen-binding fragment is used in an immunoassay. In some embodiments, an immobilized anti-TIM-3 antibody or antigen-binding fragment is used in purification of the target antigen (e.g., human TIM-3).

6.3 Polynucleotides and Vectors

Also provided herein are polynucleotides that encode a polypeptide (e.g., an anti-TIM-3 antibody or antigen-binding fragment) described herein. The term "polynucleotide that encode a polypeptide" encompasses a polynucleotide which includes only coding sequences for the polypeptide as well as a polynucleotide which includes additional coding and/or non-coding sequences. The polynucleotides of the disclosure can be in the form of RNA or in the form of DNA. DNA can be cDNA, genomic DNA, or synthetic DNA, and can be double-stranded or single-stranded. Single stranded DNA can be the coding strand or non-coding (anti-sense) strand. The polynucleotides of the disclosure can be mRNA.

Expressly contemplated herein are polynucleotides encode any anti-TIM-3 antibody or antigen-binding fragment disclosed herein. For illustrative purposes, in some embodiments, the polynucleotides provided herein encode an anti-TIM-3 antibody or antigen-binding fragment comprising (a) a VL comprising (1) a VL CDR1 having an amino acid sequence selected from the group consisting of SEQ ID NOs:86-93 and 129-137; (2) a VL CDR2 having an amino acid sequence selected from the group consisting of SEQ ID NOs:94-100 and 138-144; and (3) a VL CDR3 having an amino acid sequence selected from the group consisting of SEQ ID NOs:47-55, 145-153 and 198-206; or a variant thereof having up to about 5 amino acid substitutions, additions, and/or deletions in the VL CDRs; and/or (b) a VH comprising (1) a VH CDR1 having an amino acid sequence selected from the group consisting of SEQ ID NOs:101-108 and 154-161; (2) a VH CDR2 having an amino acid sequence selected from the group consisting of SEQ ID NOs:109-118 and 162-170; and (3) a VH CDR3 having an amino acid sequence selected from the group consisting of SEQ ID NOs:119-128 and 171-179; or a variant thereof having up to about 5 amino acid substitutions, additions, and/or deletions in the VH CDRs. In some embodiments, the polynucleotides provided herein encode an anti-TIM-3 antibody or antigen-binding fragment comprising (a) a VL comprising (1) a VL CDR1 having an amino acid sequence selected from the group consisting of SEQ ID NOs:31-38; (2) a VL CDR2 having an amino acid sequence selected from the group consisting of SEQ ID NOs:39-46; and (3) a VL CDR3 having an amino acid sequence selected from the group consisting of SEQ ID NOs:47-55; or a variant thereof having up to about 5 amino acid substitutions, additions, and/or deletions in the VL CDRs; and/or (b) a VH comprising (1) a VH CDR1 having an amino acid sequence selected from the group consisting of SEQ ID NOs:56-63; (2) a VH CDR2 having an amino acid sequence selected from the group consisting of SEQ ID NOs:64-73; and (3) a VH CDR3 having an amino acid sequence selected from the group consisting of SEQ ID NOs:74-83; or a variant thereof having up to about 5 amino acid substitutions, additions, and/or deletions in the VH CDRs.

In some embodiments, the polynucleotides provided herein encode an anti-TIM-3 antibody or antigen-binding fragment comprising (a) a VL having at least 85%, at least 90%, at least 95%, at least 98%, or 100% sequence identity to an amino acid sequence selected from the group consisting of SEQ ID NOs:1-10, 21, 180-188, and 207-215; and/or (b) a VH having at least 85%, at least 90%, at least 95%, at least 98%, or 100% sequence identity to an amino acid sequence selected from the group consisting of SEQ ID NOs: 11-20, 22-29, and 189-197. The polynucleotides can be in the form of DNA. The polynucleotides can be in the form of mRNA.

In some embodiments, the polynucleotides provided herein encode an anti-TIM-3 antibody or antigen-binding fragment disclosed herein comprising a VL and a VH, wherein the VL comprises VL CDR1, CDR2 and CDR3 and the VH comprises VH CDR1, CDR2 and CDR3, and wherein the VL CDR1, VL CDR2, VL CDR3, VH CDR1, VH CDR2 and VH CDR3 have the amino acid sequences of (1) SEQ ID NOs:86, 94, 47, 101, 109, and 119, respectively; (2) SEQ ID NOs:87, 95, 48, 102, 110, and 120, respectively; (3) SEQ ID NOs:88, 96, 49, 103, 111, and 121, respectively; (4) SEQ ID NOs:89, 97, 50, 104, 112, and 122, respectively; (5) SEQ ID NOs:90, 94, 51, 105, 113, and 123, respectively; (6) SEQ ID NOs:91, 98, 52, 106, 114, and 124, respectively; (7) SEQ ID NOs:91, 98, 53, 106, 115, and 125, respectively; (8) SEQ ID NOs:92, 99, 54, 107, 116, and 126, respectively; (9) SEQ ID NOs:93, 100, 55, 108, 117, and 127, respectively; (10) SEQ ID NOs:91, 98, 52, 106, 118, and 128, respectively; (11) SEQ ID NOs:129, 138, 145, 106, 162, and 171, respectively; (12) SEQ ID NOs:130, 139, 146, 154, 163, and 172, respectively; (13) SEQ ID NOs:131, 140, 147, 155, 164, and 173, respectively; (14) SEQ ID NOs:132, 141, 148, 156, 165, and 174, respectively; (15) SEQ ID NOs:133, 139, 149, 157, 166, and 175, respectively; (16) SEQ ID NOs:134, 142, 150, 158, 167, and 176, respectively; (17) SEQ ID NOs:135, 143, 151, 159, 168, and 177, respectively; (18) SEQ ID NOs:136, 144, 152, 160, 169, and 178, respectively; (19) SEQ ID NOs:137, 100, 153, 161, 170, and 179, respectively; (20) SEQ ID NOs:86, 94, 198, 101, 109, and 119, respectively; (21) SEQ ID NOs:86, 94, 199, 101, 109, and 119, respectively; (22) SEQ ID NOs:86, 94, 200, 101, 109, and 119, respectively; (23) SEQ ID NOs:86, 94, 201, 101, 109, and 119, respectively; (24) SEQ ID NOs:86, 94, 202, 101, 109, and 119, respectively; (25) SEQ ID NOs:86, 94, 203, 101, 109, and 119, respectively; (26) SEQ ID NOs:86, 94, 204, 101, 109, and 119, respectively; (27) SEQ ID NOs:86, 94, 205, 101, 109, and 119, respectively; or (28) SEQ ID NOs:86, 94, 206, 101, 109, and 119, respectively; or a variant thereof having up to about 5 amino acid substitutions, additions, and/or deletions in the CDRs. The polynucleotides can be in the form of DNA. The polynucleotides can be in the form of mRNA.

In some embodiments, the polynucleotides provided herein encode an anti-TIM-3 antibody or antigen-binding fragment disclosed herein comprising a VL and a VH, wherein the VL comprises VL CDR1, CDR2 and CDR3 and the VH comprises VH CDR1, CDR2 and CDR3, and wherein the VL CDR1, VL CDR2, VL CDR3, VH CDR1, VH CDR2 and VH CDR3 have the amino acid sequences of (1) SEQ ID NOs:31, 39, 47, 56, 64, and 74, respectively; (2) SEQ ID NOs:32, 40, 48, 57, 65, and 75, respectively; (3) SEQ ID NOs:33, 41, 49, 58, 66, and 76, respectively; (4) SEQ ID NOs:34, 42, 50, 59, 67 and 77, respectively; (5) SEQ ID NOs:35, 43, 51, 60, 68, and 78, respectively; (6) SEQ ID NOs:36, 44, 52, 61, 69, and 79, respectively; (7) SEQ ID NOs:36, 44, 53, 61, 70, and 80, respectively; (8) SEQ ID NOs:37, 45, 54, 62, 71, and 81, respectively; (9) SEQ ID NOs:38, 46, 55, 63, 72, and 82, respectively; or (10) SEQ ID NOs:36, 44, 52, 61, 73, and 83, respectively; or a variant thereof having up to about 5 amino acid substitutions, additions, and/or deletions in the CDRs. The polynucleotides can be in the form of DNA. The polynucleotides can be in the form of mRNA In some embodiments, the polynucleotides provided herein encode an anti-TIM-3 antibody or antigen-binding fragment disclosed herein comprising a VL and a VH, wherein the VL and VH have the amino acid sequences of (1) SEQ ID NOs:1 and 11, respectively; (2) SEQ ID NOs:2 and 12, respectively; (3) SEQ ID NOs:3 and 13, respectively; (4) SEQ ID NOs:4 and 14, respectively; (5) SEQ ID NOs:5 and 15, respectively; (6) SEQ ID NOs:6 and 16, respectively; (7) SEQ ID NOs:7 and 17, respectively; (8) SEQ ID NOs:8 and 18, respectively; (9) SEQ ID NOs:9 and 19, respectively; (10) SEQ ID NOs:10 and 20, respectively; (11) SEQ ID NOs:180 and 189, respectively; (12) SEQ ID NOs:181 and 190, respectively; (13) SEQ ID NOs:182 and 191, respectively; (14) SEQ ID NOs:183 and 192, respectively; (15) SEQ ID NOs:184 and 193, respectively; (16) SEQ ID NOs:185 and 194, respectively; (17) SEQ ID NOs:186 and 195, respectively; (18) SEQ ID NOs:187 and 196, respectively; or (19) SEQ ID NOs:188 and 197, respectively.

In some embodiments, the polynucleotides provided herein encode an anti-TIM-3 antibody or antigen-binding fragment disclosed herein comprising a VL and a VH, wherein the VL has an amino acid sequence selected from the group consisting of SEQ ID NO:21 and 207-215 and the VH has an amino acid sequence selected from the group consisting of SEQ ID NOs:22-29. In some embodiments, the VL and VH have the amino acid sequences of (1) SEQ ID NOs:21 and 28 (or 22, 23, 24, 25, 26, 27, or 29), respectively; (2) SEQ ID NOs:207 and 28 (or 22, 23, 24, 25, 26, 27, or 29), respectively; (3) SEQ ID NOs:208 and 28 (or 22, 23, 24, 25, 26, 27, or 29), respectively; (4) SEQ ID NOs:209 and 28 (or 22, 23, 24, 25, 26, 27, or 29), respectively; (5) SEQ ID NOs:210 and 28 (or 22, 23, 24, 25, 26, 27, or 29), respectively; (6) SEQ ID NOs:211 and 28 (or 22, 23, 24, 25, 26, 27, or 29), respectively; (7) SEQ ID NOs:212 and 28 (or 22, 23, 24, 25, 26, 27, or 29), respectively; (8) SEQ ID NOs:213 and 28 (or 22, 23, 24, 25, 26, 27, or 29), respectively; (9) SEQ ID NOs:214 and 28 (or 22, 23, 24, 25, 26, 27, or 29), respectively; (10) SEQ ID NOs:215 and 28 (or 22, 23, 24, 25, 26, 27, or 29), respectively. The polynucleotides can be in the form of DNA. The polynucleotides can be in the form of mRNA.

In some embodiments, the VL and VH are connected by a linker. In some embodiments, the linker has the amino acid sequence of (GGGGS)n, n=1, 2, 3, 4, or 5 (SEQ ID NO:216). In some embodiments, the linker has the amino acid sequence of (EAAAK)n, n=1, 2, 3, 4, or 5 (SEQ ID NO:217). In some embodiments, the linker has the amino acid sequence of GGGGSGGGGSGGGGS (SEQ ID NO:30).

In some embodiments, the polynucleotides provided herein encode an anti-TIM-3 antibody or antigen-binding fragment disclosed herein comprising a VL having at least 85%, at least 90%, at least 95%, at least 98%, or 100% sequence identity to an amino acid sequence selected from the group consisting of SEQ ID NOs:1-10, 21, 180-188, and 207-215. Also provided is a polynucleotide that hybridizes to a polynucleotide having a nucleotide sequence encoding an anti-TIM-3 antibody or antigen-binding fragment disclosed herein comprising a VL having at least 85%, at least 90%, at least 95%, at least 98%, or 100% sequence identity to an amino acid sequence selected from the group consisting of SEQ ID NOs:1-10, 21, 180-188, and 207-215. In some embodiments, the polynucleotides provided herein encode an anti-TIM-3 antibody or antigen-binding fragment disclosed herein comprising a VH having at least 85%, at least 90%, at least 95%, at least 98%, or 100% sequence identity to an amino acid sequence selected from the group consisting of SEQ ID NOs:11-20, 22-29 and 189-197. Also provided is a polynucleotide that hybridizes to a polynucleotide having a nucleotide sequence encoding an anti-TIM-3 antibody or antigen-binding fragment disclosed herein comprising a VH having at least 85%, at least 90%, at least 95%, at least 98%, or 100% sequence identity to an amino acid sequence selected from the group consisting of SEQ ID NOs:11-20, 22-29 and 189-197. In some embodiments, the hybridization is under conditions of high stringency as is known to those skilled in the art. The polynucleotides can be in the form of DNA. The polynucleotides can be in the form of mRNA.

The present disclosure also provides variants of the polynucleotides described herein, wherein the variants encode, for example, fragments, analogs, and/or derivatives of an anti-TIM-3 antibody or antigen-binding fragment disclosed herein. In some embodiments, the present disclosure provides a polynucleotide having a nucleotide sequence at least about 80% identical, at least about 85% identical, at least about 90% identical, at least about 95% identical, at least about 96% identical, at least about 97% identical, at least about 98% identical, or at least about 99% identical to a polynucleotide sequence encoding an anti-TIM-3 antibody or antigen-binding fragment described herein. In some embodiments, the present disclosure provides a polynucleotide having a nucleotide sequence at least about 80% identical, at least about 85% identical, at least about 90% identical, at least about 95% identical, at least about 96% identical, at least about 97% identical, at least about 98% identical, or at least about 99% identical to a polynucleotide sequence encoding an anti-TIM-3 antibody or antigen-binding fragment described herein.

As used herein, the phrase "a polynucleotide having a nucleotide sequence at least about 95% identical to a polynucleotide sequence" means that the nucleotide sequence of the polynucleotide is identical to a reference sequence except that the polynucleotide sequence can include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. These mutations of the reference sequence can occur at the 5' or 3' terminal positions of the reference nucleotide sequence or anywhere between those terminal positions, interspersed either individually among nucleotides in the reference sequence or in one or more contiguous groups within the reference sequence.

The polynucleotide variants can contain alterations in the coding regions, non-coding regions, or both. In some embodiments, a polynucleotide variant contains alterations which produce silent substitutions, additions, or deletions, but does not alter the properties or activities of the encoded polypeptide. In some embodiments, a polynucleotide variant comprises silent substitutions that results in no change to the amino acid sequence of the polypeptide (due to the degeneracy of the genetic code). Polynucleotide variants can be produced for a variety of reasons, for example, to optimize codon expression for a particular host (e.g., change codons in the human mRNA to those preferred by a bacterial host such as E. coli). In some embodiments, a polynucleotide variant comprises at least one silent mutation in a non-coding or a coding region of the sequence.

In some embodiments, a polynucleotide variant is produced to modulate or alter expression (or expression levels) of the encoded polypeptide. In some embodiments, a polynucleotide variant is produced to increase expression of the encoded polypeptide. In some embodiments, a polynucleotide variant is produced to decrease expression of the encoded polypeptide. In some embodiments, a polynucleotide variant has increased expression of the encoded polypeptide as compared to a parental polynucleotide sequence. In some embodiments, a polynucleotide variant has decreased expression of the encoded polypeptide as compared to a parental polynucleotide sequence.

In some embodiments, a polynucleotide comprises the coding sequence for a polypeptide (e.g., an antibody) fused in the same reading frame to a polynucleotide which aids in expression and secretion of a polypeptide from a host cell (e.g., a leader sequence which functions as a secretory sequence for controlling transport of a polypeptide). The polypeptide can have the leader sequence cleaved by the host cell to form a "mature" form of the polypeptide.

In some embodiments, a polynucleotide comprises the coding sequence for a polypeptide (e.g., an antibody) fused in the same reading frame to a marker or tag sequence. For example, in some embodiments, a marker sequence is a hexa-histidine tag (HIS-tag) that allows for efficient purification of the polypeptide fused to the marker. In some embodiments, a marker sequence is a hemagglutinin (HA) tag derived from the influenza hemagglutinin protein when a mammalian host (e.g., COS-7 cells) is used. In some embodiments, the marker sequence is a FLAG™ tag. In some embodiments, a marker can be used in conjunction with other markers or tags.

In some embodiments, a polynucleotide is isolated. In some embodiments, a polynucleotide is substantially pure.

Vectors and cells comprising the polynucleotides described herein are also provided. In some embodiments, provided herein are vectors comprising a polynucleotide provided herein. The vectors can be expression vectors. In some embodiments, vectors provided herein comprise a polynucleotide encoding an anti-TIM-3 antibody or antigen-binding fragment described herein. In some embodiments, vectors provided herein comprise a polynucleotide encoding a polypeptide that is part of an anti-TIM-3 antibody or antigen-binding fragment described herein.

In some embodiments, provided herein are recombinant expression vectors, which can be used to amplify and express a polynucleotide encoding an anti-TIM-3 antibody or antigen-binding fragment described herein. For example, a recombinant expression vector can be a replicable DNA construct that includes synthetic or cDNA-derived DNA fragments encoding a polypeptide chain of an anti-TIM-3 antibody, operatively linked to suitable transcriptional and/or translational regulatory elements derived from mammalian, microbial, viral or insect genes. In some embodiments, a viral vector is used. DNA regions are "operatively linked" when they are functionally related to each other. For example, a promoter is operatively linked to a coding sequence if it controls the transcription of the sequence; or a ribosome binding site is operatively linked to a coding sequence if it is positioned so as to permit translation. In some embodiments, structural elements intended for use in certain expression systems include a leader sequence enabling extracellular secretion of translated protein by a host cell. In some embodiments, in situations where recombinant protein is expressed without a leader or transport sequence, a polypeptide can include an N-terminal methionine residue.

A wide variety of expression host/vector combinations can be employed. Useful expression vectors for eukaryotic hosts include, for example, vectors comprising expression control sequences from SV40, bovine papilloma virus, adenovirus, and cytomegalovirus. Useful expression vectors for bacterial hosts include known bacterial plasmids, such as plasmids from E. coli, including pCR1, pBR322, pMB9 and their derivatives, and wider host range plasmids, such as M13 and other filamentous single-stranded DNA phages.

In some embodiments, an anti-TIM-3 antibody or antigen-binding fragment described herein is expressed from one or more vectors. Suitable host cells for expression include prokaryotes, yeast cells, insect cells, or higher eukaryotic cells under the control of appropriate promoters. Appropriate cloning and expression vectors for use with bacterial, fungal, yeast, and mammalian cellular hosts, as well as methods of protein production, including antibody production are well-known in the art.

Examples of suitable mammalian host cell lines include, but are not limited to, COS-7 (monkey kidney-derived), L-929 (murine fibroblast-derived), C127 (murine mammary tumor-derived), 3T3 (murine fibroblast-derived), CHO (Chinese hamster ovary-derived), HeLa (human cervical cancer-derived), BHK (hamster kidney fibroblast-derived). HEK-293 (human embryonic kidney-derived) cell lines and variants thereof. Mammalian expression vectors can comprise non-transcribed elements such as an origin of replication, a suitable promoter and enhancer linked to the gene to be expressed, and other 5' or 3' flanking non-transcribed sequences, and 5' or 3' non-translated sequences, such as necessary ribosome binding sites, a polyadenylation site, splice donor and acceptor sites, and transcriptional termination sequences. Expression of recombinant proteins in insect cell culture systems (e.g., baculovirus) also offers a robust method for producing correctly folded and biologically functional proteins. Baculovirus systems for production of heterologous proteins in insect cells are well-known to those of skill in the art.

The present disclosure also provides host cells comprising the polypeptides described herein, polynucleotides encoding polypeptides described herein, or vectors comprising such polynucleotides. In some embodiments, provided herein are host cells comprising a vector comprising a polynucleotide disclosed herein. In some embodiments, host cells provided herein comprise a vector comprising a polynucleotide encoding an anti-TIM-3 antibody or antigen-binding fragment described herein. In some embodiments, host cells provided herein comprise a vector comprising a polynucleotide encoding a polypeptide that is part of an anti-TIM-3 antibody or antigen-binding fragment described herein. In some embodiments, host cells provided herein comprise a polynucleotide encoding an anti-TIM-3 antibody or antigen-binding fragment described herein. In some embodiments, the cells produce the anti-TIM-3 antibodies or antigen-binding fragments described herein.

6.4 Methods of Production

Polynucleotides provided herein can be prepared, manipulated, and/or expressed using any of the well-established techniques known and available in the art. Many vectors can be used. Examples of vectors are plasmid, autonomously replicating sequences, and transposable elements. Exemplary transposon systems such as Sleeping Beauty and PiggyBac can be used, which can be stably integrated into the genome (e.g., Ivics et al., Cell, 91 (4): 501-510 (1997): Cadifianos et al., (2007) Nucleic Acids Research. 35 (12): e87). Additional exemplary vectors include, without limitation, plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses. Examples of categories of animal viruses useful as vectors include, without limitation, retrovirus (including lentivirus), adenovirus, adeno-associated virus, herpesvirus (e.g., herpes simplex virus), poxvirus, baculovirus, papillomavirus, and papovavirus (e.g., SV40). Examples of expression vectors are pClneo vectors (Promega) for expression in mammalian cells; pLenti4/V5-DEST™, pLenti6/V5-DEST®, and pLenti6.2/V5-GW/lacZ (Invitrogen) for lentivirus-mediated gene transfer and expression in mammalian cells.

In some embodiments, the vector is an episomal vector or a vector that is maintained extrachromosomally. As used herein, the term "episomal" refers to a vector that is able to replicate without integration into host's chromosomal DNA and without gradual loss from a dividing host cell also meaning that said vector replicates extrachromosomally or episomally. The vector is engineered to harbor the sequence coding for the origin of DNA replication or "ori" from a lymphotrophic herpes virus or a gamma herpesvirus, an adenovirus. SV40, a bovine papilloma virus, or a yeast, specifically a replication origin of a lymphotrophic herpes virus or a gamma herpesvirus corresponding to oriP of EBV. In some embodiments, the lymphotrophic herpes virus may be Epstein Barr virus (EBV), Kaposi's sarcoma herpes virus (KSHV), Herpes virus saimiri (HS), or Marek's disease virus (MDV). Epstein Barr virus (EBV) and Kaposi's sarcoma herpes virus (KSHV) are also examples of a gamma herpesvirus. Typically, the host cell comprises the viral replication transactivator protein that activates the replication.

"Expression control sequences," "control elements," or "regulatory sequences" present in an expression vector are those non-translated regions of the vector-origin of replication, selection cassettes, promoters, enhancers, translation initiation signals (Shine Dalgamo sequence or Kozak sequence) introns, a polyadenylation sequence, 5' and 3' untranslated regions-which interact with host cellular proteins to carry out transcription and translation. Such elements can vary in their strength and specificity. Depending on the vector system and host utilized, any number of suitable transcription and translation elements, including ubiquitous promoters and inducible promoters can be used.

Illustrative ubiquitous expression control sequences that can be used in present disclosure include, but are not limited to, a cytomegalovirus (CMV) immediate early promoter, a viral simian virus 40 (SV40) promoter (e.g., early or late), a Moloney murine leukemia virus (MoMLV) LTR promoter, a Rous sarcoma virus (RSV) LTR, a herpes simplex virus (HSV) (thymidine kinase) promoter, H5, P7.5, and P11 promoters from vaccinia virus, an elongation factor 1-alpha (EFla) promoter, early growth response 1 (EGR1), ferritin H (FerH), ferritin L (FerL), Glyceraldehyde 3-phosphate dehydrogenase (GAPDH), eukaryotic translation initiation factor 4A1 (EIF4A1), heat shock 70 kDa protein 5 (HSPA5), heat shock protein 90 kDa beta, member 1 (HSP90B1), heat shock protein 70 kDa (HSP70), β-kinesin (β-KIN), the human ROSA 26 locus (Irions et al., *Nature Biotechnology* 25, 1477-1482 (2007)), a Ubiquitin C promoter (UBC), a phosphoglycerate kinase-1 (PGK) promoter, a cytomegalovirus enhancer/chicken β-actin (CAG) promoter, and a β-actin promoter.

Illustrative examples of inducible promoters/systems include, but are not limited to, steroid-inducible promoters such as promoters for genes encoding glucocorticoid or estrogen receptors (inducible by treatment with the corresponding hormone), metallothionine promoter (inducible by treatment with various heavy metals). MX-1 promoter (inducible by interferon), the "GeneSwitch" mifepristone-regulatable system (Sirin et al., 2003, *Gene,* 323:67), the cumate inducible gene switch (WO 2002/088346), tetracycline-dependent regulatory systems, etc. The anti-TIM-3 antibodies or antigen-binding fragments described herein can be produced by any method known in the art, including chemical synthesis and recombinant expression techniques. The practice of the invention employs, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described in the references cited herein and are fully explained in the literature. See. e.g., Maniatis et al. (1982) MOLECULAR CLONING: A LABORATORY MANUAL, Cold Spring Harbor Laboratory Press: Sambrook et al. (1989), MOLECULAR CLONING: A LABORATORY MANUAL, Second Edition, Cold Spring Harbor Laboratory Press; Sambrook et al. (2001) MOLECULAR CLONING: A LABORATORY MANUAL, Cold Spring Harbor Laboratory Press, Cold Spring Harbor, NY: Ausubel et al., CURRENT PROTOCOLS IN MOLECULAR BIOLOGY, John Wiley & Sons (1987 and annual updates); CURRENT PROTOCOLS IN IMMUNOLOGY, John Wiley & Sons (1987 and annual updates) Gait (ed.) (1984) OLIGONUCLEOTIDE SYNTHESIS: A PRACTICAL APPROACH, IRL Press; Eckstein (ed.) (1991) OLIGONUCLEOTIDES AND ANALOGUES: A PRACTICAL APPROACH, IRL Press; Birren et al. (eds.) (1999) GENOME ANALYSIS: A LABORATORY MANUAL, Cold Spring Harbor Laboratory Press; Borrebaeck (ed.) (1995) ANTIBODY ENGINEERING, Second Edition, Oxford University Press: Lo (ed.) (2006) ANTIBODY ENGINEERING: METHODS AND PROTOCOLS (METHODS IN MOLECULAR BIOLOGY): Vol. 248, Humana Press, Inc; each of which is incorporated herein by reference in its entirety.

The polypeptides described herein (e.g., the anti-TIM-3 antibodies or antigen-binding fragments) can be produced and isolated using methods known in the art. Peptides can be synthesized, in whole or in part, using chemical methods (see, e.g., Caruthers (1980). *Nucleic Acids Res. Symp. Ser.* 215; Horn (1980); and Banga. A. K., THERAPEUTIC PEPTIDES AND PROTEINS, FORMULATION, PROCESSING AND DELIVERY SYSTEMS (1995) Technomic Publishing Co., Lancaster, PA). Peptide synthesis can be performed using various solid phase techniques (see, e.g., Roberge, *Science* 269:202 (1995); Merrifield, *Methods. Enzymol.* 289:3 (1997)) and automated synthesis may be achieved, e.g., using the ABI 431A Peptide Synthesizer (Perkin Elmer) in accordance with the manufacturer's instructions. Peptides can also be synthesized using combinatorial methodologies. Synthetic residues and polypeptides can be synthesized using a variety of procedures and methodologies known in the art (see, e.g., ORGANIC SYNTHESES COLLECTIVE VOLUMES, Gilman, et al. (Eds) John Wiley & Sons, Inc., NY). Modified peptides can be produced by chemical modification methods (see, for example, Belousov, *Nucleic Acids Res.* 25:3440 (1997); *Frenkel, Free Radic. Biol. Med.* 19:373 (1995); and Blommers, *Biochemistry* 33:7886 (1994)). Peptide sequence variations, derivatives, substitutions and modifications can also be made using methods such as oligonucleotide-mediated (site-directed) mutagenesis, alanine scanning, and PCR based mutagenesis. Site-directed mutagenesis (Carter et al., *Nucl. Acids Res.,* 13:4331 (1986); Zoller et al., *Nucl. Acids Res.* 10:6487 (1987)), cassette mutagenesis (Wells et al., Gene 34:315 (1985)), restriction selection mutagenesis (Wells et al., *Philos. Trans. R. Soc. London SerA* 317:415 (1986)) and other techniques can be performed on cloned DNA to produce invention peptide sequences, variants, fusions and chimeras, and variations, derivatives, substitutions and modifications thereof.

The polypeptides described herein can be prepared using a wide variety of techniques known in the art including the use of hybridoma and recombinant technologies, or a combination thereof. In some embodiments, a recombinant expression vector is used to express a polynucleotide encoding a polypeptide described herein. For example, a recombinant expression vector can be a replicable DNA construct that includes synthetic or cDNA-derived DNA fragments encoding a polypeptide operatively linked to suitable transcriptional and/or translational regulatory elements derived from mammalian, microbial, viral or insect genes. In some embodiments, coding sequences of polypeptides disclosed herein can be ligated into such expression vectors for their expression in mammalian cells. In some embodiments, a viral vector is used. DNA regions are "operatively linked" when they are functionally related to each other. For example, a promoter is operatively linked to a coding sequence if it controls the transcription of the sequence; or a ribosome binding site is operatively linked to a coding sequence if it is positioned so as to permit translation. In some embodiments, structural elements intended for use in yeast expression systems include a leader sequence enabling extracellular secretion of translated protein by a host cell. In some embodiments, in situations where recombinant protein is expressed without a leader or transport sequence, a polypeptide can include an N-terminal methionine residue.

A wide variety of expression host/vector combinations can be employed. Suitable host cells for expression include prokaryotes, yeast cells, insect cells, or higher eukaryotic cells under the control of appropriate promoters. Appropriate cloning and expression vectors for use with bacterial, fungal, yeast, and mammalian cellular hosts, as well as methods of protein production, including antibody production are well-known in the art. Useful expression vectors for bacterial hosts include known bacterial plasmids, such as plasmids from *E. coli*, including pCR1, pBR322, pMB9 and their derivatives, and wider host range plasmids, such as M13 and other filamentous single-stranded DNA phages.

Useful expression vectors for eukaryotic hosts include, for example, vectors comprising expression control sequences from SV40, bovine papilloma virus, adenovirus, and cytomegalovirus. Examples of suitable mammalian host cell lines include, but are not limited to, COS-7 (monkey kidney-derived), L-929 (murine fibroblast-derived), C127 (murine mammary tumor-derived), 3T3 (murine fibroblast-derived), CHO (Chinese hamster ovary-derived). HeLa (human cervical cancer-derived), BHK (hamster kidney fibroblast-derived), HEK-293 (human embryonic kidney-derived) cell lines and variants thereof. Mammalian expression vectors can comprise non-transcribed elements such as an origin of replication, a suitable promoter and enhancer linked to the gene to be expressed, and other 5' or 3' flanking non-transcribed sequences, and 5' or 3' non-translated sequences, such as necessary ribosome binding sites, a polyadenylation site, splice donor and acceptor sites, and transcriptional termination sequences. Expression of recombinant proteins in insect cell culture systems (e.g., baculovirus) also offers a robust method for producing correctly folded and biologically functional proteins. Baculovirus systems for production of heterologous proteins in insect cells are well-known to those of skill in the art.

Provided herein are anti-TIM-3 antibodies and antigen-binding fragments thereof that include but are not limited to monoclonal antibodies, polyclonal antibodies, synthetic antibodies, human antibodies, humanized antibodies, and antigen-binding fragments thereof.

Methods of antibody production are well-known in the art. See for example, in Harlow et al., Antibodies: A Laboratory Manual, (Cold Spring Harbor Laboratory Press, 2nd ed. 1988); Hammerling et al., in: MONOCLONAL ANTIBODIES AND T-CELL HYBRIDOMAS 563 681 (Elsevier, N.Y., 1981), each of which is incorporated herein by reference in its entirety. For in vivo use of antibodies in humans, it may be preferable to use human antibodies. Completely human antibodies are particularly desirable for therapeutic treatment of human subjects. Human antibodies can be made by a variety of methods known in the art including phage display methods using antibody libraries derived from human immunoglobulin sequences, including improvements to these techniques. See, also, U.S. Pat. Nos. 4,444,887 and 4,716,111; and PCT publications WO 98/46645, WO 98/50433. WO 98/24893, WO98/16654, WO 96/34096, WO 96/33735, and WO 91/10741; each of which is incorporated herein by reference in its entirety. A human antibody can also be an antibody wherein the heavy and light chains are encoded by a nucleotide sequence derived from one or more sources of human DNA.

Human antibodies can also be produced using transgenic mice which are incapable of expressing functional endogenous immunoglobulins, but which can express human immunoglobulin genes. For example, the human heavy and light chain immunoglobulin gene complexes can be introduced randomly or by homologous recombination into mouse embryonic stem cells. Alternatively, the human variable region, constant region, and diversity region can be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. For example, it has been described that the homozygous deletion of the antibody heavy chain joining region (JH) gene in chimeric and germ-line mutant mice results in complete inhibition of endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. For example, anti-TIM-3 antibodies directed against the human TIM-3 antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies, including, but not limited to, IgG1 (gamma 1) and IgG3. For an overview of this technology for producing human antibodies, see, Lonberg and Huszar (*Int. Rev. Immunol.,* 13:65-93 (1995)). For a detailed discussion of this technology for producing human antibodies and human monoclonal antibodies and protocols for producing such antibodies, see, e.g., PCT Publication Nos. WO 98/24893, WO 96/34096, and WO 96/33735; and U.S. Pat. Nos. 5,413,923; 5,625,126; 5,633,425; 5,569,825; 5,661,016; 5,545,806; 5,814,318; and 5,939,598, each of which is incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above. For a specific discussion of transfer of a human germ-line immunoglobulin gene array in germ-line mutant mice that will result in the production of human antibodies upon antigen challenge see, e.g., Jakobovits et al., *Proc. Natl. Acad. Sci. USA,* 90:2551 (1993); Jakobovits et al., *Nature,* 362:255-258 (1993); Bruggermann et al., *Year in Immunol.,* 7:33 (1993); and Duchosal et al., *Nature,* 355:258 (1992).

Human antibodies can also be derived from phage-display libraries (Hoogenboom et al., *J. Mol. Biol.,* 227:381 (1991); Marks et al., *J. Mol. Biol.,* 222:581-597 (1991); Vaughan et al., *Nature Biotech.,* 14:309 (1996)). Phage display technology (McCafferty et al., *Nature,* 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats: for their review see, e.g., Johnson and Chiswell, *Current Opinion in Structural Biology* 3:564-571 (1993). Several sources of V-gene segments can be used for phage display. Clackson et al., *Nature,* 352:624-628 (1991) isolated a diverse array of anti-oxazolone antibodies from a small random combinatorial library of V genes derived from the spleens of unimmunized mice. A repertoire of V genes from unimmunized human donors can be constructed and antibodies to a diverse array of antigens (including self-antigens) can be isolated essentially following the techniques described by Marks et al., *J. Mol. Biol.,* 222:581-597 (1991), or Griffith et al., *EMBO J.,* 12:725-734 (1993). See, also, U.S. Pat. Nos. 5,565,332 and 5,573,905, each of which is incorporated herein by reference in its entirety.

Human antibodies can also be generated by in vitro activated B cells (see, U.S. Pat. Nos. 5,567,610 and 5,229,275, each of which is incorporated herein by reference in its entirety). Human antibodies can also be generated in vitro using hybridoma techniques such as, but not limited to, that described by Roder et al. (*Methods Enzymol.,* 121:140-167 (1986)).

Alternatively, in some embodiments, a non-human antibody is humanized, where specific sequences or regions of the antibody are modified to increase similarity to an antibody naturally produced in a human. In some embodiment, the antigen binding domain portion is humanized.

A humanized antibody can be produced using a variety of techniques known in the art, including but not limited to, CDR-grafting (see, e.g., European Patent No. EP 239,400;

International Publication No. WO 91/09967, and U.S. Pat. Nos. 5,225,539, 5,530,101, and 5,585,089, each of which is incorporated herein in its entirety by reference), veneering or resurfacing (see, e.g., European Patent Nos. EP 592,106 and EP 519,596: Padlan, 1991, *Molecular Immunology.* 28(4/5): 489-498; Studnicka et al., 1994, *Protein Engineering*, 7(6): 805-814; and Roguska et al., 1994, *PNAS,* 91:969-973, each of which is incorporated herein by its entirety by reference), chain shuffling (see, e.g., U.S. Pat. No. 5,565,332, which is incorporated herein in its entirety by reference), and techniques disclosed in, e.g., U.S. Patent Application Publication No. US2005/0042664, U.S. Patent Application Publication No. US2005/0048617, U.S. Pat. Nos. 6,407,213, 5,766,886, International Publication No. WO 9317105, Tan et al., *J. Immunol.,* 169:1119-25 (2002), Caldas et al., *Protein Eng.,* 13(5):353-60 (2000), Morea et al., *Methods,* 20(3):267-79 (2000), Baca et al., *J. Biol. Chem.,* 272(16):10678-84 (1997). Roguska et al., *Protein Eng.,* 9(10):895-904 (1996), Couto et al., *Cancer Res.,* 55 (23 Supp):5973s-5977s (1995), Couto et al., *Cancer Res.,* 55(8):1717-22 (1995). Sandhu J S, *Gene,* 150(2):409-10 (1994), and Pedersen et al., *J. Mol. Biol.,* 235(3):959-73 (1994), each of which is incorporated herein in its entirety by reference. Often, framework residues in the framework regions can be substituted with the corresponding residue from the CDR donor antibody to alter, preferably improve, antigen binding. These framework substitutions are identified by methods well-known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, *Nature,* 332:323, which are incorporated herein by reference in their entireties.)

A humanized antibody has one or more amino acid residues introduced into it from a source which is nonhuman. These nonhuman amino acid residues are often referred to as "import" residues, which are typically taken from an "import" variable domain. Thus, humanized antibodies comprise one or more CDRs from nonhuman immunoglobulin molecules and framework regions from human. Humanization of antibodies is well-known in the art and can essentially be performed following the method of Winter and co-workers (Jones et al., *Nature,* 321:522-525 (1986): Riechmann et al., *Nature,* 332:323-327 (1988); Verhoeyen et al., *Science,* 239:1534-1536 (1988)), by substituting rodent CDRs or CDR sequences for the corresponding sequences of a human antibody, i.e., CDR-grafting (EP 239,400; PCT Publication No. WO 91/09967; and U.S. Pat. Nos. 4,816, 567; 6,331,415; 5,225,539; 5,530,101; 5,585,089; 6,548, 640, the contents of which are incorporated herein by reference herein in their entirety). In such humanized chimeric antibodies, substantially less than an intact human variable domain has been substituted by the corresponding sequence from a nonhuman species. In practice, humanized antibodies are typically human antibodies in which some CDR residues and possibly some FR residues are substituted by residues from analogous sites in rodent antibodies. Humanization of antibodies can also be achieved by veneering or resurfacing (EP 592,106; EP 519,596; Padlan, 1991, Molecular Immunology, 28(4/5):489-498; Studnicka et al., *Protein Engineering,* 7(6):805-814 (1994); and Roguska et al., *PNAS,* 91:969-973 (1994)) or chain shuffling (U.S. Pat. No. 5,565,332), the contents of which are incorporated herein by reference herein in their entirety.

The choice of human variable domains, both light and heavy, to be used in making the humanized antibodies is to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., *J. Immunol.,* 151:22% (1993), Chothia et al., *J. Mol. Biol.,* 196.901 (1987), the contents of which are incorporated herein by reference herein in their entirety). Another method uses a particular framework derived from the consensus sequence of all human antibodies of a particular subgroup of light or heavy chains. The same framework may be used for several different humanized antibodies (Carter et al., *Proc. Natl. Acad. Sci. USA,* 89:4285 (1992); Presta et al., *J. Immunol.,* 151:2623 (1993), the contents of which are incorporated herein by reference herein in their entirety).

Antibodies can be humanized with retention of high affinity for the target antigen and other favorable biological properties. For example, humanized antibodies can be prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind the target antigen. In this way, FR residues can be selected and combined from the recipient and import sequences so that the desired antibody characteristic, such as increased affinity for the target antigen, is achieved. In general, the CDR residues are directly and most substantially involved in influencing antigen binding.

A humanized antibody retains a similar antigenic specificity as the original antibody, for example, the ability to bind human TIM-3 antigen. However, using certain methods of humanization, the affinity and/or specificity of binding of the antibody for a particular antigen can be increased using methods of "directed evolution," as described by Wu et al., *J. Mol. Biol.,* 294:151 (1999), the contents of which are incorporated herein by reference herein in their entirety.

6.5 Pharmaceutical Compositions

Provided herein are also pharmaceutical compositions comprising the anti-TIM-3 antibodies or antigen-binding fragments disclosed herein. In some embodiments, the pharmaceutical composition comprises a therapeutically effective amount of the anti-TIM-3 antibodies or antigen-binding fragments disclosed herein and a pharmaceutically acceptable carrier. In some embodiments, the pharmaceutical compositions are useful in immunotherapy. In some embodiments, the pharmaceutical compositions are useful in immuno-oncology. In some embodiments, the pharmaceutical compositions are useful in inhibiting tumor growth in a subject (e.g., a human patient). In some embodiments, the pharmaceutical compositions are useful in treating cancer in a subject (e.g., a human patient).

In some embodiments, the pharmaceutical compositions provided herein comprise anti-TIM-3 antibodies or antigen-binding fragments provided herein. The anti-TIM-3 antibodies or antigen-binding fragments can be present at various concentrations. In some embodiments, the pharmaceutical compositions provided herein comprise soluble anti-TIM-3 antibodies or antigen-binding fragments provided herein at 1-1000 mg/ml. In some embodiments, the pharmaceutical compositions comprise soluble anti-TIM-3 antibodies or antigen-binding fragments provided herein at 10-500 mg/ml, 10-400 mg/ml, 10-300 mg/ml, 10-200 mg/ml, 10-100 mg/ml, 20-100 mg/ml, or 50-100 mg/ml. In some embodiments, the pharmaceutical compositions provided herein comprise anti-TIM-3 antibodies or antigen-binding fragments provided herein at about 10 mg/ml, about 20 mg/ml, about 30 mg/ml, about 40 mg/ml, about 50 mg/ml, about 60 mg/ml, about 70 mg/ml, about 80 mg/ml, about 90 mg/ml, about 100 mg/ml, about 120 mg/ml, about 150 mg/ml, about 180 mg/ml, about 200 mg/ml, about 300 mg/ml, about 500 mg/ml, about 800 mg/ml, or about 100 mg/ml. Dosages can be readily adjusted by those skilled in the art; for example, a decrease in purity may require an increase in dosage.

Provided herein are also kits for preparation of pharmaceutical compositions having the anti-TIM-3 antibodies or antigen-binding fragments disclosed herein. In some embodiments, the kit comprises the anti-TIM-3 antibodies or antigen-binding fragments disclosed herein and a pharmaceutically acceptable carrier in one or more containers. In another embodiment, the kits can comprise anti-TIM-3 antibodies or antigen-binding fragments disclosed herein for administration to a subject. In specific embodiments, the kits comprise instructions regarding the preparation and/or administration of the anti-TIM-3 antibodies or antigen-binding fragments.

In some embodiments, provided herein is a pharmaceutical composition comprising anti-TIM-3 antibodies or antigen-binding fragments or cells provided herein wherein the composition is suitable for local administration. In some embodiments, local administration comprises intratumoral injection, peritumoral injection, juxtatumoral injection, intralesional injection and/or injection into a tumor draining lymph node, or essentially any tumor-targeted injection where the antitumor agent is expected to leak into primary lymph nodes adjacent to targeted solid tumor.

Pharmaceutically acceptable carriers that can be used in compositions provided herein include any and all solvents, dispersion media, coatings, antibacterial and antifungal agents, isotonic and absorption delaying agents, and the like that are physiologically compatible. In some embodiments, the carrier is suitable for intravenous, intramuscular, subcutaneous, parenteral, spinal or epidermal administration (e.g., by injection or infusion). Depending on the route of administration, the active ingredient (i.e., anti-TIM-3 antibodies or antigen-binding fragments or immune effector cells provided herein), can be coated in a material to protect the active ingredient from the action of acids and other natural conditions that can inactivate the active ingredient.

Provided herein are also pharmaceutical compositions or formulations that improve the stability of the anti-TIM-3 antibodies or antigen-binding fragments to allow for their long-term storage. In some embodiments, the pharmaceutical composition or formulation disclosed herein comprises; (a) anti-TIM-3 antibodies or antigen-binding fragments disclosed herein; (b) a buffering agent; (c) a stabilizing agent; (d) a salt; (e) a bulking agent; and/or (f) a surfactant. In some embodiments, the pharmaceutical composition or formulation is stable for at least 1 month, at least 2 months, at least 3 months, at least 6 months, at least 1 year, at least 2 years, at least 3 years, at least 5 years or more. In some embodiments, the pharmaceutical composition or formulation is stable when stored at 4° C., 25° C., or 40° C.

Buffering agents useful in the pharmaceutical compositions or formulations disclosed herein can be a weak acid or base used to maintain the acidity (pH) of a solution near a chosen value after the addition of another acid or base. Suitable buffering agents can maximize the stability of the pharmaceutical formulations by maintaining pH control of the formulation. Suitable buffering agents can also ensure physiological compatibility or optimize solubility. Rheology, viscosity and other properties can also depend on the pH of the formulation. Common buffering agents include, but are not limited to, histidine, citrate, succinate, acetate and phosphate. In some embodiments, a buffering agent comprises histidine (e.g., L-histidine) with isotonicity agents and potentially pH adjustment with an acid or a base known in the art. In certain embodiments, the buffering agent is L-histidine. In certain embodiments, the pH of the formulation is maintained between about 2 and about 10, or between about 4 and about 8.

Stabilizing agents are added to a pharmaceutical product to stabilize that product. Such agents can stabilize proteins in different ways. Common stabilizing agents include, but are not limited to, amino acids such as glycine, alanine, lysine, arginine, or threonine, carbohydrates such as glucose, sucrose, trehalose, raffinose, or maltose, polyols such as glycerol, mannitol, sorbitol, cyclodextrins or destrans of any kind and molecular weight, or PEG. In some embodiments, the stabilizing agent is chosen to maximize the stability of FIX polypeptide in lyophilized preparations. In certain embodiments, the stabilizing agent is sucrose and/or arginine.

Bulking agents can be added to a pharmaceutical composition or formulation to add volume and mass to the product, thereby facilitating precise metering and handling thereof. Common bulking agents include, but are not limited to, lactose, sucrose, glucose, mannitol, sorbitol, calcium carbonate, or magnesium stearate.

Surfactants are amphipathic substances with lyophilic and lyophobic groups. A surfactant can be anionic, cationic, zwitterionic, or nonionic. Examples of nonionic surfactants include, but are not limited to, alkyl ethoxylate, nonylphenol ethoxylate, amine ethoxylate, polyethylene oxide, polypropylene oxide, fatty alcohols such as cetyl alcohol or oleyl alcohol, cocamide MEA, cocamide DEA, polysorbates, or dodecyl dimethylamine oxide. In some embodiments, the surfactant is polysorbate 20 or polysorbate 80.

The pharmaceutical compositions disclosed herein can further comprise one or more of a buffer system, a preservative, a tonicity agent, a chelating agent, a stabilizer and/or a surfactant, as well as various combinations thereof. The use of preservatives, isotonic agents, chelating agents, stabilizers and surfactants in pharmaceutical compositions is well-known to the skilled person. Reference may be made to *Remington: The Science and Practice of Pharmacy,* $19^{th}$ edition, 1995.

In some embodiments, the pharmaceutical composition is an aqueous formulation. Such a formulation is typically a solution or a suspension, but can also include colloids, dispersions, emulsions, and multi-phase materials. The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In some embodiments, the pharmaceutical compositions disclosed herein are freeze-dried, to which the physician or the patient adds solvents and/or diluents prior to use.

Pharmaceutical compositions disclosed herein can also include a pharmaceutically acceptable antioxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that can be employed in the pharmaceutical compositions or formulations described herein include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions can also contain adjuvants such as preservatives, wetting agents, emulsifying agents and dispersing agents. Prevention of presence of microorganisms can be ensured both by sterilization procedures, supra, and by the inclusion of various antibacterial and antifungal agents, for example, paraben, chlorobutanol, phenol sorbic acid, and the like. It can also be desirable to include isotonic agents, such as sugars, sodium chloride, and the like into the compositions. In addition, prolonged absorption of the injectable pharmaceutical form can be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions described herein is contemplated. A pharmaceutical composition or formulation can comprise a preservative or can be devoid of a preservative. Supplementary active compounds can be incorporated into the compositions.

Pharmaceutical compositions or formulations typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, the compositions can include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated herein. In the case of sterile powders for the preparation of sterile injectable solutions, some methods of preparation are vacuum drying and freeze-drying (lyophilization) that yield a powder of the active ingredient plus any additional desired ingredient from a previously sterile-filtered solution thereof.

The amount of active ingredient which can be combined with a carrier material in the pharmaceutical compositions or formulations disclosed herein can vary. In some embodiments, the amount of active ingredient which can be combined with a carrier material is the amount that produces a therapeutic effect. Generally, out of one hundred percent, this amount will range from about 0.01 percent to about ninety-nine percent of active ingredient, from about 0.1 percent to about 70 percent, or from about 1 percent to about 30 percent of active ingredient in combination with a pharmaceutically acceptable carrier.

The pharmaceutical compositions disclosed herein can be prepared with carriers that protect the active ingredient against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and poly lactic acid. Many methods for the preparation of such formulations are patented or generally known to those skilled in the art. See. e.g., Sustained and *Controlled Release Drug Delivery Systems*, J. R. Robinson, ed., Marcel Dekker, Inc., New York, 1978.

In some embodiments, the anti-TIM-3 antibodies or antigen-binding fragments or immune effector cells (e.g., T cells) described herein can be formulated to ensure proper distribution in vivo. For example, the blood-brain barrier (BBB) excludes many highly hydrophilic compounds. To ensure that the activate ingredient described herein cross the BBB (if desired, e.g., for brain cancers), they can be formulated, for example, in liposomes. For methods of manufacturing liposomes, see. e.g., U.S. Pat. Nos. 4,522,811; 5,374,548; and 5,399,331. The liposomes can comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see. e.g., U.S. Pat. No. 5,416,016 to Low et al) mannosides (Umezawa et al, (1988) *Biochem. Biophys. Res. Commun.* 153: 1038); antibodies (P. G. Bloeman et al. (1995) *FEBS Lett.* 357: 140; M. Owais et al. (1995) *Antimicrob. Agents Chemother.* 39: 180); surfactant protein A receptor (Briscoe et al. (1995) *Am. J. Physiol.* 1233: 134): p120 (Schreier et al. (1994) *J. Biol. Chem.* 269:9090); see also K. Keinanen; M. L. Laukkanen (1994) *FEBS Lett.* 346: 123; J. J. Killion; I. J. Fidler (1994) *Immunomethods* 4:273.

Anti-TIM-3 antibodies or antigen-binding fragments described herein can be tested for binding to human TIM-3 by, for example, standard ELISA. Briefly, microtiter plates are coated with purified TIM-3, and then blocked with bovine serum albumin. Dilutions of antibody (e.g., dilutions of plasma from TIM-3-immunized mice) are added to each well and incubated. The plates are washed and incubated with secondary reagent (e.g., for human antibodies, a goat-anti-human IgG Fc-specific polyclonal reagent) conjugated to horseradish peroxidase (HRP). After washing, the plates can be developed and analyzed by a spectrophotometer. Sera from immunized mice can then be further screened by flow cytometry for binding to a cell line expressing human TIM-3, but not to a control cell line that does not express TIM-3. Briefly, the binding of anti-TIM-3 antibodies can be assessed by incubating TIM-3 expressing CHO cells with the anti-TIM-3 antibody. The cells can be washed and binding can be detected with an anti-human IgG Ab. Flow cytometric analyses can be performed using a FACScan flow cytometry (Becton Dickinson, San Jose, CA). Mice which develop the highest titers can be used for fusions.

An ELISA assay as described above can be used to screen for antibodies and, thus, hybridomas that produce antibodies that show positive reactivity with the TIM-3 immunogen Hybridomas that produce antibodies that bind with high affinity to TIM-3 can then be subcloned and further characterized. One clone from each hybridoma, which retains the reactivity of the parent cells (by ELISA), can then be chosen for making a cell bank, and for antibody purification.

To purify anti-TIM-3 antibodies, selected hybridomas can be grown for monoclonal antibody purification. Supernatants can be filtered and concentrated before affinity chromatography. Eluted IgG can be checked by gel electrophoresis and high-performance liquid chromatography to ensure purity. The buffer solution can be exchanged, and the concentration can be determined. The monoclonal antibodies can be aliquoted and stored.

To determine if the selected anti-TIM-3 monoclonal antibodies bind to unique epitopes, each antibody can be biotinylated using commercially available reagents (Pierce. Rockford, IL). Biotinylated MAb binding can be detected with a streptavidin labeled probe. Competition studies using unlabeled monoclonal antibodies and biotinylated monoclonal antibodies can be performed using TIM-3 coated-ELISA plates as described above.

To determine the isotype of purified antibodies, isotype ELISAs can be performed using reagents specific for antibodies of a particular isotype. For example, to determine the isotype of a human monoclonal antibody, wells of microtiter plates can be coated with 1 pg/ml of anti-human immunoglobulin overnight at 4° C. After blocking with 1% BSA, the plates are reacted with 1 fig/ml or less of test monoclonal antibodies or purified isotype controls, at ambient temperature for one to two hours. The wells can then be reacted with either human IgG1 or human IgM-specific alkaline phosphatase-conjugated probes. Plates are developed and analyzed as described above.

To test the binding of monoclonal antibodies to live cells expressing TIM-3, flow cytometry can be used, as described in the Examples. Briefly, cell lines expressing membrane-bound TIM-3 (grown under standard growth conditions) are mixed with various concentrations of monoclonal antibodies in PBS containing 0.1% BSA at 4° C. for 1 hour. After washing, the cells are reacted with Fluorescein-labeled anti-IgG antibody under the same conditions as the primary antibody staining. The samples can be analyzed by FACScan instrument using light and side scatter properties to gate on single cells and binding of the labeled antibodies is determined. An alternative assay using fluorescence microscopy can be used (in addition to or instead of) the flow cytometry assay. Cells can be stained exactly as described above and examined by fluorescence microscopy. This method allows visualization of individual cells, but can have diminished sensitivity depending on the density of the antigen.

Anti-TIM-3 antibodies or antigen-binding fragments can be further tested for reactivity with the TIM-3 antigen by Western blotting. Briefly, cell extracts from cells expressing TIM-3 can be prepared and subjected to sodium dodecyl sulfate polyacrylamide gel electrophoresis. After electrophoresis, the separated antigens will be transferred to nitrocellulose membranes, blocked with 20% mouse serum, and probed with the monoclonal antibodies to be tested. IgG binding can be detected using anti-IgG alkaline phosphatase and developed with BCIP/NBT substrate tablets (Sigma Chem. Co., St. Louis. MO).

Methods for analyzing binding affinity, cross-reactivity, and binding kinetics of various anti-TIM-3 antibodies include standard assays known in the art, for example, biolayer interferometry (BLI) using, for example, Gator system (Probe Life) or the Octet-96 system (Sartorius AG), or BIACORE™ surface plasmon resonance (SPR) analysis using a BIACORE™ 2000 SPR instrument (Biacore AB, Uppsala, Sweden).

A variety of assays can be used to characterize the biological activity of anti-TIM-3 antibodies (which can be used, e.g., for comparing different anti-TIM-3 antibodies), such as those described herein:

(1) T cell activation assays, such as assays using purified T cells obtained from PBMCs of human donors. Assays can be conducted with total T cells or subpopulations thereof, e.g., hl cells. T cytotoxic cells, Treg cells, CD4+ T cells, CD8+ T cells, provided that they express TIM-3. Activation may be measured by determining the level of secretion of certain cytokines, e.g., interferon-g or IL-2 or the level of proliferation of the T cells. Without wanting to be limited to a particular mechanism of action, binding of anti-TIM-3 antibodies to TIM-3 on T cells may prevent binding of TIM-3 to a TIM-3 ligand (TIM-3 putative ligands include Galectin-9, HMGB 1, Semaphorin-4A, CEACAM-1, ILT-4 and phosphatidylserine) and thereby prevent TIM-3 mediated signaling in the T cell thereby preventing negatively regulation of T cells by TIM-3. Exemplary assays, including Th1 assays, TIL assays and mixed lymphocyte reactions (MLRs) are well known in the art.

(2) assays measuring stimulation of macrophages, e.g., M1 or M2 macrophage.

(3) assays measuring secretion of myeloid-associated cytokines, e.g., TNFα, IL-1β, GM-CSF, IL-6, IL-2, IL-10, CCL2, CCL3, CCL4 or CCL5 from TIM-3 positive myeloid cells. In some embodiments, anti-TIM-3 antibodies stimulate the secretion of TNFα, IL-1β, GM-CSF, IL-6, and IL-2 and/or inhibit the secretion of IL-10, CCL2, CCL3, CCL4 or CCL5 from TIM-3 positive myeloid cells.

Generally, any method for testing the biological activity of an agent that inhibits immune responses can be used to characterize the biological activity of anti-TIM-3 antibodies or antigen-binding fragments, e.g., those described in the literature (including patents and patent applications) relating to TIM-3.

6.6 Methods and Uses

The antibodies or antigen-binding fragments, compositions and methods described herein have numerous in vitro and in vivo utilities involving, for example, enhancement of immune response, such as by inhibiting (or antagonizing) TIM-3 (e.g., signaling), or detection of TIM-3. In some embodiments, the anti-TIM-3 antibodies or antigen-binding fragments described herein are humanized antibodies or antigen-binding fragments. For example, anti-TIM-3 antibodies or antigen-binding fragments described herein can be administered to cells in culture, in vitro or ex vivo, or to human subjects, e.g., in vivo, to enhance immunity in a variety of diseases. Accordingly, provided herein are methods of modifying an immune response in a subject comprising administering to the subject an anti-TIM-3 antibody, or antigen binding portion thereof, described herein such that the immune response in the subject is modified. In some embodiments, the response is enhanced, stimulated or up-regulated.

In some embodiments, provided herein are methods of inducing or stimulating immune cell activation comprising contacting an immune cell with an effective amount of an anti-TIM-3 antibody or antigen binding fragment described herein. In some embodiments, provided herein are methods of inducing or stimulating immune cell proliferation comprising contacting an immune cell with an effective amount of an anti-TIM-3 antibody or antigen binding fragment described herein. In some embodiments, provided herein are methods of reducing TIM-3 mediated suppression of an immune cell proliferation comprising contacting an immune cell with an effective amount of an anti-TIM-3 antibody or antigen binding fragment described herein. In some embodiments, provided herein are methods of inhibiting the interaction between TIM-3 and a TIM-3 ligand (e.g., phosphatidylserine) on an immune cell comprising contacting the immune cell with an effective amount of an anti-TIM-3 antibody or antigen binding fragment described herein. In some embodiments, provided herein are methods of increasing cytokine (e.g., IFN-γ) production by an immune cell comprising contacting an immune cell with an effective amount of an anti-TIM-3 antibody or antigen binding fragment described herein.

The immune cells can be, for example, T cells such as $CD4^+$ T cells, $CD8^+$ T cells, T helper (Th) cells (e.g., Th1 cells), T cytotoxic (Tc) cells or TILs. The immune cells can also be NK cells, NKT cells, or myeloid cells.

Subjects suitable for the present methods include human patients in whom enhancement of an immune response would be desirable. The methods are particularly suitable for treating human patients having a disorder that can be treated by augmenting an immune response (e.g., a T-cell mediated immune response, e.g., an antigen specific T cell response). In some embodiments, the methods are particularly suitable for treatment of cancer in vivo. To achieve antigen-specific enhancement of immunity, anti-TIM-3 antibodies or antigen-binding fragments described herein can be administered together with an antigen of interest or the antigen can already be present in the subject to be treated (e.g., a tumor-bearing or virus-bearing subject). When antibodies to TIM-3 are administered together with another agent, the two can be administered separately or simultaneously.

Also encompassed are methods for detecting the presence of human TIM-3 antigen in a sample, or measuring the amount of human TIM-3 antigen, comprising contacting the sample, and a control sample, with a monoclonal antibody, e.g., a humanized monoclonal antibody, or an antigen binding portion thereof, which specifically binds to human TIM-3, under conditions that allow for formation of a complex between the antibody or antigen-binding fragment and human TIM-3. The formation of a complex is then detected, wherein a difference complex formation between the sample compared to the control sample is indicative the presence of human TIM-3 antigen in the sample. Moreover, the anti-TIM-3 antibodies or antigen-binding fragments described herein can be used to purify human TIM-3 via immunoaffinity purification.

Given the ability of anti-TIM-3 antibodies or antigen-binding fragments described herein to stimulate or co-stimulate T cell responses, e.g., antigen-specific T cell responses, such as by inhibiting negative effects of TIM-3, provided herein are in vitro and in vivo methods of using the anti-TIM-3 antibodies or antigen-binding fragments described herein to stimulate, enhance or upregulate antigen-specific T cell responses, e.g., anti-tumor T cell responses.

In some embodiments, CD3 stimulation is also provided (e.g., by coincubation with a cell expressing membrane CD3), which stimulation can be provided at the same time, before, or after stimulation with an anti-TIM-3 antibody or antigen-binding fragment. For example, provided herein are methods of stimulating an antigen-specific T cell response comprising contacting said T cell with an anti-TIM-3 antibody or antigen-binding fragment described herein, and optionally with an anti-CD3 antibody, such that an antigen-specific T cell response is stimulated.

Any suitable indicator of an antigen-specific T cell response can be used to measure the antigen-specific T cell response. Non-limiting examples of such suitable indicators include increased T cell proliferation in the presence of the antibody and/or increase cytokine production in the presence of the antibody. In some embodiments, interleukin-2 and/or interferon-γ production by the antigen-specific T cell is stimulated.

Further encompassed are methods of stimulating an immune response (e.g., an antigen-specific T cell response) in a subject comprising administering an anti-TIM-3 antibody or antigen-binding fragment described herein to the subject such that an immune response (e.g., an antigen-specific T cell response) in the subject is stimulated. In some embodiments, the subject is a tumor-bearing subject and an immune response against the tumor is stimulated. A tumor can be a solid tumor or a liquid tumor, e.g., a hematological malignancy. In some embodiments, a tumor is an immunogenic tumor. In some embodiments, a tumor is non-immunogenic. In some embodiments, a tumor is PD-L1 positive. In some embodiments a tumor is PD-L1 negative. A subject can also be a virus-bearing subject and an immune response against the virus is stimulated.

Further provided are methods for inhibiting growth of tumor cells in a subject comprising administering to the subject an anti-TIM-3 antibody or antigen-binding fragment described herein such that growth of the tumor is inhibited in the subject. Also provided are methods of treating a viral infection in a subject comprising administering to the subject an anti-TIM-3 antibody described herein such that the viral infection is treated in the subject.

In some embodiments, an anti-TIM-3 antibody is given to a subject as an adjunctive therapy. Treatments of subjects having cancer with an anti-TIM-3 antibody can lead to prolonged survival, e.g., long-term durable response relative to the current standard of care; long term survival of at least 3 months, 6 months, 9 months, 1, 2, 3, 4, 5, 10 or more years, or recurrence-free survival of at least 3 months, 6 months, 9 months, 1, 2, 3, 4, 5, or 10 or more years. In some embodiments, treatment of a subject having cancer with an anti-TIM-3 antibody or antigen-binding fragment prevents recurrence of cancer or delays recurrence of cancer by, e.g., 3 months, 6 months, 9 months, 1, 2, 3, 4, 5, or 10 or more years. An anti-TIM-3 treatment can be used as a first-, second-, or third-line treatment.

Treatment of a subject having cancer with an anti-TIM-3 antibody or antigen-binding fragment described herein, e.g., humanized 3E6, can result in, e.g., stable disease, partial response, increased overall survival, increased disease free survival, or enhanced progression free survival.

In some embodiments, an anti-TIM-3 antibody described herein is not significantly toxic. For example, a TIM-3 antibody is not significantly toxic to an organ of a human, e.g., one or more of the liver, kidney, brain, lungs, and heart, as determined, e.g., in clinical trials. In some embodiments, a TIM-3 antibody does not significantly trigger an undesirable immune response, e.g., autoimmunity or inflammation.

In some embodiments, treatment of a subject with an anti-TIM-3 antagonist (e.g., an anti-TIM-3 antibody or antigen-binding fragment described herein) does not result in overstimulation of the immune system to the extent that the subject's immune system then attacks the subject itself (e.g., autoimmune response) or results in, e.g., anaphylaxis. Thus, in some embodiments, anti-TIM-3 antibodies do not cause anaphylaxis.

In some embodiments, treatment of a subject with an anti-TIM-3 antibody or antigen-binding fragment described herein, e.g., an antibody comprising the CDRs or variable regions of 3E6 or a variant thereof (e.g., as described herein) or other anti-TIM-3 antibodies described herein, does not cause significant inflammatory reactions, e.g., immune-mediated pneumonitis, immune-mediated colitis, immune mediated hepatitis, immune-mediated nephritis or renal dysfunction, immune-mediated hypophysitis, immune-mediated hypothyroidism and hyperthyroidism, or other immune-mediated adverse reactions. In some embodiments, an anti-TIM-3 antibody or antigen-binding fragment comprising the CDRs of variable regions of 3E6 or a variant thereof (e.g., as described herein) causes fewer inflammatory reactions, e.g., immune-mediated pneumonitis, immune-mediated colitis, immune mediated hepatitis, immune-mediated nephritis or renal dysfunction, immune-mediated hypophysitis, immune-mediated hypothyroidism and hyperthyroidism, anaphylaxis or other immune-mediated adverse reactions, than other anti-TIM-3 antibodies. In some embodiments, treatment of a subject with an anti-TIM-3 antibody described herein, e.g., an antibody comprising the CDRs or variable regions of 3E6 or a variant thereof (e.g., as described herein) or other anti-TIM-3 antibodies described herein, does not cause significant cardiac disorders, e.g., ventricular arrhythmia; eye disorders, e.g., iridocyclitis; infusion-related reactions; increased amylase, increased lipase; nervous system disorders, e.g., dizziness, peripheral and sensory neuropathy; skin and subcutaneous tissue disorders, e.g., rash, pruritus, exfoliative dermatitis, erythema multiforme, vitiligo or psoriasis; respiratory, thoracic and mediastinal disorders, e.g., cough; fatigue; nausea; decreased appetite; constipation; arthralgia; or diarrhea.

In some embodiments, an anti-TIM-3 antibody or antigen-binding fragment provides synergistic anti-tumor effects in combination with another cancer therapy, such as a compound that stimulates the immune system (e.g., an immuno-oncology agent), e.g., a compound described herein or a compound modulating a target described herein.

The present disclosure also provides methods of uses of the anti-TIM-3 antibodies or antigen-binding fragments, polynucleotides encoding such anti-TIM-3 antibodies or antigen-binding fragments, vectors comprising such polynucleotides, or pharmaceutical compositions having such antibodies or antigen-binding fragments disclosed herein in treating cancer. In some embodiments, the anti-TIM-3 antibodies or antigen-binding fragments can specifically target TIM-3-expressing cancer cells in vivo, thereby delivering their therapeutic effect of eliminating, lysing and/or killing cancer cells. In some embodiments, the anti-TIM-3 antibodies or antigen-binding fragments can reduce the immunosuppressive effects mediated by TIM-3 signaling pathway, thereby promoting the activities of immune cells in eliminating, lysing and/or killing cancer cells. In some embodiments, the methods include administering a therapeutically effective amount of the anti-TIM-3 antibodies or antigen-binding fragments disclosed herein to a subject in need thereof.

In some embodiments, provided herein are methods of treating tumor or cancer in a subject in need thereof, comprising administering to the subject a therapeutically effective amount of the anti-TIM-3 antibodies or antigen-binding fragments disclosed herein. In some embodiments, provided herein are uses of the anti-TIM-3 antibodies or antigen-binding fragments disclosed herein in the treatment of tumor or cancer. In some embodiments, provided herein are uses of the anti-TIM-3 antibodies or antigen-binding fragments provided herein for the preparation of a medicament for the treatment of tumor or cancer.

In some embodiments, provided herein are methods of treating tumor or cancer in a subject in need thereof, comprising administering to the subject a therapeutically effective amount of the pharmaceutical composition disclosed herein. In some embodiments, provided herein are uses of the pharmaceutical composition disclosed herein in treatment of tumor or cancer. In some embodiments, provided herein are uses of the pharmaceutical composition provided herein for the preparation of a medicament for the treatment of tumor or cancer.

Actual dosage levels of the active ingredients (i.e., the anti-TIM-3 antibodies or antigen-binding fragments) in the pharmaceutical compositions described herein can be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions described herein, the route of administration, the time of administration, the rate of excretion, the duration of the treatment, other drugs, compounds and/or materials used in combination with the particular compositions employed, the age, sex, weight, condition, general health and prior medical history of the patient being treated, and like factors well known in the medical arts.

The anti-TIM-3 antibodies or antigen-binding fragments can be administered as a sustained release formulation, in which case less frequent administration is required. Dosage and frequency vary depending on the half-life of the anti-TIM-3 antibodies or antigen-binding fragments in the patient. In therapeutic applications, a relatively high dosage at relatively short intervals is sometimes required until progression of the disease is reduced or terminated, and until the patient shows partial or complete amelioration of symptoms of disease.

The anti-TIM-3 antibodies or antigen-binding fragments or pharmaceutical compositions provided herein can be administered to a subject by any methods known in the art, including, but not limited to, pleural administration, intravenous administration, subcutaneous administration, intranodal administration, intratumoral administration, intramuscular administration, intradermal administration, intrathecal administration, intrapleural administration, intraperitoneal administration, intracranial administration, spinal or other parenteral routes of administration, for example by injection or infusion, or direct administration to the thymus. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. In some embodiments, subcutaneous administration is adopted. In some embodiments, intravenous administration is adopted. In some embodiments, oral administration is adopted. In one embodiment, the antibodies or antigen-binding fragments provided herein can be delivered regionally to a tumor using well known methods, including but not limited to, hepatic or aortic pump; limb, lung or liver perfusion; in the portal vein; through a venous shunt; in a cavity or in a vein that is nearby a tumor, and the like. In another embodiment, the antibodies or antigen-binding fragments provided herein can be administered systemically. In a preferred embodiment, the antibodies or antigen-binding fragments are administered regionally at the site of a tumor. The antibodies or antigen-binding fragments can also be administered intratumorally, for example, by direct injection of the cells at the site of a tumor and/or into the tumor vasculature. For example, in the case of malignant pleural disease, mesothelioma or lung cancer, administration is preferably by intrapleural administration (see Adusumilli et al., *Science Translational Medicine* 6(261):261ra151 (2014)). One skilled in the art can select a suitable mode of administration based on the type of cancer and/or location of a tumor to be treated. The antibodies or antigen-binding fragments can be introduced by injection or catheter. In one embodiment, the antibodies or antigen-binding fragments are pleurally administered to the subject in need, for example, using an intrapleural catheter.

Cancers or tumors to be treated using the anti-TIM-3 antibodies or antigen-binding fragments or pharmaceutical compositions provided herein comprise those typically responsive to immunotherapy and those that are not typically responsive to immunotherapy. Cancers that can be treated also include TIM-3 positive cancers. In some embodiments, the cancer has a high degree of microsatellite instability. In some embodiments, the cancer is a metastatic cancer, refractory cancer, or recurrent cancer.

In some embodiments, cancers or tumors that can be treated with the anti-TIM-3 antibodies or antigen-binding fragments or pharmaceutical compositions disclosed herein are hematological cancers. The hematological cancers can be TIM-3-expressing hematological cancers. In some embodiments, the hematological cancer can be leukemia, lymphoma, multiple myeloma (MM), or myelodysplastic syndrome (MDS). In some embodiments, the hematological cancer can be acute leukemia, acute myeloid leukemia (AML), B-acute lymphoid leukemia (B-ALL), T-acute lymphoid leukemia (T-ALL), B cell precursor acute lymphoblastic leukemia (BCP-ALL), blastic plasmacytoid dendritic cell neoplasm (BPDCN), acute lymphocytic leukemia, acute myeloblastic leukemia, acute promyelocytic leukemia, acute myelomonocytic leukemia, acute monocytic leukemia, acute erythroleukemia, chronic leukemia, chronic myeloid leukemia (CML), chronic myelocytic leukemia, chronic lymphocytic leukemia, chronic myelomonocytic leukemia (CMML), natural killer cell leukemia (NK leukemia), Hodgkin's disease, non-Hodgkin's disease, Waldenstrom's macroglobulinemia, lymphocytic lymphoma, primary CNS lymphoma, T-cell lymphoma, natural killer cell lymphoma (NK lymphoma), cutaneous T-Cell lymphoma (CTCL), or peripheral T-cell lymphoma (PTCL). In some embodiments, anti-TIM-3 antibodies or antigen-binding fragments or pharmaceutical compositions disclosed herein can be used to treat MDS. In some embodiments, anti-TIM-3 antibodies or antigen-binding fragments or pharmaceutical compositions disclosed herein can be used to treat leukemia. In some embodiments, the leukemia is AML.

In some embodiments, provided herein are methods of treating TIM-3-expressing leukemia in a subject in need thereof, comprising administering to the subject a therapeutically effective amount of the anti-TIM-3 antibodies or antigen-binding fragments or the pharmaceutical compositions disclosed herein.

In some embodiments, cancers or tumors that can be treated with the anti-TIM-3 antibodies or antigen-binding fragments or pharmaceutical compositions disclosed herein are solid tumors. In some embodiments, the cancer or tumor can be carcinomas, sarcoma, melanoma (e.g., cutaneous or intraocular malignant melanoma), glioma, glioblastoma, brain and spinal cord tumors, germ cell tumors, neuroendocrine tumors, carcinoid tumors, gastric cancer, esophageal cancer, liver cancer, lung cancer (e.g., small cell lung cancer, or non-small cell lung cancer), head and neck cancer, skin cancer, nasopharyngeal cancer, kidney cancer, colorectal cancer, breast cancer, pancreatic cancer, testicular cancer, cervical cancer, ovarian cancer, uterine cancer, prostate cancer (for example, hormone refractory prostate adenocarcinoma), bladder cancer, colon cancer, endocrine cancer, basal cell cancer, squamous cell cancer, dermatofibrosarcoma protuberans, mesothelioma, Merkel cell carcinoma, bone cancer, intestinal cancer, renal cancer (for example, clear cell carcinoma), throat cancer, rectal cancer, cancer of the anal region, brain cancer, stomach cancer, carcinoma of the fallopian tubes, carcinoma of the endometrium, carcinoma of the cervix, carcinoma of the vagina, carcinoma of the vulva, cancer of the small intestine, cancer of the thyroid gland, cancer of the parathyroid gland, cancer of the adrenal gland, sarcoma of soft tissue, cancer of the urethra, cancer of the penis, solid tumors of childhood, cancer of ureter, carcinoma of the renal pelvis, neoplasm of the central nervous system (CNS), spinal axis tumor, brain stem glioma, pituitary adenoma. Kaposi's sarcoma, epidermoid cancer, fibrosarcoma, myxosarcoma, liposarcoma, chondrosarcoma, osteogenic sarcoma, synovial sarcoma, chordoma, angiosarcoma, endotheliosarcoma, lymphangiosarcoma, lymphangioendotheliosarcoma, synovioma, Ewing's tumor, leiomyosarcoma, rhabdomyosarcoma, squamous cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, hepatoma, bile duct carcinoma, choriocarcinoma, seminoma, embryonal carcinoma, Wilm's tumor, epithelial carcinoma, glioma, astrocytoma, medulloblastoma, craniopharyngioma, ependymoma, pinealoma, hemangioblastoma, acoustic neuroma, oligodendroglioma, schwannoma, meningioma, neuroblastoma, or retinoblastoma.

In some embodiments, the cancer or tumor that can be treated with the anti-TIM-3 antibodies or antigen-binding fragments or pharmaceutical compositions disclosed herein is selected from the group consisting of renal cell carcinoma (RCC), non-small cell lung carcinoma (NSCLC), squamous cell carcinoma of the head and neck (SCCHN), triple negative breast cancer (TNBC), gastric/stomach adenocarcinoma (STAD), pancreatic adenocarcinoma (PAAD), colon adenocarcinoma (COAD), or rectum adenocarcinoma (READ). In some embodiments, the cancer or tumor is RCC. In some embodiments, the cancer or tumor is NSCLC. In some embodiments, the cancer or tumor is SCCHN. In some embodiments, the cancer or tumor is TNBC. In some embodiments, the cancer or tumor is STAD. In some embodiments, the cancer or tumor is PAAD. In some embodiments, the cancer or tumor is COAD. In some embodiments, the cancer or tumor is READ.

In cancer treatment, eliminating cancer or tumor cells in a subject can occur, but any clinical improvement constitutes a benefit. An anti-tumor effect can be manifested by a decrease in tumor volume, a decrease in the number of tumor cells, a decrease in the number of metastases, an increase in life expectancy, or amelioration of various physiological symptoms associated with the cancerous condition. An anti-tumor effect can also be manifested by the ability of the antibodies or antigen binding fragments, or pharmaceutical compositions provided herein in prevention of the occurrence of tumor in the first place. In some embodiments, an "anti-tumor effect" can be manifested by the reduction in cancer-induced immunosuppression. Clinical improvement comprises decreased risk or rate of progression or reduction in pathological consequences of the cancer or tumor. It is also understood that a method of treating cancer can include any effect that ameliorates a sign or symptom associated with cancer. Such signs or symptoms include, but are not limited to, reducing tumor burden, including inhibiting growth of a tumor, slowing the growth rate of a tumor, reducing the size of a tumor, reducing the number of tumors, eliminating a tumor, all of which can be measured using routine tumor imaging techniques well known in the art. Other signs or symptoms associated with cancer include, but are not limited to, fatigue, pain, weight loss, and other signs or symptoms associated with various cancers.

In some embodiments, the methods or uses provided herein can reduce tumor burden. Thus, administration of the anti-TIM-3 antibodies or antigen-binding fragments or pharmaceutical compositions disclosed herein can reduce the number of tumor cells, reduce tumor size, and/or eradicate the tumor in the subject. Methods for monitoring patient response to administration of a pharmaceutical composition disclosed herein are known in the art and can be employed in accordance with methods disclosed herein.

In some embodiments, an anti-tumor effect is observed in a subject having a tumor or cancer who has been administered with an anti-TIM-3 antibody or antigen-binding fragment described herein as a single therapy, namely, not in combination with another therapeutic (e.g., an anti-PD-1 antibody or anti-PD-L1 antibody). In some embodiments, tumor burden is reduced in a subject having a tumor or cancer who has been administered with an anti-TIM-3 antibody or antigen-binding fragment described herein as a single therapy, namely, not in combination with another therapeutic (e.g., an anti-PD-1 antibody or anti-PD-L1 antibody).

In the methods disclosed herein, a therapeutically effective amount of the anti-TIM-3 antibodies or antigen-binding fragments or pharmaceutical compositions disclosed herein is administered to a subject in need of cancer treatment. The subject can be a mammal. In some embodiments, the subject is a human. In some embodiments, these individuals have no clinically measurable tumor. However, they are suspected of being at risk for progression of the disease, either near the original tumor site, or by metastases. This group can be further subdivided into high-risk and low-risk individuals. The subdivision is made on the basis of features observed before or after the initial treatment. These features are known in the clinical arts and are suitably defined for different types of cancers. Features typical of high-risk subgroups are those in which the tumor has invaded neighboring tissues, or who show involvement of lymph nodes.

Anti-TIM-3 antibodies or antigen-binding fragments or pharmaceutical compositions provided herein can be administered with medical devices known in the art. For example, in some embodiments, a needleless hypodermic injection device can be used, such as the devices disclosed in U.S. Pat. Nos. 5,399,163; 5,383,851; 5,312,335; 5,064,413; 4,941,880; 4,790,824; or 4,596,556. Examples of well-known implants and modules for use described herein include: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In some embodiments, an anti-TIM-3 antibody or antigen-binding fragment is administered to patients having a cancer that exhibited an inadequate response to, or progressed on, a prior treatment. e.g., a prior treatment with an immuno-oncology or immunotherapy drug, or patients having a cancer that is refractory or resistant, either intrinsically refractory or resistant (e.g., refractory to a PD-1 pathway antagonist), or a wherein the resistance or refractory state is acquired. For example, subjects who are not responsive or not sufficiently responsive to a first therapy or who see disease progression following treatment, e.g., anti-PD-1 treatment, can be treated by administration of an anti-TIM-3 antibody alone or in combination with another therapy (e.g., with an anti-PD-1 therapy).

In some embodiments, an anti-TIM-3 antibody or antigen-binding fragment is administered to patients who have not previously received (i.e., been treated with) an immuno-oncology agent, e.g., a PD-1 pathway antagonist.

In some embodiments, a method of treating cancer in a subject comprises first determining whether the subject is TIM-3 positive. e.g., has tumor cells or TILs that express TIM-3, and if the subject has TIM-3 positive cancer or TIL cells, then administering to the subject an anti-TIM-3 antibody, e.g., described herein. A method of treating a subject having cancer with an anti-TIM-3 antibody can comprise administering to a subject who has cancer cells or TIL cells that express TIM-3, a therapeutically effective amount of a TIM-3 antibody. Also provided herein are methods for predicting whether a subject will respond to treatment with an anti-TIM-3 antibody, wherein the methods comprise determining the level of TIM-3 in cancer or TIL cells of the patient, and if cancer or TIL cells of the subject are TIM-3 positive, then the subject is likely to respond to a treatment with a TIM-3 antibody.

In some embodiments, a method of treating cancer in a subject comprises first determining whether the subject is PD-L1 or PD-1 positive, e.g., has tumor cells or TILs that express PD-L1 or PD-1, and if the subject has PD-L1 or PD-1 positive cancer or TIL cells, then administering to the subject an anti-TIM-3 antibody or antigen-binding fragment (and optionally a PD-1 or PD-L1 antagonist), e.g., described herein. A method of treating a subject having cancer with an anti-TIM.3 antibody (and optionally a PD-1 or PD-L1 antagonist) can comprise administering to a subject who has cancer cells or TIL cells that express PD-L1 or PD-1, a therapeutically effective amount of a TIM-3 antibody or antigen-binding fragment (and optionally a PD-1 or PD-L1 antagonist). Also provided herein are methods for predicting whether a subject will respond to treatment with an anti-TIM-3 antibody (and optionally a PD-1 or PD-L1 antagonist), wherein the methods comprise determining the level of PD-L1 or PD-1 in cancer or TIL cells of the patient, and if cancer or TIL cells of the subject are PD-L1 or PD-1 positive, then the subject is likely to respond to a treatment with a TIM-3 antibody (and optionally a PD-1 or PD-L1 antagonist).

An anti-TIM-3 antibody can be administered with a standard of care treatment. An anti-TIM-3 antibody can be administered as a maintenance therapy, e.g., a therapy that is intended to prevent the occurrence or recurrence of tumors.

An anti-TIM-3 antibody can be administered with another treatment, e.g., radiation, surgery, or chemotherapy. For example, an anti-TIM-3 antibody adjunctive therapy can be administered w % ben there is a risk that micrometastases can be present and/or in order to reduce the risk of a relapse.

An anti-TIM-3 antibody or antigen-binding fragment can be administered as a monotherapy, or as the only immunostimulating therapy. An anti-TIM-3 antibody or antigen-binding fragment can also be combined with an immunogenic agent, such as cancerous cells, purified tumor antigens (including recombinant proteins, peptides, and carbohydrate molecules), cells, and cells transfected with genes encoding immune stimulating cytokines (He et al., (2004) *J. Immunol.* 173:4919-28). Non-limiting examples of tumor vaccines that can be used include peptides of melanoma antigens, such as peptides of gp100, MAGE antigens, Trp-2. MARTI and/or tyrosinase, or tumor cells transfected to express the cytokine GM-CSF (discussed further below).

In humans, some tumors have been shown to be immunogenic such as melanomas. By lowering the threshold of T cell activation via TIM-3 inhibition, the tumor responses in the host can be activated, allowing treatment of non-immunogenic tumors or those having limited immunogenicity.

An anti-TIM-3 antibody, e.g., an anti-TIM-3 antibody described herein, can be combined with a vaccination protocol. Many experimental strategies for vaccination against tumors have been devised (see Rosenberg, S., 2000, DEVELOPMENT OF CANCER VACCINES, ASCO Educational Book Spring; 60-62; Logothetis, C. 2000, ASCO Educational Book Spring: 300-302; Khayat, D. 2000, ASCO Educational Book Spring: 414-428; Foon, K. 2000, ASCO Educational Book Spring: 730-738: see also Restifo, N, and Sznol, M., Cancer Vaccines, Ch. 61, pp. 3023-3043 in DeVita et al. (eds.), 1997, Cancer: Principles and Practice of Oncology, Fifth Edition). In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al. (1993) *Proc. Natl. Acad. Sci U.S.A.* 90: 3539-43).

Dendritic cells (DC) are potent antigen presenting cells that can be used to prime antigen-specific responses. DCs can be produced ex vivo and loaded with various protein and peptide antigens as well as tumor cell extracts (Nestle et al. (1998) *Nature Medicine* 4: 328-332). DCs can also be transduced by genetic means to express these tumor antigens as well. DCs have also been fused directly to tumor cells for the purposes of immunization (Kugler et al. (2000) *Nature Medicine* 6:332-336). As a method of vaccination, DC immunization can be effectively combined with TIM-3 inhibition to activate more potent anti-tumor responses.

Combination therapy using agents with different mechanisms of action can result in additive or synergetic effects. Combination therapy can allow for a lower dose of each agent than is used in monotherapy, thereby reducing toxic side effects and/or increasing the therapeutic index of the agent disclosed herein. Combination therapy can decrease the likelihood that resistant cancer cells will develop. In some embodiments, the additional therapy results in an increase in the therapeutic index of the antibodies or antigen-binding fragments, or pharmaceutical compositions described herein. In some embodiments, the additional therapy results in a decrease in the toxicity and/or side effects of the antibodies or antigen-binding fragments or pharmaceutical compositions described herein. In some embodiments, the anti-TIM-3 antibodies or antigen-binding fragments, or pharmaceutical compositions described herein can be administered in combination with an additional therapy. In some embodiments, the additional therapy can be surgical resection, radiotherapy, or chemotherapy.

TIM-3 inhibition can also be combined with standard cancer treatments (e.g., surgery, radiation, and chemotherapy). TIM-3 inhibition can be effectively combined with chemotherapeutic regimes. In these instances, it can be possible to reduce the dose of chemotherapeutic reagent administered (Mokyr et al (1998) *Cancer Research* 58: 5301-5304). An example of such a combination is an anti-TIM-3 antibody in combination with decarbazine for the treatment of melanoma. Another example of such a combination is an anti-TIM-3 antibody in combination with interleukin-2 (IL-2) for the treatment of melanoma. The scientific rationale behind the combined use of TIM-3 inhibition and chemotherapy is that cell death, that is a consequence of the cytotoxic action of most chemotherapeutic compounds, should result in increased levels of tumor antigen in the antigen presentation pathway. Other combination therapies that can result in synergy with TIM-3 inhibition through cell death are radiation, surgery, and hormone deprivation. Each of these protocols creates a source of tumor antigen in the host. Angiogenesis inhibitors can also be combined with TIM-3 inhibition. Inhibition of angiogenesis leads to tumor cell death which can feed tumor antigen into host antigen presentation pathways.

The anti-TIM-3 antibodies described herein can also be used in combination with bispecific antibodies that target Fcα or Fcγ receptor-expressing effectors cells to tumor cells (see, e.g., U.S. Pat. Nos. 5,922,845 and 5,837,243). Bispecific antibodies can be used to target two separate antigens. For example, an anti-Fc receptor/anti-tumor antigen (e.g., Her-2/neu) bispecific antibodies have been used to target macrophages to sites of tumor. This targeting can more effectively activate tumor specific responses. The T cell arm of these responses would be augmented by the inhibition of TIM-3. Alternatively, antigen can be delivered directly to DCs by the use of bispecific antibodies which bind to tumor antigen and a dendritic cell specific cell surface marker.

Tumors evade host immune surveillance by a large variety of mechanisms. Many of these mechanisms can be overcome by the inactivation of proteins which are expressed by the tumors and which are immunosuppressive. These include among others TGF-β (Kehrl el al. (1986)*J. Exp. Med* 163: 1037-1050), IL-10 (Howard & O'Garra (1992) *Immunology Today* 13: 198-200), and Fas ligand (Hahne et al. (1996) *Science* 274: 1363-1365). Antibodies to each of these entities can be used in combination with anti-TIM-3 antibodies or antigen-binding fragments to counteract the effects of the immunosuppressive agent and favor tumor immune responses by the host.

Bone marrow transplantation is currently being used to treat a variety of tumors of hematopoietic origin. While graft versus host disease is a consequence of this treatment, therapeutic benefit can be obtained from graft vs. tumor responses. TIM-3 inhibition can be used to increase the effectiveness of the donor engrafted tumor specific T cells.

There are also several experimental treatment protocols that involve ex vivo activation and expansion of antigen specific T cells and adoptive transfer of these cells into recipients in order to stimulate antigen-specific T cells against tumor (Greenberg & Riddell (1999) *Science* 285: 546-51). These methods can also be used to activate T cell responses to infectious agents such as CMV. Ex vivo activation in the presence of anti-TIM-3 antibodies can increase the frequency and activity of the adoptively transferred T cells.

Provided herein are methods of combination therapy in which an anti-TIM-3 antibody is co-administered with one or more additional agents, e.g., small molecule drugs, antibodies, or antigen binding portions thereof, that are effective in stimulating immune responses to thereby further enhance, stimulate or upregulate immune responses in a subject.

Generally, an anti-TIM-3 antibody or antigen-binding fragment, e.g., described herein, can be combined with (i) an agonist of a stimulatory (e.g., co-stimulatory) molecule (e.g., receptor or ligand) and/or (ii) an antagonist of an inhibitory signal or molecule (e.g., receptor or ligand) on immune cells, such as T cells, both of which result in amplifying immune responses, such as antigen-specific T cell responses. In some embodiments, an immuno-oncology agent is (i) an agonist of a stimulatory (including a co-stimulatory) molecule (e.g., receptor or ligand) or (ii) an antagonist of an inhibitory (including a co-inhibitory) molecule (e.g., receptor or ligand) on cells, e.g., those inhibiting T cell activation or those involved in innate immunity, e.g., NK cells, and wherein the immuno-oncology agent enhances innate immunity. Such immuno-oncology agents are often referred to as immune checkpoint regulators, e.g., immune checkpoint inhibitor or immune checkpoint stimulator.

In some embodiments, an anti-TIM-3 antibody or antigen-binding fragment is administered with an agent that targets a stimulatory or inhibitory molecule that is a member of the immunoglobulin super family (IgSF). For example, anti-TIM-3 antibodies or antigen-binding fragments, e.g., described herein, can be administered to a subject with an agent that targets a member of the IgSF family to increase an immune response. For example, an anti-TIM-3 antibody or antigen-binding fragment can be administered with an agent that targets (or binds specifically to) a member of the B7 family of membrane-bound ligands that includes B7-1, B7-2, B7-H1 (PD-L1), B7-DC (PD-L2), B7-H2 (ICOS-L), B7-H3, B7-H4, B7-H5 (VISTA), and B7-H6 or a co-stimulatory or co-inhibitory receptor or ligand binding specifically to a B7 family member.

An anti-TIM-3 antibody or antigen-binding fragment can also be administered with an agent that targets a member of the TNF and TNFR family of molecules (ligands or receptors), such as CD40 and CD40L, OX-40, OX-40L, CD70, CD27L, CD30, CD30L, 4-1BBL, CD137, TRAIL/Apo2-L, TRAILR1/DR4, TRAILR2/DR5, TRAILR3, TRAILR4, OPG, RANK, RANKL, TWEAKR/Fn 14, TWEAK, BAFFR, EDAR, XEDAR, TACT, APRIL, BCMA, LTpR, LIGHT, DcR3, HVEM, VEGI/TLIA, TRAMP/D R3, EDA1, EDA2, TNFR1, Lymphotoxin a/TNFp, TNFR2, TNF a, LTpR, Lymphotoxin a 1b2, FAS, FASL, RELT, DR6, TROY, and NGFR (see, e.g., Tansey (2009) *Drug Discovery Today* 00: 1).

T cell responses can be stimulated by a combination of anti-TIM-3 antibodies or antigen-binding fragments having the CDRs of, e.g., 3E6, 4H2, 16H1, 18C6, 19D11, CH 5 #, CH 8 #, CH 9 #, CH 10 #, CH 11 #, 3F2, 36A2, 36B11, 38F8, 38A8, 40F11, 50H9, 84G10, or 39D1 and one or more of the following agents:

(1) An antagonist (inhibitor or blocking agent) of a protein that inhibits T cell activation (e.g., immune checkpoint inhibitors), such as CTLA-4, PD-1, PD-L1, PD-L2, GITR, and LAG-3, Galectin 9, CEACAM-1, CEACAM-5, BTLA, CD69, Galectin-1, TIGIT, CD113, GPR56, VISTA, B7-H3, B7-H4, 2B4, CD48, GARP, PD1H, LAIR1, TIM-1, and TIM-4; and/or (2) An agonist of a protein that stimulates T cell activation, such as B7-1, B7-2, CD28, 4-1BB (CD137), 4-1BBL, GITR, ICOS, ICOS-L, OX40, OX40L, CD70, CD27, CD40, DR3 and CD28H.

Exemplary agents that modulate one of the above proteins and can be combined with anti-TIM-3 antibodies, e.g., those described herein, for treating cancer, include: YERVOY® (ipilimumab) or Tremelimumab (to CTLA-4), galiximab (to B7.1), BMS-936558 (to PD-1), MK-3475 (to PD-1), atezolizumab (TECENTRIQ®), AMP224 (to B7DC), BMS-936559 (to B7-H1), MPDL3280A (to B7-H1), MEDI-570 (to ICOS), AMG557 (to B7H2), MGA271 (to B7H3), IMP321 (to LAG-3), BMS-663513 (to CD137), PF-05082566 (to CD137), CDX-1127 (to CD27), anti-OX40 (Providence Health Services), huMAbOX40L (to OX40L), Atacicept (to TACI), CP-870893 (to CD40), Lucatumumab (to CD40), Dacetuzumab (to CD40), Muromonab-CD3 (to CD3); anti-GITR antibodies MK4166, TRX518, Medil873, INBRX-110, LK2-145, GWN-323, GITRL-Fc, or any combination thereof.

Other molecules that can be combined with anti-TIM-3 antibodies or antigen-binding fragments for the treatment of cancer include antagonists of inhibitory receptors on NK cells or agonists of activating receptors on NK cells. For example, anti-TIM-3 antibodies or antigen-binding fragments can be combined with antagonists of KIR (e.g., lirilumab).

T cell activation is also regulated by soluble cytokines, and anti-TIM-3 antibodies or antigen-binding fragments can be administered to a subject, e.g., having cancer, with antagonists of cytokines that inhibit T cell activation or agonists of cytokines that stimulate T cell activation.

In some embodiments, anti-TIM-3 antibodies or antigen-binding fragments can be used in combination with (i) antagonists (or inhibitors or blocking agents) of proteins of the IgSF family or B7 family or the TNF family that inhibit T cell activation or antagonists of cytokines that inhibit T cell activation (e.g., IL-6, IL-10, TGF-β. VEGF; "immunosuppressive cytokines") and/or (ii) agonists of stimulatory receptors of the IgSF family. B7 family or the TNF family or of cytokines that stimulate T cell activation, for stimulating an immune response, e.g., for treating proliferative diseases, such as cancer.

Yet other agents for combination therapies include agents that inhibit or deplete macrophages or monocytes, including but not limited to CSF-1R antagonists such as CSF-1R antagonist antibodies including RG7155 (WO 11/70024, WO11/107553, WO11/131407, WO13/87699, W013/1 19716, WO13/132044) or FPA-008 (WO11/140249; WO13169264: WO14/036357).

Anti-TIM-3 antibodies or antigen-binding fragments can also be administered with agents that inhibit TGF-β signaling. In some embodiments, the agent is an antibody that specifically binds a latent TGF-β or a GARP/TGF-§ complex. In some embodiments, the agent is an antibody that specifically binds a TGF-β receptor.

Additional agents that can be combined with an anti-TIM-3 antibody or antigen-binding fragment include agents that enhance tumor antigen presentation, e.g., dendritic cell vaccines, GM-CSF secreting cellular vaccines, CpG oligonucleotides, and imiquimod, or therapies that enhance the immunogenicity of tumor cells (e.g., anthracy dines).

Yet other therapies that can be combined with an anti-TIM-3 antibody or antigen-binding fragment include therapies that deplete or block Treg cells, e.g., an agent that specifically binds to CD25.

Another therapy that can be combined with an anti-TIM-3 antibody is a therapy that inhibits a metabolic enzyme such as indoleamine dioxigenase (IDO), dioxigenase, arginase, or nitric oxide synthetase.

Another class of agents that can be used with an anti-TIM-3 antibody or antigen-binding fragment includes agents that inhibit the formation of adenosine, e.g., CD73 inhibitors, or inhibit the adenosine A2A receptor.

Other therapies that can be combined with an anti-TIM-3 antibody or antigen-binding fragment for treating cancer include therapies that reverse/prevent T cell anergy or exhaustion and therapies that trigger an innate immune activation and/or inflammation at a tumor site.

Other therapies that can be combined with an anti-TIM-3 antibody or antigen-binding fragment for treating cancer include therapies that block IL-8, e.g., with HuMax-IL8.

An anti-TIM-3 antibody or antigen-binding fragment can be combined with more than one immuno-oncology agent, and can be, e.g., combined with a combinatorial approach that targets multiple elements of the immune pathway, such as one or more of the following: a therapy that enhances tumor antigen presentation (e.g., dendritic cell vaccine, GM-CSF secreting cellular vaccines. CpG oligonucleotides, imiquimod); a therapy that inhibits negative immune regulation e.g., by inhibiting CTLA-4 and/or PD1/PD-L1/PD-L2 pathway and/or depleting or blocking Tregs or other immune suppressing cells; a therapy that stimulates positive immune regulation, e.g., with agonists that stimulate the CD-137, OX-40, and/or CD40 or GITR pathway and/or stimulate T cell effector function; a therapy that increases systemically the frequency of anti-tumor T cells; a therapy that depletes or inhibits Tregs, such as Tregs in the tumor, e.g., using an antagonist of CD25 (e.g., daclizumab) or by ex vivo anti-CD25 bead depletion; a therapy that impacts the function of suppressor myeloid cells in the tumor; a therapy that enhances immunogenicity of tumor cells (e.g., anthracy dines); adoptive T cell or NK cell transfer including genetically modified cells, e.g., cells modified by chimeric antigen receptors (CAR-T therapy); a therapy that inhibits a metabolic enzyme such as indoleamine dioxigenase (IDO), dioxigenase, arginase, or nitric oxide synthetase; a therapy that reverses/prevents T cell anergy or exhaustion; a therapy that triggers an innate immune activation and/or inflammation at a tumor site; administration of immune stimulatory cytokines; or blocking of immuno repressive cytokines.

Anti-TIM-3 antibodies or antigen-binding fragments described herein can be used together with one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell anergy or exhaustion) and agents that trigger innate immune activation and/or inflammation at tumor sites.

In some embodiments, an anti-TIM-3 antibody or antigen-binding fragment is administered to a subject together with a BRAF inhibitor if the subject is BRAF V600 mutation positive.

Suitable PD-1 antagonists for use in the combination therapy described herein, include, without limitation, ligands, antibodies (e.g., monoclonal antibodies and bispecific antibodies), and multivalent agents. In some embodiments, the PD-1 antagonist is a fusion protein, e.g., an Fc fusion protein, such as AMP-244. In some embodiments, the PD-1 antagonist is an anti-PD-1 or anti-PD-L1 antibody.

An exemplary anti-PD-1 antibody is nivolumab (BMS-936558) or an antibody that comprises the CDRs or variable regions of one of antibodies 17D8, 2D3, 4H1, 5C4, 7D3, 5F4 and 4A11 described in WO 2006/121168. In some embodiments, an anti-PD-1 antibody is MK-3475 (Lambrolizumab) described in WO2012/145493; AMP-514 described in WO 2012/145493; or PDROO1. Further known PD-1 antibodies and other PD-1 inhibitors include those described in WO 2009/014708, WO 03/099196, WO 2009/114335, WO 2011/066389, WO 2011/161699, WO 2012/145493, U.S. Pat. Nos. 7,635,757 and 8,217,149, and U.S. Patent Publication No. 2009/0317368. Any of the anti-PD-1 antibodies disclosed in WO2013/173223 can also be used. An anti-PD-1 antibody that competes for binding with, and/or binds to the same epitope on PD-1 as, as one of these antibodies can also be used in combination treatments.

In some embodiments, the anti-PD-L1 antibody useful for the combination therapy is BMS-936559 (referred to as 12A4 in WO 2007/005874 and U.S. Pat. No. 7,943,743), or an antibody that comprises the CDRs or variable regions of 3G10, 12A4, 10A5, 5F8, 10H10, 1B12, 7H1, 11E6, 12B7 and 13G4, which are described in PCT Publication WO 07/005874 and U.S. Pat. No. 7,943,743. In some embodiments an anti-PD-L1 antibody is MED14736 (also known as durvalumab and Anti-B7-HI), MPDL3280A (also known as atezolizumab and RG7446), MSB0010718C (also known as avelumab; WO2013/79174), or rHigM12B7. Any of the anti-PD-L1 antibodies disclosed in WO2013/173223, WO2011/066389, WO2012/145493, U.S. Pat. Nos. 7,635, 757 and 8,217,149 and U.S. Publication No. 2009/145493 can also be used. Anti-PD-L1 antibodies that compete with and/or bind to the same epitope as that of any of these antibodies can also be used in combination treatments.

In some embodiments, the anti-TIM-3 antibody or antigen-binding fragment of the disclosure can be used with a CTLA-4 antagonist, e.g., an anti-CTLA-4 antibody. In some embodiments, an anti-CTLA-4 antibody is an antibody selected from the group of: YERVOY® (ipilimumab or antibody 10D1, described in PCT Publication WO 01/14424), tremelimumab (formerly ticilimumab, CP-675, 206), monoclonal or an anti-CTLA-4 antibody described in any of the following publications: WO 98/42752; WO 00/37504; U.S. Pat. No. 6,207,156; Hurwitz et al. (1998) Pro. Natl. Acad. Sci. USA 95(17): 10067-10071: Camacho et al. (2004) J. Clin. Oncology 22(145): Abstract No. 2505 (antibody CP-675206); and Mokyr el al. (1998) Cancer Res. 58:5301-5304. Any of the anti-CTLA-4 antibodies disclosed in WO2013/173223 can also be used.

In some embodiments, an anti-TIM-3 antibody or antigen-binding fragment of the disclosure is used in combination with a LAG3 antagonist. Examples of anti-LAG3 antibodies include antibodies comprising the CDRs or variable regions of antibodies 25F7, 26H10, 25E3, 8B7, 11F2 or 17E5, which are described in U.S. Patent Publication No. US2011/0150892, WO10/19570 and WO2014/008218. In some embodiments, an anti-LAG-3 antibody is BMS-986016. Other art recognized anti-LAG-3 antibodies that can be used include IMP731 and IMP-321, described in US 2011/007023, WO08/132601, and WO09/44273. Anti-LAG-3 antibodies that compete with and/or bind to the same epitope as that of any of these antibodies can also be used in combination treatments.

In some embodiments, an anti-TIM-3 antibody or antigen-binding fragment of the disclosure can be administered in combination with a CD 137 (4-1BB) agonist, such as an agonistic CD137 antibody. Suitable CD137 antibodies include, for example, urelumab or PF-05082566 (WO12/32433).

In some embodiments, an anti-TIM-3 antibody or antigen-binding fragment can be administered in combination with an OX40 agonist, such as an agonistic OX40 antibody. Suitable OX40 antibodies include, for example, MEDI-6383, MEDI-6469 or MOXR0916 (RG7888; WO06/029879).

In some embodiments, an anti-TIM-3 antibody or antigen-binding fragment is administered in combination with a CD40 agonist, such as an agonistic CD40 antibody. In some embodiments, the immuno-oncology agent is a CD40 antagonist, such as an antagonistic CD40 antibody. Suitable CD40 antibodies include, for example, lucatumumab (HCD122), dacetuzumab (SGN-40), CP-870,893 or Chi Lob 7/4.

In some embodiments, an anti-TIM-3 antibody or antigen-binding fragment is administered in combination with a CD27 agonist, such as an agonistic CD27 antibody. Suitable CD27 antibodies include, for example, varlilumab (CDX-1127).

In some embodiments, the anti-TIM-3 antibody or antigen-binding fragment is administered together with an anti-GITR antibody. e.g., an antibody having the CDR sequences of 6C8, e.g., a humanized antibody having the CDRs of 6C8, as described, e.g., in WO2006/105021; an antibody comprising the CDRs of an anti-GITR antibody described in WO2011/028683; an antibody comprising the CDRs of an anti-GITR antibody described in JP2008278814, an antibody comprising the CDRs of an anti-GITR antibody described in WO2015/031667, WO2015/187835, WO2015/184099, WO2016/054638, WO2016/057841 or WO2016/057846 or other anti-GITR antibody described or referred to herein.

In some embodiments, an anti-TIM-3 antibody or antigen-binding fragment is administered in combination with MGA271 (to B7H3) (WO11/109400).

In some embodiments, an anti-TIM-3 antibody or antigen-binding fragment is administered in combination with a KIR antagonist, such as lirilumab.

In some embodiments, an anti-TIM-3 antibody or antigen-binding fragment is administered in combination with an IDO antagonist. Suitable IDO antagonists include, for example, INCB-024360 (WO2006/122150, WO07/75598, WO08/36653, WO08/36642), indoximod. NLG-919 (WO09/73620, WO09/1156652, WO11/56652, WO12/142237) or F001287.

In some embodiments, an anti-TIM-3 antibody or antigen-binding fragment is administered in combination with a Toll-like receptor agonist, e.g., a TLR2/4 agonist (e.g., Bacillus Calmette-Guerin); a TLR7 agonist (e.g., Hiltonol or Imiquimod); a TLR7/8 agonist (e.g., Resiquimod), or a TLR9 agonist (e.g., CpG7909).

In some embodiments, an anti-TIM-3 antibody or antigen-binding fragment is administered in combination with a TGF-β inhibitor, e.g., GC1008, LY2157299, TEW7197, or IMC-TRI.

The anti-TIM-3 antibodies or antigen-binding fragments and combination therapies described herein can also be used in conjunction with other well-known therapies that are selected for their particular usefulness against the indication being treated (e.g., cancer). Combinations of the anti-TIM-3 antibodies described herein can be used sequentially with known pharmaceutically acceptable agent(s).

For example, the anti-TIM-3 antibodies or antigen-binding fragments and combination therapies described herein can be used in combination (e.g., simultaneously or separately) with an additional treatment, such as irradiation and/or chemotherapy, e.g., using camptothecin (CPT-11), 5-fluorouracil (5-FU), cisplatin, doxorubicin, irinotecan, paclitaxel, gemcitabine, cisplatin, paclitaxel, carboplatin-paclitaxel (Taxol), doxorubicin, or camptothecin+apo21/TRAIL (a 6x combo)), one or more proteasome inhibitors (e.g., bortezomib or MG132), one or more Bcl-2 inhibitors (e.g., BH31-2' (bcl-xl inhibitor), indoleamine dioxygenase-1 inhibitor (e.g., INCB24360, indoximod, NLG-919, or F001287), AT-101 (R-(−)-gossypol derivative), ABT-263 (small molecule), GX-15-070 (obatoclax), or MCL-1 (myeloid leukemia cell differentiation protein-1) antagonists), iAP (inhibitor of apoptosis protein) antagonists (e.g., smac7, smac4, small molecule smac mimetic, synthetic smac peptides (see Fulda ei al., *Nat Med* 2002, 8:808-15), ISIS23722 (LY2181308), or AEG-35156 (GEM-640)), HDAC (histone deacetylase) inhibitors, anti-CD20 antibodies (e.g., rituximab), angiogenesis inhibitors (e.g., bevacizumab), anti-angiogenic agents targeting VEGF and VEGFR (e.g., Avastin), synthetic triterpenoids (see Hyer et al, *Cancer Research* 2005:65:4799-808), c-FLIP (cellular FLICE-inhibitorv protein) modulators (e.g., natural and synthetic ligands of PPARy (peroxisome proliferator-activated receptor y), 5809354 or 5569100), kinase inhibitors (e.g., Sorafenib), Trastuzumab, Cetuximab, Temsirolimus, mTOR inhibitors such as rapamycin and temsirolimus, Bortezomib, JAK2 inhibitors, HSP90 inhibitors, PI3K-AKT inhibitors, Lenalildomide, GSK3P inhibitors, IAP inhibitors and/or genotoxic drugs.

The anti-TIM-3 antibodies or antigen-binding fragments and combination therapies described herein can further be used in combination with one or more anti-proliferative cytotoxic agents. Classes of compounds that can be used as anti-proliferative cytotoxic agents include, but are not limited to, the following:

Alkylating agents (including, without limitation, nitrogen mustards, ethylenimine derivatives, alkyl sulfonates, nitrosoureas and triazenes): Uracil mustard, Chlormethine, Cyclophosphamide (CYTOXAN®) fosfamide, Melphalan, Chlorambucil, Pipobroman, Triethylenemelamine, Triethylenethiophosphoramine, Busulfan, Carmustine, Lomustine, Streptozocin, Dacarbazine, and Temozolomide.

Antimetabolites (including, without limitation, folic acid antagonists, pyrimidine analogs, purine analogs and adenosine deaminase inhibitors): Methotrexate, 5-Fluorouracil, Floxuridine, Cytarabine, 6-Mercaptopurine, 6-Ihioguanine, Fludarabine phosphate, Pentostatine, and Gemcitabine.

Suitable anti-proliferative agents for combining with anti-TIM-3 antibodies or antigen-binding fragments, without limitation, taxanes, paclitaxel (paclitaxel is commercially available as TAXOL®), docetaxel, discodermolide (DDM), dictyostatin (DCT), Peloruside A, epothilones, epothilone A, epothilone B, epothilone C, epothilone D, epothilone E, epothilone F, furanoepothilone D, desoxyepothilone Bl, dehydrodesoxy epothilone B, dehydrodesoxy epothilones B, C12,13-cyclopropyl-epothilone A, C6-C8 bridged epothilone A, trans-9,10-dehydroepothilone D, cis-9,10-dehydroepothilone D, 16-desmethylepothilone B, epothilone BIO, discoderomolide, patupilone (EPO-906), KOS-862, KOS-1584, ZK-EPO, ABJ-789, XAA296A (Discodermolide), TZT-1027 (soblidotin), ILX-651 (tasidotin hydrochloride), Halichondrin B, Eribulin mesylate (E-7389), Hemiasterlin (HTI-286), E-7974, Cyrptophycins, LY-355703, Maytansinoid immunoconjugates (DM-1), MKC-1, ABT-751, T1-38067, T-900607, SB-715992 (ispinesib), SB-743921, MK-0731, STA-5312, eleutherobin, 17beta-acetoxy-2-ethoxy-6-oxo-B-homo-estra-1, 3, 5(10)-trien-3-ol, cyclostreptin, isolaulimalide, laulimalide, 4-epi-7-dihydroxy-14, 16-didemethyl-(+)-discodermolides, and cryptothilone 1, in addition to other microtubuline stabilizing agents known in the art.

Where it is desirable to render aberrantly proliferative cells quiescent in conjunction with or prior to treatment with anti-TIM-3 antibodies or antigen-binding fragments described herein, hormones and steroids (including synthetic analogs), such as 17a-Ethinylestradiol, Diethylstilbestrol, Testosterone, Prednisone, Fluoxymesterone, Dromostanolone propionate, Testolactone, Megestrolacetate, Methylprednisolone, Methyl-testosterone, Prednisolone, Triamcinolone, Chlorotrianisene, Hydroxyprogesterone, Aminoglutethimide, Estramustine, Medroxyprogesteroneacetate, Leuprolide. Flutamide, Toremifene, ZOLADEX®, can also be administered to the patient. When employing the methods or compositions described herein, other agents used in the modulation of tumor growth or metastasis in a clinical setting, such as antimimetics, can also be administered as desired.

In some embodiments, the combination of the anti-TIM-3 antibody or antigen-binding fragment and a second agent discussed herein can be administered concurrently as a single composition in a pharmaceutically acceptable carrier, or concurrently as separate compositions with the anti-TIM-3 antibody or antigen-binding fragment and the second agent in a pharmaceutically acceptable carrier. In some embodiments, the combination of the anti-TIM-3 antibody and the second agent can be administered sequentially. The administration of the two agents can start at times that are, e.g., 30 minutes, 60 minutes, 90 minutes, 120 minutes, 3 hours, 6 hours, 12 hours, 24 hours, 36 hours, 48 hours, 3 days, 5 days, 7 days, or one or more weeks apart, or administration of the second agent can start, e.g., 30 minutes, 60 minutes, 90 minutes, 120 minutes, 3 hours, 6 hours, 12 hours, 24 hours, 36 hours, 48 hours, 3 days, 5 days, 7 days, or one or more weeks after the first agent has been administered.

In some embodiments, an anti-neoplastic antibody that can be combined with an anti-TIM-3 antibody or antigen-binding fragment and/or a second agent includes RITUXANV (rituximab), HERCEPTIN® (trastuzumab), BEXXAR® (tositumomab), ZEVALIN® (ibritumomab), CAMPATH® (alemtuzunab), LYMPHOCIDE® (epratuzumab), AVASTIN® (bevacizumab), and TARCEVA® (erlotinib), or any combination thereof. In some embodiments, the second antibody useful for the combination therapy with an anti-TEVB antibody can be an antibody drug conjugate.

In some embodiments, an anti-TIM-3 antibody or antigen-binding fragment alone or in combination with another agent is used concurrently or sequentially with bone marrow transplantation to treat a variety of tumors of hematopoietic origin.

Provided herein are methods for altering an adverse event associated with treatment of a hyperproliferative disease (e.g., cancer) with an immunostimulatory agent, comprising administering an anti-TIM-3 antibody or antigen-binding fragment with or without a second agent, to a subject. For example, the methods described herein provide for a method of reducing the incidence of immunostimulatory therapeutic antibody-induced colitis or diarrhea by administering a non-absorbable steroid to the patient. As used herein, a "non-absorbable steroid" is a glucocorticoid that exhibits extensive first pass metabolism such that, following metabolism in the liver, the bioavailability of the steroid is low, i.e., less than about 20%. In some embodiments described herein, the nonabsorbable steroid is budesonide. Budesonide is a locally-acting glucocorticosteroid, which is extensively metabolized, primarily by the liver, following oral administration. ENTOCORT EC® (Astra-Zeneca) is a pH- and time-dependent oral formulation of budesonide developed to optimize drug delivery to the ileum and throughout the colon. ENTOCORT EC® is approved in the U.S. for the treatment of mild to moderate Crohn's disease involving the ileum and/or ascending colon. In some embodiments, an anti-TEVB antibody in conjunction with a non-absorbable steroid can be further combined with a salicylate. Salicylates include 5-ASA agents such as, for example: sulfasalazine (AZULFIDINE®, Pharmacia & Up John); olsalazine (DJ-PENTUM®, Pharmacia & Up John); balsalazide (COLAZAL®, Salix Pharmaceuticals, Inc.); and mesalamine (ASACOL®, Procter & Gamble Pharmaceuticals; PENTASA®, Shire US; CANASA®, Axcan Scandipharm, Inc.; ROWASA®, Solvay).

The additional therapy can be administered prior to, concurrently with, or subsequent to administration of the anti-TIM-3 antibodies or antigen-binding fragments, cells, or pharmaceutical compositions described herein. Combined administration can include co-administration, either in a single pharmaceutical formulation or using separate formulations, or consecutive administration in either order but generally within a time period such that all active agents can exert their biological activities simultaneously. A person skilled in the art can readily determine appropriate regimens for administering a pharmaceutical composition described herein and an additional therapy in combination, including the timing and dosing of an additional agent to be used in a combination therapy, based on the needs of the subject being treated.

7. EXPERIMENTAL

The examples provided below are for purposes of illustration only, which are not intended to be limiting unless otherwise specified. Thus, the invention should in no way be construed as being limited to the following examples, but rather, should be construed to encompass any and all variations which become evident as a result of the teaching provided herein.

7.1 Example 1: Preparation of Anti-Human TIM-3 Monoclonal Antibody

Human TIM-3 extracellular domain fragment comprising amino acid resides (Met 1-Arg 200) was used as immunogen, and the anti-human TIM-3 monoclonal antibody was produced by immunizing 7-week old BalB/C mice with the immunogen and Freunds Adjuvant (SIGMA). Animals with high antibody titer in serum were selected for cell fusion. Hybridoma cells were obtained by fusing mouse splenocytes with SP2/0 (ATCC, CRL8287TM) through an optimized PEG-mediated fusion procedure. After FACS screening assay, the positive hybridoma cells were selected for breed conservation and a series of subcloning. Anti-TIM-3 antibodies produced by Clones 3E6, 4H2, 16H1, 18C6, 19D11, 3F2, 36A2, 36B11, 38F8, 38A8, 40F111, 50H9, 84G10, or 39D1 were sequenced, and the sequences of respective antibodies are provided in Tables 1-3 above.

7.2 Example 2: Biological Screening Anti-TIM-3 Single Chain Variable Fragments (scFv)

Panning of anti-TIM-3 scFv Phage Display Library Mice were immunized using the method described in Example 1. Sera from different mice were titered for reactivity against TIM-3. Spleen from high-titer mice were processed to extract total RNA. Antibody heavy and light chain transcripts were reverse transcribed, amplified with Reverse Transcription Polymerase Chain Reaction (RT-PCR) and then used to construct phage display libraries of anti-TIM-3 scFvs. The immunoaffinity columns were prepared by coating each column with 10 µg TIM-3-his in 4 ml coating buffer overnight at 4° C. 4% milk in PBS-T was used to block immunoaffinity columns and phage display library separately, by incubation at 37° C. for 1 hour. Phage display library was then added to immunoaffinity columns and incubated at 37° C. for 1 hour with shaking to allow binding between anti-TIM-3 scFv with coated TIM-3. Unbound phages were removed by washing with PBS-T. The columns were eluted with 0.1 M Glycine-HCl pH 2.2, and the elute was adjusted to approximately pH 7.0 with 1.5 M TRIS-HCl, pH 7.4. Then, the elute was used to infect 10 mL of ER2738 that had been allowed to grow to an O.D. of 0.5-0.8. The elute-bacteria mixture was allowed to stand at 37° C. for 30 minutes and then incubated with shaking at 150 rpm at 37° C. for 1 hour. Afterwards, 1% bacterial culture was serially diluted and plated onto plates to determine yield. The rest was palleted, resuspended, and plated onto 2YTATG plates and cultured at 37° C. overnight. On the next day, colonies were transferred to 2YTATG liquid medium and allowed to grow to exponential phase. Then, M13KO7 accessory phage was added and allowed to infect for 40 minutes before the culture was collected by centrifugation. Pallets were resuspended with fresh 2YTAmp and cultured overnight at 30° C., followed by sedimentation purification in PEG6000-NaCl for the next round of panning. A total of 3 rounds of enrichment panning were performed.

Screening of anti-TIM3 scFv fragments. After 3 rounds of panning, monoclonal colonies well-separated from other colonies were picked into 96-deep well plates containing 2YTAmp liquid medium and allowed to grow to exponential phase at 220 rpm at 37° C. with shaking, and then incubated at 30° C. overnight at 220 rpm. Bacterial culture supernatant was collected by centrifugation at 4000 rpm, 15 minutes and ELISA was used to measure TIM-3 binding affinity. Clones with high TIM-3 binding affinity were selected, including clones CH5 #, CH8 #, CH9 #, CH10 #, and CH11 #. The sequences of respective antibodies are provided in Tables 1-3 above.

7.3 Example 3: Humanization of Anti-TIM-3 Antibodies

The germlines closest to Clones 3E6 were selected from IMGT database to serve as the templates for humanization. Kabat numbering for CDRs were adopted. CDRs from Clones 3E6 were grafted to the corresponding human templates. The sequences of humanized VH and VL regions of are provided in Tables 4a-4b above.

To express the humanized antibodies: primers were designed for genetical engineering; VH and VL regions were obtained by PCR and cloned into expression vectors that contained signal peptide and nucleic acid sequences encoding the constant regions (CH1-FC/CL); the heavy chain and light chain of the antibodies were transfected into 293F cells for expression. Affinity was measured using Octet-96. The binding affinities of the humanized antibodies are provided below.

TABLE 5

Binding affinities of humanized antibodies.

| Clone | $K_D$ (M) |
|---|---|
| 3E6 VH1/3E6 VL0 | 4.67E−07 |
| 3E6 VH2/3E6 VL0 | 2.21E−09 |
| 3E6 VH3/3E6 VL0 | 1.98E−09 |
| 3E6 VH4/3E6 VL0 | 1.87E−09 |
| 3E6 VH5/3E6 VL0 | 1.78E−09 |
| 3E6 VH6/3E6 VL0 | 1.46E−09 |
| 3E6 VH7/3E6 VL0 | 1.96E−09 |

7.4 Example 4: Affinity Maturation

Affinity maturation procedures included the following steps: the parental Fab was constructed and its binding against target antigen was validated; precise mutagenesis for residues in all six CDRs was performed; single clones were selected to express soluble Fabs for ELISA screening and off-rate ranking; the beneficial mutations were selected and combined library was constructed; ELISA screening and off-rate ranking were performed; the top affinity-matured antibody clones were selected (Table 1c above); the DNA encoding the selected antibody clones was synthesized and subcloned to expression vectors; the selected antibodies were expressed in HEK29 cells, purified and their affinities with human TIM-3 were measured.

TABLE 6

Binding affinities of affinity matured antibodies.

| | ka (1/Ms) | kd (1/s) | $K_D$ (M) | Rmax (RU) | Chi$^2$ (RU$^2$) |
|---|---|---|---|---|---|
| 3E6L-v1 | 4.33E+05 | 5.26E−04 | 1.22E−09 | 42.1 | 0.143 |
| 3E6L-v2 | 4.82E+05 | 6.13E−04 | 1.27E−09 | 50.6 | 0.432 |
| 3E6L-v3 | 4.65E+05 | 3.55E−04 | 7.64E−10 | 67.4 | 0.739 |
| 3E6L-v4 | 1.49E+05 | 5.63E−04 | 3.79E−09 | 58.63 | 0.0262 |
| 3E6L-v5 | 4.55E+05 | 6.46E−04 | 1.42E−09 | 57.22 | 0.154 |
| 3E6L-v6 | 9.19E+05 | 6.88E−04 | 7.48E−10 | 75.4 | 3.11 |
| 3E6L-v7 | 8.83E+05 | 5.62E−04 | 6.37E−10 | 71.2 | 1.59 |
| 3E6L-v8 | 6.27E+05 | 5.71E−04 | 9.11E−10 | 79.7 | 0.916 |
| 3E6L-v9 | 9.93E+05 | 4.39E−04 | 4.42E−10 | 64.5 | 0.338 |

7.5 Example 5: Purification of Antibody

The culture solution of cells transfected with the antibody was centrifuged at high speed and the supernatant was collected. After filtration with a 0.45 µm filter membrane, the first step of purification was carried out by affinity chromatography. Protein A that interacted with Fc or derivative packing (such as GE's Mabselect) was used as chromatographic medium. 10 times the column volume of equilibration buffer (1×PBS: 5.6 mmol/L Na2HPO4, 1.06 mmol/L KH2PO4, 154 mmol/L NaCl, pH7.2) was used, and the cell supernatant was then loaded and combined. The flow rate was adjusted such that it took 1 minute for the sample to go through the column. The column was washed with 1×PBS until the UV absorption of A280 dropped to the baseline and eluted with elution buffer (50 mM PBS: 50 mmol/L Na2HPO4, 1.06 mmol/L KH2PO4, 154 mmol/L NaCl, pH 3.0). The sample at the elution peak according to the A280 ultraviolet absorption was collected, neutralized with 1M NaOH, concentrated by ultrafiltration and filtered with a 0.22 μm membrane. The purity of the antibody was determined to be greater than 95% by SEC-HPLC, and the sequence confirmed by LS-MS.

7.6 Example 6: Binding Kinetics of Anti-TIM-3 Antibody to Human TIM-3 Protein Anti-TIM-3 antibodies were coupled to the surface of the HFC sensor (Probe Life), and human TIM-3 recombinant protein, as the mobile phase, was 1:2 serially diluted with a maximum concentration of 50 nM. The association and dissociation between TIM-3 protein and the antibody on the surface of the sensor were measured. Specifically, the HFC sensor was prewetted in SD buffer (PBS containing 0.02% Tween-20 and 0.2% BSA) for 10 minutes, and then balanced in a sample buffer containing antibodies for 1 minute, allowing antibodies to be coupled to the sensor surface. The antibody-coupled HFC sensor was balanced in the SD buffer solution for 1 minute, and then incubated in the buffer solution containing different concentrations of TIM-3-his for 120s to measure the association of TIM-3-his protein to captured antibody. Finally, the sensor combining the antigen and antibody was placed in SD buffer and waited for 300s to measure dissociation of TIM-3-his protein from the antibodies captured on sensor. Data was fitted using a 1:1 model, and the association rate ($k_{on}$) and the dissociation rate ($k_{off}$) were calculated. The equilibrium dissociation constant ($K_D$) was calculated by the ratio koff/Kon.

TABLE 7

Binding kinetics of anti-TIM-3 antibodies to TIM-3 protein.

| Loading | $k_{off}$(1/s) | $k_{on}$(1/Ms) | $K_D$(M) | Full R2 |
|---|---|---|---|---|
| 3E6 | 2.84E−04 | 1.24E+06 | 2.30E−10 | |
| 4H2 | 5.58E−04 | 1.32E+06 | 4.24E−10 | |
| 16H1 | 2.18E−04 | 1.30E+06 | 1.68E−10 | |
| 18C6 | 1.20E−04 | 5.80E+05 | 2.07E−10 | 0.997 |
| 19D11 | 3.70E−04 | 6.13E+05 | 6.04E−10 | 0.953 |
| CH 5# | 1.53E−03 | 8.13E+03 | 1.88E−07 | 0.941 |
| CH 8# | 2.53E−03 | 4.93E+03 | 5.12E−07 | 0.943 |
| CH 9# | 2.87E−03 | 5.19E+03 | 5.53E−07 | 0.935 |
| CH 10# | 1.48E−03 | 3.86E+04 | 3.82E−08 | 0.982 |
| CH 11# | 7.05E−04 | 3.69E+04 | 1.91E−08 | 0.991 |
| 3F2 | 6.60E−04 | 5.96E+05 | 1.11E−09 | 0.987 |
| 36A12 | 5.59E−04 | 5.53E+05 | 1.01E−09 | 0.992 |
| 36B11 | 3.83E−04 | 8.85E+05 | 4.32E−10 | 0.982 |
| 38A8 | 1.26E−03 | 9.28E+05 | 1.36E−09 | 0.987 |
| 38F8 | 2.55E−03 | 1.47E+06 | 1.74E−09 | 0.982 |
| 39D1 | 1.41E−03 | 1.25E+06 | 1.13E−09 | 0.968 |
| 40F11 | 1.90E−03 | 8.57E+05 | 2.21E−09 | 0.988 |
| 50H9 | 9.03E−03 | 1.51E+06 | 6.00E−09 | 0.816 |
| 84G10 | 1.97E−03 | 6.92E+05 | 2.84E−09 | 0.987 |

7.7 Example 7: Cross-Reactivity of Anti-TIM-3 Antibodies to Mouse or Cynomolgus TIM-3

Briefly, serially diluted anti-TIM-3 antibodies were incubated with cell lines stably expressing mouse TIM-3 or cynomolgus TIM-3 ($10^5$ cells/well). Then, PE-labelled mouse anti-human IgG antibody (Biolegend) was used as detection antibody. A flow cytometer (Canto II, BD, USA) was used to measure fluorescence. As demonstrated in FIG. 1A, antibodies 3E6, 4H2, I6H1, 39D1 cross-reacted with cynomolgus TIM-3. As shown in FIG. 1B, none of the tested antibodies cross-reacted with mouse TIM-3. Certain humanized antibodies were tested, including h3E6 IgG1 and h3E6 IgG1 LALA (L234A/L235A mutant). As shown in FIG. 2, neither h3E6 IgG1 nor h3E6 IgG1 LALA cross-reacted with cynomolgus TIM-3. It was further confirmed that neither h3E6 IgG1 nor h3E6 IgG1 LALA cross-reacted with mouse TIM-3 (data not shown).

7.8 Example 8: Binding of Various Isotypes of Anti-TIM-3 Antibodies to Human or Mouse Fc Receptors The binding of humanized anti-TIM-3 antibody 3E6 of different isotypes (IgG1, IgG1 LALA, IgG2, and IgG4) to mouse Fc receptor (CD16, CD32B, FCRN, or FCGR4) or human Fc receptor (CD32a H167, CD32a R167, CD32b, Cd16a 176F, Cd16a 176V, FCRN) was detected using biomolecular interaction system Gator (Probe Life). Biotinylated-Fc receptor was coupled to the surface of the SA sensor (Probe Life), and humanized anti-TIM-3 antibodies of different isotypes were used as the mobile phase. The binding between Fc receptor and the antibody on the surface of the sensor were measured. Specifically, the SA sensor was prewetted in SD buffer (PBS containing 0.02% Tween-20 and 0.2% BSA) for 10 minutes and then balanced in a sample buffer containing the Fc receptor for 10 minutes, allowing the Fc receptor to be coupled to the sensor surface. The Fc receptor-coupled SA sensor was balanced in the SD buffer solution for 2 minutes, and then incubated in the buffer solution containing antibodies for 5 min to measure the association of antibody to captured Fc receptor. Finally, the sensor combining the Fc receptor and antibody was placed in SD buffer and waited for 100s to measure dissociation between the two proteins.

The amounts of antibodies associated to the receptors were reflected as the "Response (nm)" in FIGS. 7A-7B. As shown in FIG. 7A (human Fc receptors) and FIG. 7B (mouse Fc receptors), various isotypes of humanized 3E6 bound to different Fc receptors at different levels.

7.9 Example 9: Anti-TIM-3 Antibodies Blocked TIM-3 Binding to Phosphatidylserine Hydrogen peroxide was first used to induce 293T apoptosis. Then, serially diluted anti-TIM-3 antibodies or isotype controls in 1× Annexin-V buffer (10 mM HEPES, 140 mM NaCl and 2.5 mM $CaCl_2$), pH adjusted to 7.4) were incubated with recombinant human TIM-3-Fc (Sino Biological, 10390-H38H) for 30 minutes at room temperature. 293T cells undergoing apoptosis were added to the antibody: TIM-3-Fc mixture with a final concentration of 1×$10^5$ cells per well and incubated for 1 hour at 4° C. After the cells were washed once, PE-labelled goat anti-mouse IgG antibody was added and incubated for 1 hour at 4° C. Finally, samples were washed once with 1× Annexin-V buffer and fluorescence was measured with a flow cytometer (Canto II, BD, USA). As shown in FIG. 3, anti-TIM-3 antibodies 3E6, 4H2, 16H1, CH 10 #, and 19D11 blocked TIM-3 binding to phosphatidylserine on the apoptotic cells.

7.10 Example 10: Anti-TIM-3 Antibodies Induced TIM-3 Internalization

TIM-3 expressing NK cells were used to measure TIM-3 internalization induced by anti-TIM-3 antibodies. Briefly, serially diluted anti-TIM-3 antibodies were incubated with NK cells ($1\times10^5$) for 18 hours at 37° C., or at 4° C. TIM-3 cell surface expression was detected with PE-labelled goat anti-human IgGκ antibody using flow cytometry. As shown in FIG. 4, anti-TIM-3 antibodies 3E6, 4H2, and 16H1 all induced internalization of TIM-3 in NK cells. Additionally, T cells and tumor cells, specifically, Pfeiffer cells (human lymphoma) were also used in the internalization study, and it was observed that 3E6, 4H2, and 16H1 all induced internalization of TIM-3 in T cells, but only 4H2 induced internalization of TIM-3 in Pfeiffer cells. Results are summarized below.

TABLE 8

TIM-3 Internalization induced by anti-TIM-3 antibodies

| Anti-TIM-3 | NK Cells | T Cells | Pfeiffer cells |
| --- | --- | --- | --- |
| 3E6 | YES | YES | NO |
| 4H2 | YES | YES | YES |
| 16H1 | YES | YES | NO |

7.11 Example 11: Anti-TIM-3 Antibodies Increased Secretion of IFN-γ in PBMC

T-cells activated with an anti-CD3 mAb (OKT3) were used to measure activities of anti-TIM-3 antibodies. To prepare activated PBMCs, 1 μg/ml OKT3 was used to coat plates by incubating overnight at 4° C. On the next day, coating solution containing OKT3 was discarded, and thawed PMBCs were added to OKT3-coated plates. 293T/OS8 cells were used as target cells. At its N-terminus, OS8 included an anti-human CD3 mAb OKT3 scfv, which could directly interact with the TCR/CD3 complex and activate T-cells. After three days of culture, activated PBMCs were mixed with 293T/OS8 target cells at a ratio of 5:1 (activated PBMC: 293T/OS8) and serially diluted anti-TIM-3 antibodies were added. As shown in FIG. 5A, anti-TIM-3 antibodies 3E6, 4H2, 16H1, 18C6, 19D11, CH 10 #, CH 11 #, 38A8, 38F8, 3F2, and 39D1 all increased IFN-γ secretion (measured by ELISA) in the co-culture of 293T/OS8 target cells and effector cells. The activities of the affinity matured antibodies were also confirmed using the same procedures (FIG. 5B).

7.12 Example 12: Anti-TIM-3 Antibodies Enhanced NK Cells-Mediated Cellular Cytotoxicity To verify that the humanized anti-TIM-3 antibodies could enhance NK cell-mediated cellular cytotoxicity, NK cells were isolated from PBMCs of healthy donors using NK Cell Isolation Kit from Miltenyi Biotec according to manufacturer's instruction. After stimulation with human IL-2 (1000 U/ml) for 1 day. NK cells were incubated with anti-TIM-3 antibodies for 20 minutes at room temperature. Then, CFSE-labelled K562 cells were added to the mixture and incubated for 2 hours at 37° C. CD107a expression (which indicated NK cell activation) was then detected with flow cytometry. As shown in FIG. 6, anti-TIM-3 antibodies 3E6, 4H2, and 16H1 increased CD107a expression measured by both Mean Fluorescence Intensity (MFI) and percentage cells expressing CD107a, to a greater extent than reference antibodies TSR022 and MBG453, demonstrating that these antibodies were capable of enhancing the activity (cytotoxicity) of NK cells, and with greater activities compared to reference antibodies.

7.13 Example 13: Anti-TIM-3 Antibodies Inhibit Tumor Growth in Mouse Models

Human CD34+ hematopoietic stem cell-engrafted NPG™ mice were subcutaneously implanted with human non-small cell lung cancer cells. Treatment with a humanized 3E6 was initiated after tumors had reached a size of approximately 75 mm$^3$ in volume. Tumor diameters were measured two times a week. Tumor volumes were calculated according to the formula lss/2, with "l" being the longest diameter and "s" the short diameter thereto. Inhibition of tumor volume in the test groups relative to the vehicle control group was calculated as the ratio of the median relative tumor volumes (T/C). Tumor volume were significantly reduced by twice administration of the humanized 3E6. Both HCC827 and MDA-MB-231 cancer cell lines were tested and similar reduction in tumor size was observed.

Following the same procedure, pancreatic cancer cell line BxPC-3 was also tested and similar reduction in tumor size was observed. Different isotypes if humanized 3E6 were tested, including IgG1 LALA (L234A and L235A), IgG2 and IgG4. As shown in FIG. 8, humanized 3E6 of different isotypes all effectively reduced tumor volume as compared to vehicle control. Additionally, various cytokines (IL-4, IL-2, IL-1β, TNF-α, IL-17A, IL-6, IL-10, IFN-γ, IL-12p70, and TGF-β) in the endpoint mouse serum samples were measured. As shown in FIG. 9, humanized 3E6 IgG1 LALA significantly increased the levels of IL-17A, IL-6, IL-10, IFN-γ, perforin, and granulysin in mouse serum samples.

Additionally, humanized 3E6 of different isotypes also inhibited tumor growth in TIM3-humanized C57BL/6 mice that were subcutaneously implanted with murine colon adenocarcinoma cells MC38 (FIG. 10).

As such, in vivo anti-tumor efficacy of the humanized anti-TIM-3 antibodies disclosed herein were separately demonstrated in mouse models having lung cancer, breast cancer, pancreatic cancer, and colon cancer.

7.14 Example 14: Epitope Binning

Antibodies were diluted with PBS to 2 μg/mL. 50 μl antibody solution was added to each well of the 96-well plate, which was incubated at 4° C. overnight. The plate was then washed with wash buffer (0.05% Tween in PBS) three times and blocked with 5% skim milk in PBS at 37° C. for two hours. The biotinylated human TIM-3 and antibodies were preincubated at room temperature for half an hour and then added to the plate. The plate was then incubated at room temperature for 1 hour and washed three times with wash buffer. 50 μl streptavidin HRP (1:1000, BD) was then added to each well at room temperature and incubated for about 1 hour. 50 μl of TMB substrate was added to each well, and the reaction was then terminated with 50 μl HCL after 1-5 minutes. Absorbance was read at 450 nm and IC50 value was analyzed.

As shown in Table 9, antibodies 3E6, 4H2, 16H1, and CH10 # competitively inhibited the reference antibodies (e.g., MBG453 and TSR022) from binding to human TIM-3 to various extent, indicating that their epitopes on human TIM-3 overlap with those recognized by the reference antibodies. To the contrary, 19D1 and CH 11 # showed little inhibition of the reference antibodies' binding to human TIM-3, indicating that their epitopes on TIM-3 have little to none overlap with those of the reference antibodies. Furthermore, MBG453 and/or TSR022 only reduced antibodies 3E6, 4H2 16H1, and CH10 # from binding to human TIM-3 to a small percentage (less than 50%, or less than 20%), indicating that these four antibodies bind to at least one additional epitope on human TIM-3 that are not recognized by MBG453 and/or TSR022.

TABLE 9

Epitope Binning of anti-TIM-3 antibodies

| inhibit percentage | | 3E6 | 4H2 | 16H1 | 19D11 | analyte CH 10# | CH 11# | MBG453 | TSR022 |
|---|---|---|---|---|---|---|---|---|---|
| solid phage | 3E6 | 100.00% | 99.59% | 26.27% | 38.70% | 50.07% | 67.12% | 24.91% | 16.43% |
| | 4H2 | 99.94% | 100.00% | 28.95% | 39.00% | 56.75% | 62.49% | 28.03% | 16.72% |
| | 16H1 | 59.99% | 64.69% | 100.00% | 0.06% | 15.09% | 8.26% | 81.66% | 4.02% |
| | 19D11 | 100.00% | 100.00% | 0.00% | 100.00% | 100.00% | 100.00% | 0.00% | 10.29% |
| | CH 10# | 98.24% | 98.58% | 45.81% | 98.09% | 100.00% | 99.73% | 35.43% | 48.55% |
| | CH 11# | 97.82% | 99.64% | 0.00% | 99.41% | 98.17% | 100.00% | 29.39% | 0.00% |
| | MBG453 | 94.27% | 95.93% | 99.16% | 4.39% | 15.82% | 8.29% | 100.00% | 94.82% |
| | TSR022 | 95.84% | 98.07% | 70.22% | 0.00% | 40.47% | 0.00% | 99.06% | 100.00% |

$$\text{Percent Inhibition} = \frac{(\text{negative control} - X)}{(\text{negative control} - \text{positive control})} \times 100\%$$

7.15 Example 15: Structure Determination

Step 1: Protein expression and purification; The coding sequence of target antigen (human TIM-3 Isoform 1) was cloned into an expression vector after codon optimization. A purification tag was attached to the N or C terminus of the antigen, and an enzyme digestion site was introduced between the tag and protein. The protein was induced to express in the form of inclusion body in E. coli. Cells were cultured in LB medium at 37° C. until OD600 reached 0.6-1.0. At this time, 1 mM IPTG was added, incubated at 37° C., and 120 rpm for 4 h to induce protein expression. The bacteria were collected by centrifugation. The collected bacteria were lysed and target protein obtained by affinity purification. Finally, SDS-PAGE, LC-MS and Size-exclusion chromatography (SEC) were used to identify the purified protein.

The antibody (3E6 Fab) was digested with papain or trypsin, and the digested antibody was centrifuged at 13000 rpm for 5 min. Superdex 200 Increase 10/300 GL columns were used to separate the components and collect the target samples.

Step 2: Complex Formation and Crystallization: The purified antigen-antibody complex was crystallized by the sitting drop method. The crystallization kit produced by Hampton Research company was used: 15 µL crystallization reagent was used as buffer and applied to wells in a 96-well crystal plate. Mosquito LCP protein crystallization screening instrument was used to add sample: 200 nL protein+180 nL crystallization solution+20 nL lysozyme crystal seed. The 96-well plate sealed with the MicroAMP Optical Adhesive membrane was placed in a constant temperature incubator at 4° C./20'C and crystal growth was observed regularly.

Step 3: Data Collection and Structure Determination: Before the collection of crystal diffraction data, the crystals were first transferred to cryo-protectant, then stored in the liquid nitrogen in Universal VI-Puck and sent to a synchrotron radiation source for data collection. The collected diffraction data were processed using HKL3000 software.

Homology models of target antigen and Fab were selected respectively, and PHASER & Molrep program in CCP4 software package was used to carry out molecular replacement to obtain the initial structure of the complex. Then, the REFMAC program in CCP4 software package was used to correct the model, and COOT program was used to adjust the model manually. The final structure was obtained through several cycles and provided in FIG. 11A.

As provided in FIG. 11B and Table 10, we further mapped the interactive between specific residues on human TIM-3 and the specific residues on the VH CDRs and VL CDRs of the h3E6 Fab. As shown, h3E6 Fab bound to amino acids 71-82 of human TIM-3 via CDR1-3 of the VH and CDR2 of the VL.

TABLE 10

Epitope Mapping of anti-TIM-3 antibodies

| TIM3(A): HC | | |
|---|---|---|
| TIM3 ATOMS | HC ATOMS | H bond (Å) |
| 71(ASP) | 100(TYR) | 2.88 |
| 74(ASP) | 102(SER), 104(TRP) | water-mediated interaction, 3.5 |
| 75(VAL) | 101(ARG) | 3.31 |
| 76(ASN) | 33(PHE) | 2.43 |
| 78(TRP) | 54(HIS), 55(SER) | 3.25, water-mediated interaction |
| 79(THR) | 101(ARG) | 3.3 |
| 82(TYR) | 101(ARG) | 2.57, 3.5 |

| TIM3(A): LC | | |
|---|---|---|
| TIM3 ATOMS | LC ATOMS | H bond (Å) |
| 73(ARG) | 56(SER) | 3.38 |

Additionally, the complexes of human TIM-3 bound with both h3E6 Fab and another anti-TIM-3 antibody were also crystalized and the structures shown in FIGS. 12A-12B. FIG. 12A shows the structure of the complex of human TIM-3, h3E6 Fab and the anti-TIM-3 Fab 6TXZ (PDB ID:6TXZ or M6903 Fab, Merck KGaA). Zhang et al., Oncoimmunology, 2020: 9(1): 1744921). FIG. 12B shows the structure of the complex of TIM-3, h3E6 Fab, and the anti-TIM-3 Fab 7KQL (PDB ID:7KQL). As shown, h3E6 bound to an epitope on human TIM-3 distinct from the epitope bound by either 6TXZ or 7KQL.

7.16 Example 16: Anti-TIM-3 Antibodies Activate Myeloid Cells In Vitro

To confirm that anti-TIM-3 antibodies provided herein (e.g., h3E6 of different isotypes) can further enhance innate immunity by activating myeloid cells, 0.5-1×10⁵ myeloid cells (macrophages and dendritic cells in parallel experiments) are plated in 96-round well plates, and the cell incubated with serial dilution antibodies at least for 2 hrs. The cells are primed with ultrapure LPS for several hours followed by stimulated with ATP or nigericin (e.g., 3 µM) for 0.5-5 h. Then, the supernatants are analyzed for human IL-1β, IL-18, IL-6, or TNFα levels according to the manufacturer's instructions. The anti-TIM-3 antibodies provided herein are expected to enhance the activity of the myeloid cells and result in enhanced levels of cytokines in the supernatants.

An anti-TIM-3 Fab that binds to a different epitope on human TIM-3 (e.g., one that does not involve D71, N76 or Y82) as control. For example, Fab 6TXZ or Fab 7KQL can be used. The control antibody is expected to have less (even no) activity in promoting the activity of myeloid cells compared to h3E6.

7.17 Exemplary Embodiments

Embodiment 1. An antibody or antigen-binding fragment thereof that specifically binds human TIM-3, comprising:
  (a) a light chain variable region (VL) comprising
    (1) a light chain CDR1 (VL CDR1) having an amino acid sequence selected from the group consisting of SEQ ID NOs:86-93 and 129-137;
    (2) a light chain CDR2 (VL CDR2) having an amino acid sequence selected from the group consisting of SEQ ID NOs:94-100 and 138-144; and
    (3) a light chain CDR3 (VL CDR3) having an amino acid sequence selected from the group consisting of SEQ ID NOs:47-55, 145-153 and 198-206;
    or a variant thereof having up to about 3 amino acid substitutions, additions, and/or deletions in the VL CDRs; and/or
  (b) a heavy chain variable region (VH) comprising
    (1) a heavy chain CDR1 (VH CDR1) having an amino acid sequence selected from the group consisting of SEQ ID NOs:101-108 and 154-161;
    (2) a heavy chain CDR2 (VH CDR2) having an amino acid sequence selected from the group consisting of SEQ ID NOs:109-118 and 162-170; and
    (3) a heavy chain CDR3 (VH CDR3) having an amino acid sequence selected from the group consisting of SEQ ID NOs:119-128 and 171-179;
    or a variant thereof having up to about 3 amino acid substitutions, additions, and/or deletions in the VH CDRs.

Embodiment 2. The antibody or antigen-binding fragment of Embodiment 1, wherein
  (a) the VL CDR1, CDR2 and CDR3 have
    (1) the amino acid sequences of SEQ ID NOs:86, 94, and 47, respectively;
    (2) the amino acid sequences of SEQ ID NOs:87, 95, and 48, respectively;
    (3) the amino acid sequences of SEQ ID NOs:88, %, and 49, respectively;
    (4) the amino acid sequences of SEQ ID NOs:89, 97, and 50, respectively;
    (5) the amino acid sequences of SEQ ID NOs:90, 94, and 51, respectively;
    (6) the amino acid sequences of SEQ ID NOs:91, 98, and 52, respectively;
    (7) the amino acid sequences of SEQ ID NOs:91, 98, and 53, respectively;
    (8) the amino acid sequences of SEQ ID NOs:92, 99, and 54, respectively;
    (9) the amino acid sequences of SEQ ID NOs:93, 10, and 55, respectively;
    (10) the amino acid sequences of SEQ ID NOs:129, 138, and 145, respectively;
    (11) the amino acid sequences of SEQ ID NOs:130, 139, and 146, respectively;
    (12) the amino acid sequences of SEQ ID NOs:131, 140, and 147, respectively;
    (13) the amino acid sequences of SEQ ID NOs:132, 141, and 148, respectively;
    (14) the amino acid sequences of SEQ ID NOs:133, 139, and 149, respectively;
    (15) the amino acid sequences of SEQ ID NOs:134, 142, and 150, respectively;
    (16) the amino acid sequences of SEQ ID NOs:135, 143, and 151, respectively;
    (17) the amino acid sequences of SEQ ID NOs:136, 144, and 152, respectively;
    (18) the amino acid sequences of SEQ ID NOs:137, 100, and 153, respectively;
    (19) the amino acid sequences of SEQ ID NOs:86, 94, and 198, respectively;
    (20) the amino acid sequences of SEQ ID NOs:86, 94, and 199, respectively;
    (21) the amino acid sequences of SEQ ID NOs:86, 94, and 200, respectively;
    (22) the amino acid sequences of SEQ ID NOs:86, 94, and 201, respectively;
    (23) the amino acid sequences of SEQ ID NOs:86, 94, and 202, respectively;
    (24) the amino acid sequences of SEQ ID NOs:86, 94, and 203, respectively;
    (25) the amino acid sequences of SEQ ID NOs:86, 94, and 204, respectively;
    (26) the amino acid sequences of SEQ ID NOs:86, 94, and 205, respectively; or
    (27) the amino acid sequences of SEQ ID NOs:86, 94, and 206, respectively;
    or a variant thereof having up to about 3 amino acid substitutions, additions, and/or deletions in the VL CDRs; and/or
  (b) the VH CDR1, CDR2 and CDR3 have
    (1) the amino acid sequences of SEQ ID NOs:101, 109, and 119, respectively;
    (2) the amino acid sequences of SEQ ID NOs:102, 110, and 120, respectively;
    (3) the amino acid sequences of SEQ ID NOs:103, 111, and 121, respectively;
    (4) the amino acid sequences of SEQ ID NOs:104, 112, and 122, respectively;
    (5) the amino acid sequences of SEQ ID NOs:105, 113, and 123, respectively;
    (6) the amino acid sequences of SEQ ID NOs:106, 114, and 124, respectively;
    (7) the amino acid sequences of SEQ ID NOs:106, 115, and 125, respectively;
    (8) the amino acid sequences of SEQ ID NOs:107, 116, and 126, respectively;
    (9) the amino acid sequences of SEQ ID NOs:108, 117, and 127, respectively;
    (10) the amino acid sequences of SEQ ID NOs:106, 118, and 128, respectively;
    (11) the amino acid sequences of SEQ ID NOs:106, 162, and 171, respectively;

(12) the amino acid sequences of SEQ ID NOs:154, 163, and 172, respectively;
(13) the amino acid sequences of SEQ ID NOs:155, 164, and 173, respectively;
(14) the amino acid sequences of SEQ ID NOs:156, 165, and 174, respectively;
(15) the amino acid sequences of SEQ ID NOs:157, 166, and 175, respectively;
(16) the amino acid sequences of SEQ ID NOs:158, 167, and 176, respectively;
(17) the amino acid sequences of SEQ ID NOs:159, 168, and 177, respectively;
(18) the amino acid sequences of SEQ ID NOs:160, 169, and 178, respectively; or
(19) the amino acid sequences of SEQ ID NOs:161, 170, and 179, respectively;
or a variant thereof having up to about 3 amino acid substitutions, additions, and/or deletions in the VH CDRs.

Embodiment 3. The antibody or antigen-binding fragment of Embodiment 1, wherein
(1) the VL CDR1, CDR2, and CDR3 have the amino acid sequences of SEQ ID NOs:86, 94, and 47, respectively; and/or the VH CDR1, CDR2, and CDR3 have the amino acid sequences of SEQ ID NOs:101, 109, and 119, respectively;
(2) the VL CDR1, CDR2, and CDR3 have the amino acid sequences of SEQ ID NOs:87, 95, and 48, respectively; and/or the VH CDR1, CDR2, and CDR3 have the amino acid sequences of SEQ ID NOs:102, 110, and 120, respectively;
(3) the VL CDR1, CDR2, and CDR3 have the amino acid sequences of SEQ ID NOs:88, 96, and 49, respectively; and/or the VH CDR1, CDR2, and CDR3 have the amino acid sequences of SEQ ID NOs:103, 111, and 121, respectively;
(4) the VL CDR1, CDR2, and CDR3 have the amino acid sequences of SEQ ID NOs:89, 97, and 50, respectively; and/or the VH CDR1, CDR2, and CDR3 have the amino acid sequences of SEQ ID NOs:104, 112, and 122, respectively;
(5) the VL CDR1, CDR2, and CDR3 have the amino acid sequences of SEQ ID NOs:90, 94, and 51, respectively; and/or the VH CDR1, CDR2, and CDR3 have the amino acid sequences of SEQ ID NOs:105, 113, and 123, respectively;
(6) the VL CDR1, CDR2, and CDR3 have the amino acid sequences of SEQ ID NOs:91, 98, and 52, respectively; and/or the VH CDR1, CDR2, and CDR3 have the amino acid sequences of SEQ ID NOs:106, 114, and 124, respectively,
(7) the VL CDR1, CDR2, and CDR3 have the amino acid sequences of SEQ ID NOs:91, 98, and 53, respectively; and/or the VH CDR1, CDR2, and CDR3 have the amino acid sequences of SEQ ID NOs:106, 115, and 125, respectively;
(8) the VL CDR1. CDR2, and CDR3 have the amino acid sequences of SEQ ID NOs:92, 99, and 54, respectively; and/or the VH CDR1, CDR2, and CDR3 have the amino acid sequences of SEQ ID NOs:107, 116, and 126, respectively;
(9) the VL CDR1, CDR2, and CDR3 have the amino acid sequences of SEQ ID NOs:93, 100, and 55, respectively; and/or the VH CDR1, CDR2, and CDR3 have the amino acid sequences of SEQ ID NOs:108, 117, and 127, respectively,
(10) the VL CDR1, CDR2, and CDR3 have the amino acid sequences of SEQ ID NOs:91, 98, and 52, respectively; and/or the VH CDR1, CDR2, and CDR3 have the amino acid sequences of SEQ ID NOs:106, 118, and 128, respectively;
(11) the VL CDR1, CDR2, and CDR3 have the amino acid sequences of SEQ ID NOs:129, 138, and 145, respectively; and/or the VH CDR1, CDR2, and CDR3 have the amino acid sequences of SEQ ID NOs:106, 162, and 171, respectively;
(12) the VL CDR1, CDR2, and CDR3 have the amino acid sequences of SEQ ID NOs:130, 139, and 146, respectively; and/or the VH CDR1, CDR2, and CDR3 have the amino acid sequences of SEQ ID NOs:154, 163, and 172, respectively;
(13) the VL CDR1, CDR2, and CDR3 have the amino acid sequences of SEQ ID NOs:131, 140, and 147, respectively; and/or the VH CDR1. CDR2, and CDR3 have the amino acid sequences of SEQ ID NOs:155, 164, and 173, respectively;
(14) the VL CDR1, CDR2, and CDR3 have the amino acid sequences of SEQ ID NOs:132, 141, and 148, respectively; and/or the VH CDR1, CDR2, and CDR3 have the amino acid sequences of SEQ ID NOs:156, 165, and 174, respectively;
(15) the VL CDR1, CDR2, and CDR3 have the amino acid sequences of SEQ ID NOs:133, 139, and 149, respectively; and/or the VH CDR1, CDR2, and CDR3 have the amino acid sequences of SEQ ID NOs:157, 166, and 175, respectively;
(16) the VL CDR1, CDR2, and CDR3 have the amino acid sequences of SEQ ID NOs:134, 142, and 150, respectively; and/or the VH CDR1, CDR2, and CDR3 have the amino acid sequences of SEQ ID NOs:158, 167, and 176, respectively;
(17) the VL CDR1, CDR2, and CDR3 have the amino acid sequences of SEQ ID NOs:135, 143, and 151, respectively; and/or the VH CDR1, CDR2, and CDR3 have the amino acid sequences of SEQ ID NOs:159, 168, and 177, respectively;
(18) the VL CDR1, CDR2, and CDR3 have the amino acid sequences of SEQ ID NOs:136, 144, and 152, respectively; and/or the VH CDR1, CDR2, and CDR3 have the amino acid sequences of SEQ ID NOs:160, 169, and 178, respectively;
(19) the VL CDR1, CDR2, and CDR3 have the amino acid sequences of SEQ ID NOs:137, 100, and 153, respectively; and/or the VH CDR1, CDR2, and CDR3 have the amino acid sequences of SEQ ID NOs:161, 170, and 179, respectively;
(20) the VL CDR1, CDR2, and CDR3 have the amino acid sequences of SEQ ID NOs:86, 94, and 198, respectively; and/or the VH CDR1, CDR2, and CDR3 have the amino acid sequences of SEQ ID NOs:101, 109, and 119, respectively;
(21) the VL CDR1, CDR2, and CDR3 have the amino acid sequences of SEQ ID NOs:86, 94, and 199, respectively; and/or the VH CDR1, CDR2, and CDR3 have the amino acid sequences of SEQ ID NOs:101, 109, and 119, respectively;
(22) the VL CDR1, CDR2, and CDR3 have the amino acid sequences of SEQ ID NOs:86, 94, and 200, respectively; and/or the VH CDR1, CDR2, and CDR3 have the amino acid sequences of SEQ ID NOs:101, 109, and 119, respectively;
(23) the VL CDR1, CDR2, and CDR3 have the amino acid sequences of SEQ ID NOs:86, 94, and 201, respectively; and/or the VH CDR1, CDR2, and CDR3 have the amino acid sequences of SEQ ID NOs:101, 109, and 119, respectively;

(24) the VL CDR1, CDR2, and CDR3 have the amino acid sequences of SEQ ID NOs:86, 94, and 202, respectively; and/or the VH CDR1, CDR2, and CDR3 have the amino acid sequences of SEQ ID NOs:101, 109, and 119, respectively;

(25) the VL CDR1, CDR2, and CDR3 have the amino acid sequences of SEQ ID NOs:86, 94, and 203, respectively; and/or the VH CDR1, CDR2, and CDR3 have the amino acid sequences of SEQ ID NOs:101, 109, and 119, respectively;

(26) the VL CDR1, CDR2, and CDR3 have the amino acid sequences of SEQ ID NOs:86, 94, and 204, respectively; and/or the VH CDR1, CDR2, and CDR3 have the amino acid sequences of SEQ ID NOs:101, 109, and 119, respectively;

(27) the VL CDR1, CDR2, and CDR3 have the amino acid sequences of SEQ ID NOs:86, 94, and 205, respectively; and/or the VH CDR1, CDR2, and CDR3 have the amino acid sequences of SEQ ID NOs:101, 109, and 119, respectively; or

(28) the VL CDR1, CDR2, and CDR3 have the amino acid sequences of SEQ ID NOs:86, 94, and 206, respectively; and/or the VH CDR1, CDR2, and CDR3 have the amino acid sequences of SEQ ID NOs:101, 109, and 119, respectively.

Embodiment 4. The antibody or antigen-binding fragment of Embodiment 1, comprising a VL CDR1, a VL CDR2, a VH CDR1, a VH CDR2 and a VH CDR3 having the amino acid sequences of SEQ ID NOs:86, 94, 101, 109, and 119, respectively, and a VL CDR3 having an amino acid sequence selected from the group consisting of SEQ ID NOs:47 and 198-206; or a variant thereof having up to about 3 amino acid substitutions, additions, and/or deletions in the VL CDRs and up to about 3 amino acid substitutions, additions, and/or deletions in the VH CDRs.

Embodiment 5. The antibody or antigen-binding fragment of Embodiment 4, wherein the F residue of VH CDR1 (amino acid 3 of SEQ ID NO:101), H and S resides of VH CDR2 (amino acids 4 and 5 of SEQ ID NO:109), Y, R, S and W residues of VH CDR3 (amino acids 2, 3, 4, and 6 of SEQ ID NO:119), and S residue of VL CDR2 (amino acid 7 of SEQ ID NO:94) are not mutated.

Embodiment 6. The antibody or antigen-binding fragment of Embodiment 4, comprising a VL CDR1, a VL CDR2, a VL CDR3, a VH CDR1, a VH CDR2 and a VH CDR3 having the amino acid sequences of SEQ ID NOs:86, 94, 47, 101, 109, and 119, respectively.

Embodiment 7. An antibody or antigen-binding fragment thereof that specifically binds human TIM-3, comprising:
(a) a VL having at least 85%, at least 90%, at least 95%, at least 98%, or 100% sequence identity to an amino acid sequence selected from the group consisting of SEQ ID NOs:1-10 and 180-188; and/or
(b) a VH having at least 85%, at least 90%, at least 95%, at least 98%, or 100% sequence identity to an amino acid sequence selected from the group consisting of SEQ ID NOs:11-20 and 189-197.

Embodiment 8. The antibody or antigen-binding fragment of Embodiment 7 comprising a VL and a VH, wherein the VL and VH each have at least 85%, at least 90%, at least 95%, at least 98%, or 100% sequence identity to the amino acid sequences of (1) SEQ ID NOs:1 and 11, respectively; (2) SEQ ID NOs:2 and 12, respectively; (3) SEQ ID NOs:3 and 13, respectively; (4) SEQ ID NOs:4 and 14, respectively; (5) SEQ ID NOs:5 and 15, respectively; (6) SEQ ID NOs:6 and 16, respectively; (7) SEQ ID NOs:7 and 17, respectively; (8) SEQ ID NOs:8 and 18, respectively; (9) SEQ ID NOs:9 and 19, respectively; (10) SEQ ID NOs:10 and 20, respectively; (11) SEQ ID NOs:180 and 189, respectively; (12) SEQ ID NOs:181 and 190, respectively; (13) SEQ ID NOs:182 and 191, respectively; (14) SEQ ID NOs:183 and 192, respectively; (15) SEQ ID NOs:184 and 193, respectively; (16) SEQ ID NOs:185 and 194, respectively; (17) SEQ ID NOs:186 and 195, respectively; (18) SEQ ID NOs:187 and 196, respectively; or (19) SEQ ID NOs:188 and 197, respectively.

Embodiment 9. The antibody or antigen-binding fragment of Embodiment 7 comprising a VL and a VH, wherein the VL and VH each have at least 85%, at least 90%, at least 95%, at least 98%, or 100% sequence identity to the amino acid sequences of SEQ ID NOs:1 and 11, respectively.

Embodiment 10. An antibody or antigen-binding fragment thereof that specifically binds human TIM-3, comprising:
(a) a VL having at least 85%, at least 90%, at least 95%, at least 98%, or 100% sequence identity to an amino acid sequence selected from the group consisting of SEQ ID NOs:21 and 207-215; and/or
(b) a VH having at least 85%, at least 90%, at least 95%, at least 98%, or 100% sequence identity to an amino acid sequence selected from the group consisting of SEQ ID NOs:22-29.

Embodiment 11. An antibody or antigen-binding fragment thereof that specifically binds human TIM-3, comprising
(a) a VL comprising VL CDR1, CDR2, and CDR3 from a VL having an amino acid sequence selected from the group consisting of SEQ ID NOs:1-10 and 180-188; and/or
(b) a VH comprising VH CDR1, CDR2, and CDR3 from a VH having an amino acid sequence selected from the group consisting of SEQ ID NOs:11-20 and 189-197.

Embodiment 12. The antibody or antigen-binding fragment thereof. Embodiment 11, comprising
(1) a VL comprising VL CDR1, CDR2, and CDR3 from a VL having the amino acid sequence of SEQ ID NO:1, and/or a VH comprising VH CDR1, CDR2, and CDR3 from a VH having the amino acid sequence of SEQ ID NO:11;
(2) a VL comprising VL CDR1, CDR2, and CDR3 from a VL having the amino acid sequence of SEQ ID NO:2, and/or a VH comprising VH CDR1, CDR2, and CDR3 from a VH having the amino acid sequence of SEQ ID NO:12;
(3) a VL comprising VL CDR1, CDR2, and CDR3 from a VL having the amino acid sequence of SEQ ID NO:3, and/or a VH comprising VH CDR1, CDR2, and CDR3 from a VH having the amino acid sequence of SEQ ID NO:13;
(4) a VL comprising VL CDR1, CDR2, and CDR3 from a VL having the amino acid sequence of SEQ ID NO:4, and/or a VH comprising VH CDR1, CDR2, and CDR3 from a VH having the amino acid sequence of SEQ ID NO:14;
(5) a VL comprising VL CDR1, CDR2, and CDR3 from a VL having the amino acid sequence of SEQ ID NO:5, and/or a VH comprising VH CDR1, CDR2, and CDR3 from a VH having the amino acid sequence of SEQ ID NO:15;
(6) a VL comprising VL CDR1, CDR2, and CDR3 from a VL having the amino acid sequence of SEQ ID NO:6, and/or a VH comprising VH CDR1, CDR2, and CDR3 from a VH having the amino acid sequence of SEQ ID NO:16;

(7) a VL comprising VL CDR1, CDR2, and CDR3 from a VL having the amino acid sequence of SEQ ID NO:7, and/or a VH comprising VH CDR1, CDR2, and CDR3 from a VH having the amino acid sequence of SEQ ID NO:17;

(8) a VL comprising VL CDR1, CDR2, and CDR3 from a VL having the amino acid sequence of SEQ ID NO:8, and/or a VH comprising VH CDR1, CDR2, and CDR3 from a VH having the amino acid sequence of SEQ ID NO:18;

(9) a VL comprising VL CDR1, CDR2, and CDR3 from a VL having the amino acid sequence of SEQ ID NO:9, and/or a VH comprising VH CDR1, CDR2, and CDR3 from a VH having the amino acid sequence of SEQ ID NO:19;

(10) a VL comprising VL CDR1, CDR2, and CDR3 from a VL having the amino acid sequence of SEQ ID NO:10, and/or a VH comprising VH CDR1, CDR2, and CDR3 from a VH having the amino acid sequence of SEQ ID NO:20;

(11) a VL comprising VL CDR1, CDR2, and CDR3 from a VL having the amino acid sequence of SEQ ID NO:180, and/or a VH comprising VH CDR1, CDR2, and CDR3 from a VH having the amino acid sequence of SEQ ID NO:189;

(12) a VL comprising VL CDR1, CDR2, and CDR3 from a VL having the amino acid sequence of SEQ ID NO:181, and/or a VH comprising VH CDR1, CDR2, and CDR3 from a VH having the amino acid sequence of SEQ ID NO:190;

(13) a VL comprising VL CDR1, CDR2, and CDR3 from a VL having the amino acid sequence of SEQ ID NO:182, and/or a VH comprising VH CDR1, CDR2, and CDR3 from a VH having the amino acid sequence of SEQ ID NO:191;

(14) a VL comprising VL CDR1, CDR2, and CDR3 from a VL having the amino acid sequence of SEQ ID NO:183, and/or a VH comprising VH CDR1, CDR2, and CDR3 from a VH having the amino acid sequence of SEQ ID NO:192;

(15) a VL comprising VL CDR1, CDR2, and CDR3 from a VL having the amino acid sequence of SEQ ID NO:184, and/or a VH comprising VH CDR1, CDR2, and CDR3 from a VH having the amino acid sequence of SEQ ID NO:193;

(16) a VL comprising VL CDR1, CDR2, and CDR3 from a VL having the amino acid sequence of SEQ ID NO:185, and/or a VH comprising VH CDR1, CDR2, and CDR3 from a VH having the amino acid sequence of SEQ ID NO:194;

(17) a VL comprising VL CDR1, CDR2, and CDR3 from a VL having the amino acid sequence of SEQ ID NO:186, and/or a VH comprising VH CDR1, CDR2, and CDR3 from a VH having the amino acid sequence of SEQ ID NO:195;

(18) a VL comprising VL CDR1, CDR2, and CDR3 from a VL having the amino acid sequence of SEQ ID NO:187, and/or a VH comprising VH CDR1, CDR2, and CDR3 from a VH having the amino acid sequence of SEQ ID NO:196; or

(19) a VL comprising VL CDR1, CDR2, and CDR3 from a VL having the amino acid sequence of SEQ ID NO:188, and/or a VH comprising VH CDR1, CDR2, and CDR3 from a VH having the amino acid sequence of SEQ ID NO:197.

Embodiment 13. An antibody or antigen-binding fragment thereof that specifically binds human TIM-3 comprising a VL and a VH, wherein the VL comprises VL CDR1, CDR2, and CDR3 from a VL having an amino acid sequence selected from the group consisting of SEQ ID NOs:21 and 207-215, and the VH comprises VH CDR1, CDR2, and CDR3 from a VH having an amino acid sequence selected from the group consisting of SEQ ID NOs:22-29.

Embodiment 14. An antibody or antigen-binding fragment thereof that competes with the antibody or antigen-binding fragment of any one of Embodiments 1 to 13 for binding to human TIM-3.

Embodiment 15. An antibody or antigen-binding fragment thereof that specifically binds human TIM-3, wherein the antibody or antigen-binding fragment specifically binds to an epitope comprising at least one of the amino acids 71-82 of human TIM-3.

Embodiment 16. The antibody or antigen-binding fragment of Embodiment 15 that specifically binds to at least one of the following amino acid residues of human TIM-3: D71, R73, D74, V75, N76, W78, T79, and Y82.

Embodiment 17. The antibody or antigen-binding fragment of Embodiment 15 that specifically binds to at least two, at least three, at least four, at least five, at least six, at least seven or eight of the following residues of human TIM-3: D71, R73, D74, V75, N76, W78, T79, and Y82.

Embodiment 18. The antibody or antigen-binding fragment of Embodiment 15 that specifically binds to at least D71, N76, or Y82 of human TIM-3.

Embodiment 19. The antibody or antigen-binding fragment of any one of Embodiments 1 to 18 that does not specifically bind to an epitope outside amino acids 71-82 of human TIM-3.

Embodiment 20. The antibody or antigen-binding fragment of any one of Embodiments 1 to 19, that binds human TIM-3 with a $K_D$ that is $5 \times 10^{-8}$ or less.

Embodiment 21. The antibody or antigen-binding fragment of Embodiment 20, that binds human TIM-3 with a $K_D$ that ranges from $10^{-11}$ M to $5 \times 10^{-9}$ M.

Embodiment 22. The antibody or antigen-binding fragment of any one of Embodiments 1 to 21, that blocks the interaction between TIM-3 and a TIM-3 ligand.

Embodiment 23. The method of Embodiment 22, wherein the TIM-3 ligand is phosphatidylserine, CEACAM1, HMGB1, or any combination thereof.

Embodiment 24. The antibody or antigen-binding fragment of any one of Embodiments 1 to 23 that (1) inhibits TIM-3 mediated T cell suppression, (2) inhibits TIM-3 mediated myeloid cell suppression, (3) inhibits TIM-3 mediated suppression of inflammasome activation, or any combination thereof.

Embodiment 25. The antibody or antigen-binding fragment of any one of Embodiments 1 to 24 that is a monoclonal antibody or antigen-binding fragment.

Embodiment 26. The antibody or antigen-binding fragment of any one of Embodiments 1 to 25 that is selected from the group consisting of an IgG1 antibody, an IgG2 antibody, an IgG3 antibody, and an IgG4 antibody.

Embodiment 27. The antibody or antigen-binding fragment of Embodiment 26 that is an IgG1 antibody Embodiment 28. The antibody or antigen-binding fragment of any one of Embodiments 1 to 25 that is selected from the group consisting of a Fab, a Fab', a F(ab'), a Fv, a scFv, a (scFv)₂, a single domain antibody (sdAb), and a heavy chain antibody (HCAb).

Embodiment 29. The antibody or antigen-binding fragment of any one of Embodiments 1 to 28 that is a chimeric antibody or antigen-binding fragment, a humanized antibody or antigen-binding fragment, or a human antibody or antigen-binding fragment.

Embodiment 30. The antibody or antigen-binding fragment of Embodiment 29 that is a humanized antibody or antigen-binding fragment.

Embodiment 31. The antibody or antigen-binding fragment of any one of Embodiments 1 to 30 that is a bispecific antibody or a multispecific antibody.

Embodiment 32. The antibody or antigen-binding fragment of Embodiment 31 that is a bispecific antibody that further specifically binds PD-1, PD-L1, CEACAM1, or CEACAM5.

Embodiment 33. A polynucleotide encoding the antibody or antigen-binding fragment of any one of Embodiments 1 to 32.

Embodiment 34. A vector comprising the polynucleotide of Embodiment 33.

Embodiment 35. A host cell comprising the polynucleotide of Embodiment 33, or the vector of Embodiment 34.

Embodiment 36. A pharmaceutical composition comprising a therapeutically effective amount of the antibody or antigen-binding fragment of any one of Embodiments 1 to 32, and a pharmaceutically acceptable carrier.

Embodiment 37. A method of inducing or stimulating immune cell activation and/or proliferation, comprising contacting an immune cell with an effective amount of the antibody or antigen-binding fragment of any one of Embodiments 1 to 32.

Embodiment 38. A method of reducing TIM-3-mediated suppression of an immune cell comprising contacting the immune cell with an effective amount of the antibody or antigen-binding fragment of any one of Embodiments 1 to 32.

Embodiment 39. The method of any Embodiment 37 or 38, wherein the immune cell is a T cell, an NK cell, an NKT cell, or a myeloid cell.

Embodiment 40. The method of Embodiment 39, wherein the immune cell is a T cell.

Embodiment 41. The method of Embodiment 39, wherein the immune cell is a NK cell.

Embodiment 42. The method of Embodiment 39, wherein the immune cell is a myeloid cell, wherein the myeloid cell is a macrophage or a dendritic cell.

Embodiment 43. A method of stimulating anti-tumor immunity in a subject in need thereof, comprising administering to the subject an effective amount of the antibody or antigen-binding fragment of any one of Embodiments 1 to 32 or the pharmaceutical composition of Embodiment 36.

Embodiment 44. A method of inhibiting tumor cell growth in a subject in need thereof, comprising administering to the subject a therapeutically effective amount of the antibody or antigen-binding fragment of any one of Embodiments 1 to 32 or the pharmaceutical composition of Embodiment 36.

Embodiment 45. A method of treating cancer in a subject in need thereof, comprising administering to the subject a therapeutically effective amount of the antibody or antigen-binding fragment of any one of Embodiments 1 to 32 or the pharmaceutical composition of Embodiment 36.

Embodiment 46. The method of Embodiment 44 or 45, further comprising administering an additional therapy to the subject.

Embodiment 47. The method of Embodiment 46, wherein the additional therapy comprises an antibody that specifically binds PD-L1, PD-1, CEACAM1, CTLA4, CEACAM5, latent TGF-β, TGF-β receptor, CD70, B7H4, or B7H3.

Embodiment 48. The method of Embodiment 46, wherein the additional therapy comprises irradiation or chemotherapy.

Embodiment 49. The method of any one of Embodiments 43 to 48, wherein the subject is a human.

Embodiment 50. Use of the antibody or antigen-binding fragment of any one of Embodiments 1 to 32 in cancer treatment.

Embodiment 51. Use of the antibody or antigen-binding fragment of any one of Embodiments 1 to 32 for the preparation of a medicament for the treatment of cancer.

Embodiment 52. The method or use of any one of Embodiments 45 to 51, wherein the cancer is a hematological cancer.

Embodiment 53. The method of Embodiment 52, wherein the hematological cancer is acute myelogenous leukemia (AML) or myelodysplastic syndromes (MDS).

Embodiment 54. The method or use of any one of Embodiments 45 to 51, wherein the cancer is a solid tumor.

Embodiment 55. The method or use of Embodiment 54, wherein the cancer is melanoma, lung cancer, head and neck cancer, colorectal cancer, pancreatic cancer, gastric cancer, kidney cancer, bladder cancer, prostate cancer, breast cancer, ovarian cancer, uterine/cervical cancer, testicular cancer, thyroid cancer, esophageal cancer, soft tissue sarcoma, liver cancer, gallbladder cancer, cervical cancer, duodenal cancer, bone cancer, neuroendocrine cancer, intestinal cancer, skin cancer, or germ cell cancer.

Embodiment 56. The method or use of Embodiment 54, wherein the cancer is selected from the group consisting of renal cell carcinoma (RCC), non-small cell lung carcinoma (NSCLC), squamous cell carcinoma of the head and neck (SCCHN), triple negative breast cancer (TNBC), gastric/stomach adenocarcinoma (STAD), pancreatic adenocarcinoma (PAAD), colon adenocarcinoma (COAD), or rectum adenocarcinoma (READ).

Embodiment 57. The method or use of any one of Embodiments 45 to 56, wherein the cancer has a high degree of microsatellite instability.

Embodiment 58. The method or use of any one of Embodiments 45 to 57, wherein the cancer is a metastatic cancer, refractory cancer, or recurrent cancer.

SEQUENCE LISTING

```
Sequence total quantity: 217
SEQ ID NO: 1            moltype = AA  length = 106
FEATURE                 Location/Qualifiers
REGION                  1..106
                        note = 3E6 VL
source                  1..106
```

```
                            mol_type = protein
                            organism = synthetic construct
SEQUENCE: 1
DIIMTQSQKF MSTSVGDRVS VTCKASQNVG ANVAWYQQKP RQSPKALIYS ASYRYSGVPD    60
RFTGSGSGTD FTLTISNVQS EDLAEYFCQQ YNSYPTFGGG TKLEIK                  106

SEQ ID NO: 2                moltype = AA  length = 107
FEATURE                     Location/Qualifiers
REGION                      1..107
                            note = 4H2 VL
source                      1..107
                            mol_type = protein
                            organism = synthetic construct
SEQUENCE: 2
DIQMTQSPSS LSASLGGKVT ITCKASQDIN KYIAWYQHKP GKGPRLLIHY TSTLQPGIPS    60
RFSGSGSGTD YSFSISNLEP EDFATYYCLQ YDNLLFTFGS GTKLEIK                 107

SEQ ID NO: 3                moltype = AA  length = 107
FEATURE                     Location/Qualifiers
REGION                      1..107
                            note = 16H1 VL
source                      1..107
                            mol_type = protein
                            organism = synthetic construct
SEQUENCE: 3
DIVMTQSHKF MSTSIEDRVS ITCKASQDVS AAVAWYQQKP GQTPKLLIYS TFYRYIGVPD    60
RFTGSGSGTD FTFTITSVQA EDLAVYFCQQ HYSVPWTFGG GTKLEIK                 107

SEQ ID NO: 4                moltype = AA  length = 113
FEATURE                     Location/Qualifiers
REGION                      1..113
                            note = 18C6 VL
source                      1..113
                            mol_type = protein
                            organism = synthetic construct
SEQUENCE: 4
DVVMTQTPLS LPVSLGDQAS ISCRSSQSLV HSNGNTYLHW FLQKPGQSPK LLIYKVSNRF    60
SGVPDRFSGS GSGTDFTLKI SRVEAEDLGV YFCCQSTHVP PLTFGAGTKL ELK          113

SEQ ID NO: 5                moltype = AA  length = 108
FEATURE                     Location/Qualifiers
REGION                      1..108
                            note = 19D11 VL
source                      1..108
                            mol_type = protein
                            organism = synthetic construct
SEQUENCE: 5
DIVMTQSQKF MSTSVGDRVS VTCKASQNVG TNVAWYQQKP GQSPKTLIYS ASYRYSGVPD    60
RFTGSGSGTD FTLTISNVQS EDLAEYFCQQ YNSYPLVTFG TGTKLELK                108

SEQ ID NO: 6                moltype = AA  length = 111
FEATURE                     Location/Qualifiers
REGION                      1..111
                            note = CH 5# VL
source                      1..111
                            mol_type = protein
                            organism = synthetic construct
SEQUENCE: 6
DIELTQSPAS LAVSLGQRAT ISCRASESVE YYGTSLMQWY QQKPGQPPKL LIYAASNVES    60
GVPARFSGSV SGTDFSLNIH PVEEDDIAMY FCQQSRKVPI TFGSGTKLEI K            111

SEQ ID NO: 7                moltype = AA  length = 111
FEATURE                     Location/Qualifiers
REGION                      1..111
                            note = CH 8# VL
source                      1..111
                            mol_type = protein
                            organism = synthetic construct
SEQUENCE: 7
DIELTQSPAS LAVSLGQRAT ISCRASESVE YYGTSLMQWY QQKPGQPPKL LIYAASNVES    60
GVAARFSGSG SGTDFSLNIH PVEEDDIAMY FCQPSRKVPY TFGGGTKLEI K            111

SEQ ID NO: 8                moltype = AA  length = 106
FEATURE                     Location/Qualifiers
REGION                      1..106
                            note = CH 9# VL
source                      1..106
                            mol_type = protein
                            organism = synthetic construct
```

```
SEQUENCE: 8
DIELTQSPAI LSASPGEKVT MTCRASSSVS YMHWYQQKPG SSPKPWIYAT SNLASGVPAR    60
FSGSGSGTSY SLTISRVEAE DAATYYCQQW SSNPLTFGAG TKLEIK                  106

SEQ ID NO: 9               moltype = AA   length = 108
FEATURE                    Location/Qualifiers
REGION                     1..108
                           note = CH 10# VL
source                     1..108
                           mol_type = protein
                           organism = synthetic construct
SEQUENCE: 9
DIELTQSPAL MAASPGEKVT ITCSASSSVS SSYLHWYQQK PGSSPKLWIY STSNLASGVP    60
ARFSGSGSGT SYSLTISSME AEDAATYYCQ QWSSYPLTFG AGTKLEIK                108

SEQ ID NO: 10              moltype = AA   length = 111
FEATURE                    Location/Qualifiers
REGION                     1..111
                           note = CH 11# VL
source                     1..111
                           mol_type = protein
                           organism = synthetic construct
SEQUENCE: 10
DIELTQSPAS LAVSLGQRAT ISCRASESVE YYGTSLMQWY QQKPGQPPKL LIYAASNVES    60
GVPARFSGSV SGTDFSLNIH PVEEDDIAVY FCQQSRKVPI TFGSGTKLEL K            111

SEQ ID NO: 11              moltype = AA   length = 118
FEATURE                    Location/Qualifiers
REGION                     1..118
                           note = 3E6 VH
source                     1..118
                           mol_type = protein
                           organism = synthetic construct
SEQUENCE: 11
DVQLQEAGPG LVKPSQSLSL NCTVTGYSIT SGFAWNWIRQ FPGNKLEWMG YISHSGSTSY    60
NPSLKSRISI TRDTSKNQFF LQLNSVTTED TATYYCARGY RSPWFAYWGQ GTLVTVSA    118

SEQ ID NO: 12              moltype = AA   length = 114
FEATURE                    Location/Qualifiers
REGION                     1..114
                           note = 4H2 VH
source                     1..114
                           mol_type = protein
                           organism = synthetic construct
SEQUENCE: 12
EVQLQESGPS LVKPSQTLSL TCSVTGDSIT SGYWNWIRKF PGNKLEYMGY INYSGSTYYN    60
PSLKSRISIT RDTSKNQYYL QLNSVTTEDT ATYYCATGNH FDYWGQGTTL TVSS         114

SEQ ID NO: 13              moltype = AA   length = 119
FEATURE                    Location/Qualifiers
REGION                     1..119
                           note = 16H1 VH
source                     1..119
                           mol_type = protein
                           organism = synthetic construct
SEQUENCE: 13
QVQLQQSGPQ LVRPGSSVQI SCKTSGYSFT SYLMHWVRQR PGQGLEWIGS IDPSDSEISL    60
NQKFMDKATL TVDKSSSTAN MQFSSPTSED SAVYFCARDF GYVAWFVYWG QGTLVTVSA   119

SEQ ID NO: 14              moltype = AA   length = 114
FEATURE                    Location/Qualifiers
REGION                     1..114
                           note = 18C6 VH
source                     1..114
                           mol_type = protein
                           organism = synthetic construct
SEQUENCE: 14
QVQLQQPGAE IVMPGASVKM SCKASGYKFT DFLMHWVKQR PGQGLEWIGA IDTSDSYASY    60
NQKFKGKATL TLDESSSTAY MQLSSLTSED SAVYYCSREA MDYWGQGTSV TVSS         114

SEQ ID NO: 15              moltype = AA   length = 118
FEATURE                    Location/Qualifiers
REGION                     1..118
                           note = 19D11 VH
source                     1..118
                           mol_type = protein
                           organism = synthetic construct
SEQUENCE: 15
DVQLQESGPD LVKPSQSLSL TCTVTGYSIT SGYSWHWIRQ FPGNKLEWMG YIYFSGSTNY    60
```

```
NPSLKSRISI TRDTSKNQFF LQLNSVTTED TATYYCARGY RSAWFAYWGQ GTLVTVSA    118

SEQ ID NO: 16           moltype = AA  length = 121
FEATURE                 Location/Qualifiers
REGION                  1..121
                        note = CH 5# VH
source                  1..121
                        mol_type = protein
                        organism = synthetic construct
SEQUENCE: 16
QVQLQQSGPD LVKPGASVKI SCKASGYSFT GYYMHWVKQS HGKSLEWIGR VNPNNGGTDY    60
DQKFKGKAIL SVDKSSNTAY MELRSLTSED SAVYYCAREG EYFDYYAMDY WGQGTTVTVS   120
S                                                                   121

SEQ ID NO: 17           moltype = AA  length = 121
FEATURE                 Location/Qualifiers
REGION                  1..121
                        note = CH 8# VH
source                  1..121
                        mol_type = protein
                        organism = synthetic construct
SEQUENCE: 17
QVKLQQSGPD LVKPGASVKI SCKASGYSFT GYYMHWVKQS HGKSLEWIGR VYPNNGGTSY    60
NQKFKGKAIL TVDKSSSTAY MELRSLTSED SAVYYCAREG EYFDYFAMDY WGQGTTVTVS   120
S                                                                   121

SEQ ID NO: 18           moltype = AA  length = 118
FEATURE                 Location/Qualifiers
REGION                  1..118
                        note = CH 9# VH
source                  1..118
                        mol_type = protein
                        organism = synthetic construct
SEQUENCE: 18
QVKLQESGPG LVAPSQSLSI TCTVSGFSLT GYGVHWVRQP PGKGLEWLGM IWGDGSTDYN    60
SALKSRLSIS KDNSKSQVFL KMNSLQTDDT ARYYCARDRG NHWYFDVWGQ GTTVTVSS    118

SEQ ID NO: 19           moltype = AA  length = 118
FEATURE                 Location/Qualifiers
REGION                  1..118
                        note = CH 10# VH
source                  1..118
                        mol_type = protein
                        organism = synthetic construct
SEQUENCE: 19
QVQLQQSGAE LMKPGASVKI SCKAIGYTFS SYWIEWVKQR PGHGLEWIGE ISPGRGSTNY    60
NEKFKGKATF TADTSSNTAY MQLSSLTSED SAVYYCARDY YGSIFDVWGQ GTTVTVSS    118

SEQ ID NO: 20           moltype = AA  length = 121
FEATURE                 Location/Qualifiers
REGION                  1..121
                        note = CH 11# VH
source                  1..121
                        mol_type = protein
                        organism = synthetic construct
SEQUENCE: 20
QVKLQQSGPD LVKPGASVKI SCKASGYSFT GYYMHWVKQS HGKSLEWIGR VNPNNGGTTY    60
KQKFKGKVIL TVDKSSSTAY MELRSLTSED SAVYYCAREG EYFDYYTMDY WGQGTTVTVS   120
S                                                                   121

SEQ ID NO: 21           moltype = AA  length = 106
FEATURE                 Location/Qualifiers
REGION                  1..106
                        note = 3E6 VL0
source                  1..106
                        mol_type = protein
                        organism = synthetic construct
SEQUENCE: 21
DIQMTQSPSS LSASVGDRVT ITCKASQNVG ANVAWYQQKP GKAPKSLIYS ASYRYSGVPS    60
RFSGSGSGTD FTLTISSLQP EDFATYYCQQ YNSYPTFGGG TKVEIK                 106

SEQ ID NO: 22           moltype = AA  length = 118
FEATURE                 Location/Qualifiers
REGION                  1..118
                        note = 3E6 VH0
source                  1..118
                        mol_type = protein
                        organism = synthetic construct
SEQUENCE: 22
```

```
QVQLQESGPG LVKPSQTLSL TCTVSGYSIT SGFAWNWIRQ PPGKGLEWIG YISHSGSTSY    60
NPSLKSRVTI SVDTSKNQFS LKLSSVTAAD TAVYYCARGY RSPWFAYWGQ GTTVTVSS    118

SEQ ID NO: 23           moltype = AA  length = 118
FEATURE                 Location/Qualifiers
REGION                  1..118
                        note = 3E6 VH1
source                  1..118
                        mol_type = protein
                        organism = synthetic construct
SEQUENCE: 23
QVQLQESGPG LVKPSQTLSL TCTVSGYSIT SGFAWNWIRQ PPGNGLEWMG YISHSGSTSY    60
NPSLKSRVTI SVDTSKNQFS LKLSSVTAAD TAVYYCARGY RSPWFAYWGQ GTTVTVSS    118

SEQ ID NO: 24           moltype = AA  length = 118
FEATURE                 Location/Qualifiers
REGION                  1..118
                        note = 3E6 VH2
source                  1..118
                        mol_type = protein
                        organism = synthetic construct
SEQUENCE: 24
QVQLQESGPG LVKPSQTLSL TCTVSGYSIT SGFAWNWIRQ PPGKGLEWMG YISHSGSTSY    60
NPSLKSRVTI SVDTSKNQFS LKLSSVTAAD TAVYYCARGY RSPWFAYWGQ GTTVTVSS    118

SEQ ID NO: 25           moltype = AA  length = 118
FEATURE                 Location/Qualifiers
REGION                  1..118
                        note = 3E6 VH3
source                  1..118
                        mol_type = protein
                        organism = synthetic construct
SEQUENCE: 25
QVQLQESGPG LVKPSQTLSL TCTVSGYSIT SGFAWNWIRQ PPGNGLEWIG YISHSGSTSY    60
NPSLKSRVTI SVDTSKNQFS LKLSSVTAAD TAVYYCARGY RSPWFAYWGQ GTTVTVSS    118

SEQ ID NO: 26           moltype = AA  length = 118
FEATURE                 Location/Qualifiers
REGION                  1..118
                        note = 3E6 VH4
source                  1..118
                        mol_type = protein
                        organism = synthetic construct
SEQUENCE: 26
QVQLQESGPG LVKPSQTLSL TCTVSGYSIT SGFAWNWIRQ PPGNGLEWIG YISHSGSTSY    60
NPSLKSRITI SVDTSKNQFS LKLSSVTAAD TAVYYCARGY RSPWFAYWGQ GTTVTVSS    118

SEQ ID NO: 27           moltype = AA  length = 118
FEATURE                 Location/Qualifiers
REGION                  1..118
                        note = 3E6 VH5
source                  1..118
                        mol_type = protein
                        organism = synthetic construct
SEQUENCE: 27
QVQLQESGPG LVKPSQTLSL TCTVSGYSIT SGFAWNWIRQ PPGNGLEWIG YISHSGSTSY    60
NPSLKSRITI SRDTSKNQFS LKLSSVTAAD TAVYYCARGY RSPWFAYWGQ GTTVTVSS    118

SEQ ID NO: 28           moltype = AA  length = 118
FEATURE                 Location/Qualifiers
REGION                  1..118
                        note = 3E6 VH6
source                  1..118
                        mol_type = protein
                        organism = synthetic construct
SEQUENCE: 28
QVQLQESGPG LVKPSQTLSL TCTVSGYSIT SGFAWNWIRQ PPGKGLEWMG YISHSGSTSY    60
NPSLKSRITI SVDTSKNQFS LKLSSVTAAD TAVYYCARGY RSPWFAYWGQ GTTVTVSS    118

SEQ ID NO: 29           moltype = AA  length = 118
FEATURE                 Location/Qualifiers
REGION                  1..118
                        note = 3E6 VH7
source                  1..118
                        mol_type = protein
                        organism = synthetic construct
SEQUENCE: 29
QVQLQESGPG LVKPSQTLSL TCTVSGYSIT SGFAWNWIRQ PPGKGLEWMG YISHSGSTSY    60
NPSLKSRITI SRDTSKNQFS LKLSSVTAAD TAVYYCARGY RSPWFAYWGQ GTTVTVSS    118
```

```
SEQ ID NO: 30           moltype = AA   length = 15
FEATURE                 Location/Qualifiers
REGION                  1..15
                        note = Linker
source                  1..15
                        mol_type = protein
                        organism = synthetic construct
SEQUENCE: 30
GGGGSGGGGS GGGGS                                                        15

SEQ ID NO: 31           moltype = AA   length = 13
FEATURE                 Location/Qualifiers
REGION                  1..13
                        note = 3E6 VL CDR1
source                  1..13
                        mol_type = protein
                        organism = synthetic construct
SEQUENCE: 31
KASQNVGANV AWY                                                          13

SEQ ID NO: 32           moltype = AA   length = 13
FEATURE                 Location/Qualifiers
REGION                  1..13
                        note = 4H2 VL CDR1
source                  1..13
                        mol_type = protein
                        organism = synthetic construct
SEQUENCE: 32
KASQDINKYI AWY                                                          13

SEQ ID NO: 33           moltype = AA   length = 13
FEATURE                 Location/Qualifiers
REGION                  1..13
                        note = 16H1 VL CDR1
source                  1..13
                        mol_type = protein
                        organism = synthetic construct
SEQUENCE: 33
KASQDVSAAV AWY                                                          13

SEQ ID NO: 34           moltype = AA   length = 18
FEATURE                 Location/Qualifiers
REGION                  1..18
                        note = 18C6 VL CDR1
source                  1..18
                        mol_type = protein
                        organism = synthetic construct
SEQUENCE: 34
RSSQSLVHSN GNTYLHWF                                                     18

SEQ ID NO: 35           moltype = AA   length = 13
FEATURE                 Location/Qualifiers
REGION                  1..13
                        note = 19D11 VL CDR1
source                  1..13
                        mol_type = protein
                        organism = synthetic construct
SEQUENCE: 35
KASQNVGTNV AWY                                                          13

SEQ ID NO: 36           moltype = AA   length = 17
FEATURE                 Location/Qualifiers
REGION                  1..17
                        note = CH 5#, CH 8# , CH 11# VL CDR1
source                  1..17
                        mol_type = protein
                        organism = synthetic construct
SEQUENCE: 36
RASESVEYYG TSLMQWY                                                      17

SEQ ID NO: 37           moltype = AA   length = 12
FEATURE                 Location/Qualifiers
REGION                  1..12
                        note = CH 9# VL CDR1
source                  1..12
                        mol_type = protein
                        organism = synthetic construct
SEQUENCE: 37
```

```
RASSSVSYMH WY                                                                       12

SEQ ID NO: 38           moltype = AA   length = 14
FEATURE                 Location/Qualifiers
REGION                  1..14
                        note = CH 10# VL CDR1
source                  1..14
                        mol_type = protein
                        organism = synthetic construct
SEQUENCE: 38
SASSSVSSSY LHWY                                                                     14

SEQ ID NO: 39           moltype = AA   length = 11
FEATURE                 Location/Qualifiers
REGION                  1..11
                        note = 3E6 VL CDR2
source                  1..11
                        mol_type = protein
                        organism = synthetic construct
SEQUENCE: 39
ALIYSASYRY S                                                                        11

SEQ ID NO: 40           moltype = AA   length = 11
FEATURE                 Location/Qualifiers
REGION                  1..11
                        note = 4H2 VL CDR2
source                  1..11
                        mol_type = protein
                        organism = synthetic construct
SEQUENCE: 40
LLIHYTSTLQ P                                                                        11

SEQ ID NO: 41           moltype = AA   length = 11
FEATURE                 Location/Qualifiers
REGION                  1..11
                        note = 16H1 VL CDR2
source                  1..11
                        mol_type = protein
                        organism = synthetic construct
SEQUENCE: 41
LLIYSTFYRY I                                                                        11

SEQ ID NO: 42           moltype = AA   length = 11
FEATURE                 Location/Qualifiers
REGION                  1..11
                        note = 18C6 VL CDR2
source                  1..11
                        mol_type = protein
                        organism = synthetic construct
SEQUENCE: 42
LLIYKVSNRF S                                                                        11

SEQ ID NO: 43           moltype = AA   length = 11
FEATURE                 Location/Qualifiers
REGION                  1..11
                        note = 19D11 VL CDR2
source                  1..11
                        mol_type = protein
                        organism = synthetic construct
SEQUENCE: 43
TLIYSASYRY S                                                                        11

SEQ ID NO: 44           moltype = AA   length = 11
FEATURE                 Location/Qualifiers
REGION                  1..11
                        note = CH 5#, CH 8# , CH 11# VL CDR2
source                  1..11
                        mol_type = protein
                        organism = synthetic construct
SEQUENCE: 44
LLIYAASNVE S                                                                        11

SEQ ID NO: 45           moltype = AA   length = 11
FEATURE                 Location/Qualifiers
REGION                  1..11
                        note = CH 9# VL CDR2
source                  1..11
                        mol_type = protein
                        organism = synthetic construct
```

```
SEQUENCE: 45
PWIYATSNLA S                                                              11

SEQ ID NO: 46           moltype = AA  length = 11
FEATURE                 Location/Qualifiers
REGION                  1..11
                        note = CH 10# VL CDR2
source                  1..11
                        mol_type = protein
                        organism = synthetic construct
SEQUENCE: 46
LWIYSTSNLA S                                                              11

SEQ ID NO: 47           moltype = AA  length = 8
FEATURE                 Location/Qualifiers
REGION                  1..8
                        note = 3E6 VL CDR3
source                  1..8
                        mol_type = protein
                        organism = synthetic construct
SEQUENCE: 47
QQYNSYPT                                                                   8

SEQ ID NO: 48           moltype = AA  length = 9
FEATURE                 Location/Qualifiers
REGION                  1..9
                        note = 4H2 VL CDR3
source                  1..9
                        mol_type = protein
                        organism = synthetic construct
SEQUENCE: 48
LQYDNLLFT                                                                  9

SEQ ID NO: 49           moltype = AA  length = 9
FEATURE                 Location/Qualifiers
REGION                  1..9
                        note = 16H1 VL CDR3
source                  1..9
                        mol_type = protein
                        organism = synthetic construct
SEQUENCE: 49
QQHYSVPWT                                                                  9

SEQ ID NO: 50           moltype = AA  length = 10
FEATURE                 Location/Qualifiers
REGION                  1..10
                        note = 18C6 VL CDR3
source                  1..10
                        mol_type = protein
                        organism = synthetic construct
SEQUENCE: 50
CQSTHVPPLT                                                                10

SEQ ID NO: 51           moltype = AA  length = 10
FEATURE                 Location/Qualifiers
REGION                  1..10
                        note = 19D11 VL CDR3
source                  1..10
                        mol_type = protein
                        organism = synthetic construct
SEQUENCE: 51
QQYNSYPLVT                                                                10

SEQ ID NO: 52           moltype = AA  length = 9
FEATURE                 Location/Qualifiers
REGION                  1..9
                        note = CH 5#, CH 11# VL CDR3
source                  1..9
                        mol_type = protein
                        organism = synthetic construct
SEQUENCE: 52
QQSRKVPIT                                                                  9

SEQ ID NO: 53           moltype = AA  length = 9
FEATURE                 Location/Qualifiers
REGION                  1..9
                        note = CH 8# VL CDR3
source                  1..9
                        mol_type = protein
```

```
                                  -continued organism = synthetic construct
SEQUENCE: 53
QPSRKVPYT                                                                9

SEQ ID NO: 54           moltype = AA   length = 9
FEATURE                 Location/Qualifiers
REGION                  1..9
                        note = CH 9# VL CDR3
source                  1..9
                        mol_type = protein
                        organism = synthetic construct
SEQUENCE: 54
QQWSSNPLT                                                                9

SEQ ID NO: 55           moltype = AA   length = 9
FEATURE                 Location/Qualifiers
REGION                  1..9
                        note = CH 10# VL CDR3
source                  1..9
                        mol_type = protein
                        organism = synthetic construct
SEQUENCE: 55
QQWSSYPLT                                                                9

SEQ ID NO: 56           moltype = AA   length = 11
FEATURE                 Location/Qualifiers
REGION                  1..11
                        note = 3E6 VH CDR1
source                  1..11
                        mol_type = protein
                        organism = synthetic construct
SEQUENCE: 56
GYSITSGFAW N                                                            11

SEQ ID NO: 57           moltype = AA   length = 10
FEATURE                 Location/Qualifiers
REGION                  1..10
                        note = 4H2 VH CDR1
source                  1..10
                        mol_type = protein
                        organism = synthetic construct
SEQUENCE: 57
GDSITSGYWN                                                              10

SEQ ID NO: 58           moltype = AA   length = 10
FEATURE                 Location/Qualifiers
REGION                  1..10
                        note = 16H1 VH CDR1
source                  1..10
                        mol_type = protein
                        organism = synthetic construct
SEQUENCE: 58
GYSFTSYLMH                                                              10

SEQ ID NO: 59           moltype = AA   length = 10
FEATURE                 Location/Qualifiers
REGION                  1..10
                        note = 18C6 VH CDR1
source                  1..10
                        mol_type = protein
                        organism = synthetic construct
SEQUENCE: 59
GYKFTDFLMH                                                              10

SEQ ID NO: 60           moltype = AA   length = 11
FEATURE                 Location/Qualifiers
REGION                  1..11
                        note = 19D11 VH CDR1
source                  1..11
                        mol_type = protein
                        organism = synthetic construct
SEQUENCE: 60
GYSITSGYSW H                                                            11

SEQ ID NO: 61           moltype = AA   length = 10
FEATURE                 Location/Qualifiers
REGION                  1..10
                        note = CH 5#, CH 8#, CH 11# VH CDR1
source                  1..10
```

```
                        mol_type = protein
                        organism = synthetic construct
SEQUENCE: 61
GYSFTGYYMH                                                                  10

SEQ ID NO: 62           moltype = AA   length = 10
FEATURE                 Location/Qualifiers
REGION                  1..10
                        note = CH 9# VH CDR1
source                  1..10
                        mol_type = protein
                        organism = synthetic construct
SEQUENCE: 62
GFSLTGYGVH                                                                  10

SEQ ID NO: 63           moltype = AA   length = 10
FEATURE                 Location/Qualifiers
REGION                  1..10
                        note = CH 10# VH CDR1
source                  1..10
                        mol_type = protein
                        organism = synthetic construct
SEQUENCE: 63
GYTFSSYWIE                                                                  10

SEQ ID NO: 64           moltype = AA   length = 17
FEATURE                 Location/Qualifiers
REGION                  1..17
                        note = 3E6 VH CDR2
source                  1..17
                        mol_type = protein
                        organism = synthetic construct
SEQUENCE: 64
GYISHSGSTS YNPSLKS                                                          17

SEQ ID NO: 65           moltype = AA   length = 17
FEATURE                 Location/Qualifiers
REGION                  1..17
                        note = 4H2 VH CDR2
source                  1..17
                        mol_type = protein
                        organism = synthetic construct
SEQUENCE: 65
GYINYSGSTY YNPSLKS                                                          17

SEQ ID NO: 66           moltype = AA   length = 18
FEATURE                 Location/Qualifiers
REGION                  1..18
                        note = 16H1 VH CDR2
source                  1..18
                        mol_type = protein
                        organism = synthetic construct
SEQUENCE: 66
GSIDPSDSEI SLNQKFMD                                                         18

SEQ ID NO: 67           moltype = AA   length = 18
FEATURE                 Location/Qualifiers
REGION                  1..18
                        note = 18C6 VH CDR2
source                  1..18
                        mol_type = protein
                        organism = synthetic construct
SEQUENCE: 67
GAIDTSDSYA SYNQKFKG                                                         18

SEQ ID NO: 68           moltype = AA   length = 17
FEATURE                 Location/Qualifiers
REGION                  1..17
                        note = 19D11 VH CDR2
source                  1..17
                        mol_type = protein
                        organism = synthetic construct
SEQUENCE: 68
GYIYFSGSTN YNPSLKS                                                          17

SEQ ID NO: 69           moltype = AA   length = 18
FEATURE                 Location/Qualifiers
REGION                  1..18
                        note = CH 5# VH CDR2
```

```
source                        1..18
                              mol_type = protein
                              organism = synthetic construct
SEQUENCE: 69
GRVNPNNGGT DYDQKFKG                                                     18

SEQ ID NO: 70                 moltype = AA   length = 18
FEATURE                       Location/Qualifiers
REGION                        1..18
                              note = CH 8# VH CDR2
source                        1..18
                              mol_type = protein
                              organism = synthetic construct
SEQUENCE: 70
GRVYPNNGGT SYNQKFKG                                                     18

SEQ ID NO: 71                 moltype = AA   length = 17
FEATURE                       Location/Qualifiers
REGION                        1..17
                              note = CH 9# VH CDR2
source                        1..17
                              mol_type = protein
                              organism = synthetic construct
SEQUENCE: 71
GMIWGDGSTD YNSALKS                                                      17

SEQ ID NO: 72                 moltype = AA   length = 18
FEATURE                       Location/Qualifiers
REGION                        1..18
                              note = CH 10# VH CDR2
source                        1..18
                              mol_type = protein
                              organism = synthetic construct
SEQUENCE: 72
GEISPGRGST NYNEKFKG                                                     18

SEQ ID NO: 73                 moltype = AA   length = 18
FEATURE                       Location/Qualifiers
REGION                        1..18
                              note = CH 11# VH CDR2
source                        1..18
                              mol_type = protein
                              organism = synthetic construct
SEQUENCE: 73
GRVNPNNGGT TYKQKFKG                                                     18

SEQ ID NO: 74                 moltype = AA   length = 11
FEATURE                       Location/Qualifiers
REGION                        1..11
                              note = 3E6 VH CDR3
source                        1..11
                              mol_type = protein
                              organism = synthetic construct
SEQUENCE: 74
ARGYRSPWFA Y                                                            11

SEQ ID NO: 75                 moltype = AA   length = 8
FEATURE                       Location/Qualifiers
REGION                        1..8
                              note = 4H2 VH CDR3
source                        1..8
                              mol_type = protein
                              organism = synthetic construct
SEQUENCE: 75
ATGNHFDY                                                                8

SEQ ID NO: 76                 moltype = AA   length = 12
FEATURE                       Location/Qualifiers
REGION                        1..12
                              note = 16H1 VH CDR3
source                        1..12
                              mol_type = protein
                              organism = synthetic construct
SEQUENCE: 76
ARDFGYVAWF VY                                                           12

SEQ ID NO: 77                 moltype = AA   length = 7
FEATURE                       Location/Qualifiers
REGION                        1..7
```

```
                        note = 18C6 VH CDR3
source                  1..7
                        mol_type = protein
                        organism = synthetic construct
SEQUENCE: 77
SREAMDY                                                             7

SEQ ID NO: 78           moltype = AA  length = 11
FEATURE                 Location/Qualifiers
REGION                  1..11
                        note = 19D11 VH CDR3
source                  1..11
                        mol_type = protein
                        organism = synthetic construct
SEQUENCE: 78
ARGYRSAWFA Y                                                       11

SEQ ID NO: 79           moltype = AA  length = 14
FEATURE                 Location/Qualifiers
REGION                  1..14
                        note = CH 5# VH CDR3
source                  1..14
                        mol_type = protein
                        organism = synthetic construct
SEQUENCE: 79
AREGEYFDYY AMDY                                                    14

SEQ ID NO: 80           moltype = AA  length = 14
FEATURE                 Location/Qualifiers
REGION                  1..14
                        note = CH 8# VH CDR3
source                  1..14
                        mol_type = protein
                        organism = synthetic construct
SEQUENCE: 80
AREGEYFDYF AMDY                                                    14

SEQ ID NO: 81           moltype = AA  length = 12
FEATURE                 Location/Qualifiers
REGION                  1..12
                        note = CH 9# VH CDR3
source                  1..12
                        mol_type = protein
                        organism = synthetic construct
SEQUENCE: 81
ARDRGNHWYF DV                                                      12

SEQ ID NO: 82           moltype = AA  length = 11
FEATURE                 Location/Qualifiers
REGION                  1..11
                        note = CH 10# VH CDR3
source                  1..11
                        mol_type = protein
                        organism = synthetic construct
SEQUENCE: 82
ARDYYGSIFD V                                                       11

SEQ ID NO: 83           moltype = AA  length = 14
FEATURE                 Location/Qualifiers
REGION                  1..14
                        note = CH 11# VH CDR3
source                  1..14
                        mol_type = protein
                        organism = synthetic construct
SEQUENCE: 83
AREGEYFDYY TMDY                                                    14

SEQ ID NO: 84           moltype = AA  length = 301
FEATURE                 Location/Qualifiers
REGION                  1..301
                        note = Human Tim-3 Isoform 1
source                  1..301
                        mol_type = protein
                        organism = synthetic construct
SEQUENCE: 84
MFSHLPFDCV LLLLLLLLTR SSEVEYRAEV GQNAYLPCFY TPAAPGNLVP VCWGKGACPV    60
FECGNVVLRT DERDVNYWTS RYWLNGDFRK GDVSLTIENV TLADSGIYCC RIQIPGIMND   120
EKFNLKLVIK PAKVTPAPTR QRDFTAAFPR MLTTRGHGPA ETQTLGSLPD INLTQISTLA   180
NELRDSRLAN DLRDSGATIR IGIYIGAGIC AGLALALIFG ALIFKWYSHS KEKIQNLSLI   240
```

```
SLANLPPSGL ANAVAEGIRS EENIYTIEEN VYEVEEPNEY YCYVSSRQQP SQPLGCRFAM    300
P                                                                   301

SEQ ID NO: 85            moltype = AA  length = 142
FEATURE                  Location/Qualifiers
REGION                   1..142
                         note = Human Tim-3 Isoform 2
source                   1..142
                         mol_type = protein
                         organism = synthetic construct
SEQUENCE: 85
MFSHLPFDCV LLLLLLLLTR SSEVEYRAEV GQNAYLPCFY TPAAPGNLVP VCWGKGACPV    60
FECGNVVLRT DERDVNYWTS RYWLNGDFRK GDVSLTIENV TLADSGIYCC RIQIPGIMND    120
EKFNLKLVIK PGEWTFACHL YE                                            142

SEQ ID NO: 86            moltype = AA  length = 11
FEATURE                  Location/Qualifiers
REGION                   1..11
                         note = 3E6 VL CDR1
source                   1..11
                         mol_type = protein
                         organism = synthetic construct
SEQUENCE: 86
KASQNVGANV A                                                        11

SEQ ID NO: 87            moltype = AA  length = 11
FEATURE                  Location/Qualifiers
REGION                   1..11
                         note = 4H2 VL CDR1
source                   1..11
                         mol_type = protein
                         organism = synthetic construct
SEQUENCE: 87
KASQDINKYI A                                                        11

SEQ ID NO: 88            moltype = AA  length = 11
FEATURE                  Location/Qualifiers
REGION                   1..11
                         note = 16H1 VL CDR1
source                   1..11
                         mol_type = protein
                         organism = synthetic construct
SEQUENCE: 88
KASQDVSAAV A                                                        11

SEQ ID NO: 89            moltype = AA  length = 16
FEATURE                  Location/Qualifiers
REGION                   1..16
                         note = 18C6 VL CDR1
source                   1..16
                         mol_type = protein
                         organism = synthetic construct
SEQUENCE: 89
RSSQSLVHSN GNTYLH                                                   16

SEQ ID NO: 90            moltype = AA  length = 11
FEATURE                  Location/Qualifiers
REGION                   1..11
                         note = 19D11 VL CDR1
source                   1..11
                         mol_type = protein
                         organism = synthetic construct
SEQUENCE: 90
KASQNVGTNV A                                                        11

SEQ ID NO: 91            moltype = AA  length = 15
FEATURE                  Location/Qualifiers
REGION                   1..15
                         note = CH 5#, CH 8#, CH 11# VL CDR1
source                   1..15
                         mol_type = protein
                         organism = synthetic construct
SEQUENCE: 91
RASESVEYYG TSLMQ                                                    15

SEQ ID NO: 92            moltype = AA  length = 10
FEATURE                  Location/Qualifiers
REGION                   1..10
                         note = CH 9# VL CDR1
```

```
source                    1..10
                          mol_type = protein
                          organism = synthetic construct
SEQUENCE: 92
RASSSVSYMH                                                          10

SEQ ID NO: 93             moltype = AA  length = 12
FEATURE                   Location/Qualifiers
REGION                    1..12
                          note = CH 10# VL CDR1
source                    1..12
                          mol_type = protein
                          organism = synthetic construct
SEQUENCE: 93
SASSSVSSSYLH                                                        12

SEQ ID NO: 94             moltype = AA  length = 7
FEATURE                   Location/Qualifiers
REGION                    1..7
                          note = 3E6, 19D11 VL CDR2
source                    1..7
                          mol_type = protein
                          organism = synthetic construct
SEQUENCE: 94
SASYRYS                                                             7

SEQ ID NO: 95             moltype = AA  length = 7
FEATURE                   Location/Qualifiers
REGION                    1..7
                          note = 4H2 VL CDR2
source                    1..7
                          mol_type = protein
                          organism = synthetic construct
SEQUENCE: 95
YTSTLQP                                                             7

SEQ ID NO: 96             moltype = AA  length = 7
FEATURE                   Location/Qualifiers
REGION                    1..7
                          note = 16H1 VL CDR2
source                    1..7
                          mol_type = protein
                          organism = synthetic construct
SEQUENCE: 96
STFYRYI                                                             7

SEQ ID NO: 97             moltype = AA  length = 7
FEATURE                   Location/Qualifiers
REGION                    1..7
                          note = 18C6 VL CDR2
source                    1..7
                          mol_type = protein
                          organism = synthetic construct
SEQUENCE: 97
KVSNRFS                                                             7

SEQ ID NO: 98             moltype = AA  length = 7
FEATURE                   Location/Qualifiers
REGION                    1..7
                          note = CH 5#, CH 8#, CH 11# VL CDR2
source                    1..7
                          mol_type = protein
                          organism = synthetic construct
SEQUENCE: 98
AASNVES                                                             7

SEQ ID NO: 99             moltype = AA  length = 7
FEATURE                   Location/Qualifiers
REGION                    1..7
                          note = CH 9# VL CDR2
source                    1..7
                          mol_type = protein
                          organism = synthetic construct
SEQUENCE: 99
ATSNLAS                                                             7

SEQ ID NO: 100            moltype = AA  length = 7
FEATURE                   Location/Qualifiers
REGION                    1..7
```

|  |  |  |
|---|---|---|
| source | note = CH 10#, 39D1 VL CDR2<br>1..7<br>mol_type = protein<br>organism = synthetic construct | |
| SEQUENCE: 100<br>STSNLAS | | 7 |
| SEQ ID NO: 101<br>FEATURE<br>REGION<br>source | moltype = AA  length = 6<br>Location/Qualifiers<br>1..6<br>note = 3E6 VH CDR1<br>1..6<br>mol_type = protein<br>organism = synthetic construct | |
| SEQUENCE: 101<br>SGFAWN | | 6 |
| SEQ ID NO: 102<br>FEATURE<br>REGION<br>source | moltype = AA  length = 5<br>Location/Qualifiers<br>1..5<br>note = 4H2 VH CDR1<br>1..5<br>mol_type = protein<br>organism = synthetic construct | |
| SEQUENCE: 102<br>SGYWN | | 5 |
| SEQ ID NO: 103<br>FEATURE<br>REGION<br>source | moltype = AA  length = 5<br>Location/Qualifiers<br>1..5<br>note = 16H1 VH CDR1<br>1..5<br>mol_type = protein<br>organism = synthetic construct | |
| SEQUENCE: 103<br>SYLMH | | 5 |
| SEQ ID NO: 104<br>FEATURE<br>REGION<br>source | moltype = AA  length = 5<br>Location/Qualifiers<br>1..5<br>note = 18C6 VH CDR1<br>1..5<br>mol_type = protein<br>organism = synthetic construct | |
| SEQUENCE: 104<br>DFLMH | | 5 |
| SEQ ID NO: 105<br>FEATURE<br>REGION<br>source | moltype = AA  length = 6<br>Location/Qualifiers<br>1..6<br>note = 19D11 VH CDR1<br>1..6<br>mol_type = protein<br>organism = synthetic construct | |
| SEQUENCE: 105<br>SGYSWH | | 6 |
| SEQ ID NO: 106<br>FEATURE<br>REGION<br>source | moltype = AA  length = 5<br>Location/Qualifiers<br>1..5<br>note = CH 5#, CH 8#, CH 11#, 3F2 VH CDR1<br>1..5<br>mol_type = protein<br>organism = synthetic construct | |
| SEQUENCE: 106<br>GYYMH | | 5 |
| SEQ ID NO: 107<br>FEATURE<br>REGION<br>source | moltype = AA  length = 5<br>Location/Qualifiers<br>1..5<br>note = CH 9# VH CDR1<br>1..5<br>mol_type = protein<br>organism = synthetic construct | |
| SEQUENCE: 107<br>GYGVH | | 5 |
| SEQ ID NO: 108<br>FEATURE | moltype = AA  length = 5<br>Location/Qualifiers | |

```
REGION                  1..5
                        note = CH 10# VH CDR1
source                  1..5
                        mol_type = protein
                        organism = synthetic construct
SEQUENCE: 108
SYWIE                                                                    5

SEQ ID NO: 109          moltype = AA  length = 16
FEATURE                 Location/Qualifiers
REGION                  1..16
                        note = 3E6 VH CDR2
source                  1..16
                        mol_type = protein
                        organism = synthetic construct
SEQUENCE: 109
YISHSGSTSY NPSLKS                                                        16

SEQ ID NO: 110          moltype = AA  length = 16
FEATURE                 Location/Qualifiers
REGION                  1..16
                        note = 4H2 VH CDR2
source                  1..16
                        mol_type = protein
                        organism = synthetic construct
SEQUENCE: 110
YINYSGSTYY NPSLKS                                                        16

SEQ ID NO: 111          moltype = AA  length = 17
FEATURE                 Location/Qualifiers
REGION                  1..17
                        note = 16H1 VH CDR2
source                  1..17
                        mol_type = protein
                        organism = synthetic construct
SEQUENCE: 111
SIDPSDSEIS LNQKFMD                                                       17

SEQ ID NO: 112          moltype = AA  length = 17
FEATURE                 Location/Qualifiers
REGION                  1..17
                        note = 18C6 VH CDR2
source                  1..17
                        mol_type = protein
                        organism = synthetic construct
SEQUENCE: 112
AIDTSDSYAS YNQKFKG                                                       17

SEQ ID NO: 113          moltype = AA  length = 16
FEATURE                 Location/Qualifiers
REGION                  1..16
                        note = 19D11 VH CDR2
source                  1..16
                        mol_type = protein
                        organism = synthetic construct
SEQUENCE: 113
YIYFSGSTNY NPSLKS                                                        16

SEQ ID NO: 114          moltype = AA  length = 17
FEATURE                 Location/Qualifiers
REGION                  1..17
                        note = CH 5# VH CDR2
source                  1..17
                        mol_type = protein
                        organism = synthetic construct
SEQUENCE: 114
RVNPNNGGTD YDQKFKG                                                       17

SEQ ID NO: 115          moltype = AA  length = 17
FEATURE                 Location/Qualifiers
REGION                  1..17
                        note = CH 8# VH CDR2
source                  1..17
                        mol_type = protein
                        organism = synthetic construct
SEQUENCE: 115
RVYPNNGGTS YNQKFKG                                                       17

SEQ ID NO: 116          moltype = AA  length = 16
```

```
FEATURE                 Location/Qualifiers
REGION                  1..16
                        note = CH 9# VH CDR2
source                  1..16
                        mol_type = protein
                        organism = synthetic construct
SEQUENCE: 116
MIWGDGSTDY NSALKS                                                          16

SEQ ID NO: 117          moltype = AA  length = 17
FEATURE                 Location/Qualifiers
REGION                  1..17
                        note = CH 10# VH CDR2
source                  1..17
                        mol_type = protein
                        organism = synthetic construct
SEQUENCE: 117
EISPGRGSTN YNEKFKG                                                         17

SEQ ID NO: 118          moltype = AA  length = 17
FEATURE                 Location/Qualifiers
REGION                  1..17
                        note = CH 11# VH CDR2
source                  1..17
                        mol_type = protein
                        organism = synthetic construct
SEQUENCE: 118
RVNPNNGGTT YKQKFKG                                                         17

SEQ ID NO: 119          moltype = AA  length = 9
FEATURE                 Location/Qualifiers
REGION                  1..9
                        note = 3E6 VH CDR3
source                  1..9
                        mol_type = protein
                        organism = synthetic construct
SEQUENCE: 119
GYRSPWFAY                                                                   9

SEQ ID NO: 120          moltype = AA  length = 6
FEATURE                 Location/Qualifiers
REGION                  1..6
                        note = 4H2 VH CDR3
source                  1..6
                        mol_type = protein
                        organism = synthetic construct
SEQUENCE: 120
GNHFDY                                                                      6

SEQ ID NO: 121          moltype = AA  length = 10
FEATURE                 Location/Qualifiers
REGION                  1..10
                        note = 16H1 VH CDR3
source                  1..10
                        mol_type = protein
                        organism = synthetic construct
SEQUENCE: 121
DFGYVAWFVY                                                                 10

SEQ ID NO: 122          moltype = AA  length = 5
FEATURE                 Location/Qualifiers
REGION                  1..5
                        note = 18C6 VH CDR3
source                  1..5
                        mol_type = protein
                        organism = synthetic construct
SEQUENCE: 122
EAMDY                                                                       5

SEQ ID NO: 123          moltype = AA  length = 9
FEATURE                 Location/Qualifiers
REGION                  1..9
                        note = 19D11 VH CDR3
source                  1..9
                        mol_type = protein
                        organism = synthetic construct
SEQUENCE: 123
GYRSAWFAY                                                                   9
```

```
SEQ ID NO: 124          moltype = AA  length = 12
FEATURE                 Location/Qualifiers
REGION                  1..12
                        note = CH 5# VH CDR3
source                  1..12
                        mol_type = protein
                        organism = synthetic construct
SEQUENCE: 124
EGEYFDYYAM DY                                                            12

SEQ ID NO: 125          moltype = AA  length = 12
FEATURE                 Location/Qualifiers
REGION                  1..12
                        note = CH 8# VH CDR3
source                  1..12
                        mol_type = protein
                        organism = synthetic construct
SEQUENCE: 125
EGEYFDYFAM DY                                                            12

SEQ ID NO: 126          moltype = AA  length = 10
FEATURE                 Location/Qualifiers
REGION                  1..10
                        note = CH 9# VH CDR3
source                  1..10
                        mol_type = protein
                        organism = synthetic construct
SEQUENCE: 126
DRGNHWYFDV                                                               10

SEQ ID NO: 127          moltype = AA  length = 9
FEATURE                 Location/Qualifiers
REGION                  1..9
                        note = CH 10# VH CDR3
source                  1..9
                        mol_type = protein
                        organism = synthetic construct
SEQUENCE: 127
DYYGSIFDV                                                                9

SEQ ID NO: 128          moltype = AA  length = 12
FEATURE                 Location/Qualifiers
REGION                  1..12
                        note = CH 11# VH CDR3
source                  1..12
                        mol_type = protein
                        organism = synthetic construct
SEQUENCE: 128
EGEYFDYYTM DY                                                            12

SEQ ID NO: 129          moltype = AA  length = 17
FEATURE                 Location/Qualifiers
REGION                  1..17
                        note = 3F2 VL CDR1
source                  1..17
                        mol_type = protein
                        organism = synthetic construct
SEQUENCE: 129
KSSQSVLYSS NQKNYLA                                                       17

SEQ ID NO: 130          moltype = AA  length = 17
FEATURE                 Location/Qualifiers
REGION                  1..17
                        note = 36A2 VL CDR1
source                  1..17
                        mol_type = protein
                        organism = synthetic construct
SEQUENCE: 130
KSSQSVLHSS NQKNFLA                                                       17

SEQ ID NO: 131          moltype = AA  length = 12
FEATURE                 Location/Qualifiers
REGION                  1..12
                        note = 36B11 VL CDR1
source                  1..12
                        mol_type = protein
                        organism = synthetic construct
SEQUENCE: 131
SASSGISSSY LY                                                            12
```

```
SEQ ID NO: 132            moltype = AA   length = 11
FEATURE                   Location/Qualifiers
REGION                    1..11
                          note = 38F8 VL CDR1
source                    1..11
                          mol_type = protein
                          organism = synthetic construct
SEQUENCE: 132
RASQDISNYL N                                                                   11

SEQ ID NO: 133            moltype = AA   length = 17
FEATURE                   Location/Qualifiers
REGION                    1..17
                          note = 38A8 VL CDR1
source                    1..17
                          mol_type = protein
                          organism = synthetic construct
SEQUENCE: 133
KSSQSLLNSR TRKNYLA                                                             17

SEQ ID NO: 134            moltype = AA   length = 12
FEATURE                   Location/Qualifiers
REGION                    1..12
                          note = 40F11 VL CDR1
source                    1..12
                          mol_type = protein
                          organism = synthetic construct
SEQUENCE: 134
RASSIVSSSY LH                                                                  12

SEQ ID NO: 135            moltype = AA   length = 11
FEATURE                   Location/Qualifiers
REGION                    1..11
                          note = 50H9 VL CDR1
source                    1..11
                          mol_type = protein
                          organism = synthetic construct
SEQUENCE: 135
QASQGSSVNL N                                                                   11

SEQ ID NO: 136            moltype = AA   length = 11
FEATURE                   Location/Qualifiers
REGION                    1..11
                          note = 84G10 VL CDR1
source                    1..11
                          mol_type = protein
                          organism = synthetic construct
SEQUENCE: 136
RASENINSYL A                                                                   11

SEQ ID NO: 137            moltype = AA   length = 10
FEATURE                   Location/Qualifiers
REGION                    1..10
                          note = 39D1 VL CDR1
source                    1..10
                          mol_type = protein
                          organism = synthetic construct
SEQUENCE: 137
SASSSVRFMH                                                                     10

SEQ ID NO: 138            moltype = AA   length = 7
FEATURE                   Location/Qualifiers
REGION                    1..7
                          note = 3F2 VL CDR2
source                    1..7
                          mol_type = protein
                          organism = synthetic construct
SEQUENCE: 138
WASFRES                                                                         7

SEQ ID NO: 139            moltype = AA   length = 7
FEATURE                   Location/Qualifiers
REGION                    1..7
                          note = 36A2, 38A8 VL CDR2
source                    1..7
                          mol_type = protein
                          organism = synthetic construct
SEQUENCE: 139
```

```
WASTRES                                                                7

SEQ ID NO: 140        moltype = AA  length = 7
FEATURE               Location/Qualifiers
REGION                1..7
                      note = 36B11 VL CDR2
source                1..7
                      mol_type = protein
                      organism = synthetic construct
SEQUENCE: 140
GTSNLAS                                                                7

SEQ ID NO: 141        moltype = AA  length = 7
FEATURE               Location/Qualifiers
REGION                1..7
                      note = 38F8 VL CDR2
source                1..7
                      mol_type = protein
                      organism = synthetic construct
SEQUENCE: 141
HTSRLYS                                                                7

SEQ ID NO: 142        moltype = AA  length = 7
FEATURE               Location/Qualifiers
REGION                1..7
                      note = 40F11 VL CDR2
source                1..7
                      mol_type = protein
                      organism = synthetic construct
SEQUENCE: 142
STSNLPS                                                                7

SEQ ID NO: 143        moltype = AA  length = 7
FEATURE               Location/Qualifiers
REGION                1..7
                      note = 50H9 VL CDR2
source                1..7
                      mol_type = protein
                      organism = synthetic construct
SEQUENCE: 143
GSNILED                                                                7

SEQ ID NO: 144        moltype = AA  length = 7
FEATURE               Location/Qualifiers
REGION                1..7
                      note = 84G10 VL CDR2
source                1..7
                      mol_type = protein
                      organism = synthetic construct
SEQUENCE: 144
HAKTLAS                                                                7

SEQ ID NO: 145        moltype = AA  length = 8
FEATURE               Location/Qualifiers
REGION                1..8
                      note = 3F2 VL CDR3
source                1..8
                      mol_type = protein
                      organism = synthetic construct
SEQUENCE: 145
HQSLSSYT                                                               8

SEQ ID NO: 146        moltype = AA  length = 8
FEATURE               Location/Qualifiers
REGION                1..8
                      note = 36A2 VL CDR3
source                1..8
                      mol_type = protein
                      organism = synthetic construct
SEQUENCE: 146
HQYLSSLT                                                               8

SEQ ID NO: 147        moltype = AA  length = 9
FEATURE               Location/Qualifiers
REGION                1..9
                      note = 36B11 VL CDR3
source                1..9
                      mol_type = protein
                      organism = synthetic construct
```

```
SEQUENCE: 147
HQWSNYPYT                                                                               9

SEQ ID NO: 148          moltype = AA  length = 9
FEATURE                 Location/Qualifiers
REGION                  1..9
                        note = 38F8 VL CDR3
source                  1..9
                        mol_type = protein
                        organism = synthetic construct
SEQUENCE: 148
QQGNTLPLT                                                                               9

SEQ ID NO: 149          moltype = AA  length = 8
FEATURE                 Location/Qualifiers
REGION                  1..8
                        note = 38A8 VL CDR3
source                  1..8
                        mol_type = protein
                        organism = synthetic construct
SEQUENCE: 149
KQSYSLLT                                                                                8

SEQ ID NO: 150          moltype = AA  length = 9
FEATURE                 Location/Qualifiers
REGION                  1..9
                        note = 40F11 VL CDR3
source                  1..9
                        mol_type = protein
                        organism = synthetic construct
SEQUENCE: 150
QQYSGYPYT                                                                               9

SEQ ID NO: 151          moltype = AA  length = 9
FEATURE                 Location/Qualifiers
REGION                  1..9
                        note = 50H9 VL CDR3
source                  1..9
                        mol_type = protein
                        organism = synthetic construct
SEQUENCE: 151
LQHSYLPYT                                                                               9

SEQ ID NO: 152          moltype = AA  length = 9
FEATURE                 Location/Qualifiers
REGION                  1..9
                        note = 84G10 VL CDR3
source                  1..9
                        mol_type = protein
                        organism = synthetic construct
SEQUENCE: 152
QHHYGTPLT                                                                               9

SEQ ID NO: 153          moltype = AA  length = 9
FEATURE                 Location/Qualifiers
REGION                  1..9
                        note = 39D1 VL CDR3
source                  1..9
                        mol_type = protein
                        organism = synthetic construct
SEQUENCE: 153
QQRSSYPPT                                                                               9

SEQ ID NO: 154          moltype = AA  length = 5
FEATURE                 Location/Qualifiers
REGION                  1..5
                        note = 36A2 VH CDR1
source                  1..5
                        mol_type = protein
                        organism = synthetic construct
SEQUENCE: 154
SFEMH                                                                                   5

SEQ ID NO: 155          moltype = AA  length = 7
FEATURE                 Location/Qualifiers
REGION                  1..7
                        note = 36B11 VH CDR1
source                  1..7
                        mol_type = protein
```

```
                              organism = synthetic construct
SEQUENCE: 155
TSGMGVG                                                                  7

SEQ ID NO: 156              moltype = AA  length = 5
FEATURE                     Location/Qualifiers
REGION                      1..5
                            note = 38F8 VH CDR1
source                      1..5
                            mol_type = protein
                            organism = synthetic construct
SEQUENCE: 156
DYSMD                                                                    5

SEQ ID NO: 157              moltype = AA  length = 5
FEATURE                     Location/Qualifiers
REGION                      1..5
                            note = 38A8 VH CDR1
source                      1..5
                            mol_type = protein
                            organism = synthetic construct
SEQUENCE: 157
TYNMH                                                                    5

SEQ ID NO: 158              moltype = AA  length = 5
FEATURE                     Location/Qualifiers
REGION                      1..5
                            note = 40F11 VH CDR1
source                      1..5
                            mol_type = protein
                            organism = synthetic construct
SEQUENCE: 158
TAEMQ                                                                    5

SEQ ID NO: 159              moltype = AA  length = 5
FEATURE                     Location/Qualifiers
REGION                      1..5
                            note = 50H9 VH CDR1
source                      1..5
                            mol_type = protein
                            organism = synthetic construct
SEQUENCE: 159
TNGMS                                                                    5

SEQ ID NO: 160              moltype = AA  length = 5
FEATURE                     Location/Qualifiers
REGION                      1..5
                            note = 84G10 VH CDR1
source                      1..5
                            mol_type = protein
                            organism = synthetic construct
SEQUENCE: 160
SYWMN                                                                    5

SEQ ID NO: 161              moltype = AA  length = 6
FEATURE                     Location/Qualifiers
REGION                      1..6
                            note = 39D1 VH CDR1
source                      1..6
                            mol_type = protein
                            organism = synthetic construct
SEQUENCE: 161
SSYWIE                                                                   6

SEQ ID NO: 162              moltype = AA  length = 17
FEATURE                     Location/Qualifiers
REGION                      1..17
                            note = 3F2 VH CDR2
source                      1..17
                            mol_type = protein
                            organism = synthetic construct
SEQUENCE: 162
YISCYNGATN YNQKFKG                                                      17

SEQ ID NO: 163              moltype = AA  length = 17
FEATURE                     Location/Qualifiers
REGION                      1..17
                            note = 36A2 VH CDR2
source                      1..17
```

```
                              mol_type = protein
                              organism = synthetic construct
SEQUENCE: 163
YISGGSTTIY YADTMKG                                                              17

SEQ ID NO: 164                moltype = AA   length = 16
FEATURE                       Location/Qualifiers
REGION                        1..16
                              note = 36B11 VH CDR2
source                        1..16
                              mol_type = protein
                              organism = synthetic construct
SEQUENCE: 164
HIWWDDVKRY NPALKS                                                               16

SEQ ID NO: 165                moltype = AA   length = 17
FEATURE                       Location/Qualifiers
REGION                        1..17
                              note = 38F8 VH CDR2
source                        1..17
                              mol_type = protein
                              organism = synthetic construct
SEQUENCE: 165
DINPNYDSLS YNQKFKG                                                              17

SEQ ID NO: 166                moltype = AA   length = 17
FEATURE                       Location/Qualifiers
REGION                        1..17
                              note = 38A8 VH CDR2
source                        1..17
                              mol_type = protein
                              organism = synthetic construct
SEQUENCE: 166
GIYPGNGDTS YNQKFKG                                                              17

SEQ ID NO: 167                moltype = AA   length = 17
FEATURE                       Location/Qualifiers
REGION                        1..17
                              note = 40F11 VH CDR2
source                        1..17
                              mol_type = protein
                              organism = synthetic construct
SEQUENCE: 167
WINTRSGVPK YAEDFKG                                                              17

SEQ ID NO: 168                moltype = AA   length = 17
FEATURE                       Location/Qualifiers
REGION                        1..17
                              note = 50H9 VH CDR2
source                        1..17
                              mol_type = protein
                              organism = synthetic construct
SEQUENCE: 168
TISSGGSNTY YPDSVKG                                                              17

SEQ ID NO: 169                moltype = AA   length = 17
FEATURE                       Location/Qualifiers
REGION                        1..17
                              note = 84G10 VH CDR2
source                        1..17
                              mol_type = protein
                              organism = synthetic construct
SEQUENCE: 169
QIYPGEGDTN YNGKFKG                                                              17

SEQ ID NO: 170                moltype = AA   length = 17
FEATURE                       Location/Qualifiers
REGION                        1..17
                              note = 39D1 VH CDR2
source                        1..17
                              mol_type = protein
                              organism = synthetic construct
SEQUENCE: 170
EILPGSGSIN YNEKFKG                                                              17

SEQ ID NO: 171                moltype = AA   length = 9
FEATURE                       Location/Qualifiers
REGION                        1..9
                              note = 3F2 VH CDR3
```

```
source                  1..9
                        mol_type = protein
                        organism = synthetic construct
SEQUENCE: 171
DYYLSVMDY                                                                         9

SEQ ID NO: 172          moltype = AA  length = 8
FEATURE                 Location/Qualifiers
REGION                  1..8
                        note = 36A2 VH CDR3
source                  1..8
                        mol_type = protein
                        organism = synthetic construct
SEQUENCE: 172
SYYGLLDY                                                                          8

SEQ ID NO: 173          moltype = AA  length = 10
FEATURE                 Location/Qualifiers
REGION                  1..10
                        note = 36B11 VH CDR3
source                  1..10
                        mol_type = protein
                        organism = synthetic construct
SEQUENCE: 173
TFITTTTMDY                                                                       10

SEQ ID NO: 174          moltype = AA  length = 10
FEATURE                 Location/Qualifiers
REGION                  1..10
                        note = 38F8 VH CDR3
source                  1..10
                        mol_type = protein
                        organism = synthetic construct
SEQUENCE: 174
RGYGKDYFDF                                                                       10

SEQ ID NO: 175          moltype = AA  length = 10
FEATURE                 Location/Qualifiers
REGION                  1..10
                        note = 38A8 VH CDR3
source                  1..10
                        mol_type = protein
                        organism = synthetic construct
SEQUENCE: 175
SYYTFDAMDC                                                                       10

SEQ ID NO: 176          moltype = AA  length = 7
FEATURE                 Location/Qualifiers
REGION                  1..7
                        note = 40F11 VH CDR3
source                  1..7
                        mol_type = protein
                        organism = synthetic construct
SEQUENCE: 176
GTYAMDY                                                                           7

SEQ ID NO: 177          moltype = AA  length = 9
FEATURE                 Location/Qualifiers
REGION                  1..9
                        note = 50H9 VH CDR3
source                  1..9
                        mol_type = protein
                        organism = synthetic construct
SEQUENCE: 177
RSELGPFAY                                                                         9

SEQ ID NO: 178          moltype = AA  length = 13
FEATURE                 Location/Qualifiers
REGION                  1..13
                        note = 84G10 VH CDR3
source                  1..13
                        mol_type = protein
                        organism = synthetic construct
SEQUENCE: 178
GHFYGSSYDW FAY                                                                   13

SEQ ID NO: 179          moltype = AA  length = 8
FEATURE                 Location/Qualifiers
REGION                  1..8
```

```
                        note = 39D1 VH CDR3
source                  1..8
                        mol_type = protein
                        organism = synthetic construct
SEQUENCE: 179
SYYYVMDY                                                                  8

SEQ ID NO: 180          moltype = AA  length = 112
FEATURE                 Location/Qualifiers
REGION                  1..112
                        note = 3F2 VL
source                  1..112
                        mol_type = protein
                        organism = synthetic construct
SEQUENCE: 180
NIMMTQSPSS LAVSAGEKVT MSCKSSQSVL YSSNQKNYLA WYQQKPGQSP KLLIYWASFR        60
ESGVPDRFTG SGSGTDFTLT ISSVQAEDLA VYYCHQSLSS YTFGGGTKLE IK                112

SEQ ID NO: 181          moltype = AA  length = 112
FEATURE                 Location/Qualifiers
REGION                  1..112
                        note = 36A2 VL
source                  1..112
                        mol_type = protein
                        organism = synthetic construct
SEQUENCE: 181
NIMMTQSPSS LSVSTGEKVT MSCKSSQSVL HSSNQKNFLA WFQQKPGQSP KLLIYWASTR        60
ESGVPDRFTG SGSGTDFTLT INNVQPEDLA VYYCHQYLSS LTFGAGTKLE LK                112

SEQ ID NO: 182          moltype = AA  length = 108
FEATURE                 Location/Qualifiers
REGION                  1..108
                        note = 36B11 VL
source                  1..108
                        mol_type = protein
                        organism = synthetic construct
SEQUENCE: 182
QIVLTQSPTI MSASPGEKVT LTCSASSGIS SSYLYWYQQK PGSSPKLWIY GTSNLASGVP        60
ARFSGSGSGT SYSLTISSLE AEDAASYFCH QWSNYPYTFG GGTKLEIK                    108

SEQ ID NO: 183          moltype = AA  length = 107
FEATURE                 Location/Qualifiers
REGION                  1..107
                        note = 38F8 VL
source                  1..107
                        mol_type = protein
                        organism = synthetic construct
SEQUENCE: 183
TWGMTQTTSS LSASLGDRVT ISCRASQDIS NYLNWYQQKP DGTVKLLIYH TSRLYSGVPS        60
RFTGSGSGTD YSLTISNLEQ EDIATYFCQQ GNTLPLTFGA GTKLELK                     107

SEQ ID NO: 184          moltype = AA  length = 112
FEATURE                 Location/Qualifiers
REGION                  1..112
                        note = 38A8 VL
source                  1..112
                        mol_type = protein
                        organism = synthetic construct
SEQUENCE: 184
DIVMSQSPSS LAVSAGEKVT MSCKSSQSLL NSRTRKNYLA WYQQKPGRSP KLLIYWASTR        60
ESGVPDRFTG GGSGTDFTLT ISSVQAEDLA VYYCKQSYSL LTFGAGTKLE LK                112

SEQ ID NO: 185          moltype = AA  length = 108
FEATURE                 Location/Qualifiers
REGION                  1..108
                        note = 40F11 VL
source                  1..108
                        mol_type = protein
                        organism = synthetic construct
SEQUENCE: 185
ENVLTQSPAI MSASPGEKVT MTCRASSIVS SSYLHWYQQK SGASPKLWIY STSNLPSGVP        60
ARFSGSGSGT FYSLTVSSVE SEDAATYYCQ QYSGYPYTFG GGTKLEIK                    108

SEQ ID NO: 186          moltype = AA  length = 107
FEATURE                 Location/Qualifiers
REGION                  1..107
                        note = 50H9 VL
source                  1..107
                        mol_type = protein
```

```
                        organism = synthetic construct
SEQUENCE: 186
DVQMIQSPSS LSASLGDIVT MTCQASQGSS VNLNWFQQKP GKSPKLLIHG SNILEDGVPS    60
RFSGSRYGTD FTLTISSLEN EDMATYFCLQ HSYLPYTFGG GTKLEIK                  107

SEQ ID NO: 187          moltype = AA   length = 107
FEATURE                 Location/Qualifiers
REGION                  1..107
                        note = 84G10 VL
source                  1..107
                        mol_type = protein
                        organism = synthetic construct
SEQUENCE: 187
DIQMTQSPAS LSASVGETVT ITCRASENIN SYLAWYQQKQ GKSPQLLVYH AKTLASGVPS    60
RFSGSGSGTQ FSLKINSLQP EDFGSYYCQH HYGTPLTFGA GARLELK                  107

SEQ ID NO: 188          moltype = AA   length = 106
FEATURE                 Location/Qualifiers
REGION                  1..106
                        note = 39D1 VL
source                  1..106
                        mol_type = protein
                        organism = synthetic construct
SEQUENCE: 188
QIVLTQSPAI MSASPGEMLT ITCSASSSVR FMHWFQQKPG TSPKLWIYST SNLASGVPAR    60
FSGSGSGTSY SLTVSRMEAE DAATYYCQQR SSYPPTFGGG TKLEIK                   106

SEQ ID NO: 189          moltype = AA   length = 118
FEATURE                 Location/Qualifiers
REGION                  1..118
                        note = 3F2 VH
source                  1..118
                        mol_type = protein
                        organism = synthetic construct
SEQUENCE: 189
EVQLQQSGPE LVKTGSSVKI SCKASGYSFT GYYMHWVRQS PGKSLEWIGY ISCYNGATNY    60
NQKFKGKATF TVDTYSSTAY MQFDSLASED SAVYYCVRDY YLSVMDYWGQ GTSVTVSS      118

SEQ ID NO: 190          moltype = AA   length = 117
FEATURE                 Location/Qualifiers
REGION                  1..117
                        note = 36A2 VH
source                  1..117
                        mol_type = protein
                        organism = synthetic construct
SEQUENCE: 190
DVQLVESGGG LVQPGGSRKL SCAASGFTFS SFEMHWVRQA PETGLEWVAY ISGGSTTIYY    60
ADTMKGRFTI SRDNPENTLF LQMTSLRSED TAIYYCVRSY YGLLDYWGQG TTLTVSS       117

SEQ ID NO: 191          moltype = AA   length = 120
FEATURE                 Location/Qualifiers
REGION                  1..120
                        note = 36B11 VH
source                  1..120
                        mol_type = protein
                        organism = synthetic construct
SEQUENCE: 191
QVTLKESGPG ILQPSQTLSL TCSFSGFSLS TSGMGVGWIR QPSGKGLEWL AHIWWDDVKR    60
YNPALKSRLT ISKDTSSSQV FLKIASVDTA DTATYYCVRT FITTTMDYW GQGTSVTVSS    120

SEQ ID NO: 192          moltype = AA   length = 119
FEATURE                 Location/Qualifiers
REGION                  1..119
                        note = 38F8 VH
source                  1..119
                        mol_type = protein
                        organism = synthetic construct
SEQUENCE: 192
EVQLQQLGAE LVKPGASVKI SCKASGYIFT DYSMDWVKQS HGESLEWIGD INPNYDSLSY    60
NQKFKGKATL TVDKSSSTAY MELRSLTSED TAVYYCARRG YGKDYFDFWG QGTSLTVSS     119

SEQ ID NO: 193          moltype = AA   length = 119
FEATURE                 Location/Qualifiers
REGION                  1..119
                        note = 38A8 VH
source                  1..119
                        mol_type = protein
                        organism = synthetic construct
SEQUENCE: 193
```

```
QVQLQQPGAE LVKPGASVKM SCKASGYTFT TYNMHWVKQT PGQGLEWIGG IYPGNGDTSY    60
NQKFKGKATL TADKSSSTAY MQLSSLTSED SAVYYCARSY YTFDAMDCWG QGTSVTVSS    119

SEQ ID NO: 194              moltype = AA   length = 116
FEATURE                     Location/Qualifiers
REGION                      1..116
                            note = 40F11 VH
source                      1..116
                            mol_type = protein
                            organism = synthetic construct
SEQUENCE: 194
QIQLVQSGPE LKKPGETVRI SCKASGYTFR TAEMQWVQKM PGRGLKWIGW INTRSGVPKY    60
AEDFKGRFAL SLETSATTAY LQISNLKNED TATYFCTRGT YAMDYWGQGT SVTVSS       116

SEQ ID NO: 195              moltype = AA   length = 118
FEATURE                     Location/Qualifiers
REGION                      1..118
                            note = 50H9 VH
source                      1..118
                            mol_type = protein
                            organism = synthetic construct
SEQUENCE: 195
EVQLVESGGD LVKPGGSLKL SCAASGFTFS TNGMSWVRQI PDKRLEWVAT ISSGGSNTYY    60
PDSVKGRFTI SRDNAKNTLY LQMSSLKSED TAMYYCARRS ELGPFAYWGQ GTLVTVSA    118

SEQ ID NO: 196              moltype = AA   length = 122
FEATURE                     Location/Qualifiers
REGION                      1..122
                            note = 84G10 VH
source                      1..122
                            mol_type = protein
                            organism = synthetic construct
SEQUENCE: 196
QVQLQQSGGE LVRPGSSVKI SCKASGYAFS SYWMNWVKQR PGQGLEWIGQ IYPGEGDTNY    60
NGKFKGKATL TADKSSSTAY MQLSSLTSED SAVYFCARGH FYGSSYDWFA YWGQGTLVTV   120
SA                                                                 122

SEQ ID NO: 197              moltype = AA   length = 118
FEATURE                     Location/Qualifiers
REGION                      1..118
                            note = 39D1 VH
source                      1..118
                            mol_type = protein
                            organism = synthetic construct
SEQUENCE: 197
QVQLQQSGAE LMKPGASVKI SCKATGYTFS SSYWIEWVKQ RPGHGLEWIG EILPGSGSIN    60
YNEKFKGKAT FTADTSSNTV YMQLSSLTSD DSAVYYCARS YYYVMDYWGQ GTSVTVSS    118

SEQ ID NO: 198              moltype = AA   length = 8
FEATURE                     Location/Qualifiers
REGION                      1..8
                            note = 3E6L-v1 VL CDR3
source                      1..8
                            mol_type = protein
                            organism = synthetic construct
SEQUENCE: 198
SQVNSYNT                                                             8

SEQ ID NO: 199              moltype = AA   length = 8
FEATURE                     Location/Qualifiers
REGION                      1..8
                            note = 3E6L-v2 VL CDR3
source                      1..8
                            mol_type = protein
                            organism = synthetic construct
SEQUENCE: 199
EQVNSYPT                                                             8

SEQ ID NO: 200              moltype = AA   length = 8
FEATURE                     Location/Qualifiers
REGION                      1..8
                            note = 3E6L-v3 VL CDR3
source                      1..8
                            mol_type = protein
                            organism = synthetic construct
SEQUENCE: 200
SQYNPYNT                                                             8

SEQ ID NO: 201              moltype = AA   length = 8
```

```
FEATURE              Location/Qualifiers
REGION               1..8
                     note = 3E6L-v4 VL CDR3
source               1..8
                     mol_type = protein
                     organism = synthetic construct
SEQUENCE: 201
SQVNPYNT                                                                    8

SEQ ID NO: 202       moltype = AA  length = 8
FEATURE              Location/Qualifiers
REGION               1..8
                     note = 3E6L-v5 VL CDR3
source               1..8
                     mol_type = protein
                     organism = synthetic construct
SEQUENCE: 202
EQVNPYPT                                                                    8

SEQ ID NO: 203       moltype = AA  length = 8
FEATURE              Location/Qualifiers
REGION               1..8
                     note = 3E6L-v6 VL CDR3
source               1..8
                     mol_type = protein
                     organism = synthetic construct
SEQUENCE: 203
QQVNPYPT                                                                    8

SEQ ID NO: 204       moltype = AA  length = 8
FEATURE              Location/Qualifiers
REGION               1..8
                     note = 3E6L-v7 VL CDR3
source               1..8
                     mol_type = protein
                     organism = synthetic construct
SEQUENCE: 204
EQYNPYPT                                                                    8

SEQ ID NO: 205       moltype = AA  length = 8
FEATURE              Location/Qualifiers
REGION               1..8
                     note = 3E6L-v8 VL CDR3
source               1..8
                     mol_type = protein
                     organism = synthetic construct
SEQUENCE: 205
SQVNSYPT                                                                    8

SEQ ID NO: 206       moltype = AA  length = 8
FEATURE              Location/Qualifiers
REGION               1..8
                     note = 3E6L-v9 VL CDR3
source               1..8
                     mol_type = protein
                     organism = synthetic construct
SEQUENCE: 206
EQVQSYPT                                                                    8

SEQ ID NO: 207       moltype = AA  length = 106
FEATURE              Location/Qualifiers
REGION               1..106
                     note = 3E6 VL0-v1
source               1..106
                     mol_type = protein
                     organism = synthetic construct
SEQUENCE: 207
DIQMTQSPSS LSASVGDRVT ITCKASQNVG ANVAWYQQKP GKAPKSLIYS ASYRYSGVPS            60
RFSGSGSGTD FTLTISSLQP EDFATYYCSQ VNSYNTFGGG TKVEIK                         106

SEQ ID NO: 208       moltype = AA  length = 106
FEATURE              Location/Qualifiers
REGION               1..106
                     note = 3E6 VL0-v2
source               1..106
                     mol_type = protein
                     organism = synthetic construct
SEQUENCE: 208
DIQMTQSPSS LSASVGDRVT ITCKASQNVG ANVAWYQQKP GKAPKSLIYS ASYRYSGVPS            60
```

RFSGSGSGTD FTLTISSLQP EDFATYYCEQ VNSYPTFGGG TKVEIK                106

SEQ ID NO: 209          moltype = AA   length = 106
FEATURE                 Location/Qualifiers
REGION                  1..106
                        note = 3E6 VL0-v3
source                  1..106
                        mol_type = protein
                        organism = synthetic construct
SEQUENCE: 209
DIQMTQSPSS LSASVGDRVT ITCKASQNVG ANVAWYQQKP GKAPKSLIYS ASYRYSGVPS   60
RFSGSGSGTD FTLTISSLQP EDFATYYCSQ YNPYNTFGGG TKVEIK                106

SEQ ID NO: 210          moltype = AA   length = 106
FEATURE                 Location/Qualifiers
REGION                  1..106
                        note = 3E6 VL0-v4
source                  1..106
                        mol_type = protein
                        organism = synthetic construct
SEQUENCE: 210
DIQMTQSPSS LSASVGDRVT ITCKASQNVG ANVAWYQQKP GKAPKSLIYS ASYRYSGVPS   60
RFSGSGSGTD FTLTISSLQP EDFATYYCSQ VNPYNTFGGG TKVEIK                106

SEQ ID NO: 211          moltype = AA   length = 106
FEATURE                 Location/Qualifiers
REGION                  1..106
                        note = 3E6 VL0-v5
source                  1..106
                        mol_type = protein
                        organism = synthetic construct
SEQUENCE: 211
DIQMTQSPSS LSASVGDRVT ITCKASQNVG ANVAWYQQKP GKAPKSLIYS ASYRYSGVPS   60
RFSGSGSGTD FTLTISSLQP EDFATYYCEQ VNPYPTFGGG TKVEIK                106

SEQ ID NO: 212          moltype = AA   length = 106
FEATURE                 Location/Qualifiers
REGION                  1..106
                        note = 3E6 VL0-v6
source                  1..106
                        mol_type = protein
                        organism = synthetic construct
SEQUENCE: 212
DIQMTQSPSS LSASVGDRVT ITCKASQNVG ANVAWYQQKP GKAPKSLIYS ASYRYSGVPS   60
RFSGSGSGTD FTLTISSLQP EDFATYYCQQ VNPYPTFGGG TKVEIK                106

SEQ ID NO: 213          moltype = AA   length = 106
FEATURE                 Location/Qualifiers
REGION                  1..106
                        note = 3E6 VL0-v7
source                  1..106
                        mol_type = protein
                        organism = synthetic construct
SEQUENCE: 213
DIQMTQSPSS LSASVGDRVT ITCKASQNVG ANVAWYQQKP GKAPKSLIYS ASYRYSGVPS   60
RFSGSGSGTD FTLTISSLQP EDFATYYCEQ YNPYPTFGGG TKVEIK                106

SEQ ID NO: 214          moltype = AA   length = 106
FEATURE                 Location/Qualifiers
REGION                  1..106
                        note = 3E6 VL0-v8
source                  1..106
                        mol_type = protein
                        organism = synthetic construct
SEQUENCE: 214
DIQMTQSPSS LSASVGDRVT ITCKASQNVG ANVAWYQQKP GKAPKSLIYS ASYRYSGVPS   60
RFSGSGSGTD FTLTISSLQP EDFATYYCSQ VNSYPTFGGG TKVEIK                106

SEQ ID NO: 215          moltype = AA   length = 106
FEATURE                 Location/Qualifiers
REGION                  1..106
                        note = 3E6 VL0-v9
source                  1..106
                        mol_type = protein
                        organism = synthetic construct
SEQUENCE: 215
DIQMTQSPSS LSASVGDRVT ITCKASQNVG ANVAWYQQKP GKAPKSLIYS ASYRYSGVPS   60
RFSGSGSGTD FTLTISSLQP EDFATYYCEQ VQSYPTFGGG TKVEIK                106

```
SEQ ID NO: 216          moltype = AA  length = 5
FEATURE                 Location/Qualifiers
REGION                  1..5
                        note = Linker
REPEAT                  1..5
                        note = (GGGGS)n, n=1,2,3,4, or 5
REPEAT                  1..5
                        note = (GGGGS)n, n=1,2,3,4, or 5
source                  1..5
                        mol_type = protein
                        organism = synthetic construct
SEQUENCE: 216
GGGGS                                                                         5

SEQ ID NO: 217          moltype = AA  length = 5
FEATURE                 Location/Qualifiers
REGION                  1..5
                        note = Linker
REPEAT                  1..5
                        note = (EAAAK)n, n=1,2,3,4, or 5
source                  1..5
                        mol_type = protein
                        organism = synthetic construct
SEQUENCE: 217
EAAAK                                                                         5
```

What is claimed is:

1. An antibody or antigen-binding fragment thereof that specifically binds human TIM-3, comprising
    (a) a light chain variable region (VL) comprising a light chain CDR1 (VL CDR1) having the amino acid sequence of SEQ ID NO:86, a light chain CDR2 (VL CDR2) having the amino acid sequence of SEQ ID NO:94, and a light chain CDR3 (VL CDR3) having the amino acid sequence of SEQ ID NO:47 or the amino acid sequence of SEQ ID NO:47 in which (i) the first Q residue is substituted with S or E, (ii) the third Y residue is substituted with V, (iii) the fourth N residue is substituted with Q, (iv) the fifth S residue is substituted with P, or (v) the seventh P residue is substituted with N, or any combination of (i)-(v); and
    (b) a heavy chain variable region (VH) comprising a heavy chain CDR1 (VH CDR1) having the amino acid sequence of SEQ ID NO:101, a heavy chain CDR2 (VH CDR2) having the amino acid sequence of SEQ ID NO: 109, and a heavy chain CDR3 (VH CDR3) having the amino acid sequence of SEQ ID NO:119.

2. The antibody or antigen-binding fragment of claim 1, wherein:
    (a) the VL of the antibody or antigen-binding fragment comprises:
    (1) a VL CDR1 having the amino acid sequence of SEQ ID NO:86;
    (2) a VL CDR2 having the amino acid sequence of SEQ ID NO:94; and
    (3) a VL CDR3 having an amino acid sequence selected from the group consisting of SEQ ID NOs:47 and 198-206; and
    (b) the VH of the antibody or antigen-binding fragment comprises:
    (1) a VH CDR1 having the amino acid sequence of SEQ ID NO:101;
    (2) a VH CDR2 having the amino acid sequence of SEQ ID NO:109; and
    (3) a VH CDR3 having the amino acid sequence of SEQ ID NO:119.

3. The antibody or antigen-binding fragment of claim 2, wherein
    (1) the VL CDR1, CDR2, and CDR3 have the amino acid sequences of SEQ ID NOs:86, 94, and 47, respectively; and the VH CDR1, CDR2, and CDR3 have the amino acid sequences of SEQ ID NOs:101, 109, and 119, respectively;
    (2) the VL CDR1, CDR2, and CDR3 have the amino acid sequences of SEQ ID NOs:86, 94, and 198, respectively; and the VH CDR1, CDR2, and CDR3 have the amino acid sequences of SEQ ID NOs: 101, 109, and 119, respectively;
    (3) the VL CDR1, CDR2, and CDR3 have the amino acid sequences of SEQ ID NOs:86, 94, and 199, respectively; and the VH CDR1, CDR2, and CDR3 have the amino acid sequences of SEQ ID NOs: 101, 109, and 119, respectively;
    (4) the VL CDR1, CDR2, and CDR3 have the amino acid sequences of SEQ ID NOs:86, 94, and 200, respectively; and the VH CDR1, CDR2, and CDR3 have the amino acid sequences of SEQ ID NOs: 101, 109, and 119, respectively;
    (5) the VL CDR1, CDR2, and CDR3 have the amino acid sequences of SEQ ID NOs:86, 94, and 201, respectively; and the VH CDR1, CDR2, and CDR3 have the amino acid sequences of SEQ ID NOs: 101, 109, and 119, respectively;
    (6) the VL CDR1, CDR2, and CDR3 have the amino acid sequences of SEQ ID NOs:86, 94, and 202, respectively; and the VH CDR1, CDR2, and CDR3 have the amino acid sequences of SEQ ID NOs: 101, 109, and 119, respectively;
    (7) the VL CDR1, CDR2, and CDR3 have the amino acid sequences of SEQ ID NOs:86, 94, and 203, respectively; and the VH CDR1, CDR2, and CDR3 have the amino acid sequences of SEQ ID NOs: 101, 109, and 119, respectively;
    (8) the VL CDR1, CDR2, and CDR3 have the amino acid sequences of SEQ ID NOs:86, 94, and 204, respectively; and the VH CDR1, CDR2, and CDR3 have the amino acid sequences of SEQ ID NOs: 101, 109, and 119, respectively;

(9) the VL CDR1, CDR2, and CDR3 have the amino acid sequences of SEQ ID NOs:86, 94, and 205, respectively; and the VH CDR1, CDR2, and CDR3 have the amino acid sequences of SEQ ID NOs: 101, 109, and 119, respectively; or

(10) the VL CDR1, CDR2, and CDR3 have the amino acid sequences of SEQ ID NOs:86, 94, and 206, respectively; and the VH CDR1, CDR2, and CDR3 have the amino acid sequences of SEQ ID NOs:101, 109, and 119, respectively.

4. The antibody or antigen-binding fragment of claim 1, comprising:
(a) a VL having at least 85%, at least 90%, at least 95%, at least 98%, or 100% sequence identity to the amino acid sequence of SEQ ID NO:1; and
(b) a VH having at least 85%, at least 90%, at least 95%, at least 98%, or 100% sequence identity to the amino acid sequence of SEQ ID NO:11.

5. The antibody or antigen-binding fragment of claim 1, comprising:
(a) a VL having at least 85%, at least 90%, at least 95%, at least 98%, or 100% sequence identity to an amino acid sequence selected from the group consisting of SEQ ID NOs:21 and 207-215; and
(b) a VH having at least 85%, at least 90%, at least 95%, at least 98%, or 100% sequence identity to an amino acid sequence selected from the group consisting of SEQ ID NOs:22-29.

6. The antibody or antigen-binding fragment of claim 1 that blocks the interaction between TIM-3 and a TIM-3 ligand.

7. The antibody or antigen-binding fragment of claim 1 that (1) inhibits TIM-3 mediated T cell suppression, (2) inhibits TIM-3 mediated myeloid cell suppression, (3) inhibits TIM-3 mediated suppression of inflammasome activation, or any combination thereof.

8. The antibody or antigen-binding fragment of claim 1 that is a monoclonal antibody or antigen-binding fragment.

9. The antibody or antigen-binding fragment of claim 1 that is selected from the group consisting of an IgG1 antibody, an IgG2 antibody, an IgG3 antibody, and an IgG4 antibody.

10. The antibody or antigen-binding fragment of claim 1 that is selected from the group consisting of a Fab, a Fab', a F(ab')$_2$, a Fv, a scFv, a (scFv)$_2$, a single domain antibody (sdAb), and a heavy chain antibody (HCAb).

11. The antibody or antigen-binding fragment of claim 1 that is a chimeric antibody or antigen-binding fragment, a humanized antibody or antigen-binding fragment, or a human antibody or antigen-binding fragment.

12. A pharmaceutical composition comprising a therapeutically effective amount of the antibody or antigen-binding fragment of claim 1, and a pharmaceutically acceptable carrier.

13. The antibody or antigen-binding fragment of claim 1, wherein the VL CDR1, CDR2, and CDR3 have the amino acid sequences of SEQ ID NOs:86, 94, and 47, respectively; and the VH CDR1, CDR2, and CDR3 have the amino acid sequences of SEQ ID NOs:101, 109, and 119, respectively.

14. The antibody or antigen-binding fragment of claim 1, comprising:
(a) a VL having an amino acid sequence selected from the group consisting of SEQ ID NOs:21 and 207-215; and
(b) a VH having an amino acid sequence selected from the group consisting of SEQ ID NOs:22-29.

15. The antibody or antigen-binding fragment of claim 1, comprising:
(a) a VL having at least 85%, at least 90%, at least 95%, at least 98%, or 100% sequence identity to the amino acid sequence of SEQ ID NO:21; and
(b) a VH having at least 85%, at least 90%, at least 95%, at least 98%, or 100% sequence identity to the amino acid sequence of SEQ ID NO:28.

16. The antibody or antigen-binding fragment of claim 1, comprising:
(a) a VL having the amino acid sequence of SEQ ID NO:21; and
(b) a VH having the amino acid sequence of SEQ ID NO:28.

* * * * *